US010869889B2

(12) United States Patent
Jensen et al.

(10) Patent No.: US 10,869,889 B2
(45) Date of Patent: *Dec. 22, 2020

(54) METHOD AND COMPOSITIONS FOR CELLULAR IMMUNOTHERAPY

(71) Applicants: Fred Hutchinson Cancer Research Center, Seattle, WA (US); Seattle Children's Hospital, Seattle, WA (US)

(72) Inventors: Michael C. Jensen, Bainbridge Island, WA (US); Stanley R. Riddell, Sammamish, WA (US); Michael Hudecek, Leipzig (DE)

(73) Assignees: Fred Hutchinson Cancer Research Center, Seattle, WA (US); Seattle Children's Hospital, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/657,666

(22) Filed: Oct. 18, 2019

(65) Prior Publication Data

US 2020/0078405 A1 Mar. 12, 2020

Related U.S. Application Data

(63) Continuation of application No. 14/422,640, filed as application No. PCT/US2013/055862 on Aug. 20, 2013.

(60) Provisional application No. 61/691,117, filed on Aug. 20, 2012.

(51) Int. Cl.

| | |
|---|---|
| ***A61K 35/17*** | (2015.01) |
| ***C07K 14/705*** | (2006.01) |
| ***C07K 14/725*** | (2006.01) |
| ***C07K 14/715*** | (2006.01) |
| ***C07K 16/28*** | (2006.01) |
| ***C07K 16/32*** | (2006.01) |
| ***C07K 16/40*** | (2006.01) |

(52) U.S. Cl.

CPC ............ *A61K 35/17* (2013.01); *C07K 14/705* (2013.01); *C07K 14/7051* (2013.01); *C07K 14/70521* (2013.01); *C07K 14/7151* (2013.01); *C07K 16/2803* (2013.01); *C07K 16/32* (2013.01); *C07K 16/40* (2013.01); *C07K 2317/622* (2013.01); *C07K 2317/64* (2013.01); *C07K 2319/03* (2013.01); *C07K 2319/30* (2013.01); *C07K 2319/70* (2013.01)

(58) Field of Classification Search

None

See application file for complete search history.

(56) References Cited

U.S. PATENT DOCUMENTS

| | | | |
|---|---|---|---|
| 6,040,177 | A | 3/2000 | Riddell et al. |
| 8,822,647 | B2 | 9/2014 | Jensen |
| 2003/0148982 | A1 | 9/2003 | Brenner |
| 2008/0131415 | A1 | 6/2008 | Riddell et al. |
| 2011/0059012 | A1 | 3/2011 | Turtle et al. |
| 2013/0202622 | A1 | 8/2013 | Riddell et al. |
| 2013/0287748 | A1 | 10/2013 | June et al. |
| 2014/0314795 | A1 | 10/2014 | Riddell et al. |
| 2015/0306141 | A1 | 10/2015 | Jensen et al. |
| 2018/0200298 | A1 | 7/2018 | Jensen et al. |

FOREIGN PATENT DOCUMENTS

| | | | |
|---|---|---|---|
| WO | 92/08796 | A1 | 5/1992 |
| WO | 1992/015322 | | 9/1992 |
| WO | 94/28143 | A1 | 12/1994 |
| WO | 1995/021528 | | 8/1995 |
| WO | 02/077029 | A2 | 10/2002 |
| WO | 2010/025177 | A1 | 3/2010 |
| WO | 2011/056894 | A2 | 5/2011 |
| WO | 2012/129514 | A1 | 9/2012 |
| WO | 2013/123061 | A1 | 8/2013 |
| WO | 2013/126712 | A1 | 8/2013 |

OTHER PUBLICATIONS

Berasain et al., Mol. Biochem. Parasitol., 2003, p. 1-7.*

Adlersberg, "The Immunoglobulin Hinge (Interdomain) Region," *La Ricerca Clin. Lab.* 6:191-205 (1976).

Altvater et al., "2B4 (CD244) signaling via chimeric receptors costimulates tumor-antigen specific proliferation and in vitro expansion of human T cells," *Cancer Immunol Immunother* 58:1991-2001 (2009).

Altvater et al., "2B4 (CD244) Signaling by Recombinant Antigen-specific Chimeric Receptors Costimulates Natural Killer Cell Activation to Leukemia and Neuroblastoma Cells," *Clin Cancer Res* 15(15):4857-4866 (2009).

(Continued)

*Primary Examiner* — Ileana Popa

(74) *Attorney, Agent, or Firm* — Seed IP Law Group LLP

(57) ABSTRACT

The present invention provides nucleic acids, vectors, host cells, methods and compositions to confer and/or augment immune responses mediated by cellular immunotherapy, such as by adoptively transferring CD8+ central memory T cells or combinations of central memory T cells with CD4+ T cells that are genetically modified to express a chimeric receptor. In embodiments the genetically modified host cell comprises a nucleic acid comprising a polynucleotide coding for a ligand binding domain, a polynucleotide comprising a customized spacer region, a polynucleotide comprising a transmembrane domain, and a polynucleotide comprising an intracellular signaling domain. It has been surprisingly found that the length of the spacer region can affects the ability of chimeric receptor modified T cells to recognize target cells in vitro and affects in vivo efficacy of the chimeric receptor modified T cells. Pharmaceutical formulations produced by the method, and methods of using the same, are also described.

18 Claims, 20 Drawing Sheets

Specification includes a Sequence Listing.

(56) References Cited

OTHER PUBLICATIONS

Bejcek et al., "Development and Characterization of Three Recombinant Single Chain Antibody Fragments (scFvs) Directed against the CD19 Antigen," *Cancer Research* 55:2346-2351, 1995.
Bloom et al., "Intrachain disulfide bond in the core hinge region of human IgG4," *Protein Science* 6:407-415 (1997).
Brentjens et al., "Treatment of Chronic Lymphocytic Leukemia With Genetically Targeted Autologous T Cells: Case Report of an Unforeseen Adverse Event in a Phase I Clinical Trial," *Mol. Ther.*, 18(4):666-668 (2010).
Brezski et al., "A monoclonal antibody against hinge-cleaved lgG restores effector function to proteolytically-inactivated lgGs in vitro and in vivo," *mAbs* 6(5):1265-1273 (Sep.-Oct. 2014).
Bridgeman et al., "Building Better Chimeric Antigen Receptors for Adoptive T Cell Therapy," *Current Gene Therapy* 10:77-90 (2010).
Chang et al., "Transgene-enforced co-stimulation of CD4+ T cells leads to enhanced and sustained anti-tumor effector functioning," *Cytotherapy* 9(8):771-784 (2007).
Cheadle et al., "Natural Expression of the CD19 Antigen Impacts the Long-Term Engraftment but Not Antitumor Activity of CD19-Specific Engineered T Cells," Journal of Immunology 184, 2010, 12 pages.
Cheadle et al., "Eradication of Established B-cell Lymphoma by CD19-specific Murine T Cells is Dependent on Host Lymphopenic Environment and Can be Mediated by CD4+ and CD8+ T Cells,"*J Immunother* 32(3):207-218 (Apr. 2009).
Cheadle et al., "Killing of non-Hodgkin lymphoma cells by autologous CD19 engineered T cells," *British Journal of Haematology* 129:322-332 (2005).
Cheadle et al., "The combination of cyclophosphamide and human T cells genetically engineered to target CD19 can eradicate established B-cell lymphoma," *British Journal of Haematology* 142(1):65-68 (2008).
Chen et al., "Generation and Analysis of Random Point Mutations in an Antibody CDR2 Sequence: Many Mutated Antibodies Lose Their Ability to Bind Antigen," J. Exp. Med. 176:855-866, 1992.
Cho et al., "Structure of the extracellular region of HER2 alone and in complex with the Herceptin Fab," Nature 421:756-760, 2003.
Davis et al., "The kinetic-segregation model: TCR triggering and beyond," *Nature Immunology* 7(8):803-809 (Aug. 2006).
Fitzer-Attas et al., "Harnessing Syk Family Tyrosine Kinases as Signaling Domains for Chimeric Single Chain of the Variable Domain Receptors: Optimal Design for T Cell Activation," Journal of Immunology 160:145-154, 1998.
Gattenlöhner et al., "Rhabdomyosarcoma Lysis by T Cells Expressing a Human Autoantibody-Based Chimeric Receptor Targeting the Fetal Acetylcholine Receptor," *Cancer Res* 66(1):24-28 (2006).
Gonzalez et al., "Genetic engineering of cytolytic T lymphocytes for adoptive T-cell therapy of neuroblastoma," *The Journal of Gene Medicine* 6:704-711 (2004).
Guest et al., "The Role of Extracellular Spacer Regions in the Optimal Design of Chimeric Immune Receptors," J Immunother 28(3):203-211, 2005.
Hombach et al., "T Cell Activation by Antibody-Like Immunoreceptors: The Position of the binding Epitope within the Target Molecule Determines the Efficiency of Activation of Redirected T Cells," Journal of Immunology 178:4650-4657, 2007.
Hombach et al., "Adoptive immunotherapy with genetically engineered T cells: modification of the IgG1 Fc 'spacer' domain in the extracellular moiety of chimeric antigen receptors avoids 'off-target' activation and unintended initiation of an innate immune response," Gene Ther. 17:1206-1213, 2010.
Hoyos et al., "Engineering CD19-specific T lymphocytes with interleukin-15 and a suicide gene to enhance their anti-lymphoma/leukemia effects and safety," *Leukemia* 24:1160-1170 (2010).
Hudecek et al., "The Non-signaling Extracellular Spacer Domain of Chimeric Antigen Receptors is Decisive for *In Vivo* Antitumor Activity," *Cancer Immunol Res*. 3(2):125-135 (2014).
Hudecek et al., "The B-cell tumor-associated antigen ROR1 can be targeted with T cells modified to express a ROR1-specific chimeric antigen receptor," Blood 116:4532-4541, 2010.
Hudecek et al. "The Anti-Tumor Reactivity of ROR1-CAR Modified T Cells Depends on the Targeted Epitope, CAR-Affinity and Design of the CAR Extracellular Domain," Clinical Lymphoma, Myeloma & Leukemia 11(Supplement 2), Abstract, 3 pages (Oct. 2011).
Imai et al., "Genetic modification of primary natural killer cells overcomes inhibitory signals and induces specific killing of leukemic cells," *Blood* 106(1):376-373 (2005).
James et al., "Antigen Sensitivity of CD22-Specific Chimeric TCR is Modulated by Target Epitome Distance from the Cell Membrane," Journal of Immunology 180:7028-7038, 2008.
Jensen et al., "Antitransgene Rejection Responses Contribute to Attenuated Persistence of Adoptively Transferred CD20/CD19-Specific Chimeric Antigen Receptor Redirected T Cells in Humans," Biol. Blood Marrow Transplant 16:1245-1256 (2010).
Kahlon et al., "Specific Recognition and Killing of Glioblastoma Multiforme by Interleukin 13-Zetakine Redirected Cytolytic T Cells," *Cancer Research* 64:9160-9166 (2004).
Kalos et al., "T Cells with Chimeric Antigen Receptors Have Potent Antitumor Effects and Can Establish Memory in Patients with Advanced Leukemia," *Sci. Trans. Med*. 3 95(95ra73):1-13 (2011).
Kochenderfer et al., "Construction and Pre-clinical Evaluation of an Anti-CD19 Chimeric Antigen Receptor," *J Immunother*. 32(7):689-702 (Sep. 2009).
Kochenderfer et al., "Eradication of B-lineage cells and regression of lymphoma in a patient treated with autologous T cells genetically engineered to recognize CD19," *Blood* 116(20):4099-4102 (Nov. 18, 2010).
Koehler et al., "Engineered T Cells for the Adoptive Therapy of B-Cell Chronic Lymphocytic Leukaemia," Advances in Hematology 2012, 2012, 13 pages.
Kowolik et al., "CD28 Costimulation Provided through a CD19-Specific Chimeric Antigen Receptor Enhances In vivo Persistence and Antitumor Efficacy of Adoptively Transferred T Cells," *Cancer Res* 66(22):10995-11004 (2006).
Kradin et al., "Adoptive Immunotherapy with Interleukin-2 (IL-2) Results in Diminished IL-2 Production by Stimulated Peripheral Blood Lymphocytes," *Journal of Clinical Immunology* 9(5):378-385 (1989).
Landmeier et al., "Gene-Engineered Varicella-Zoster Virus-Reactive CD4+ *Cytotoxic T Cells Exert Tumor-Specific Effector Function*," *Cancer Res* 67(17):8335-8343 (2007).
Loskog et al., "Addition of the CD28 signaling domain to chimeric T-cell receptors enhances chimeric T-cell resistance to T regulatory cells," *Leukemia* 20:1819-1828 (2006).
Lupton et al., "Dominant Positive and Negative Selection Using a Hygromycin Phosphotransferase-Thymidine Kinase Fusion Gene," Molecular and Cellular Biology 11(6):3374-3378, 1991.
Marin et al., "Enhancement of the anti-leukemic activity of cytokine induced killer cells with an anti-CD19 chimeric receptor delivering a 4-1BB-ζ activating signal," *Experimental Hematology* 35:1388-1397 (2007).
Micklethwaite et al., "Derivation of human T lymphocytes from cord blood and peripheral blood with antiviral and antileukemic specificity from a single culture as protection against infection and relapse after stem cell transplantation," *Blood* 115(13):2695-2703 (Apr. 1, 2010).
Moritz et al., "A spacer region between the single chain antibody—and the CD3ζ-chain domain of chimeric T cell receptor components is required for efficient ligand binding and signaling activity," *Gene Therapy* 2:539-546 (1995).
Nicholson et al., "Construction and characterisation of a functional CD19 specific single chain Fv fragment for immunotherapy of B lineage leukaemia and lymphoma." *Molecular Immunology* 24(16-17):1157-1165 (1997).
Park et al., "Adoptive Transfer of Chimeric Antigen Receptor Re-directed Cytolytic T Lymphocyte Clones in Pateints with Neuroblastoma," *Molecular Therapy* 15(4):825-833 (2007).

(56) References Cited

OTHER PUBLICATIONS

Patel et al., "Impact of chimeric immune receptor extracellular protein domains on T cell function," Gene Therapy 6:412-419 (1999).
Pezzutto et al., "CD19 monoclonal antibody HD37 inhibits anti-immunoglobulin-induced B cell activation and proliferation," The Journal of Immunology 138:2793-2799, 1987.
Pule et al., "A Chimeric T Cell Antigen Receptor That Augments Cytokine Release and Supports Clonal Expansion of Primary Human T Cells," *Molecular Therapy* 12(5):933-941 (2005).
Ramos et al., "Chimeric Antigen Receptor (CAR)-Engineered Lymphocytes for Cancer Therapy," Expert Opin Biol Ther. 11(7):855-873, 2011. (32 pages).
Reddy et al., "Elimination of Fc Receptor-Dependent Effector Functions of a Modified IgG4 Monoclonal Antibody to Human CD4," *The Journal of Immunology* 164:1925-1933 (2000).
Riddell et al., "The use of anti-CD28 monoclonal antibodies to clone and expand human antigen-specific T cells," Journal of Immunological Methods 128:189-201, 1990.
Riddell et al., "The Fred Hutchinson Cancer Research Center and the University of Washington School of Medicine, Department of Medicine, Division of Oncology Oct. 7, 1991," Human Gene Therapy 3:319-338,1992.
Rossig et al., "Target Antigen Expression on a Professional Antigen-Presenting Cell Induces Superior Proliferative Antitumor T-Cell Responses via Chimeric T-Cell Receptors," *J Immunother* 29(1):21-31 (2006).
Salvoldo et al., "CD28 costimulation improves expansion and persistence of chimeric antigen receptor-modified T cells in lymphoma patients," *The Journal of Clinical Investigation* 121(5):1822-1826 (2011).
Salvoldo et al., "Epstein Barr virus-specific cytotoxic T lymphocytes expressing the anti-CD30ζ artificial chimeric T-cell receptor for immunotherapy of Hodgin disease," *Blood* 110(7):2620-2630 (2007).
Sequence Alignment 1 (2019).
Sequence Alignment 2 (2019).
Solomon et al., "Proteolytic cleavage of human IgG molecules by neutral proteases of polymorphonuclear leukocytes," Eur. J. Immunol. 8:782-785, 1978.
Tao et al., "The Differential Ability of Human IgG1 and IgG4 to Activate Complement is Determined by the COOH-terminal Sequence of the $C_H2$ Domain," *J. Exp. Med.* 173:1025-1028 (1991).
Till et al., "CD20-specific adoptive immunotherapy for lymphoma using a chimeric antigen receptor with both CD28 and 4-1BB domains: pilot clinical trial results," *Blood* 119(17):3940-3950 (2012).
Till et al., "Adoptive immunotherapy for indolent non-Hodgkin lymphoma and mantle cell lymphoma using genetically modified autologous CD20-specific T cells," Blood 112(6):2261-2271, 2008.
Vera et al., "T lymphocytes redirected against the k light chain of human immunoglobulin efficiently kill mature B lymphocyte-derived malignant cells," *Blood* 108(12):3890-3897 (2006).
Wang et al., "A transgene-encoded cell surface polypeptide for selection, in vivo tracking, and ablation of engineered cells," *Blood* 118(5):1255-1263 (2011).
Wilkie et al., "Retargeting of Human T Cells to Tumor-Associated MUC1: The Evolution of a Chimeric Antigen Receptor," Journal of Immunology 180:4901-4909, 2008.
Winkler et al., "Changing the Antigen Binding Specificity by Single Point Mutations of an Anti-p24 (HIV-1) Antibody," J. Immunol. 165:4505-4514, 2000. (11 Pages).
Yang et al. "Therapeutic Potential and Challenges of Targeting Receptor Tyrosine Kinase ROR1 with Monoclonal Antibodies in B-Cell Malignancies," *PLos One* 6(6):e21018, (15 pages) (2011).
Chmielewski et al., "CD28 cosignalling does not affect the activation threshold in a chimeric antigen receptor-redirected T-cell attack," *Gene Therapy* 18:62-72 (2011).
Zhao et al., "A Herceptin-Based Chimeric Antigen Receptor with Modified Signaling Domains Leads to Enhanced Survival of Transduced T Lymphocytes and Antitumor Activity," *The Journal of Immunology* 183:5563-5574 (2009).
Jensen et al., "CD20 is a molecular target for scFvFc:ζ receptor redirected T cells: implications for cellular immunotherapy of CD20+ malignancy," *Biology of Blood and Marrow Transplantation* 4:75-83 (1998).
Karlsson et al., "Evaluation of Intracellular Signaling Downstream Chimeric Antigen Receptors," *PLoS One* 10(12):e0144787 (20 pages) (2015).
Rossig et al., "Adoptive Cellular Immunotherapy with CD19-Specific T Cells," *Klin Padiatr* 217:351-356 (2005).
Cartellieri et al., "Chimeric Antigen Receptor-Engineered T Cells for Immunotherapy of Cancer," *Journal of Biomedicine and Biotechnology, vol. 2010, Article ID* 956304 (13 pages) (2010).

* cited by examiner

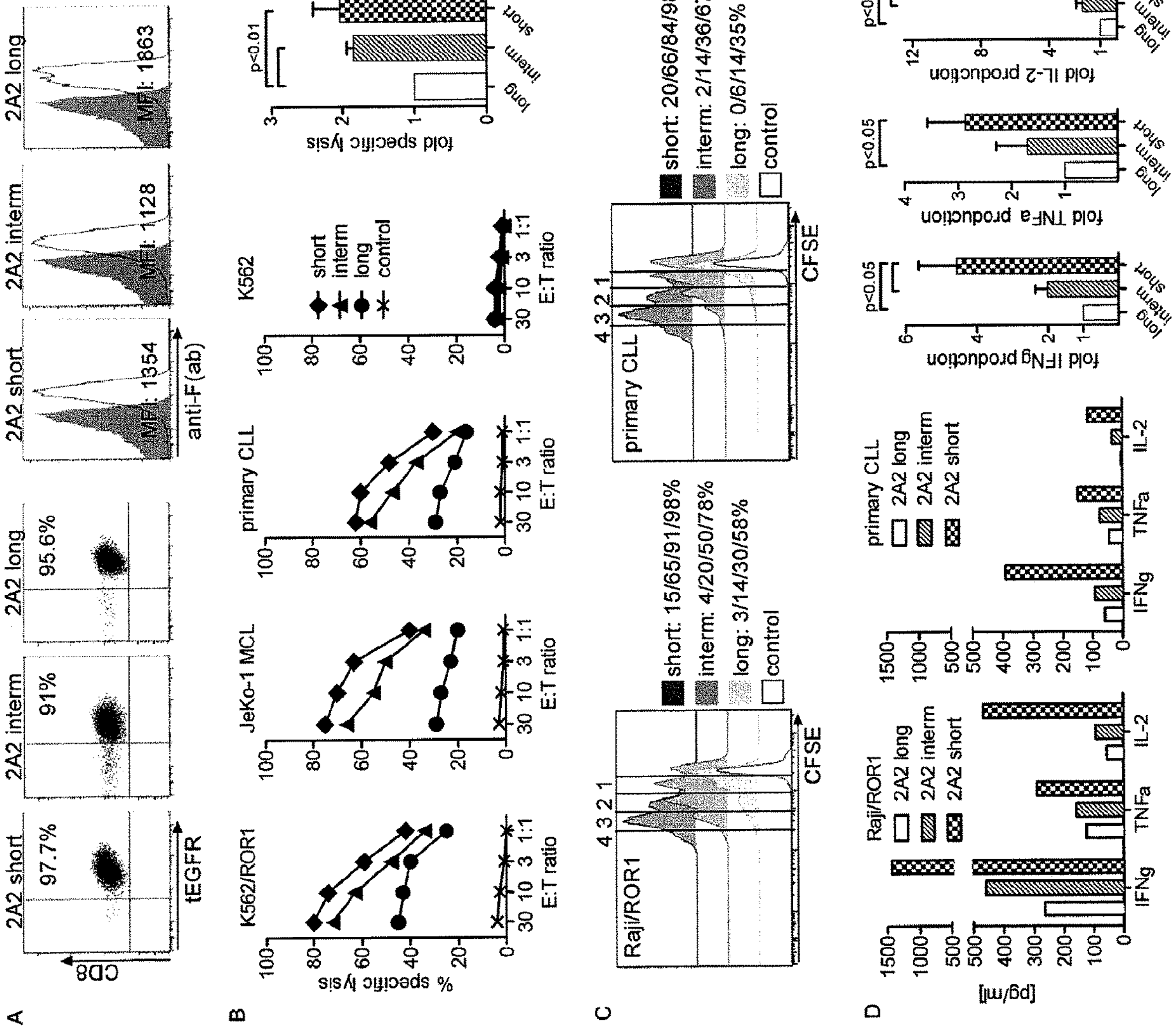

Figure 2
A
2A2 short
97.7%
2A2 interm
91%
2A2 long
95.6%
CD8
tEGFR
MFI: 1354
MFI: 1128
MFI: 1863
anti-F(ab)
B
K562/ROR1
JeKo-1 MCL
primary CLL
K562
% specific lysis
E:T ratio
short
interm
long
control
fold specific lysis
p<0.01
C
Raji/ROR1
short: 15/65/91/98%
interm: 4/20/50/78%
long: 3/14/30/58%
control
primary CLL
short: 20/66/84/98%
interm: 2/14/36/67%
long: 0/6/14/35%
CFSE
D
Raji/ROR1
2A2 long
2A2 interm
2A2 short
[pg/ml]
IFNg
TNFa
IL-2
primary CLL
fold IFNg production
fold TNFa production
fold IL-2 production
p<0.05

A)
B)
C)
D)
R11 short 4-1BB
R11 interm. 4-1BB
R11 long 4-1BB
tEGFR
CD8
51
50
45
specific lysis (%)
E:T
30
10
3
1
K562+CD19
K562+ROR1
CFSE
IFN-γ (ng/ml)
Raji+ROR1
K562+ROR1
K562+CD19

A
2A2 (28)
2A2 (4-1BB)
R12 (28)
R12 (4-1BB)
92.4%
92%
90.9%
87.9%
CD8
tEGFR
B
K562/ROR1
Raji/ROR1
K562
% specific lysis
E:T ratio
30 10 3 1:1
2A2 (28)
R12 (28)
2A2 (4-1BB)
R12 (4-1BB)
control
C
Raji/ROR1
[pg/ml]
IFNg
TNFa
IL-2
fold IL-2 production
p<0.05
D
R12 (28): 54/84/97/99%
2A2 (28): 21/41/69/87%
control
R12 (4-1BB): 2/31/76/99%
2A2 (4-1BB): 0/1/11/47%
4 3 2 1
CFSE A
Primary CLL
99.2%
CD19
ROR1
Primary CLL
0%
CD80
CD86
Raji/ROR1
80.8%
R12 ROR1
64.7%
2A2 ROR1
50.7%
CD19
66%
CD28
B
primary CLL
2A2 ROR1
R12 ROR1
CD19
control
% specific lysis
60
40
20
0
30 10 3 1:1
E:T ratio
fold specific lysis
2
1
0
p<0.05
2A2
R12
normal B cells
2A2 ROR1
R12 ROR1
CD19
control
% specific lysis
100
80
60
40
20
0
30 10 3 1:1
E:T ratio
C
primary CLL
2A2 ROR1
R12 ROR1
CD19
[pg/ml]
200
150
100
50
0
IFNγ
TNFα
IL-2
primary CLL
2A2 ROR1
R12 ROR1
p<0.05
Optical density (O.D.)
0.8
0.6
0.4
0.2
0.0
IFNγ
D
primary CLL
3 2 1
CD19: 44/80/96%
R12 ROR1: 7/25/51%
2A2 ROR1: 3/17/44%
control
CFSE A.
Her2
Herceptin fab
B.
5' LTR
EF1p
Leader sequence
Her2 scFv
VH linker VL
Spacer domain
IgG4- CH2-CH3 (L)
IgG4-CH3 (M)
hinge (S)
Signaling domain
CD28tm 41BB CD3ζ
Transduction marker
T2A EGFRt
3' LTR
C.
kDa
75
50
Mock
S
M
L
α-CD3ζ
D.
S
80.3%
M
80%
L
75.9%
EGFRt
E.
D341
Med411FH
D283
Specific Lysis [%]
Effector: Target Ratio
50:1 25.1 12.5:1 6.25:1
Mock
S
M
L

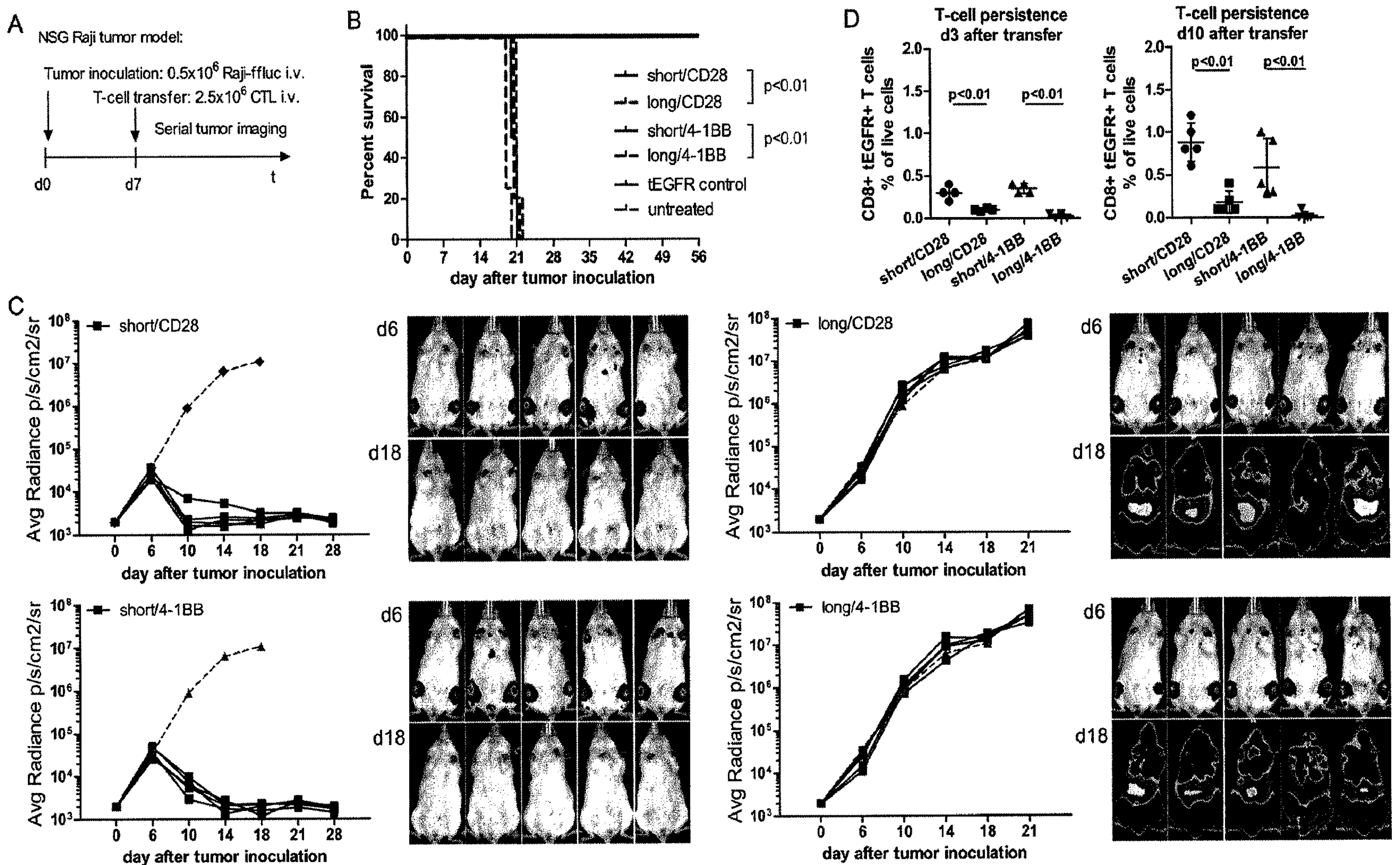
Figure 17
A
NSG Raji tumor model:
Tumor inoculation: 0.5x10^6 Raji-ffluc i.v.
T-cell transfer: 2.5x10^6 CTL i.v.
Serial tumor imaging
d0
d7
t
B
Percent survival
day after tumor inoculation
short/CD28
long/CD28
short/4-1BB
long/4-1BB
tEGFR control
untreated
p<0.01
p<0.01
D
T-cell persistence d3 after transfer
T-cell persistence d10 after transfer
CD8+ tEGFR+ T cells % of live cells
short/CD28
long/CD28
short/4-1BB
long/4-1BB
p<0.01
p<0.01
C
short/CD28
long/CD28
short/4-1BB
long/4-1BB
Avg Radiance p/s/cm2/sr
day after tumor inoculation
d6
d18

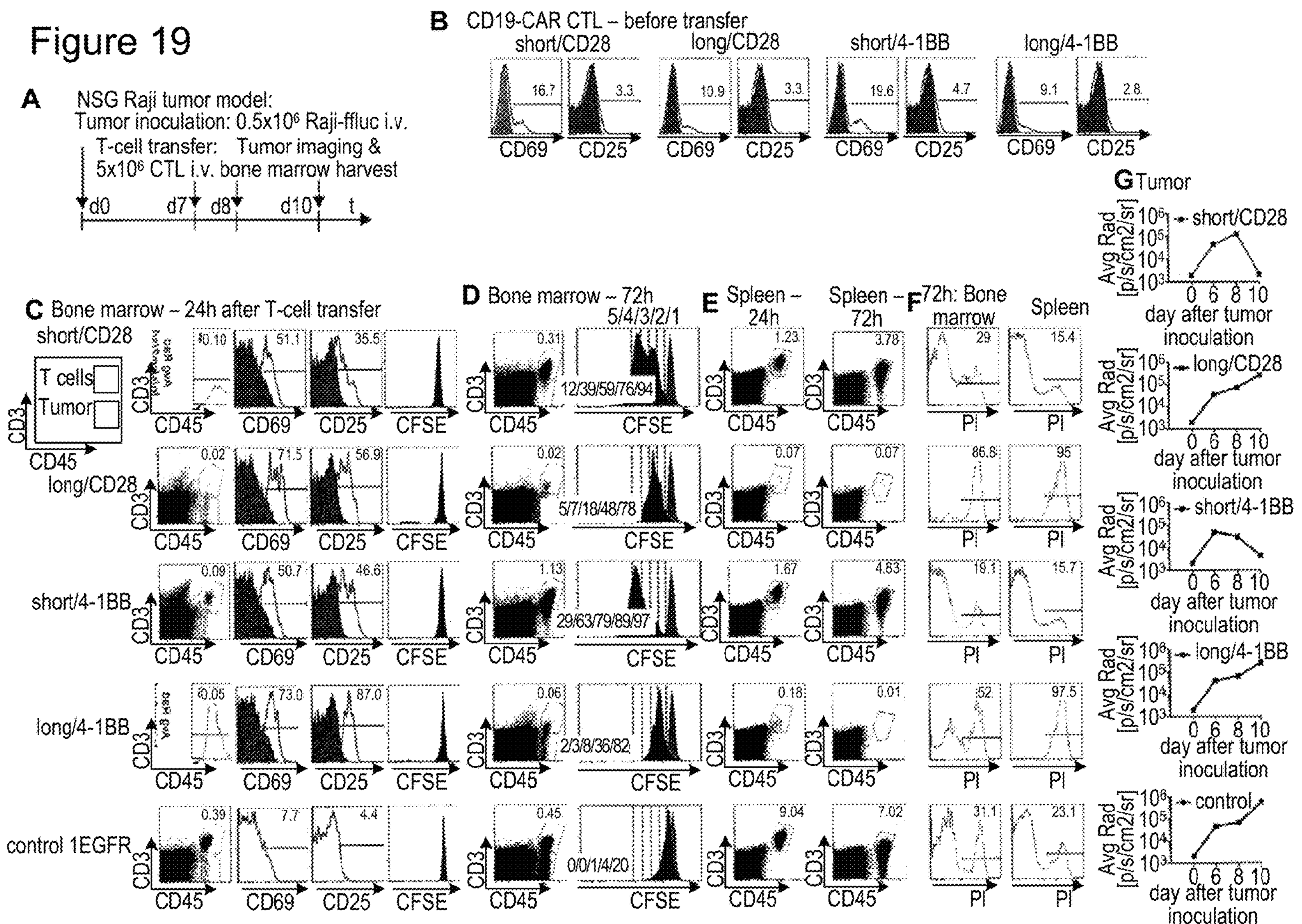
Figure 19
A
NSG Raji tumor model:
Tumor inoculation: 0.5x10⁶ Raji-ffluc i.v.
T-cell transfer: 5x10⁶ CTL i.v.
Tumor imaging & bone marrow harvest
d0
d7
d8
d10
t
B
CD19-CAR CTL – before transfer
short/CD28
long/CD28
short/4-1BB
long/4-1BB
16.7
3.3
10.9
3.3
19.6
4.7
9.1
2.8
CD69
CD25
C
Bone marrow – 24h after T-cell transfer
short/CD28
T cells
Tumor
long/CD28
short/4-1BB
long/4-1BB
control 1EGFR
CD3
CD45
CD69
CD25
CFSE
D
Bone marrow – 72h
5/4/3/2/1
12/39/59/76/94
5/7/18/48/78
29/63/79/89/97
2/3/8/36/82
0/0/1/4/20
E
Spleen – 24h
Spleen – 72h
F
72h: Bone marrow
Spleen
PI
G
Tumor
Avg Rad [p/s/cm2/sr]
short/CD28
long/CD28
short/4-1BB
long/4-1BB
control
day after tumor inoculation Figure 20
Cytotoxicity - Chromium release assay
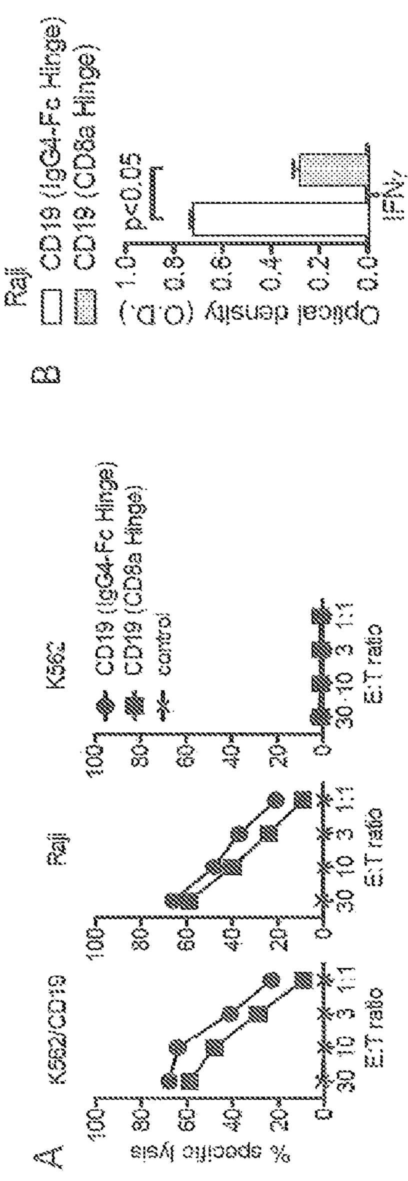
Cytokine analysis (ELISA)
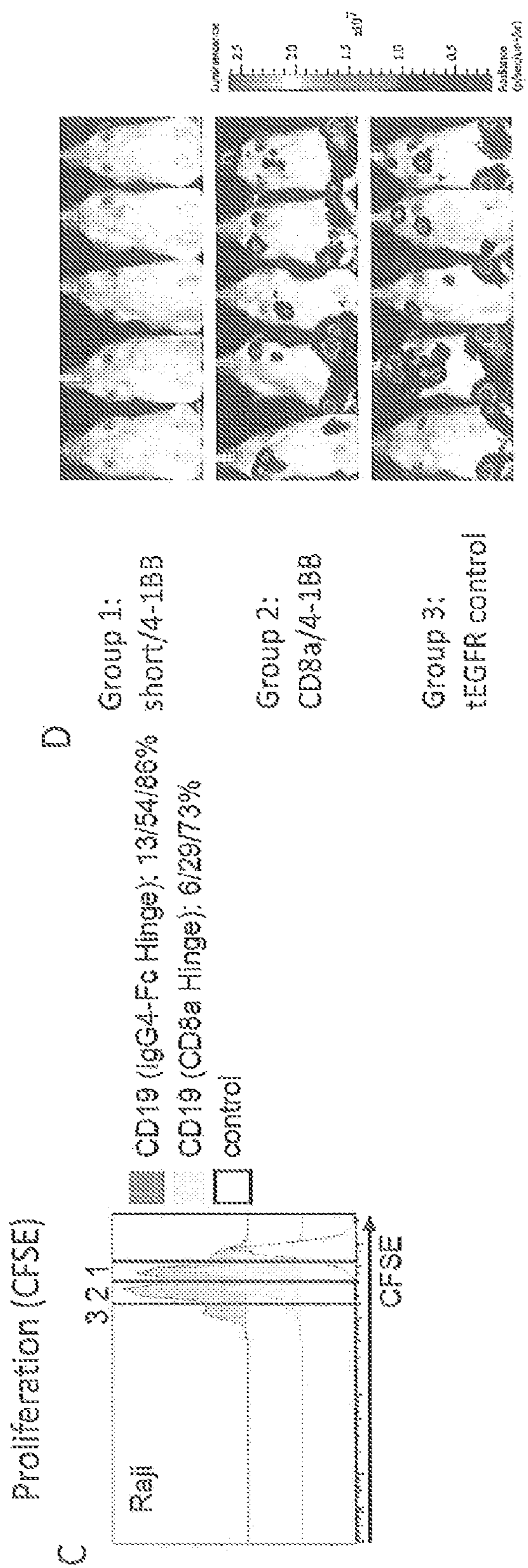

METHOD AND COMPOSITIONS FOR CELLULAR IMMUNOTHERAPY

CROSS-REFERENCES TO RELATED APPLICATIONS

The present application is a continuation application of U.S. application Ser. No. 14/422,640, filed Feb. 19, 2015, now pending, which is a U.S. national phase application of PCT/US2013/055862, filed Aug. 20, 2013, which claims priority to U.S. Provisional Application No. 61/691,117, filed Aug. 20, 2012. The disclosures of these applications are incorporated herein by reference in their entireties.

STATEMENT REGARDING FEDERALLY SPONSORED RESEARCH

This invention was made with government support under CA136551 and CA114536 awarded by the National Institutes of Health. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 360056_425C1_SEQUENCE_LISTING.txt. The text file is 160 KB, was created on Oct. 17, 2019, and is being submitted electronically via EFS-Web.

FIELD OF THE INVENTION

The present invention relates to the field of biomedicine and specifically methods useful for cancer therapy. In particular, embodiments of the invention relate to methods and compositions for carrying out cellular immunotherapy comprising T cells modified with tumor targeting receptors.

BACKGROUND OF THE INVENTION

The adoptive transfer of human T lymphocytes that are engineered by gene transfer to express chimeric antigen receptors (chimeric receptors) specific for surface molecules expressed on tumor cells has the potential to effectively treat advanced malignancies. Chimeric receptors are synthetic receptors that include an extracellular ligand binding domain, most commonly a single chain variable fragment of a monoclonal antibody (scFv) linked to intracellular signaling components, most commonly CD3ζ alone or combined with one or more costimulatory domains. Much of the research in the design of chimeric receptors has focused on defining scFvs and other ligand binding elements that target malignant cells without causing serious toxicity to essential normal tissues, and on defining the optimal composition of intracellular signaling modules to activate T cell effector functions. However, it is uncertain whether the variations in chimeric receptor design that mediate superior in vitro function will translate reproducibly into improved in vivo therapeutic activity in clinical applications of chimeric receptor-modified T cells.

There is a need to identify methods for determining elements of chimeric receptor design that are important for therapeutic activity and cell populations to genetically modify and adoptively transfer that provide enhanced survival and efficacy in vivo.

SUMMARY OF THE INVENTION

In one aspect, the present disclosure relates to methods and compositions to confer and/or augment immune responses mediated by cellular immunotherapy, such as by adoptively transferring tumor-specific, genetically modified subsets of CD8+ or CD4+ T cells alone, or in combination. The disclosure provides for chimeric receptor nucleic acids, and vectors and host cells including such nucleic acids. The nucleic acid sequence that encodes the chimeric receptor links together a number of modular components that can be excised and replaced with other components in order to customize the chimeric receptor for efficient T cell activation and recognition of a specific target molecule or an epitope on the target molecule.

In embodiments, a chimeric receptor nucleic acid comprises a polynucleotide coding for a ligand binding domain, wherein the ligand is a molecule expressed on malignant or infected cells, a polynucleotide coding for a polypeptide spacer wherein the polypeptide spacer is about 200 amino acids or less, a polynucleotide coding for a transmembrane domain; and a polynucleotide coding for intracellular signaling domains. In embodiments, the polypeptide spacer comprises a modified IgG4 hinge region containing an amino acid sequence $X_1PPX_2P$ (SEQ ID NO:1) that may be linked to other amino acid sequences including but not limited to the CH2 and CH3 or CH3 only sequences of the Ig Fc. It has been surprisingly found that the length of the spacer region that is presumed not to have signaling capability affects the in vivo efficacy of the T cells modified to express the chimeric receptor and needs to be customized for individual target molecules for optimal tumor or target cell recognition.

Another aspect of the disclosure provides an isolated chimeric receptor nucleic acid comprising: a polynucleotide coding for a ligand binding domain, wherein the ligand is a tumor specific antigen, viral antigen, or any other molecule expressed on a target cell population that is suitable to mediate recognition and elimination by a lymphocyte; a polynucleotide coding for a polypeptide spacer wherein the polypeptide spacer is of a customized length that is specific for each targeted ligand, wherein the spacer provides for enhanced T cell proliferation and/or cytokine production as compared to a reference chimeric receptor; a polynucleotide coding for a transmembrane domain; and a polynucleotide coding for one or more intracellular signaling domains. In embodiments, a long spacer is employed if the epitope on the target ligand is in a membrane proximal position and a short spacer is employed if the epitope on the target ligand is in a membrane distal position. The disclosure includes expression vectors and host cells comprising the isolated chimeric receptor as described herein.

Another aspect of the disclosure provides a chimeric receptor polypeptide comprising a ligand binding domain, wherein the ligand is a tumor specific antigen, viral antigen or any other molecule that is expressed on a target cell population and can be targeted to mediate recognition and elimination by lymphocytes; a polypeptide spacer wherein the polypeptide spacer is about 10-229 amino acids; a transmembrane domain; and one or more intracellular signaling domains. In embodiments, the polypeptide spacer comprises a modified IgG hinge region containing the amino acid sequence $X_1PPX_2P$ (SEQ ID NO:1).

In another aspect, the present disclosure provides compositions to confer and/or augment immune responses mediated by cellular immunotherapy, such as by adoptively transferring tumor-specific, subset specific genetically modified CD4+ T cells, wherein the CD4+ T cells confer and/or augment the ability of CD8+ T cells to sustain anti-tumor reactivity and increase and/or maximize tumor-specific proliferation. In embodiments, the CD4+ cells are genetically modified to express a chimeric receptor nucleic acid and/or chimeric receptor polypeptide as described herein.

In another aspect, the present disclosure provides compositions to confer and/or augment immune responses mediated by cellular immunotherapy, such as by adoptively transferring tumor-specific, subset specific genetically modified CD8+ T cells. In embodiments, the CD8+ cells express a chimeric receptor nucleic acid and/or chimeric receptor polypeptide as described herein.

In another embodiment, the present invention provides an adoptive cellular immunotherapy composition having a genetically modified CD8+ cytotoxic T lymphocyte cell preparation to confer and/or augment immune responses, wherein the cytotoxic T lymphocyte cell preparation comprises CD8+ T cells that express a chimeric receptor comprising a ligand binding domain for a ligand associated with the disease or disorder, a customized spacer region, a transmembrane domain; and an intracellular signaling domain of a T cell or other receptors, such as a costimulatory domain, and/or a genetically modified helper T lymphocyte cell preparation, wherein the helper T lymphocyte cell preparation has CD4+ T cells that express a chimeric receptor comprising an antibody variable domain specific for the ligand associated with the disease or disorder, a customized spacer region, a transmembrane domain; and one or more intracellular signaling domains.

In one embodiment, the present invention provides a method of performing cellular immunotherapy in a subject having a disease or disorder by administering to the subject a genetically modified cytotoxic T lymphocyte cell preparation that provides a cellular immune response, wherein the cytotoxic T lymphocyte cell preparation comprises CD8+ T cells that have a chimeric receptor comprising a polynucleotide coding for a ligand binding domain, wherein the ligand is a tumor specific antigen, viral antigen, or any other molecule expressed on a target cell population that is suitable to mediate recognition and elimination by a lymphocyte; a polynucleotide coding for a polypeptide spacer wherein the polypeptide spacer is of a customized length that is specific for each targeted ligand, wherein the spacer provides for enhanced T cell proliferation and/or cytokine production as compared to a reference chimeric receptor; a polynucleotide coding for a transmembrane domain; and a polynucleotide coding for one or more intracellular signaling domains. In embodiment, the ligand binding domain is an extracellular antibody variable domain specific for a ligand associated with the disease or disorder. An embodiment includes a genetically modified helper T lymphocyte cell preparation that wherein the helper T lymphocyte cell preparation comprises CD4+ T cells that have a chimeric receptor comprising an a polynucleotide coding for a ligand binding domain, wherein the ligand is a tumor specific antigen, viral antigen, or any other molecule expressed on a target cell population that is suitable to mediate recognition and elimination by a lymphocyte; a polynucleotide coding for a polypeptide spacer wherein the polypeptide spacer is of a customized length that is specific for each targeted ligand, wherein the spacer provides for enhanced T cell proliferation and/or cytokine production as compared to a reference chimeric receptor; a polynucleotide coding for a transmembrane domain; and a polynucleotide coding for one or more intracellular signaling domains. In embodiments, the genetically modified CD8+ and genetically modified CD4+ cell population are coadministered. In embodiments, the T cells are autologous or allogeneic T cells.

Various modifications of the above method are possible. For example, the chimeric receptor that is expressed by the CD4+ T cell and the CD8+ T cell can be the same or different.

In another aspect, the present invention provides a method of manufacturing an adoptive immunotherapy composition by obtaining a chimeric receptor modified tumor-specific CD8+ cytotoxic T lymphocyte cell preparation that elicits a cellular immune response and expresses an antigen-reactive chimeric receptor, wherein the modified cytotoxic T lymphocyte cell preparation comprises CD8+ T cells that have a chimeric receptor comprising a ligand binding domain, wherein the ligand is a tumor specific antigen, viral antigen, or any other molecule expressed on a target cell population that is suitable to mediate recognition and elimination by a lymphocyte; a polypeptide spacer wherein the polypeptide spacer is of a customized length that is specific for each targeted ligand, wherein the spacer provides for enhanced T cell proliferation and/or cytokine production as compared to a reference chimeric receptor; a transmembrane domain; and one or more intracellular signaling domains; and/or obtaining a modified naïve or memory CD4+ T helper cell wherein the modified helper T lymphocyte cell preparation comprises CD4+ cells that have a chimeric receptor comprising a ligand binding domain, wherein the ligand is a tumor specific antigen, viral antigen, or any other molecule expressed on a target cell population that is suitable to mediate recognition and elimination by a lymphocyte; a polypeptide spacer wherein the polypeptide spacer is of a customized length that is specific for each targeted ligand, wherein the spacer provides for enhanced T cell proliferation and/or cytokine production as compared to a reference chimeric receptor; a transmembrane domain; and one or more intracellular signaling domains.

These and other embodiments of the invention are described further in the accompanying specification, drawings and claims.

BRIEF DESCRIPTION OF THE DRAWINGS

FIG. 2: In vitro cytotoxicity, cytokine production, and proliferation of T-cells modified to express 2A2 ROR1 chimeric receptors with modified spacer length. (A) Phenotype of purified $CD8^+$ $T_{CM}$-derived cell lines modified with each of the 2A2 ROR1 chimeric receptors with long, intermediate and short spacer domain. Staining with anti-F(ab) antibody that binds to an epitope in the 2A2 scFV shows surface expression of ROR1 chimeric receptors with full length or truncated spacer. (B) Cytolytic activity of T-cells expressing the various 2A2 ROR1 chimeric receptors with long (●), intermediate (▲) and short spacer (♦), or a tEGFR control lentiviral vector against ROR1$^+$ (x) and control target cells. The bar diagram summarizes cytotoxicity data from 3 independent experiments (E:T=30:1) normalized to cytolytic activity by 2A2 ROR1 chimeric receptor 'long'=1, and analyzed by Student's t-test. (C) CFSE dye dilution was used to measure proliferation of 2A2 ROR1 chimeric receptor and tEGFR control T-cells, 72 hours after stimulation with Raji/ROR1 (left panel) and primary CLL cells (right panel) without addition of exogenous cytokines. For analysis, triplicate wells were pooled and the proliferation of live (PI$^-$), CD8$^+$ T-cells analyzed. Numbers above each histogram indicate the number of cell divisions the proliferating subset underwent, and the fraction of T-cells in each gate that underwent ≥4/3/2/1 cell divisions is provided next to each plot. (D) Multiplex cytokine assay of supernatants obtained after 24 hours from triplicate co-cultures of $5\times10^4$ T-cells expressing the various 2A2 ROR1 chimeric receptors with Raji/ROR1 and primary CLL cells. Multiplex cytokine data from 3 independent experiments were normalized (cytokine release by 2A2 ROR1 chimeric receptor 'long'=1) and analyzed by Student's t-test (right bar diagram).

ROR1 and a CD19 chimeric receptor, 72 hours after stimulation with primary CLL cells. Numbers above each histogram indicate the number of cell divisions, and the fraction of T-cells in each gate that underwent ≥3/2/1 cell divisions is provided next to each plot.

Figure 8:
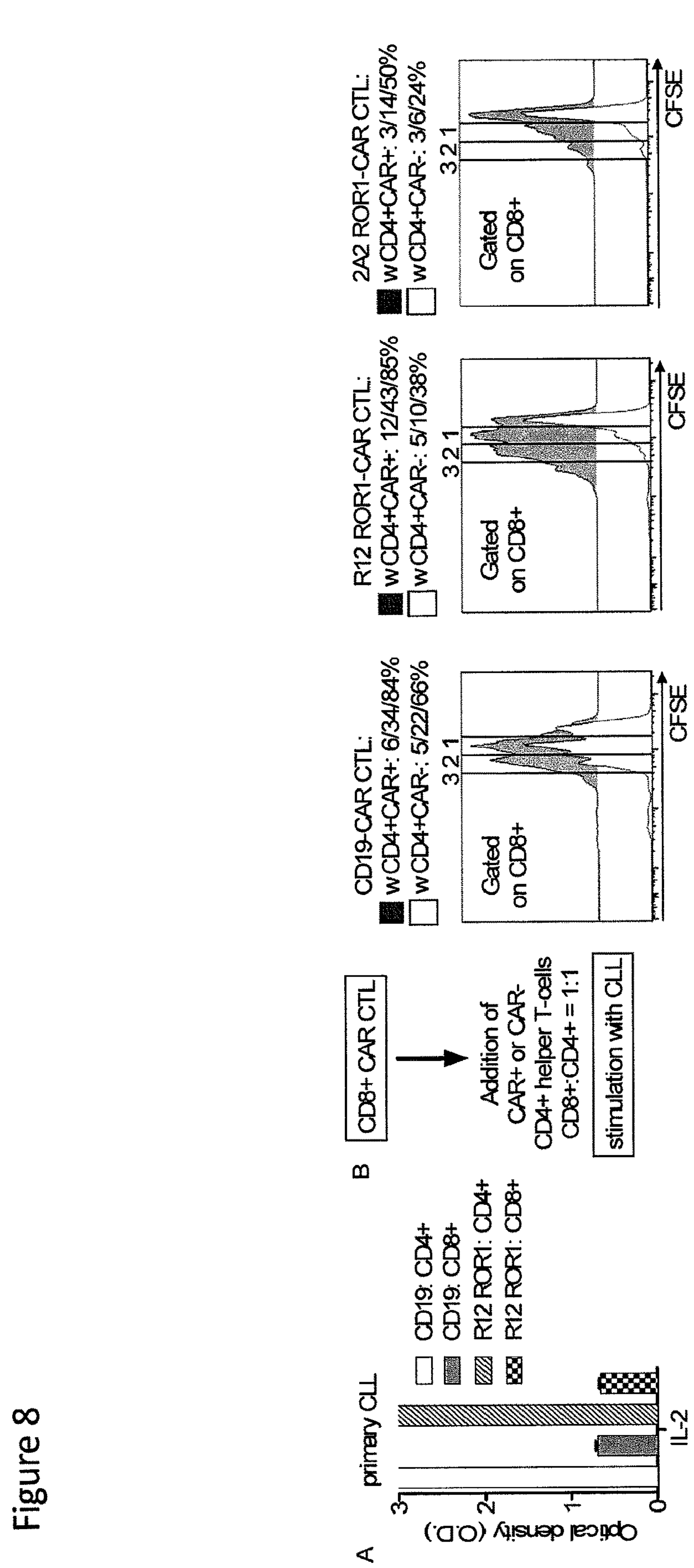

FIG. 8: The function of ROR1-chimeric receptor and CD19-chimeric receptor modified $CD8^+$ T-cells against primary CLL is augmented by chimeric receptor-modified $CD4^+$ helper T-cells. (A) ELISA for IL-2 production from triplicate co-cultures of $5\times10^4$ $CD8^+$ and $CD4^+$ T-cells expressing the R12 ROR1 and CD19-chimeric receptor respectively, incubated with primary CLL for 24-hours. O.D. of 1 corresponds to approx. 800 pg/ml. (B) Proliferation of chimeric receptor-modified $CD8^+$ T-cells in response to primary CLL is enhanced by addition of chimeric receptor-modified $CD4^+$ T-cells. CFSE-labeled $CD8^+$ T-cells expressing the 2A2 ROR1, R12 ROR1 and CD19-chimeric receptor respectively, were co-cultured with tumor cells and with 2A2 ROR1, R12 ROR1 and CD19-chimeric receptor transduced or control untransduced $CD4^+$ T-cells ($CD8^+$: $CD4^+$=1:1). Proliferation of the $CD8^+$ subset was analyzed 72 hours after stimulation. Numbers above each histogram indicate the number of cell divisions, and the fraction of T-cells in each gate that underwent ≥3/2/1 cell divisions is provided above each plot.

Figure 9:
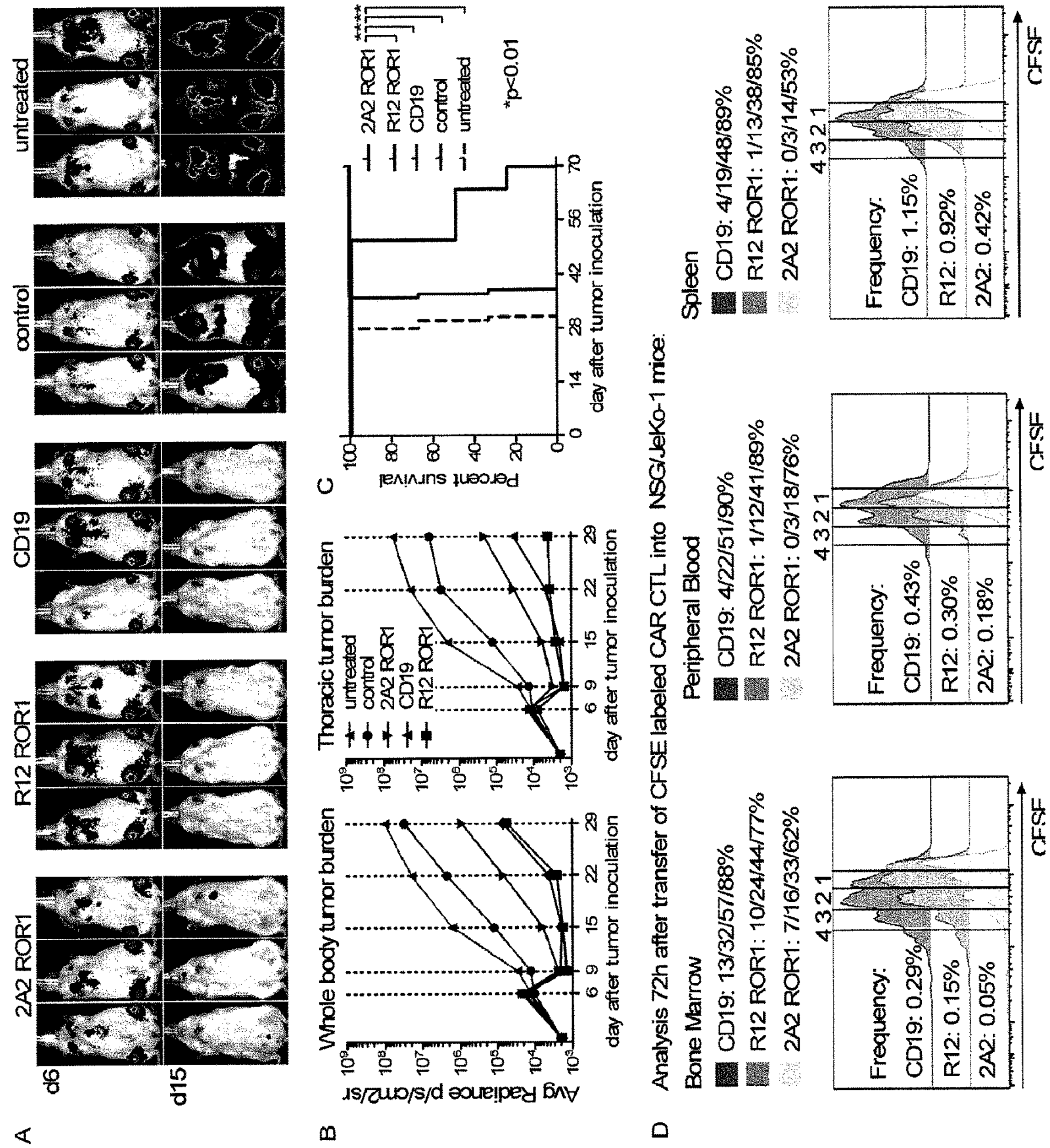

FIG. 9: In vivo anti-tumor efficacy of 2A2 ROR1, R12 ROR1 and CD19 chimeric receptor T-cells. Cohorts of mice were inoculated with $0.5\times10^6$ JeKo-1/ffluc MCL via tail vein injection, and $5\times10^6$ 2 A2 ROR1, R12 ROR1 or CD19 chimeric receptor T-cells, or T-cells expressing a tEGFR control vector were administered 7 days after tumor inoculation. All chimeric receptor constructs had the short IgG4 'Hinge-only' spacer and a 4-1BB costimulatory domain. (A, B) Serial bioluminescence imaging of tumor in cohorts of mice treated with T-cells expressing the 2A2 ROR1 chimeric receptor (▼), the high affinity R12 ROR1 chimeric receptor (■), a CD19-specific chimeric receptor (▲), with T-cells transduced with tEGFR alone (●), and untreated mice. Bioluminescence imaging showed tumor manifestations in the bone marrow and thorax and thus, signal intensity was measured in regions of interest that encompassed the entire body and thorax of each individual mouse. (C) Kaplan-Meier analysis of survival in individual treatment and control groups. Statistical analyses were performed using the log-rank test. The data shown in A-C are representative of results obtained in 2 independent experiments. (D) Proliferation of 2A2 ROR1, R12 ROR1 and CD19 chimeric receptor T-cells in vivo. Tumor bearing NSG/JeKo-1 mice received a single dose of $5\times10^6$ CFSE-labeled 2A2 ROR1, R12 ROR1 or CD19 chimeric receptor T-cells on day 7 after tumor inoculation, and 72 h later peripheral blood, bone marrow and spleen were collected from each individual mouse. The frequency and proliferation of live ($PI^-$), $CD45^+$ $CD8^+$ $tEGFR^+$ T-cells was analyzed. The frequency of 2A2 ROR1, R12 ROR1 and CD19 chimeric receptor T-cells respectively is provided on the left of each histogram as percentage of live cells, and the fraction of T-cells that underwent ≥4/3/2/1 cell divisions is provided above each plot.

Figure 10:
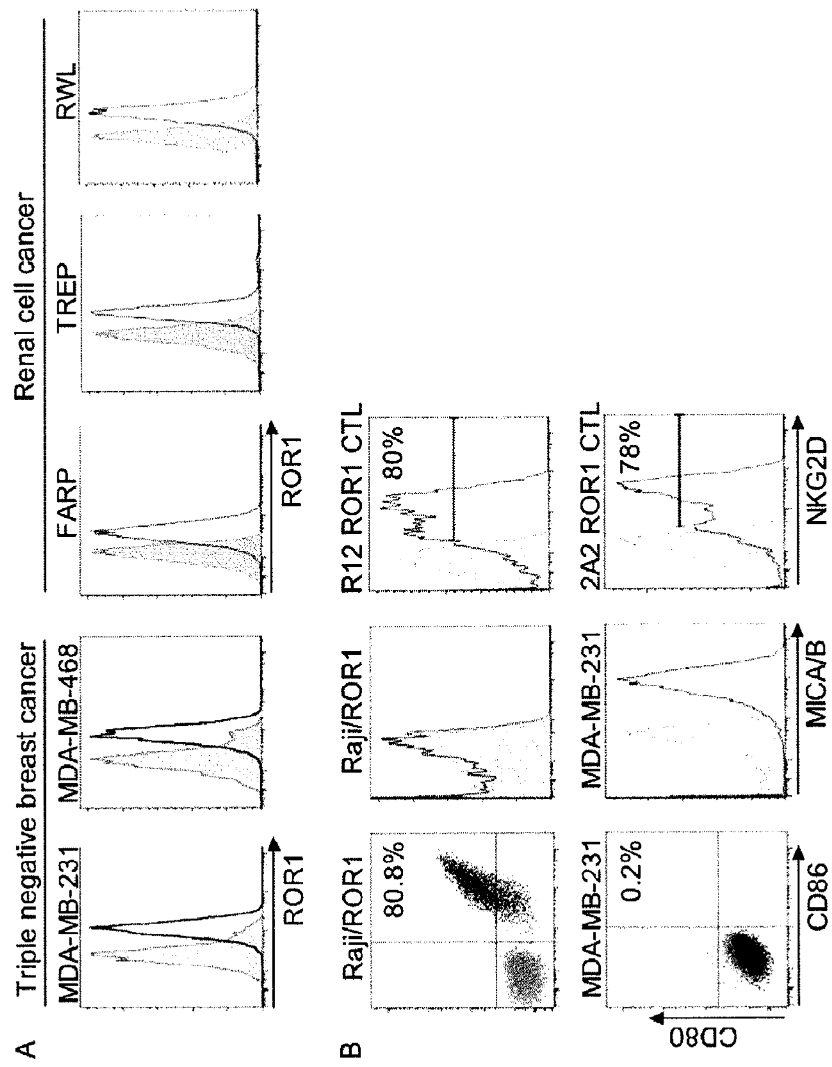

FIG. 10 Expression of ROR1 and NKG2D ligands on epithelial cancer cell lines. (A) Expression of ROR1 on the triple negative breast cancer cell lines MDA-MB-231 and 468, and the renal cell cancer lines FARP, TREP and RWL (black histograms). Staining with matched isotype control antibody is shown as grey histograms. (B) Expression of CD80/86 and the NKG2D ligands MICAS on MDA-MB-231 and Raji/ROR1 tumor cells, and NKG2D (CD314) on 2A2 and R12 ROR1-chimeric receptor T-cells. Staining with matched isotype control mAbs is shown as grey dot plots/histograms.

Figure 11:
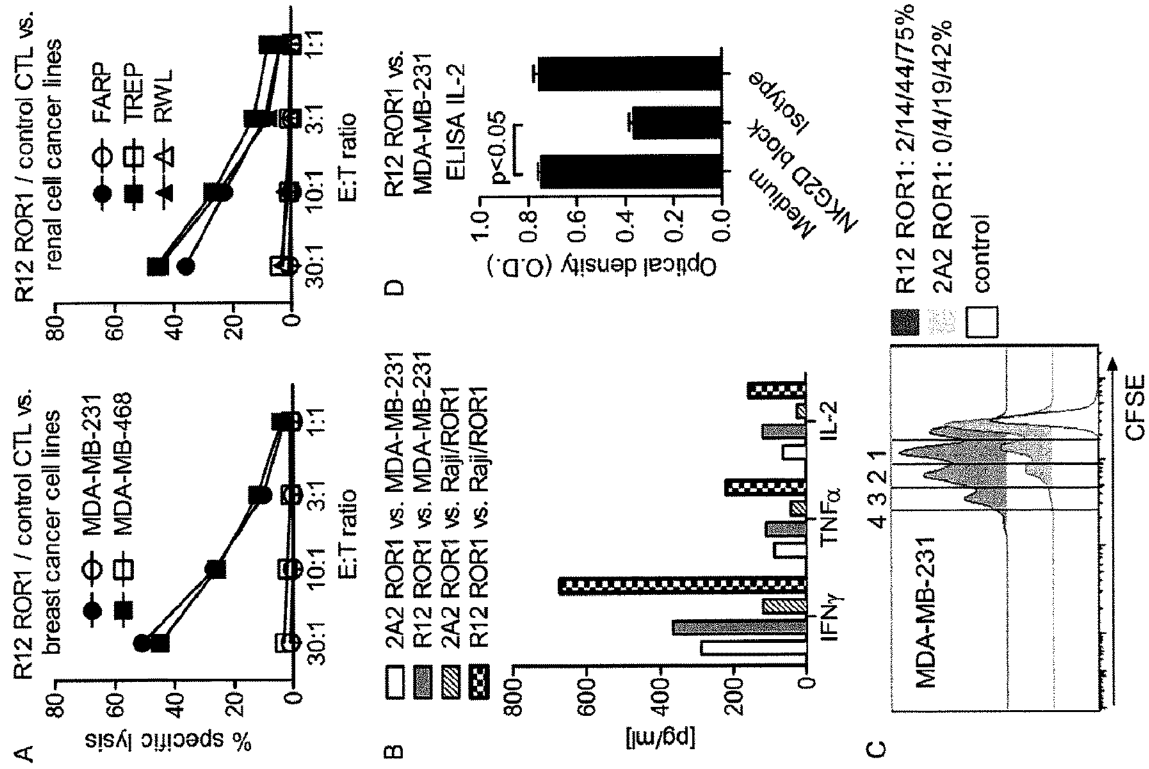

FIG. 11: ROR1-chimeric receptor modified T-cells recognize $ROR1^+$ epithelial tumor cells in vitro. (A) Chromium release assay to evaluate the cytolytic activity of R12 ROR1-chimeric receptor modified T-cells (short spacer/4-1BB costimulatory domain, closed symbols) and tEGFR control T-cells (open symbols) against $ROR1^+$ breast cancer and renal cell cancer lines. (A-D) The 2A2 and R12 ROR1-chimeric receptors had the optimal short spacer and a 4-1BB costimulatory domain. (B) Multiplex cytokine analysis after stimulation of T-cells expressing the 2A2 and R12 ROR1-chimeric receptor with MDA-MB-231 and Raji/ROR1 tumor cells. (C) Proliferation of $CD8^+$ T-cells modified with the 2A2 and R12 ROR1-chimeric receptor 72 hours after stimulation with MDA-MB-231 tumor cells. For analysis, triplicate wells were pooled and the proliferation of live ($PI^-$), $CD8^+$ T-cells analyzed. Numbers above each histogram indicate the number of cell divisions the proliferating subset underwent, and the fraction of T-cells in each gate that underwent ≥4/3/2/1 cell divisions is provided next to each histogram. (D) ELISA for IL-2 production by R12 ROR1-chimeric receptor T-cells after a 24-hour co-culture with MDA-MB-231 in plain medium, and after addition of an antibody cocktail blocking of the NKG2D pathway [anti-NKG2D (clone 1D11), anti-MICAS (clone 6D4) and anti-ULBP] or matched isotype control mAbs. O.D. of 0.6 corresponds to approximately 1900 pg/ml.

Figure 12:
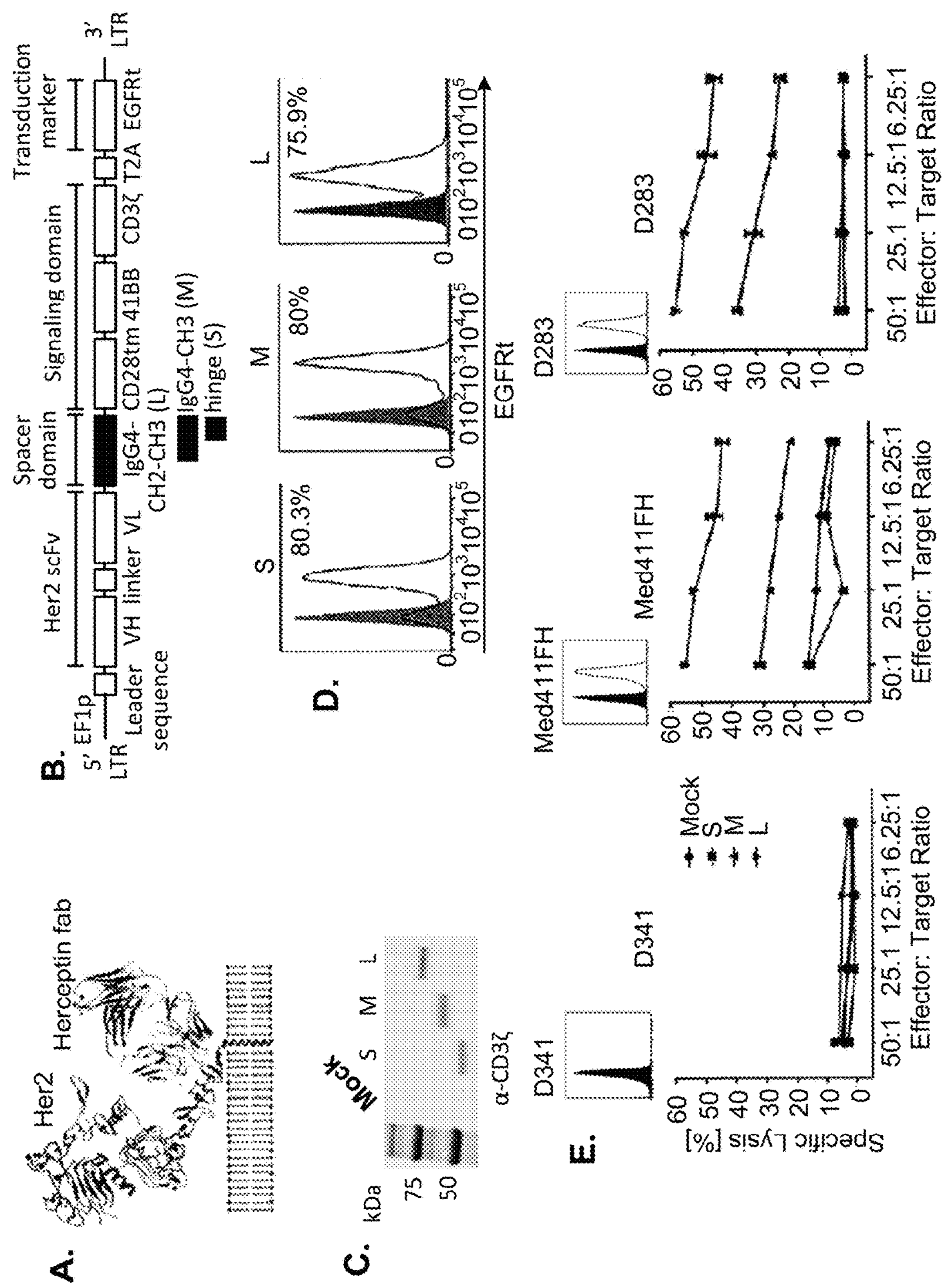

FIG. 12. Effect of extracellular spacer length on recognition and triggering of tumor cell lysis by CD8+ human T cells that express a HER2-specific chimeric receptor. A.) Depiction of Herceptin Fab epitope location on tumor cell membrane proximal epitope on human HER2, B.) Structural formats of Herceptin scFv CAR spacer length variants as—T2A—linked polypeptides with the carboxyl EGFRt marker transmembrane protein, C.) Western blot detection of short, medium, and long spacer Herceptin-CAR variant expression in human CD8+ CTL's, D.) Flow cytometric detection of EGFRt by transduced human CD8+ CTL's transduced with Herceptin CAR variants then immunomagnetically purified by Herceptin-biotin, anti-biotin microbeads, E.) Distinct cytolytic function by T cells transduced to express the Herceptin CAR variants (short—S; medium—M; and long—L) against $HER2^+$ Med411FH and D283 human medulloblastoma cell lines (D341 is a $HER2^-$ control medulloblastoma cell line, inset flow plots are tumor target lines stained with anti-HER2 specific mAb). Green=full IgG4 (Long Spacer, ▼), Blue=IgG4hinge:CH3(Medium Spacer; ▲), Red=IgG4hinge only (Short Spacer; ■).

Figure 13:
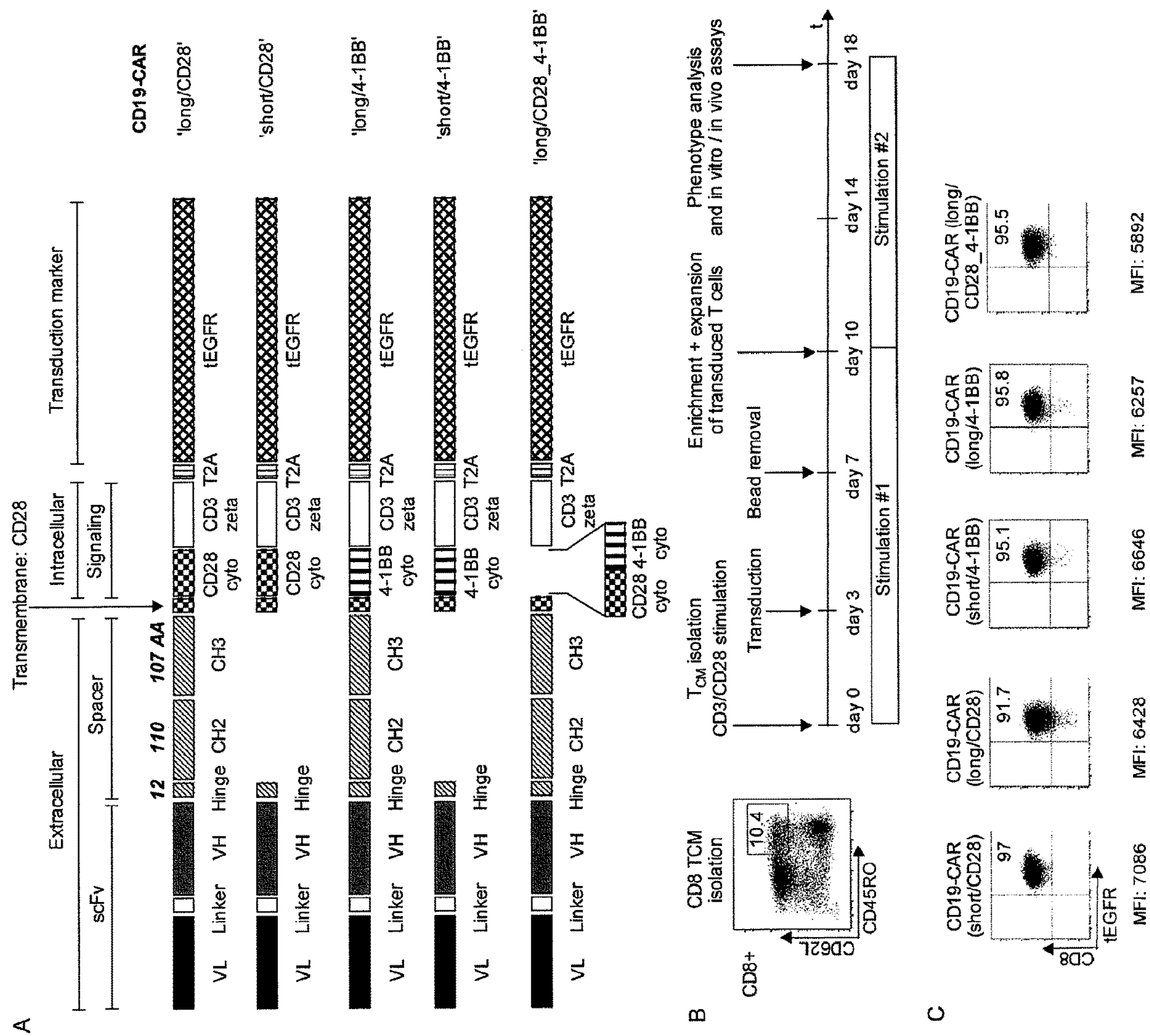

FIG. 13: CD19-chimeric receptor vectors and generation of CD19-chimeric receptor T cells. (A) Design of lentiviral transgene inserts encoding a panel of CD19-specific chimeric receptors that differ in extracellular spacer length and intracellular co-stimulation. Each chimeric receptor encoded the CD19-specific single chain variable fragment derived from the FMC63 mAb in a VL-VH orientation, an IgG4-derived spacer domain of Hinge-CH2-CH3 (long spacer, 229 AA) or Hinge only (short spacer, 12 AA), and a signaling module containing CD3ζ with CD28 or 4-1BB alone or in tandem. Each chimeric receptor cassette contains a truncated EGFR marker encoded downstream of a cleavable 2A element. (B, C) Polyclonal T cell lines modified with each of the CD19-chimeric receptor constructs were prepared from purified $CD8^+$ $CD45RO^+$ $CD62L^+$ central memory T cells ($T_{CM}$) of normal donors. Following lentiviral transduction, transgene-positive T cells in each cell line were purified using the tEGFR marker and expanded for in vitro and in vivo experiments. (D) MFI after staining for the tEGFR marker shows equivalent transgene expression in T cells modified with each of the CD19-chimeric receptors.

Figure 14:
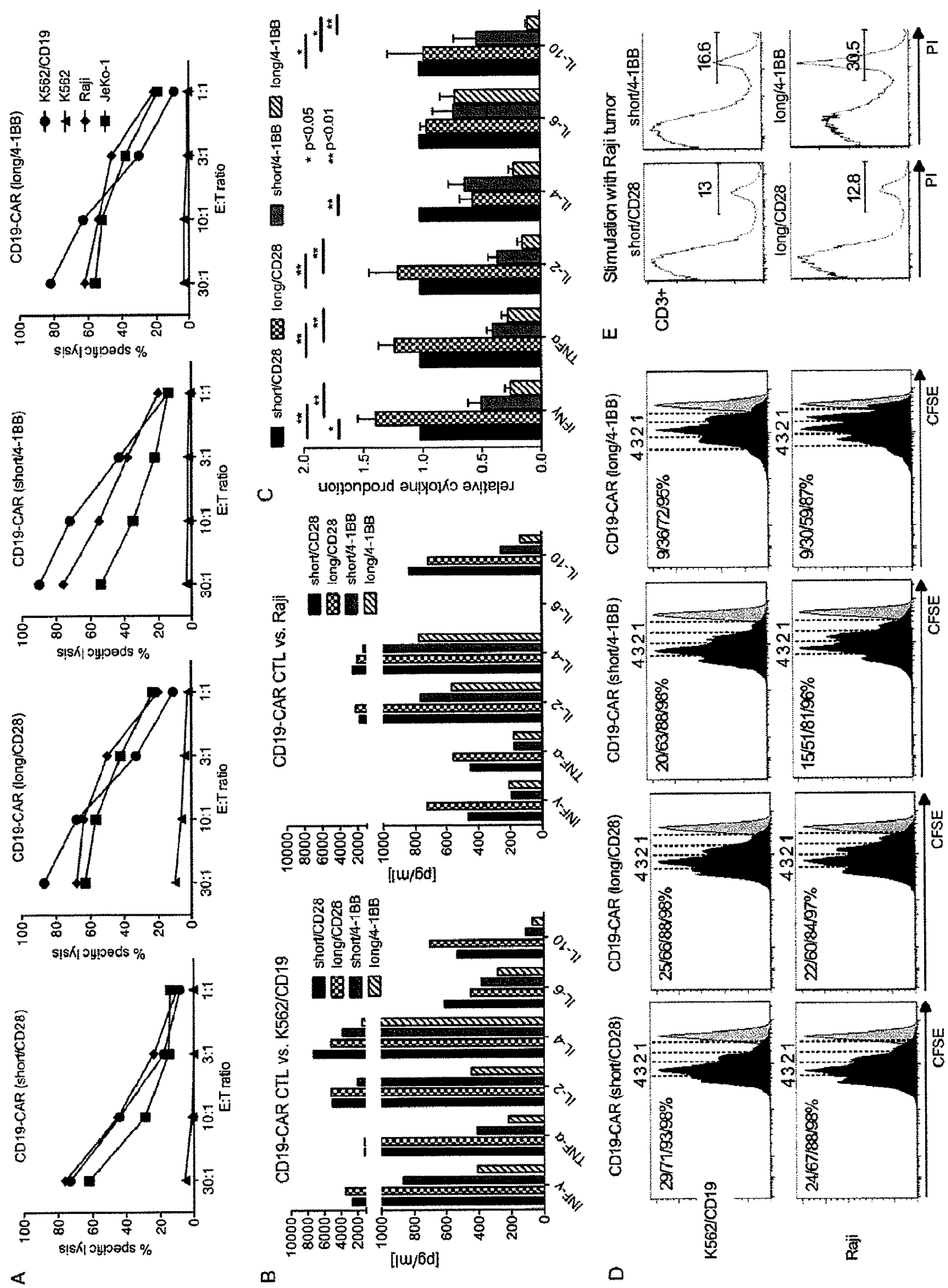

FIG. 14: In vitro cytotoxicity, cytokine production, and proliferation of T cells modified with distinct CD19-chimeric receptors. (A) Cytolytic activity of T cells expressing the various CD19-chimeric receptors against $CD19^+$ and control target cells. (B) Multiplex cytokine assay of supernatants obtained after 24 hours from triplicate co-cultures of T cells expressing the various CD19-chimeric receptors and K562 cells transfected with CD19, and $CD19^+$ Raji cells. (C) Comparison of cytokine production by T cells expressing the various CD19-chimeric receptors. Multiplex cytokine data from 6 independent experiments were normalized (cytokine release by CD19-chimeric receptor 'short/CD28' CTL=1) and analyzed by Student's t-test. (D) CFSE dye dilution was used to measure proliferation of CD19-chimeric receptor T cells 72 hours after stimulation with K562/CD19 (upper panel) and $CD19^+$ Raji tumor cells (lower panel) without addition of exogenous cytokines. For analysis, triplicate wells were pooled and the proliferation of live ($PI^-$), $CD8^+$ T cells analyzed. Numbers above each histogram indicate the number of cell divisions the proliferating subset underwent, and the fraction of T cells in each gate that underwent ≥4/3/2/1 cell divisions is provided in the upper left of each plot. (E) PI staining was performed at the end of a 72-hour co-culture of T cells expressing the various CD19-chimeric receptors with Raji tumor cells. The percentage of Pt cells within in chimeric receptor T cell line ($CD3^+$) is provided in each histogram.

Figure 15:
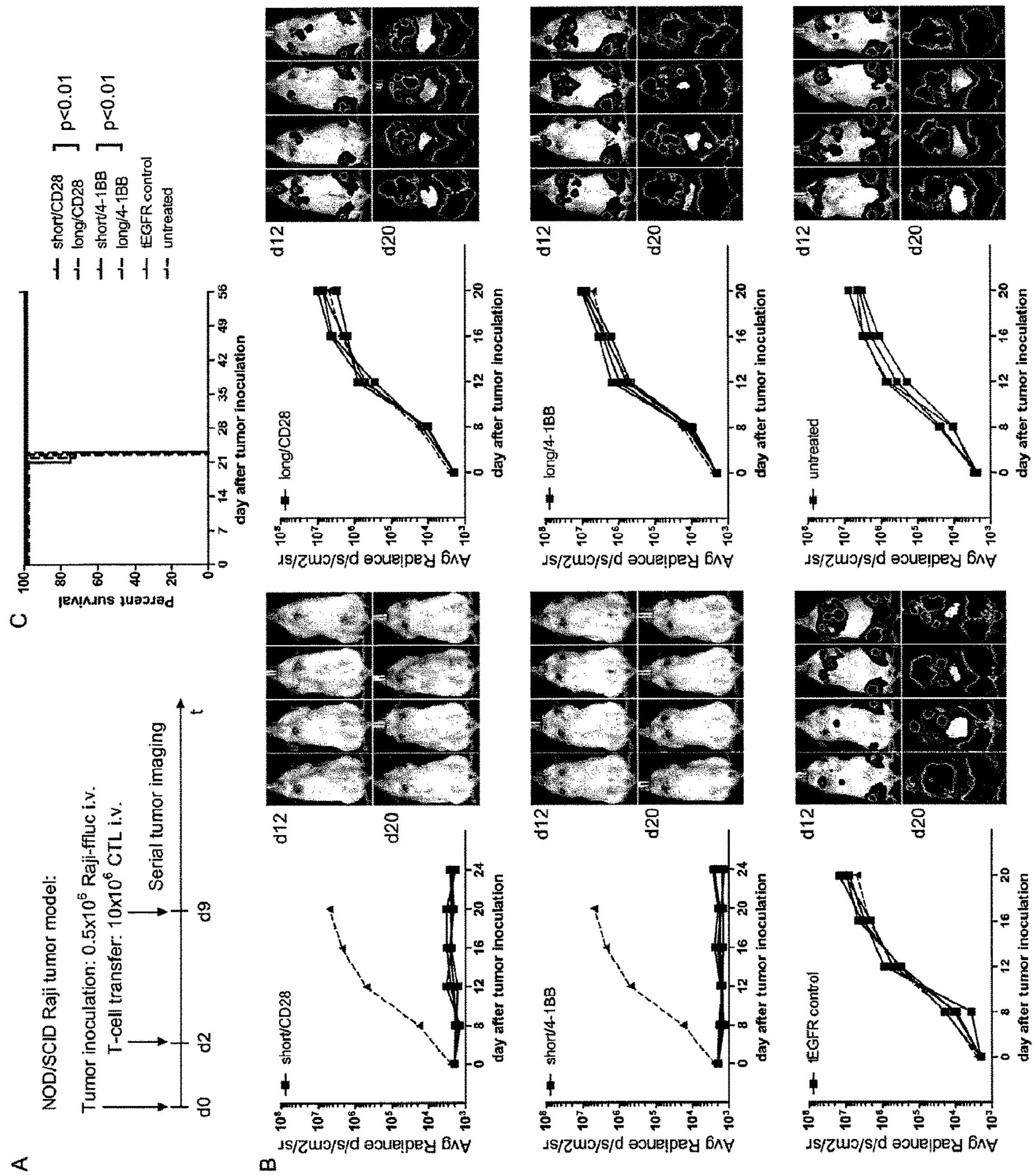

FIG. 15: CD19-chimeric receptor T cells with a short extracellular spacer domain eradicate Raji tumors in NOD/SCID mice. (A) Cohorts of mice were inoculated with Raji-ffluc via tail vein injection, and T cells transduced with CD19-chimeric receptors containing long and short spacer domains or with tEGFR alone were administered 2 and 9 days after tumor inoculation by tail vein injection. Tumor progression and distribution was evaluated by serial bioluminescence imaging after injection of luciferin substrate. (B) Serial bioluminescence imaging of tumor in cohorts of mice either treated with T cells expressing CD19-chimeric receptors with short spacer ('short/CD28' and 'short/4-1BB') and long spacer ('long/CD28' and 'long/4-1BB') domains, with T cells transduced with the tEGFR control vector, or untreated. Each diagram representing cohorts of mice treated with CD19-chimeric receptor or tEGFR transduced T cells also shows the mean of tumor progression in untreated mice for comparison (red triangles). (C) Kaplan-Meier analyses of survival of untreated mice and mice treated with T cells expressing CD19-chimeric receptors with short spacer ('short/CD28' and 'short/4-1BB'), long spacer ('long/CD28' and 'long/4-1BB') domains, and with control tEGFR. Statistical analyses were performed using the log-rank test. The data shown in B and C are representative of results obtained in 3 independent experiments.

Figure 16:
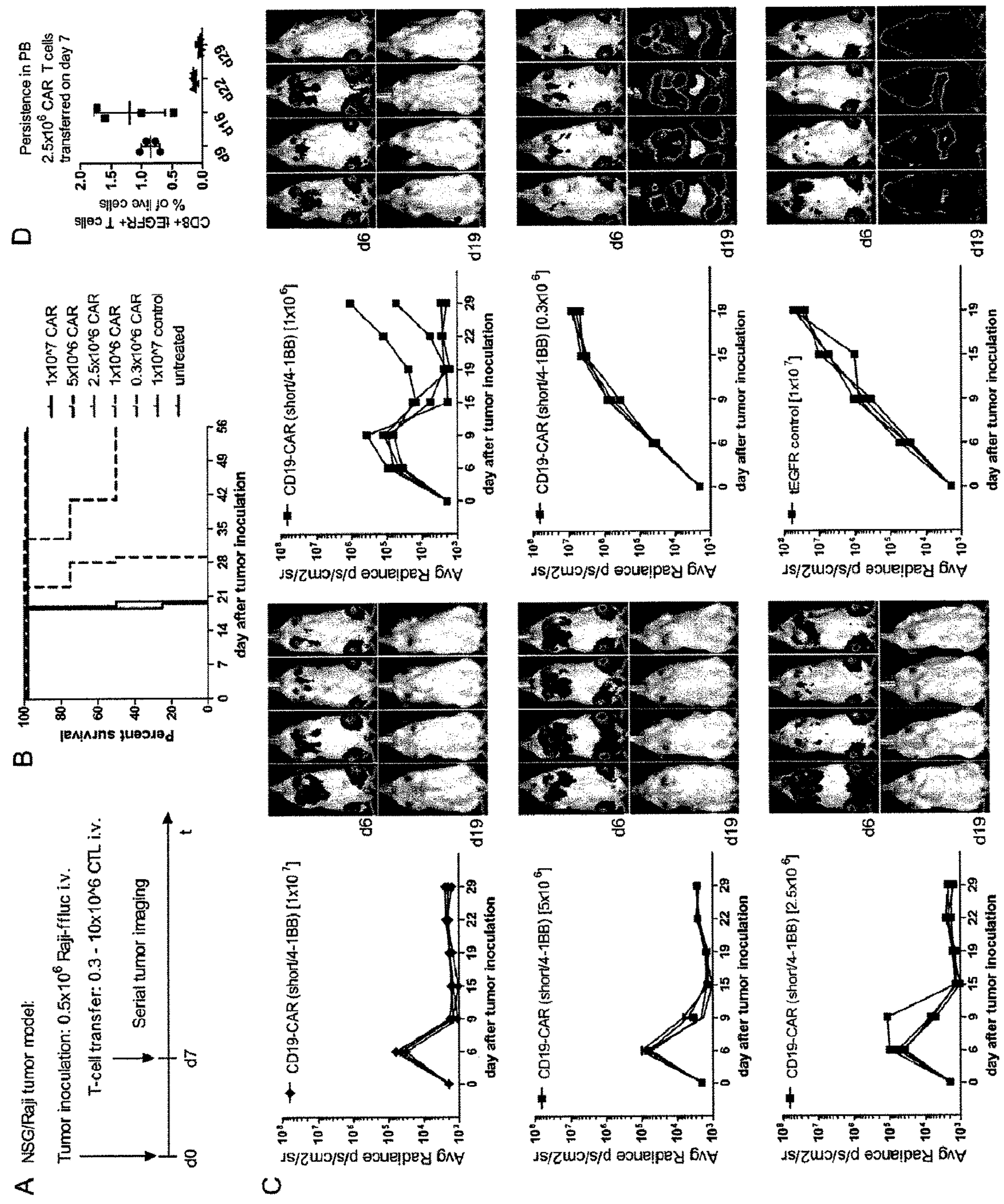

FIG. 16: CD19-chimeric receptor T cells with a short spacer (short/4-1BB) eradicate established Raji tumors in NSG mice in a dose-dependent manner. (A) Mice were inoculated with Raji-ffluc via tail vein injection and tumor engraftment confirmed by bioluminescence imaging on day 6. On day 7, mice received a single i.v. injection of various doses of T cells transduced with the CD19-chimeric receptor 'short/4-1BB' or with the tEGFR-control lentivirus. (B, C) Dose dependent anti-tumor efficacy of T cells expressing the CD19-chimeric receptor 'short/4-1BB'. A control cohort of mice received a single high dose of T cells modified with tEGFR alone. (D) Persistence of CD19-chimeric receptor T cells following adoptive transfer into NSG/Raji mice. Flow cytometric analysis of peripheral blood (eye bleeds) in the cohort of mice treated with $2.5\times10^6$ CD19-chimeric receptor 'short/4-1BB' T cells. The frequency of $CD8^+$ $tEGFR^+$ T cells is shown as percentage of live peripheral blood cells.

FIG. 17: T cells expressing CD19-chimeric receptors with a short spacer and either CD28 or 4-1BB are more effective against established lymphoma than those expressing CD19-chimeric receptors with a long spacer. (A) NSG mice were inoculated with Raji-ffluc on day 0, and treated on day 7 with one dose of $2.5\times10^6$ CD19 chimeric receptor T cells expressing short or long spacer and either CD28 or 4-1BB costimulatory domain. (B) Kaplan-Meier analyses of survival of mice in each of the treatment groups. Statistical analyses were performed using the log-rank test. (C) Bioluminescence imaging of cohorts of mice treated with T cells expressing CD19-chimeric receptors with short spacers ('short/CD28' and 'short/4-1BB'), and long spacers ('long/CD28 and long/4-1BB'). The mean tumor burden observed in untreated mice at each time point is shown in each diagram for comparison (triangles). (D) In vivo persistence of T cells expressing CD19-chimeric receptor with short spacer domain is enhanced compared to T cells expressing CD19-chimeric receptors with long spacer domain. The frequency of $CD8^+$ $tEGFR^+$ T cells in the peripheral blood obtained at day 3 and 10 after transfer was determined by flow cytometry and is shown as percentage of live ($PI^-$) peripheral blood cells. Statistical analyses were performed by Student's t-test. The data shown in B-D are representative for results obtained in 3 independent experiments.

Figure 18:
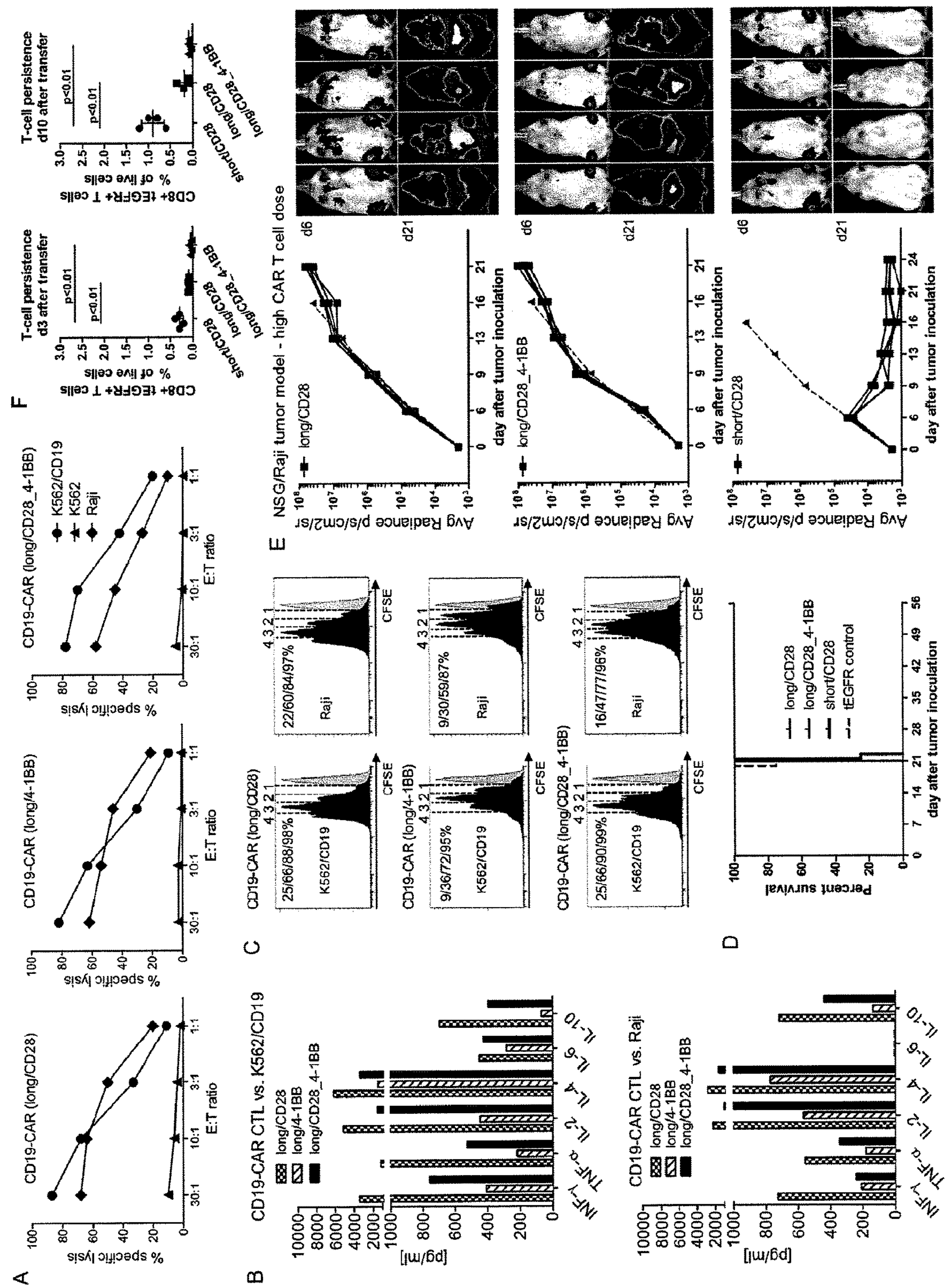

FIG. 18: Increasing chimeric receptor T cell dose or augmenting costimulatory signaling does not improve the anti-tumor efficacy of CD19-chimeric receptors with a long spacer domain against established lymphoma. (A) Cytolytic activity of T cells expressing 'long/CD28', 'long/4-1BB' and 'long/CD28_4-1BB' CD19 chimeric receptors against $CD19^+$ and control target cells. (B) Multiplex cytokine assay of supernatant obtained after 24 hours from triplicate co-cultures of K562/CD19 and Raji tumor cells with T cells expressing the various CD19-chimeric receptors. (C) Evaluation of proliferation of CD19-chimeric receptor T cells 72 hours after stimulation with $CD19^+$ tumor cells (K562/CD19—left panel; Raji—right panel) by CFSE dye dilution. For analysis, triplicate wells were pooled and the proliferation of live ($PI^-$) $CD8^+$ T cells analyzed. Numbers above each histogram indicate the number of cell divisions the proliferating subset underwent, and the fraction of T cells in each gate that underwent ≥4/3/2/1 cell divisions is provided in the upper left of each plot. (D) Kaplan-Meier analyses of survival of mice treated with T cells expressing CD19-chimeric receptors with short ('short/CD28') and long spacer domain ('long/CD28' and 'long/CD28_4-1BB'), or T cells modified with a tEGFR-encoding control lentiviral vector. Statistical analyses were performed using the log-rank test. (E) Bioluminescence imaging of cohorts of mice treated with T cells expressing CD19-chimeric receptors with short spacer ('short/CD28'), and long spacers ('long/CD28 and 'long/CD28_4-1BB'). Diagrams show mean tumor progression in untreated mice for comparison (red triangles). (F) In vivo persistence of T cells expressing the various CD19-chimeric receptors. The frequency of $CD8^+$ $tEGFR^+$ T cells in the peripheral blood obtained at day 3 and 10 after transfer was determined by flow cytometry and is shown as percentage of live ($PI^-$) peripheral blood cells. Statistical analyses were performed by Student's t-test.

FIG. 19: CD19-chimeric receptor T cells with a long spacer domain are activated by tumor in vivo but fail to increase in cell number. (A) Expression of CD69 and CD25 on T cells modified with each CD19-chimeric receptor prior to transfer into NSG/Raji mice. (B) Cohorts of mice were inoculated with Raji-ffluc tumor cells and 7 days later received CFSE-labeled CD19-chimeric receptor transduced or control T cells. Bone marrow and spleens were harvested from subgroups of mice 24 and 72 hours after T cell administration. (C, D) Multiparameter flow cytometric analysis of bone marrow mononuclear cells obtained 24 hours (C) and 72 hours (D) after T cell transfer. Dot plots show anti CD3 and anti CD45 staining after gating on $PI^-$ cells to detect viable human T cells. The $CD3^-$ $CD45^+$ gate contains Raji tumor cells. Expression of CD25 and CD69 on live ($PI^-$) $CD3^+$ $CD45^+$ T cells is shown in the histograms. (E) Frequency of $CD3^+$ $CD45^+$ T cells in spleens obtained 24 and 72 hours after T cell transfer. Dot plots are gated on live $PI^-$ splenocytes and the percentage of $CD3^+$ $CD45^+$ T cells is shown in each plot. (F) PI staining of bone marrow and splenocytes hours after T cell transfer into NSG/Raji mice. The numbers in the histograms indicate the percentage of $PI^-$ cells within the $CD3^+$ population. (G) Bioluminescence imaging of cohorts of mice treated with T cells expressing CD19-chimeric receptors with short spacer ('short/CD28' and 'short/4-1BB'), long spacers ('long/CD28 and long/4-1BB'), or control T cells.

FIG. 20: T cells expressing CD19 chimeric receptors with 4-1BB and CD3zeta and a modified IgG4-Fc hinge exhibit superior in vitro and in vivo function compared to T cells expressing CD19 chimeric receptors with 4-1BB and CD3zeta and a CD8 alpha hinge. A. Cytolytic activity of CD19 chimeric receptor modified T-cells with IgG4 Fc hinge, CD8 alpha hinge and control T cells against $Cr^{51}$-labeled K562 cells transfected with CD19, Raji lymphoma cells that express CD19, and K562 control T cells. Lysis is shown at different E/T ratios in a 4 hour $Cr^{51}$ release assay. B. Interferon gamma production by $5\times10^4$ T cells expressing a CD19 chimeric receptor with an IgG4 Fc hinge or CD8 alpha hinge after a 24-hour coculture with Raji tumor cells. O.D. of 1 corresponds to ~500 pg/ml of interferon gamma. C. CFSE dye dilution assay to measure proliferation of T cells expressing a CD19 chimeric receptor with an IgG4 Fc hinge or CD8 alpha hinge and T cells that express tEGFR alone (control) after 72 hours coculture with CD19 positive Raji lymphoma cells. Numbers above each histogram indicate the number of cell divisions the proliferating cell subset underwent. The fraction of T cells in each gate that underwent ≥3/2/1 cell divisions is provided next to the plot. D. In vivo antitumor activity of T cells expressing a CD19 chimeric receptor with an IgG4 Fc hinge (group 1) or CD8 alpha hinge (group 2) and T cells that express tEGFR alone (group 3) in NSG mice inoculated with Raji tumor cells expressing firefly luciferase (ffluc). Mice were imaged 17 days after tumor inoculation and 10 days after T cell inoculation. The data shows greater tumor burden in mice treated with control tEGFR T cells (group 3) or with CD19 chimeric receptor CD8 alpha hinge T cells (group 2) compared with mice treated with CD19 chimeric receptor IgG4 Fc hinge T cells (group 1).

DETAILED DESCRIPTION

Unless defined otherwise, all technical and scientific terms used herein have the same meaning as commonly understood by one of ordinary skill in the art to which the invention pertains.

"About" as used herein when referring to a measurable value is meant to encompass variations of ±20% or ±10%, more preferably ±5%, even more preferably ±1%, and still more preferably ±0.1% from the specified value.

"Activation", as used herein, refers to the state of a T cell that has been sufficiently stimulated to induce detectable cellular proliferation, cytokine production or expression of cell surface markers such as CD69 and CD25, or detectable effector functions.

"Activation Induced cell death" as used herein refers to a state of a T cell that is activated but is not able to proliferate for more than 2 generations and exhibits markers of apoptosis.

"Antigen" or "Ag" as used herein refers to a molecule that provokes an immune response. This immune response may involve either antibody production, or the activation of specific immunologically-competent cells, or both. It is readily apparent that an antigen can be generated synthesized, produced recombinantly or can be derived from a biological sample. Such a biological sample can include, but is not limited to a tissue sample, a tumor sample, a cell or a biological fluid.

"Anti-tumor effect" as used herein, refers to a biological effect, which can be manifested by a decrease in tumor volume, a decrease in the number of tumor cells, a decrease in the number of metastases, an increase in life expectancy, or a decrease of various physiological symptoms associated with the cancerous condition. An "anti-tumor effect" can also be manifested by a decrease in recurrence or an increase in the time before recurrence.

"Chimeric receptor" as used herein refers to a synthetically designed receptor comprising a ligand binding domain of an antibody or other protein sequence that binds to a molecule associated with the disease or disorder and is linked via a spacer domain to one or more intracellular signaling domains of a T cell or other receptors, such as a costimulatory domain.

"Co-stimulatory domain," as the term is used herein refers to a signaling moiety that provides to T cells a signal which, in addition to the primary signal provided by for instance the CD3 zeta chain of the TCR/CD3 complex, mediates a T cell response, including, but not limited to, activation, proliferation, differentiation, cytokine secretion, and the like. A co-stimulatory domain can include all or a portion of, but is not limited to, CD27, CD28, 4-1BB, OX40, CD30, CD40, ICOS, lymphocyte function-associated antigen-1 (LFA-1), CD2, CD7, LIGHT, NKG2C, B7-H3, and a ligand that specifically binds with CD83. In embodiments, the co-stimulatory domain is an intracellular signaling domain that interacts with other intracellular mediators to mediate a cell response including activation, proliferation, differentiation and cytokine secretion, and the like.

"Coding for" are used herein refers to the property of specific sequences of nucleotides in a polynucleotide, such as a gene, a cDNA, or an mRNA, to serve as templates for synthesis of other macromolecules such as a defined sequence of amino acids. Thus, a gene codes for a protein if transcription and translation of mRNA corresponding to that gene produces the protein in a cell or other biological system. A "nucleic acid sequence coding for a polypeptide" includes all nucleotide sequences that are degenerate versions of each other and that code for the same amino acid sequence.

"Cytotoxic T lymphocyte" (CTL) as used herein refers to a T lymphocyte that expresses CD8 on the surface thereof (i.e., a CD8$^+$ T cell). In some embodiments such cells are preferably "memory" T cells ($T_M$ cells) that are antigen-experienced.

"Central memory" T cell (or "$T_{CM}$") as used herein refers to an antigen experienced CTL that expresses CD62L or CCR-7 and CD45RO on the surface thereof, and does not express or has decreased expression of CD45RA as compared to naive cells. In embodiments, central memory cells are positive for expression of CD62L, CCR7, CD28, CD127, CD45RO, and CD95, and have decreased expression of CD54RA as compared to naïve cells.

"Effector memory" T cell (or "$T_{EM}$") as used herein refers to an antigen experienced T cell that does not express or has decreased expression of CD62L on the surface thereof as compared to central memory cells, and does not express or has decreased expression of CD45RA as compared to naïve cell. In embodiments, effector memory cells are negative for expression of CD62L and CCR7, compared to naïve cells or central memory cells, and have variable expression of CD28 and CD45RA.

"Naïve" T cells as used herein refers to a non antigen experienced T lymphocyte that expresses CD62L and CD45RA, and does not express CD45RO− as compared to central or effector memory cells. In some embodiments, naïve CD8+ T lymphocytes are characterized by the expression of phenotypic markers of naïve T cells including CD62L, CCR7, CD28, CD127, and CD45RA.

"Effector" "$T_E$" T cells as used herein refers to a antigen experienced cytotoxic T lymphocyte cells that do not express or have decreased expression of CD62L, CCR7, CD28, and are positive for granzyme B and perforin as compared to central memory or naïve T cells.

"Enriched" and "depleted" as used herein to describe amounts of cell types in a mixture refers to the subjecting of the mixture of the cells to a process or step which results in an increase in the number of the "enriched" type and a decrease in the number of the "depleted" cells. Thus, depending upon the source of the original population of cells subjected to the enriching process, a mixture or composition may contain about 60, 70, 80, 90, 95, or 99 percent or more (in number or count) of the "enriched" cells and about 40, 30, 20, 10, 5 or 1 percent or less (in number or count) of the "depleted" cells.

"Epitope" as used herein refers to a part of an antigen or molecule that is recognized by the immune system including antibodies, T cells, and/or B cells. Epitopes usually have at least 7 amino acids and can be linear or conformational.

"Isolated," when used to describe the various polypeptides disclosed herein, means polypeptide or nucleic acid that has been identified and separated and/or recovered from a component of its natural environment. Preferably, the isolated polypeptide or nucleic acid is free of association with all components with which it is naturally associated. Contaminant components of its natural environment are materials that would typically interfere with diagnostic or therapeutic uses for the polypeptide or nucleic acid, and may include enzymes, hormones, and other proteinaceous or non-proteinaceous solutes.

"Intracellular signaling domain" as used herein refers to all or a portion of one or more domains of a molecule (here the chimeric receptor molecule) that provides for activation of a lymphocyte. Intracellular domains of such molecules mediate a signal by interacting with cellular mediators to result in proliferation, differentiation, activation and other effector functions. In embodiments, such molecules include all or portions of CD28, CD3, 4-1BB, and combinations thereof.

"Ligand" as used herein refers to a substance that binds specifically to another substance to form a complex. Example of ligands include epitopes on antigens, molecules that bind to receptors, substrates, inhibitors, hormones, and activators. "Ligand binding domain" as used herein refers to substance or portion of a substance that binds to a ligand. Examples of ligand binding domains include antigen binding portions of antibodies, extracellular domains of receptors, and active sites of enzymes.

"Operably linked" as used herein refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Percent (%) amino acid sequence identity" with respect to the chimeric receptor polypeptide sequences identified herein is defined as the percentage of amino acid residues in a candidate sequence that are identical with the amino acid residues in the reference sequence for each of the ligand binding domain, spacer, transmembrane domain, and/or the lymphocyte activating domain, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For example, % amino acid sequence identity values generated using the WU-BLAST-2 computer program [Altschul et al., Methods in Enzymology, 266:460-480 (1996)] uses several search parameters, most of which are set to the default values. Those that are not set to default values (i.e., the adjustable parameters) are set with the following values: overlap span=1, overlap fraction=0.125, word threshold (T)=11 and scoring matrix=BLOSUM62. A % amino acid sequence identity value is determined by dividing (a) the number of matching identical amino acid residues between the each or all of the polypeptide amino acid sequence of the reference chimeric receptor sequence provided in Table 2 and the comparison amino acid sequence of interest as determined by WU-BLAST-2 by (b) the total number of amino acid residues of the polypeptide of interest.

"Chimeric receptor variant polynucleotide" or "chimeric receptor variant nucleic acid sequence" as used herein refers to a polypeptide-encoding nucleic acid molecule as defined below having at least about 80% nucleic acid sequence identity with the polynucleotide acid sequence shown in Table 1 or a specifically derived fragment thereof, such as polynucleotide coding for an antigen binding domain, a polynucleotide encoding a spacer domain, a polynucleotide coding for a transmembrane domain and/or a polynucleotide coding for a lymphocyte stimulatory domain. Ordinarily, a chimeric receptor variant of polynucleotide or fragment thereof will have at least about 80% nucleic acid sequence identity, more preferably at least about 81% nucleic acid sequence identity, more preferably at least about 82% nucleic acid sequence identity, more preferably at least about 83% nucleic acid sequence identity, more preferably at least about 84% nucleic acid sequence identity, more preferably at least about 85% nucleic acid sequence identity, more preferably at least about 86% nucleic acid sequence identity, more preferably at least about 87% nucleic acid sequence identity, more preferably at least about 88% nucleic acid sequence identity, more preferably at least about 89% nucleic acid sequence identity, more preferably at least about 90% nucleic acid sequence identity, more preferably at least about 91% nucleic acid sequence identity, more preferably at least about 92% nucleic acid sequence identity, more preferably at least about 93% nucleic acid sequence identity, more preferably at least about 94% nucleic acid sequence identity, more preferably at least about 95% nucleic acid sequence identity, more preferably at least about 96% nucleic acid sequence identity, more preferably at least about 97% nucleic acid sequence identity, more preferably at least about 98% nucleic acid sequence identity and yet more preferably at least about 99% nucleic acid sequence identity with the nucleic acid sequence as shown in Table or a derived fragment thereof. Variants do not encompass the native nucleotide sequence. In this regard, due to the degeneracy of the genetic code, one of ordinary skill in the art will immediately recognize that a large number of chimeric receptor variant polynucleotides having at least about 80% nucleic acid sequence identity to the nucleotide sequence of Table 1 will encode a polypeptide having an amino acid sequence which is identical to the amino acid sequence of Table 2.

"Substantially purified" refers to a molecule that is essentially free of other molecule types or a cell that is essentially free of other cell types. A substantially purified cell also refers to a cell, which has been separated from other cell types with which it is normally associated in its naturally occurring state. In some instances, a population of substantially purified cells refers to a homogenous population of cells.

"Not substantially found" when used in reference the presence of a tumor antigen or other molecules on normal cells refers to the percentage of a normal cell type that has the antigen or molecule, and/or the density of the antigen on the cells. In embodiments, not substantially found means that the antigen or molecule is found on less than 50% of normal cell type and/or at a 50% less density as compared to the amount of cells or antigen found on a tumor cell or other diseased cell.

"T cells" or "T lymphocytes" as used herein may be from any mammalian, preferably primate, species, including monkeys, dogs, and humans. In some embodiments the T cells are allogeneic (from the same species but different donor) as the recipient subject; in some embodiments the T cells are autologous (the donor and the recipient are the same); in some embodiments the T cells arc syngeneic (the donor and the recipients are different but are identical twins).

Modes of the Disclosure

The disclosure provides for chimeric receptor nucleic acids, and vectors and host cells including such nucleic acids. The chimeric receptor nucleic acid comprises a number of modular components that can be excised and replaced with other components in order to customize the chimeric receptor for a specific target molecule. The disclosure provides that one of the modular components is the spacer component. It has been surprisingly found that the length of the spacer region that is presumed not to have signaling capability affects the in vivo efficacy of the T cells modified to express the chimeric receptor and needs to be customized for individual target molecules for enhanced therapeutic activity.

In one aspect, methods and nucleic acid constructs are provided to design a chimeric receptor that has improved tumor recognition, increased T cell proliferation and/or cytokine production in response to the ligand as compared to a reference chimeric receptor. In embodiments, a library of nucleic acids is provided, wherein each nucleic acid codes for a spacer region that differs from the others in sequence and length. Each of the nucleic acids can then be used to form a chimeric receptor nucleic acid construct that can be tested in vivo (in an animal model) and/or in vitro so that a spacer can be selected that provides for improved tumor recognition, increased T cell proliferation and/or cytokine production in response to the ligand.

In embodiments, a chimeric receptor nucleic acid comprises a polynucleotide coding for a ligand binding domain, wherein the ligand is a tumor or viral specific antigen or molecule, a polynucleotide coding for a customized polypeptide spacer, wherein the spacer provides for enhanced T cell proliferation; a polynucleotide coding for a transmembrane domain; and a polynucleotide coding for one or more intracellular signaling domains. In embodiments, a long spacer is employed if the epitope of the target molecule is membrane proximal on the target cell and a short spacer is employed if the epitope of the target molecule is membrane distal on the target cell.

The design of a chimeric receptor can be customized depending on the type of tumor or virus, the target antigen or molecule present on the tumor, the affinity of the antibody for the target molecule, the flexibility needed for the antigen binding domain, and/or the intracellular signaling domain. In embodiments, a number of chimeric receptor constructs are tested in vitro and in in vivo models to determine the ability of T cells modified with the receptor to kill tumor cells in immunodeficient mice and to proliferate and persist after adoptive transfer. In embodiments, a chimeric receptor is selected that provides for capability of at least 30% of the cells to proliferate through at least two generations in vitro and/or within 72 hours after introduction in vivo. In embodiments, a chimeric receptor is not selected that results in greater than 50% of the cells undergoing activation induced cell death (AICD) within 72 hours in vivo in immunodeficient mice, and fails to eradicate tumor cells.

Depending on whether the target molecule is present on a subject's tumor cells, the chimeric receptor includes a ligand binding domain that specifically binds to that target molecule. In embodiments, a subject's tumor cells are characterized for cell surface tumor molecules. The target molecule may be selected based on a determination of its presence on a particular subject's tumor cells. In embodiments, a target molecule is selected that is a cell surface molecule found predominantly on tumor cells and not found on normal tissues to any substantial degree. In embodiments, an antibody is selected to bind to an epitope on the targeted cell surface molecule. In some cases, the epitope is characterized with respect to its proximity to the cell membrane. An epitope is characterized as proximal to the membrane when it is predicted or known by structural analysis to reside closer to the target cell membrane than alternative epitopes that are predicted or known by structural analysis to reside a greater distance from the target cell membrane. In embodiments, the affinity of the antibody from which the scFV is constructed is compared by binding assays, and antibodies with different affinities are examined in chimeric receptor formats expressed in T cells to determine which affinity confers optimal tumor recognition, based on superior cytotoxicity of target cells, and/or T cell cytokine production and proliferation.

In addition, the spacer region of the chimeric receptor may be varied to optimize T cell recognition of the ligand on the target cell. In embodiments, when an antibody binds to an epitope on the target cell that is very proximal to the membrane, a spacer is selected that is longer than about 15 amino acids. For example, in embodiments, if the epitope or portion thereof on the target antigen is in the first 100 amino acids of the linear sequence of the extracellular domain adjacent to the transmembrane domain, a long spacer region may be selected. In embodiments, when an antibody binds to an epitope on the target cell that is distal to the membrane, a spacer is selected that is about 119 or 15 amino acids or less. For example, in embodiments, when the epitope or portion thereof is found in the 150 amino acids of the linear sequence of the extracellular domain from the terminus, a short or intermediate spacer may be utilized. In embodiments, a spacer comprises an amino acid sequence $X_1PPX_2P$ (SEQ ID NO:1).

A variety of combinations of primary and costimulatory intracellular signaling domain may be employed to enhance the in vivo efficacy of the chimeric receptor. In embodiments, different constructs of the chimeric receptor can be tested in an in vivo animal model to determine efficacy for tumor killing. In embodiments, a costimulatory intracellular signaling domain is selected from the group consisting of CD28 and modified versions thereof, 4-1BB and modified versions thereof and combinations thereof. Other costimulatory domains, such as OX40 may be incorporated.

CD8+ central memory T cells have an intrinsic programming that allows them to persist for extended periods after administration, which makes them a preferred subset of CD8+ T cells for immunotherapy. In embodiments, CD19 specific chimeric receptor modified cytotoxic T cells prepared from sort purified CD8+ central memory T cells are administered in the presence or absence of CD4+ CD19 specific chimeric receptor-modified T cells. In embodiments, tumor-specific CD4+ T cells exert anti-tumor reactivity and provide help to tumor-specific CD8+ T cells in vitro and in vivo. In a specific embodiment, tumor-specific CD4+ T cells or $CD4^+$ T cells selected from the naïve or the central memory subsets are utilized alone or in combination with $CD8^+$ $T_{CM}$.

Nucleic Acids, Vectors, and Polypeptides

The disclosure provides a chimeric receptor nucleic acid useful for transforming or transducing lymphocytes for use in adoptive immunotherapy. In embodiments, the nucleic acid contains a number of modular components that provide for easy substitution of elements of the nucleic acid. While not meant to limit the scope of the disclosure, it is believed that the chimeric receptor for each tumor antigen is desirably customized in terms of components in order to provide for in vivo efficacy and efficient expression in mammalian cells. For example, in a specific embodiment, for efficacy of a chimeric receptor comprising a scFV that binds to a ROR1 epitope located in the membrane distal Ig/Frizzled domain, a spacer that is about 15 amino acids or less is employed. In another specific embodiment, for efficacy of a chimeric receptor comprising a scFV that binds to a ROR1 epitope located in the membrane proximal Kringle domain, a spacer that is longer than 15 amino acids is employed. In another embodiment, for efficacy of a chimeric receptor comprising a scFV that binds to CD19, a spacer that is 15 amino acids or less is employed.

In embodiments, an isolated chimeric receptor nucleic acid comprises a polynucleotide coding for a ligand binding domain, wherein the target molecule is a tumor specific antigen, a polynucleotide coding for a polypeptide spacer wherein the polypeptide spacer is about 229 amino acids or less; a polynucleotide coding for a transmembrane domain; and a polynucleotide coding for an intracellular signaling domain. In embodiments, an expression vector comprises a chimeric nucleic acid as described herein. Polypeptides encoded by all of or a portion of the chimeric receptor nucleic acids are also included herein.

Ligand Binding Domain

In embodiments, the chimeric receptor nucleic acid comprises a polynucleotide coding for a ligand binding domain. In embodiments, the ligand binding domain specifically binds to a tumor or viral specific antigen. In embodiments, the ligand binding domain is an antibody or fragment thereof. A nucleic acid sequence coding for an antibody or antibody fragment can readily be determined. In a specific embodiment, the polynucleotide codes for a single chain Fv that specifically binds CD19. In other specific embodiments, the polynucleotide codes for a single chain Fv that specifically binds ROR1. The sequences of these antibodies are known to or can readily be determined by those of skill in the art.

Tumor antigens are proteins that are produced by tumor cells that elicit an immune response. The selection of the ligand binding domain of the invention will depend on the type of cancer to be treated, and may target tumor antigens or other tumor cell surface molecules. A tumor sample from a subject may be characterized for the presence of certain biomarkers or cell surface markers. For example, breast cancer cells from a subject may be positive or negative for each of Her2Neu, Estrogen receptor, and/or the Progesterone receptor. A tumor antigen or cell surface molecule is selected that is found on the individual subject's tumor cells. Tumor antigens and cell surface molecules are well known in the art and include, for example, carcinoembryonic antigen (CEA), prostate specific antigen, PSMA, Her2/neu, estrogen receptor, progesterone receptor, ephrinB2, CD19, CD20, CD22, CD23, CD123, CS-1, ROR1, mesothelin, c-Met, GD-2, and MAGE A3 TCR. In embodiments a target molecule is a cell surface molecule that is found on tumor cells and is not substantially found on normal tissues, or restricted in its expression to non-vital normal tissues.

Other target molecules include but are not limited to antigens derived from infectious pathogens such as HIV (human immunodeficiency virus), HBV (hepatitis B virus), HPV (human papilloma virus) and Hepatitis C virus.

In one embodiment, the target molecule on the tumor comprises one or more epitopes associated with a malignant tumor. Malignant tumors express a number of proteins that can serve as target antigens for T cell receptor or chimeric receptor mediated recognition. Other target molecules belong to the group of cell transformation-related molecules such as the oncogene HER-2/Neu/ErbB2. In embodiments, the tumor antigen is selectively expressed or overexpressed on the tumor cells as compared to control cells of the same tissue type. In other embodiments, the tumor antigen is a cell surface polypeptide.

Once a tumor cell surface molecule that might be targeted with a chimeric receptor is identified, an epitope of the target molecule is selected and characterized. In embodiments, an epitope is selected that is proximal to the tumor cell membrane. In other embodiments, an epitope is selected that is distal to the tumor cell membrane. An epitope is characterized as proximal to the membrane when it is predicted or known by structural analysis to reside closer to the target cell membrane than alternative epitopes that are predicted or known by structural analysis to reside a greater distance from the target cell membrane.

Antibodies that specifically bind a tumor cell surface molecule can be prepared using methods of obtaining monoclonal antibodies, methods of phage display, methods to generate human or humanized antibodies, or methods using a transgenic animal or plant engineered to produce human antibodies. Phage display libraries of partially or fully synthetic antibodies are available and can be screened for an antibody or fragment thereof that can bind to the target molecule. Phage display libraries of human antibodies are also available. In embodiments, antibodies specifically bind to a tumor cell surface molecule and do not cross react with nonspecific components such as bovine serum albumin or other unrelated antigens. Once identified, the amino acid sequence or polynucleotide sequence coding for the antibody can be isolated and/or determined.

Antibodies or antigen binding fragments include all or a portion of polyclonal antibodies, a monoclonal antibody, a human antibody, a humanized antibody, a synthetic antibody, a chimeric antibody, a bispecific antibody, a minibody, and a linear antibody. Antibody fragments" comprise a portion of an intact antibody, preferably the antigen binding or variable region of the intact antibody and can readily be prepared. Examples of antibody fragments include Fab, Fab', F(ab')2, and Fv fragments; diabodies; linear antibodies; single-chain antibody molecules; and multispecific antibodies formed from antibody fragments.

In embodiments, a number of different antibodies that bind to a particular tumor cell surface molecule can be isolated and characterized. In embodiments, the antibodies are characterized based on epitope specificity of the targeted molecule. In addition, in some cases, antibodies that bind to the same epitope can be selected based on the affinity of the antibody for that epitope. In embodiments, an antibody has an affinity of at least 1 mM, and preferably <50 nM. In embodiments, an antibody is selected that has a higher affinity for the epitope as compared to other antibodies. For example, an antibody is selected that has at least a 2 fold, at least a 5 fold, at least a 10 fold, at least a 20 fold, at least a 30 fold, at least a 40 fold, or at least a 50 fold greater affinity than a reference antibody that binds to the same epitope.

In embodiments, target molecules are selected from the group consisting of CD19, CD20, CD22, CD23, CD123, CS-1, ROR1, mesothelin, Her2, c-Met, PSMA, GD-2, MAGE A3 TCR and combinations thereof.

In specific embodiments, the target antigen is CD19. A number of antibodies specific for CD19 are known to those of skill in the art and can be readily characterized for sequence, epitope binding, and affinity. In a specific embodiment, the chimeric receptor construct includes a scFV sequence from FMC63 antibody. In other embodiments, the scFV is a human or humanized scFv comprising a variable light chain comprising a CDRL1 sequence of RASQDISKYLN (SEQ ID NO:57), CDRL2 sequence of SRLHSGV (SEQ ID NO:58), and a CDRL3 sequence of GNTLPYTFG (SEQ ID NO:59). In other embodiments, the scFV is a human or humanized scFv comprising a variable heavy chain comprising CDRH1 sequence of DYGVS (SEQ ID NO:74), CDRH2 sequence of VIWGSETTYYNSALKS (SEQ ID NO:60), and a CDRH3 sequence of YAMDYWG (SEQ ID NO:61). The disclosure also contemplates variable regions that have at least 90% amino acid sequence identity to that of the scFv for FMC63 and that have at least the same affinity for CD19. In embodiments, the chimeric receptor has a short or intermediate spacer of 119 amino acids or less, or 12 amino acids or less. In a specific embodiment, the spacer is 12 amino acid or less and has a sequence of SEQ ID NO:4.

In embodiments, CDR regions are found within antibody regions as numbered by Kabat as follows: for the light chain; CDRL1 amino acids 24-34; CDRL2 amino acids 50-56; CDRL3 at amino acids 89-97; for the heavy chain at CDRH1 at amino acids 31-35; CDRH2 at amino acids 50-65; and for CDRH3 at amino acids 95-102. CDR regions in antibodies can be readily determined.

In specific embodiments, the target antigen is ROR1. A number of antibodies specific for ROR1 are known to those of skill in the art and can be readily characterized for sequence, epitope binding, and affinity. In a specific embodiment, the chimeric receptor construct includes a scFV sequence from R12 antibody. In other embodiments, the scFV is a human or humanized ScFv comprising a variable light chain comprising a CDRL1 sequence of ASGFDFSAYYM (SEQ ID NO:62), CDRL2 sequence of TIYPSSG (SEQ ID NO:63), and a CDRL3 sequence of ADRATYFCA (SEQ ID NO:64). In other embodiments, the scFV is a human or humanized ScFv comprising a variable heavy chain comprising CDRH1 sequence of DTIDWY (SEQ ID NO:65), CDRH2 sequence of VQSDGSYTKRPGVPDR (SEQ ID NO:66), and a CDRH3 sequence of YIGGYVFG (SEQ ID NO:67). The disclosure also contemplates variable regions that have at least 90% amino acid sequence identity to that of the scFv for R12 and that have at least the same affinity for ROR1. In embodiments, the chimeric receptor has a short or intermediate spacer of 119 amino acids or less, or 12 amino acids or less. In a specific embodiment, the spacer is 12 amino acid or less and has a sequence of SEQ ID NO:4.

In specific embodiments, the target antigen is ROR1. A number of antibodies specific for ROR1 are known to those of skill in the art and can be readily characterized for sequence, epitope binding, and affinity. In a specific embodiment, the chimeric receptor construct includes a scFV sequence from R11 antibody. In other embodiments, the scFV is a human or humanized ScFv comprising a variable light chain comprising a CDRL1 sequence of SGSDINDYPIS (SEQ ID NO:68), CDRL2 sequence of INSGGST (SEQ ID NO:69), and a CDRL3 sequence of YFCARGYS (SEQ ID NO:70). In other embodiments, the scFV is a human or humanized scFv comprising a variable heavy chain comprising CDRH1 sequence of SNLAW (SEQ ID NO:71), CDRH2 sequence of RASNLASGVPSRFSGS (SEQ ID NO:72), and a CDRH3 sequence of NVSYRTSF (SEQ ID NO:73). The disclosure also contemplates variable regions that have at least 90% amino acid sequence identity to that of the scFv for R11 and that have at least the same affinity for ROR1. In embodiments, the chimeric receptor has a long spacer of 229 amino acids or less. In a specific embodiment, the spacer is 229 amino acids and has a sequence of SEQ ID NO:50.

In specific embodiments, the target antigen is Her2. A number of antibodies specific for Her2 are known to those of skill in the art and can be readily characterized for sequence, epitope binding, and affinity. In a specific embodiment, the chimeric receptor construct includes a scFV sequence from Herceptin antibody. In other embodiments, the scFV is a human or humanized ScFv comprising a variable light chain comprising a CDRL1 sequence, CDRL2 sequence and a CDRL3 sequence of the Herceptin antibody. In other embodiments, the scFV is a human or humanized ScFv comprising a variable heavy chain comprising CDRH1 sequence, CDRH2, and a CDRH3 sequence of Herceptin. The CDR sequences can readily be determined from the amino acid sequence of Herceptin. The disclosure also contemplates variable regions that have at least 90% amino acid sequence identity to that of the scFv for Herceptin and that have at least the same affinity for Her2. In embodiments, the chimeric receptor has a long spacer of 229 amino acids or less. In a specific embodiment, the spacer is 229 amino acids and has a sequence of SEQ ID NO:50.

In embodiments, a polynucleotide coding for a ligand binding domain is operably linked to a polynucleotide coding for a spacer region. In embodiments, the polynucleotide coding for a ligand binding domain may also have one or more restriction enzyme sites at the 5' and/or 3' ends of the coding sequence in order to provide for easy excision and replacement of the polynucleotide with another polynucleotide coding for a ligand binding domain coding for a different antigen or that has different binding characteristics. For example, a restriction site, NheI, is encoded upstream of the leader sequence; and a 3' RsrII located within the hinge region allows subcloning of any desirable scFv into a chimeric receptor vector. In embodiments, the polynucleotide is codon optimized for expression in mammalian cells.

In embodiments, the polynucleotide coding for a ligand binding domain is operably linked to a signal peptide. In embodiments the signal peptide is a signal peptide for granulocyte colony stimulating factor. Polynucleotides coding for other signal peptides such as CD8 alpha can be utilized.

In embodiments, the polynucleotide coding for a ligand binding domain is operably linked to a promoter. A promoter is selected that provides for expression of the chimeric antigen receptor in a mammalian cell. In a specific embodiment the promoter is the elongation growth factor promoter (EF-1). Another example of a suitable promoter is the immediate early cytomegalovirus (CMV) promoter sequence. However, other constitutive promoter sequences may also be used, including, but not limited to the simian virus 40 (SV 40) early promoter, mouse mammary tumor virus (MMTV), human immunodeficiency virus (HIV) long terminal repeat (LTR) promoter, MuMoLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Inducible promoters are also contemplated. Examples of inducible promoters include, but are not limited to a metallothionine promoter, a glucocorticoid promoter, a progesterone promoter, and a tetracycline promoter.

A specific embodiment of a polynucleotide coding for a ligand binding domain is shown in Table 1 as the scFv from an antibody that specifically binds CD19, such as FMC63. A polynucleotide encoding for a flexible linker including the amino acids GSTSGSGKPGSGEGSTKG (SEQ ID NO:36) separates the VH and VL chains in the scFV. The amino acid sequence of the scFv including the linker is shown in Table 2. (SEQ ID NO:11) Other CD19-targeting antibodies such as SJ25C1 and HD37 are known. (SJ25C1: Bejcek et al. Cancer Res 2005, PMID 7538901; HD37: Pezutto et al. JI 1987, PMID 2437199).

Spacer

In embodiments, the chimeric receptor nucleic acid comprises a polynucleotide coding for a spacer region. It has been surprisingly found that the length of the spacer region that is presumed not to have signaling capability affects the in vivo efficacy of the T cells modified to express the chimeric receptor and needs to be customized for individual target molecules for optimal tumor or target cell recognition. In embodiments, the chimeric receptor nucleic acid comprises a polynucleotide coding for a customizable spacer region selected from a library of polynucleotides coding for spacer regions. In embodiments, a spacer length is selected based upon the location of the epitope, affinity of the antibody for the epitope, and/or the ability of the T cells expressing the chimeric receptor to proliferate in vitro and/or in vivo in response to antigen recognition.

Typically a spacer region is found between the ligand binding domain and the transmembrane domain of the chimeric receptor. In embodiments, a spacer region provides for flexibility of the ligand binding domain, allows for high expression levels in lymphocytes. A CD19-specific chimeric receptor having a spacer domain of about 229 amino acids had less antitumor activity than a CD19-specific chimeric receptor with a short spacer region comprised of the modified IgG4 hinge only. Other chimeric receptors, such as those constructed from the R12 or 2A2 scFvs also require a short spacer for optimal triggering of T cell effector functions, while a chimeric receptor constructed with the R11 ROR1 scFv requires a long spacer domain of about 229 amino acids for tumor recognition.

In embodiments, a spacer region has at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In embodiments, a spacer region has about 12 amino acids or less, about 119 amino acids or less, or about 229 amino acids or less.

In some embodiments, the spacer region is derived from a hinge region of an immunoglobulin like molecule. In embodiments, a spacer region comprises all or a portion of the hinge region from a human IgG1, human IgG2, a human IgG3, or a human IgG4, and may contain one or more amino acid substitutions. Exemplary sequences of the hinge regions are provided in Table 8. In embodiments, a portion of the hinge region includes the upper hinge amino acids found between the variable heavy chain and the core, and the core hinge amino acids including a polyproline region. Typically, the upper hinge region has about 3 to 10 amino acids. In some cases, the spacer region comprises an amino acid sequence of $X_1PPX_2P$ (SEQ ID NO:1). In embodiments, $X_1$ is a cysteine, glycine, or arginine and X2 is a cysteine or a threonine.

In embodiments, hinge region sequences can be modified in one or more amino acids in order to avoid undesirable structural interactions such as dimerization. In a specific embodiment, the spacer region comprises a portion of a modified human hinge region from IgG4, for example, as shown in Table 2 or Table 8 (SEQ ID NO:21). A representative of a polynucleotide coding for a portion of a modified IgG4 hinge region is provided in Table 1. (SEQ ID NO:4) In embodiments, a hinge region can have at least about 90%, 92%, 95%, or 100% sequence identity with a hinge region amino acid sequence identified in Table 2 or Table 8. In a specific embodiment, a portion of a human hinge region from IgG4 has an amino acid substitution in the core amino acids from CPSP to CPPC.

In some embodiments, all or a portion of the hinge region is combined with one or more domains of a constant region of an immunoglobulin. For example, a portion of a hinge region can be combined with all or a portion of a CH2 or CH3 domain or variant thereof. In embodiments, the spacer region does not include the 47-48 amino acid hinge region sequence from CD8apha or the spacer region consisting of an extracellular portion of the CD28 molecule.

In embodiments, a short spacer region has about 12 amino acids or less and comprises all or a portion of a IgG4 hinge region sequence or variant thereof, an intermediate spacer region has about 119 amino acids or less and comprises all or a portion of a IgG4 hinge region sequence and a CH3 region or variant thereof, and a long spacer has about 229 amino acids or less and comprises all or a portion of a IgG4 hinge region sequence, a CH2 region, and a CH3 region or variant thereof.

A polynucleotide coding for a spacer region can be readily prepared by synthetic or recombinant methods from the amino acid sequence. In embodiments, a polynucleotide coding for a spacer region is operably linked to a polynucleotide coding for a transmembrane region. In embodiments, the polynucleotide coding for the spacer region may also have one or more restriction enzyme sites at the 5' and/or 3' ends of the coding sequence in order to provide for easy excision and replacement of the polynucleotide with another polynucleotide coding for a different spacer region. In embodiments, the polynucleotide coding for the spacer region is codon optimized for expression in mammalian cells.

In embodiments, a library of polynucleotides, each coding for different spacer region is provided. In an embodiment, the spacer region is selected from the group consisting of a hinge region sequence from IgG1, IgG2, IgG3, or IgG4 or portion thereof, a hinge region sequence from IgG1, IgG2, IgG3, or IgG4 in combination with all or a portion of a CH2 region or variant thereof, a hinge region sequence from IgG1, IgG2, IgG3, or IgG4 in combination with all or a portion of a CH3 region or variant thereof, and a hinge region sequence from IgG1, IgG2, IgG3, or IgG4 in combination with all or a portion of a CH2 region or variant thereof, and a CH3 region or variant thereof. In embodiments, a short spacer region is a modified IgG4 hinge sequence (SEQ ID NO:4) having 12 amino acids or less, an intermediate sequence is a IgG4 hinge sequence with a CH3 sequence having 119 amino acids or less (SEQ ID NO:49); or a IgG4 hinge sequence with a CH2 and CH3 region having 229 amino acids or less (SEQ ID NO:50)

In embodiments, a method of selecting a spacer region for a chimeric receptor is provided herein. Surprisingly some chimeric receptor constructs, although effective to activate T cells and direct their killing of tumor cells in vitro, were not effective in vivo. In addition, the side effect profile of the chimeric receptor modified T cells can be such as to result in more cells undergoing activation induced cell death or causing an increase in in vivo cytokines. In embodiments, a method comprises providing a plurality of chimeric receptor nucleic acids, wherein the chimeric receptor nucleic acids differ only in the spacer region; introducing each of the chimeric receptor nucleic acids into a separate T lymphocyte population; expanding each separate lymphocyte population in vitro, and introducing each lymphocyte population into an animal bearing a tumor to determine the anti-tumor efficacy of each of the chimeric receptors when expressed in T cells, and selecting a chimeric receptor that provides anti-tumor efficacy as compared to each of the other separate lymphocyte populations modified with each of the other chimeric receptors.

Animal models of different tumors are known. Anti-tumor efficacy can be measured by identifying a decrease in tumor volume, by determining animal death, persistence of the genetically modified T cells in vivo, activation of genetically modified T cells (for example, by detecting an increase in expression of CD25 and/CD69), and/or proliferation of genetically modified T cells in vivo. In an embodiment, a chimeric receptor is selected that provides for the best anti-tumor efficacy in vivo as determined by one or more of these parameters. Lack of anti-tumor efficacy can be determined by lack of persistence of the genetically modified lymphocytes in vivo, animal death, an increase in apoptosis as measured by an increase in induction of caspase −3, and/or a decrease in proliferation of genetically modified lymphocytes.

In other embodiments, a method for selecting a spacer comprises selecting an epitope of a target molecule and characterizing the location of the epitope with respect to the cell membrane, selecting a spacer region that is long or short depending on the location of the epitope with respect to the cell membrane, selecting an antibody or fragment thereof that has an affinity for the epitope that is higher or lower as compared to a reference antibody, and determining whether the chimeric receptor construct provides for enhanced T cell proliferation or cytokine production in vitro and/or in vivo.

In some embodiments, if the target epitope or portion thereof is located proximal to the membrane it is located in the first 100 amino acids of the linear sequence of the extracellular domain adjacent to the transmembrane domain. If the epitope is located proximal to the membrane, a long spacer (e.g., 229 amino acids or less and greater than 119 amino acids) is selected. In some embodiments, if the target epitope is located distal to the membrane, it is located in the first 150 amino acids of the linear sequence of the extracellular domain terminus. If the epitope is located distal to the membrane, an intermediate or short spacer is selected (e.g. 119 amino acids or less or 12-15 amino acids or less). Alternatively, whether the epitope is proximal or distal to the membrane can be determined by modeling of the three dimensional structure or based on analysis of the crystal structure, In some embodiments, a chimeric receptor is selected that provides for at least 30% of the cells proliferating through two generations in vitro and/or in vivo. In other embodiments a chimeric receptor is not selected if it results in at least 50% of the cells undergoing activation induced cell death in 72 hours. In embodiments, a short spacer (e.g. 15 amino acids or less) is selected if the epitope is distal to the membrane. In embodiments, a long spacer (e.g. 229 amino acid or less and greater than 119 amino acids) is selected if the epitope is proximal to the membrane.

In embodiments, providing a plurality of chimeric receptor nucleic acids, wherein the chimeric receptor nucleic acids differ only in the spacer region comprises providing a chimeric receptor construct comprising a polynucleotide coding for a ligand binding domain, wherein the ligand is a tumor specific antigen, viral antigen, or any other molecule expressed on a target cell population that is suitable to mediate recognition and elimination by a lymphocyte; a polynucleotide coding for a first polypeptide spacer having a defined restriction site at the 5' and 3' end of the coding sequence for the first polypeptide spacer; a polynucleotide coding for a transmembrane domain; and a polynucleotide coding for one or more intracellular signaling domains.

In embodiments, a method further comprises providing one or more polynucleotides, each encoding a different spacer region. In embodiments, the different spacer regions are selected from the group consisting of a hinge region sequence from IgG1, IgG2, IgG3, or IgG4 or variant thereof or portion thereof, a hinge region sequence from IgG1, IgG2, IgG3, or IgG4 in combination with all or a portion of a CH2 region or variant thereof, a hinge region sequence from IgG1, IgG2, IgG3, or IgG4 in combination with all or a portion of a CH3 region or variant thereof, and a hinge region sequence from IgG1, IgG2, IgG3, or IgG4 in combination with all or a portion of a CH2 region or variant thereof and a CH3 region or variant thereof. In embodiments, CH2 or CH3 regions may be modified by one or more deletions or amino acid substitutions in order to provide for expression in lymphocytes and/or in order to minimize interactions with other molecules. In embodiments, a portion of a hinge region comprises at least the upper amino acids and the core sequence. In embodiments, a hinge region comprises the sequence $X_1PPX_2P$ (SEQ ID NO:1).

In embodiments, a method further comprises replacing the polynucleotide coding for the spacer region with a polynucleotide encoding a different spacer region to form a chimeric receptor nucleic acid with a different spacer region. The method can be repeated to form any number of chimeric receptor nucleic acids, each differing in the spacer region. In embodiments, the chimeric receptor nucleic acids differ from one another only in the spacer region.

Transmembrane Domain

In embodiments, the chimeric receptor nucleic acid comprises a polynucleotide coding for a transmembrane domain. The transmembrane domain provides for anchoring of the chimeric receptor in the membrane.

In an embodiment, the transmembrane domain that naturally is associated with one of the domains in the chimeric receptor is used. In some cases, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or a synthetic source. When the source is natural, the domain may be derived from any membrane-bound or transmembrane protein. Transmembrane regions comprise at least the transmembrane region(s) of) the alpha, beta or zeta chain of the T-cell receptor, CD28, CD3, CD45, CD4, CD8, CD9, CD16, CD22; CD33, CD37, CD64, CD80, CD86, CD134, CD137 and CD154. In a specific embodiment, the transmembrane domain comprises the amino acid sequence of the CD28 transmembrane domain as shown in Table 2. A representative polynucleotide sequence coding for the CD28 transmembrane domain is shown in Table 1 (SEQ ID NO:5).

A transmembrane domain may be synthetic or a variant of a naturally occurring transmembrane domain. In embodiments, synthetic or variant transmembrane domains comprise predominantly hydrophobic residues such as leucine and valine. In embodiments, a transmembrane domain can have at least about 80%, 85%, 90%, 95%, or 100% amino acid sequence identity with a transmembrane domain as shown in Table 2 or Table 6. Variant transmembrane domains preferably have a hydrophobic score of at least 50 as calculated by Kyte Doolittle.

A polynucleotide coding for a transmembrane domain can be readily prepared by synthetic or recombinant methods. In embodiments, a polynucleotide coding for a transmembrane domain is operably linked to a polynucleotide coding for a intracellular signaling region. In embodiments, the polynucleotide coding for a transmembrane domain may also have one or more restriction enzyme sites at the 5' and/or 3' ends of the coding sequence in order to provide for easy excision and replacement of the polynucleotide coding for a transmembrane domain with another polynucleotide coding for a different transmembrane domain. In embodiments, the polynucleotide coding for a transmembrane domain is codon optimized for expression in mammalian cells.

Intracellular Signaling Domain

In embodiments, the chimeric receptor nucleic acid comprises a polynucleotide coding for an intracellular signaling domain. The intracellular signaling domain provides for activation of one function of the transduced cell expressing the chimeric receptor upon binding to the ligand expressed on tumor cells. In embodiments, the intracellular signaling domain contains one or more intracellular signaling domains. In embodiments, the intracellular signaling domain is a portion of and/or a variant of an intracellular signaling domain that provides for activation of at least one function of the transduced cell.

Examples of intracellular signaling domains for use in a chimeric receptor of the disclosure include the cytoplasmic sequences of the CD3 zeta chain, and/or co-receptors that act in concert to initiate signal transduction following chimeric receptor engagement, as well as any derivative or variant of these sequences and any synthetic sequence that has the same functional capability. T cell activation can be said to be mediated by two distinct classes of cytoplasmic signaling sequence: those that initiate antigen-dependent primary activation and provide a T cell receptor like signal (primary cytoplasmic signaling sequences) and those that act in an antigen-independent manner to provide a secondary or co-stimulatory signal (secondary cytoplasmic signaling sequences). Primary cytoplasmic signaling sequences that act in a stimulatory manner may contain signaling motifs which are known as receptor tyrosine-based activation motifs or ITAMs. Examples of ITAM containing primary cytoplasmic signaling sequences include those derived from CD3 zeta, FcR gamma, CD3 gamma, CD3 delta, CD3 epsilon, CD5, CD22, CD79a, CD79b, and CD66d. In embodiments, the primary signaling intracellular domain can have at least about 80%, 85%, 90%, or 95% sequence identity to CD3zeta having a sequence provided in Table 2. In embodiments variants, of CD3 zeta retain at least one, two, three or all ITAM regions as shown in Table 7.

In a preferred embodiment, the intracellular signaling domain of the chimeric receptor can be designed to comprise the CD3-zeta signaling domain by itself or combined with any other desired cytoplasmic domain(s). For example, the intracellular signaling domain of the chimeric receptor can comprise a CD3zeta chain and a costimulatory signaling region.

The costimulatory signaling region refers to a portion of the chimeric receptor comprising the intracellular domain of a costimulatory molecule. A costimulatory molecule is a cell surface molecule other than an antigen receptor or their ligands that is required for a response of lymphocytes to an antigen. Examples of such molecules include CD27, CD28, 4-1BB (CD 137), OX40, CD30, CD40, lymphocyte function-associated antigen-1 (LFA-1), CD2, CD7, LIGHT, NKG2C, B7-H3, and a ligand that specifically binds with CD83. In embodiments, the costimulatory signaling domain can have at least about 80%, 85%, 90%, or 95% amino acid sequence identity to the intracellular domain of CD28 as shown in Table 5 or to 4-1BB having a sequence provided in Table 2. In an embodiment, a variant of the CD28 intracellular domain comprises an amino acid substitution at positions 186-187, wherein LL is substituted with GG.

The intracellular signaling sequences of the chimeric receptor may be linked to each other in a random or specified order. Optionally, a short oligo- or polypeptide linker, preferably between 2 and 10 amino acids in length may form the linkage. In one embodiment, the intracellular signaling domains comprises all or a portion of the signaling domain of CD3-zeta or variant thereof and all or a portion of the signaling domain of CD28 or a variant thereof. In another embodiment, the intracellular signaling domain comprises all or a portion of the signaling domain of CD3-zeta or variant thereof and all or a portion of the signaling domain of 4-1BB or variant thereof. In yet another embodiment, the intracellular signaling domain comprises all or a portion of the signaling domain of CD3-zeta or variant thereof, all or a portion of the signaling domain of CD28 or variant thereof, and all or a portion of the signaling domain of 4-1BB or variant thereof. In a specific embodiment, the amino acid sequence of the intracellular signaling domain comprising a variant of CD3zeta and a portion of the 4-1BB intracellular signaling domain is provided in Table 2. A representative nucleic acid sequence is provided in Table 1 (SEQ ID NO:6; SEQ ID NO:7).

In an embodiment, a polynucleotide coding for an intracellular signaling domain comprises a 4-1BB intracellular domain linked to a portion of a CD3zeta domain. In other embodiments, a 4-1BB intracellular domain and a CD28 intracellular domain are linked to a portion of a CD3 zeta domain.

A polynucleotide coding for an intracellular signaling domain can be readily prepared by synthetic or recombinant methods from the amino acid sequence. In embodiments, the polynucleotide coding for an intracellular signaling domain may also have one or more restriction enzyme sites at the 5' and/or 3' ends of the coding sequence in order to provide for easy excision and replacement of the polynucleotide coding for an intracellular signaling domain with another polynucleotide coding for a different intracellular signaling domain. In embodiments, the polynucleotide coding for an intracellular signaling domain is codon optimized for expression in mammalian cells.

Marker Sequences

In embodiments, the chimeric receptor nucleic acid optionally further comprises a polynucleotide sequence coding for a marker sequence. A marker sequence can provide for selection of transduced cells, and identification of transduced cells. In embodiments, the marker sequence is operably linked to a polynucleotide sequence coding for a linker sequence. In embodiments, the linker sequence is a cleavable linker sequence.

A number of different marker sequences can be employed. Typically a marker sequence has a functional characteristic that allows for selection of transduced cells and/or detection of transduced cells. In embodiments, the marker sequence is compatible with transduction of human lymphocytes.

The positive selectable marker may be a gene, which upon being introduced into the host cell, expresses a dominant phenotype permitting positive selection of cells carrying the gene. Genes of this type are known in the art, and include, inter alia, hygromycin-B phosphotransferase gene (hph) which confers resistance to hygromycin B, the amino glycoside phosphotransferase gene (neo or aph) from Tn5 which codes for resistance to the antibiotic G418, the dihydrofolate reductase (DHFR) gene, the adenosine deaminase gene (ADA), and the multi-drug resistance (MDR) gene.

In an embodiment, a chimeric receptor nucleic acid further comprises a polynucleotide coding for a marker sequence. In an embodiment, the marker sequence is a truncated epidermal growth factor receptor as shown in Table 2. An exemplary polynucleotide for the truncated epidermal growth factor receptor is shown in Table 1. (SEQ ID NO:9) In embodiments, the polynucleotide coding for the marker sequence is operably linked to a polynucleotide coding for a linker sequence. In a specific embodiment, the linker sequence is a cleavable linker sequence T2A as shown in Table 2. An exemplary polynucleotide sequence coding for the T2A linker is provided in Table 1. (SEQ ID NO:8)

A polynucleotide coding for marker sequence can be readily prepared by synthetic or recombinant methods from the amino acid sequence. In embodiments a polynucleotide coding for a marker sequence is operably linked to a polynucleotide coding for an intracellular signaling domain. In embodiments, the polynucleotide coding for a marker sequence may also have one or more restriction enzyme sites at the 5' and/or 3' ends of the coding sequence in order to provide for easy excision and replacement of the polynucleotide coding for a marker sequence with another polynucleotide coding for a different marker sequence. In embodiments, the polynucleotide coding for a marker sequence is codon optimized for expression in mammalian cells.

Vectors, Cells and Methods of Transducing Cells (a) Selection and Sorting of T Lymphocyte Populations The compositions described herein provide for CD4+ and/or CD8+ T lymphocytes. T lymphocytes can be collected in accordance with known techniques and enriched or depleted by known techniques such as affinity binding to antibodies such as flow cytometry and/or immunomagnetic selection. After enrichment and/or depletion steps, in vitro expansion of the desired T lymphocytes can be carried out in accordance with known techniques (including but not limited to those described in U.S. Pat. No. 6,040,177 to Riddell et al.), or variations thereof that will be apparent to those skilled in the art. In embodiments, the T cells are autologous T cells obtained from the patient.

For example, the desired T cell population or subpopulation may be expanded by adding an initial T lymphocyte population to a culture medium in vitro, and then adding to the culture medium feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). The non-dividing feeder cells can comprise gamma-irradiated PBMC feeder cells. In some embodiments, the PBMC are irradiated with gamma rays in the range of about 3000 to 3600 rads to prevent cell division. The order of addition of the T cells and feeder cells to the culture media can be reversed if desired. The culture can typically be incubated under conditions of temperature and the like that are suitable for the growth of T lymphocytes. For the growth of human T lymphocytes, for example, the temperature will generally be at least about 25 degrees Celsius, preferably at least about 30 degrees, more preferably about 37 degrees.

The T lymphocytes expanded include $CD8^+$ cytotoxic T lymphocytes (CTL) and $CD4^+$ helper T lymphocytes that may be specific for an antigen present on a human tumor or a pathogen.

Optionally, the expansion method may further comprise the step of adding non-dividing EBV-transformed lymphoblastoid cells (LCL) as feeder cells. LCL can be irradiated with gamma rays in the range of about 6000 to 10,000 rads. The LCL feeder cells may be provided in any suitable amount, such as a ratio of LCL feeder cells to initial T lymphocytes of at least about 10:1.

Optionally, the expansion method may further comprise the step of adding anti-CD3 and/or anti CD28 antibody to the culture medium (e.g., at a concentration of at least about 0.5 ng/ml). Optionally, the expansion method may further comprise the step of adding IL-2 and/or IL-15 to the culture medium (e.g., wherein the concentration of IL-2 is at least about 10 units/ml).

After isolation of T lymphocytes both cytotoxic and helper T lymphocytes can be sorted into naïve, memory, and effector T cell subpopulations either before or after expansion.

CD8+ cells can be obtained by using standard methods. In some embodiments, CD8+ cells are further sorted into naïve, central memory, and effector memory cells by identifying cell surface antigens that are associated with each of those types of CD8+ cells. In embodiments, memory T cells are present in both CD62L+ and CD62L− subsets of CD8+ peripheral blood lymphocytes. PBMC are sorted into CD62L-CD8+ and CD62L+CD8+ fractions after staining with anti-CD8 and anti-CD62L antibodies. In some embodiments, the expression of phenotypic markers of central memory $T_{CM}$ include CD45RO, CD62L, CCR7, CD28, CD3, and CD127 and are negative or low for granzyme B. In some embodiments, central memory T cells are CD45RO+, CD62L+, CD8+ T cells. In some embodiments, effector $T_E$ are negative for CD62L, CCR7, CD28, and CD127, and positive for granzyme B and perforin. In some embodiments, naïve CD8+ T lymphocytes are characterized by the expression of phenotypic markers of naïve T cells including CD62L, CCR7, CD28, CD3, CD127, and CD45RA.

Whether a cell or cell population is positive for a particular cell surface marker can be determined by flow cytometry using staining with a specific antibody for the surface marker and an isotype matched control antibody. A cell population negative for a marker refers to the absence of significant staining of the cell population with the specific antibody above the isotype control, positive refers to uniform staining of the cell population above the isotype control. In some embodiments, a decrease in expression of one or markers refers to loss of 1 log 10 in the mean fluorescence intensity and/or decrease of percentage of cells that exhibit the marker of at least about 20% of the cells, 25% of-the cells, 30% of the cells, 35% of the cells, 40% of the cells, 45% of the cells, 50% of the cells, 55% of the cells, 60% of the cells, 65% of the cells, 70% of the cells, 75% of the cells, 80% of the cells, 85% of the cells, 90% of the cell, 95% of the cells, and 100% of the cells and any % between 20 and 100% when compared to a reference cell population. In some embodiments, a cell population positive for one or markers refers to a percentage of cells that exhibit the marker of at least about 50% of the cells, 55% of the cells, 60% of the cells, 65% of the cells, 70% of the cells, 75% of the cells, 80% of the cells, 85% of the cells, 90% of the cell, 95% of the cells, and 100% of the cells and any % between 50 and 100% when compared to a reference cell population.

CD4+ T helper cells are sorted into naïve, central memory, and effector cells by identifying cell populations that have cell surface antigens. CD4+ lymphocytes can be obtained by standard methods. In some embodiments, naïve CD4+ T lymphocytes are CD45RO−, CD45RA+, CD62L+, CD4+ T cells. In some embodiments, central memory CD4+ cells are CD62L+ and CD45RO+. In some embodiments, effector CD4+ cells are CD62L− and CD45RO−.

In embodiments, populations of CD4+ and CD8+ that are antigen specific can be obtained by stimulating naïve or antigen specific T lymphocytes with antigen. For example, antigen-specific T cell lines or clones can be generated to Cytomegalovirus antigens by isolating T cells from infected subjects and stimulating the cells in vitro with the same antigen. Naïve T cells may also be used. Any number of antigens from tumor cells may be utilized as targets to elicit T cell responses. In some embodiments, the adoptive cellular immunotherapy compositions are useful in the treatment of a disease or disorder including a solid tumor, hematologic malignancy, breast cancer or melanoma.

(b) Modification of T Lymphocyte Populations

In some embodiments it may be desired to introduce functional genes into the T cells to be used in immunotherapy in accordance with the present disclosure. For example, the introduced gene or genes may improve the efficacy of therapy by promoting the viability and/or function of transferred T cells; or they may provide a genetic marker to permit selection and/or evaluation of in vivo survival or migration; or they may incorporate functions that improve the safety of immunotherapy, for example, by making the cell susceptible to negative selection in vivo as described by Lupton S. D. et al., *Mol. and Cell Biol.,* 11:6 (1991); and Riddell et al., *Human Gene Therapy* 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. This can be carried out in accordance with known techniques (see, e.g., U.S. Pat. No. 6,040,177 to Riddell et al. at columns 14-17) or variations thereof that will be apparent to those skilled in the art based upon the present disclosure.

In embodiments, T cells are modified with chimeric receptors as described herein. In some embodiments, the T cells are obtained from the subject to be treated. In other embodiments, the lymphocytes are obtained from allogeneic human donors, preferably healthy human donors.

In some embodiments, chimeric receptors comprise a ligand binding domain that specifically binds to a tumor cell surface molecule, a polypeptide spacer region, a transmembrane domain and an intracellular signaling domain as described herein. In embodiments, the ligand binding domain is a single-chain antibody fragment (scFv) that is derived from the variable heavy (VH) and variable light (VL) chains of a monoclonal antibody (mAb). Costimulatory signals can also be provided through the chimeric receptor by fusing the costimulatory domain of CD28 and/or 4-1BB to the CD3t chain. Chimeric receptors are specific for cell surface molecules independent from HLA, thus overcoming the limitations of TCR-recognition including HLA-restriction and low levels of HLA-expression on tumor cells.

Chimeric receptors can be constructed with a specificity for any cell surface marker by utilizing antigen binding fragments or antibody variable domains of, for example, antibody molecules. The antigen binding molecules can be linked to one or more cell signaling modules. In embodiments, cell signaling modules include CD3 transmembrane domain, CD3 intracellular signaling domains, and CD28 transmembrane domains. In embodiments, the intracellular signaling domain comprises a CD28 transmembrane and signaling domain linked to a CD3 zeta intracellular domain. In some embodiments, a chimeric receptor can also include a transduction marker such as tEGFR.

In embodiments, the same or a different chimeric receptor can be introduced into each of population of CD4+ and CD8+ T lymphocytes. In embodiments, the chimeric receptor in each of these populations has a ligand binding domain that specifically binds to the same ligand on the tumor or infected cell. The cellular signaling modules can differ. In embodiments, the intracellular signaling domain of the CD8+ cytotoxic T cells is the same as the intracellular signaling domain of the CD4+ helper T cells. In other embodiments, the intracellular signaling domain of the CD8+ cytotoxic T cells is different than the intracellular signaling domain of the CD4+ helper T cells.

In embodiments each of the CD4 or CD8 T lymphocytes can be sorted in to naïve, central memory, effector memory or effector cells prior to transduction as described herein. In alternative embodiments, each of the CD4 or CD8 T lymphocytes can be sorted in to naïve, central memory, effector memory, or effector cells after transduction.

Various transduction techniques have been developed which utilize recombinant infectious virus particles for gene delivery. This represents a currently preferred approach to the transduction of T lymphocytes of the present invention. The viral vectors which have been used in this way include virus vectors derived from simian virus 40, adenoviruses, adeno-associated virus (AAV), lentiviral vectors, and retroviruses. Thus, gene transfer and expression methods are numerous but essentially function to introduce and express genetic material in mammalian cells. Several of the above techniques have been used to transduce hematopoietic or lymphoid cells, including calcium phosphate transfection, protoplast fusion, electroporation, and infection with recombinant adenovirus, adeno-associated virus and retrovirus vectors. Primary T lymphocytes have been successfully transduced by electroporation and by retroviral or lentiviral infection.

Retroviral and lentiviral vectors provide a highly efficient method for gene transfer into eukaryotic cells. Moreover, retroviral or lentiviral integration takes place in a controlled fashion and results in the stable integration of one or a few copies of the new genetic information per cell.

It is contemplated that overexpression of a stimulatory factor (for example, a lymphokine or a cytokine) may be toxic to the treated individual. Therefore, it is within the scope of the invention to include gene segments that cause the T cells of the invention to be susceptible to negative selection in vivo. By "negative selection" is meant that the infused cell can be eliminated as a result of a change in the in vivo condition of the individual. The negative selectable phenotype may result from the insertion of a gene that confers sensitivity to an administered agent, for example, a compound. Negative selectable genes are known in the art, and include, inter alia the following: the Herpes simplex virus type I thymidine kinase (HSV-I TK) gene, which confers ganciclovir sensitivity; the cellular hypoxanthine phosphribosyltransferase (HPRT) gene, the cellular adenine phosphoribosyltransferase (APRT) gene, and bacterial cytosine deaminase.

In some embodiments it may be useful to include in the T cells a positive marker that enables the selection of cells of the negative selectable phenotype in vitro. The positive selectable marker may be a gene that upon being introduced into the host cell expresses a dominant phenotype permitting positive selection of cells carrying the gene. Genes of this type are known in the art, and include, inter alia, hygromycin-B phosphotransferase gene (hph) which confers resistance to hygromycin B, the amino glycoside phosphotransferase gene (neo or aph) from Tn5 which codes for resistance to the antibiotic G418, the dihydrofolate reductase (DHFR) gene, the adenosine deaminase gene (ADA), and the multi-drug resistance (MDR) gene.

A variety of methods can be employed for transducing T lymphocytes, as is well known in the art. In embodiments, transduction is carried out using lentiviral vectors.

In embodiments, CD4+ and CD8+ cells each can separately be modified with an expression vector encoding a chimeric receptor to form defined populations. In embodiments, these cells are then further sorted into subpopulations of naïve, central memory and effector cells as described above by sorting for cell surface antigens unique to each of those cell populations. In addition, CD4+ or CD8+ cell populations may be selected by their cytokine profile or proliferative activities. For example, CD4+ T lymphocytes that have enhanced production of cytokines such as IL-2, IL-4, IL-10, TNFα, and IFNγ as compared to sham transduced cells or transduced CD8+ cells when stimulated with antigen can be selected. In other embodiments, naïve or central memory CD4+ T cells that have enhanced production of IL-2 and/or TNFα are selected. Likewise, CD8+ cells that have enhanced IFNγ production are selected as compared to sham transduced CD8+ cells.

In embodiments, CD4+ and CD8+ cells that proliferate in response to antigen or tumor targets are selected. For example, CD4+ cells that proliferate vigorously when stimulated with antigen or tumor targets as compared to sham transduced cells, or CD8+ transduced cells are selected. In some embodiments, CD4+ and CD8+ cells are selected that are cytotoxic for antigen bearing cells. In embodiments, CD4+ are expected to be weakly cytotoxic as compared to CD8+ cells.

In a preferred embodiment, transduced lymphocytes, such as CD8+ central memory cells, are selected that provide for tumor cell killing in vivo using an animal model established for the particular type of cancer. Such animal models are known to those of skill in the art and exclude human beings. As described herein, not all chimeric receptor constructs transduced into lymphocytes confer the ability to kill tumor cells in vivo despite the ability to become activated and kill tumor cells in vitro. In particular, for some target molecules T cells having chimeric receptor constructs with a long spacer region were less effective at killing tumor cells in vivo as compared to T cells having a chimeric receptor with short spacer region. For other target molecules, T cells having chimeric receptor constructs with a short spacer region were less effective at killing tumor cells in vivo as compared to T cells having chimeric receptors with a long spacer region.

In yet other embodiments, transduced chimeric receptor expressing T cells are selected that can persist in vivo using an animal model established for the particular type of cancer. In embodiments, transduced chimeric receptor CD8+ central memory cells with a short spacer region have been shown to persist in vivo after introduction into the animal for about 3 day or more, 10 days or more, 20 days or more, 30 days or more, 40 days or more, or 50 days or more.

The disclosure contemplates that combinations of CD4+ and CD8+ T cells will be utilized in the compositions. In one embodiment, combinations of chimeric receptor transduced CD4+ cells can be combined with chimeric receptor transduced CD8+ cells of the same ligand specificity or combined with $CD8^+$ T cells that are specific for a distinct tumor ligand. In other embodiments, chimeric receptor transduced CD8+ cells are combined with chimeric receptor transduced CD4+ cells specific for a different ligand expressed on the tumor. In yet another embodiment, chimeric receptor modified CD4+ and CD8+ cells are combined. In embodiments CD8+ and CD4+ cells can be combined in different ratios for example, a 1:1 ratio of CD8+ and CD4+, a ratio of 10:1 of CD8+ to CD4+, or a ratio of 100:1 of CD8+ to CD4+. In embodiments, the combined population is tested for cell proliferation in vitro and/or in vivo, and the ratio of cells that provides for proliferation of cells is selected.

As described herein, the disclosure contemplates that CD4+ and CD8+ cells can be further separated into subpopulations, such as naïve, central memory, and effector memory cell populations. As described herein, in some embodiments, naïve CD4+ cells are CD45RO−, CD45RA+, CD62L+, CD4+ positive T cells. In some embodiments, central memory CD4+ cells are CD62L positive and CD45RO positive. In some embodiments, effector CD4+ cells are CD62L negative and CD45RO positive. Each of these populations may be independently modified with a chimeric receptor.

As described herein, in embodiments, memory T cells are present in both CD62L+ and CD62L− subsets of CD8+ peripheral blood lymphocytes. PBMC are sorted into CD62L− CD8+ and CD62L+CD8+ fractions after staining with anti-CD8 and anti-CD62L antibodies. In some embodiments, the expression of phenotypic markers of central memory T cells (TCM) include CD62L, CCR7, CD28, CD3, and CD127 and are negative or low for granzyme B. In some embodiments, central memory T cells are CD45RO+, CD62L+, CD8+ T cells. In some embodiments, effector T cells ($T_E$) are negative for CD62L, CCR7, CD28, and CD127, and positive for granzyme B and perforin. In some embodiments, naïve CD8+T lymphocytes are characterized by CD8+, CD62L+, CD45RO+, CCR7+, CD28+CD127+, and CD45RO+. Each of these populations may be independently modified with a chimeric receptor.

After transduction and/or selection for chimeric receptor bearing cells, the cell populations are preferably expanded in vitro until a sufficient number of cells are obtained to provide for at least one infusion into a human subject, typically around $10^4$ cells/kg to $10^9$ cells/kg In embodiments, the transduced cells are cultured in the presence of antigen bearing cells, anti CD3, anti CD28, and IL 2, IL-7, IL 15, IL-21 and combinations thereof.

Each of the subpopulations of CD4+ and CD8+ cells can be combined with one another. In a specific embodiment, modified naïve or central memory CD4+ cells are combined with modified central memory CD8+ T cells to provide a synergistic cytotoxic effect on antigen bearing cells, such as tumor cells.

Compositions

The disclosure provides for an adoptive cellular immunotherapy composition comprising a genetically modified T lymphocyte cell preparation as described herein.

In embodiments, the T lymphocyte cell preparation comprises CD4+ T cells that have a chimeric receptor comprising an extracellular antibody variable domain specific for a ligand associated with the disease or disorder, a customizable spacer region, a transmembrane domain, and an intracellular signaling domain of a T cell receptor or other receptors as described herein. In other embodiments, an adoptive cellular immunotherapy composition further comprises a chimeric receptor modified tumor-specific CD8+ cytotoxic T lymphocyte cell preparation that provides a cellular immune response, wherein the cytotoxic T lymphocyte cell preparation comprises CD8+ T cells that have a chimeric receptor comprising an extracellular single chain antibody specific for a ligand associated with the disease or disorder, a customizable spacer region, a transmembrane domain, and an intracellular signaling domain of a T cell receptor as described herein. In embodiments, the chimeric receptor modified T cell population of the disclosure can persist in vivo for at least about 3 days or longer.

In some embodiments, an adoptive cellular immunotherapy composition comprises a chimeric receptor modified tumor-specific CD8+ cytotoxic T lymphocyte cell preparation that provides a cellular immune response, wherein the cytotoxic T lymphocyte cell preparation comprises CD8+ T cells that have a chimeric receptor comprising an extracellular single chain antibody specific for a ligand associated with the disease or disorder, a customizable spacer region, a transmembrane domain, and an intracellular signaling domain of a T cell receptor, in combination with an antigen-reactive chimeric receptor modified naïve CD4+ T helper cell derived from CD45RO− CD62L+CD4+ T cells, and a pharmaceutically acceptable carrier.

In other embodiments, an adoptive cellular immunotherapy composition comprises an antigen specific CD8+ cytotoxic T lymphocyte cell preparation that provides a cellular immune response derived from the patient combined with an antigen-reactive chimeric receptor modified naïve CD4+ T helper cell that augments the CD8+ immune response, wherein the helper T lymphocyte cell preparation comprises CD4+ T cells that have a chimeric receptor comprising an extracellular antibody variable domain specific for the antigen associated with the disease or disorder, a customizable spacer region, a transmembrane domain, and an intracellular signaling domain of a T cell receptor.

In a further embodiment, an adoptive cellular immunotherapy composition comprises an antigen-reactive chimeric receptor modified naïve CD4+ T helper cell that augments the CD8+ immune response, wherein the helper T lymphocyte cell preparation comprises CD4+ T cells that have a chimeric receptor comprising an extracellular antibody variable domain specific for a ligand associated with a disease or disorder, a customizable spacer region, a transmembrane domain, and an intracellular signaling domain of a T cell receptor.

In embodiments, the CD4+ T helper lymphocyte cell is selected from the group consisting of naïve CD4+ T cells, central memory CD4+ T cells, effector memory CD4+ T cells, or bulk CD4+ T cells. In some embodiments, CD4+ helper lymphocyte cell is a naïve CD4+ T cell, wherein the naïve CD4+ T cell comprises a CD45RO−, CD45RA+, CD62L+CD4+ T cell. In embodiments, the CD8+ T cytotoxic lymphocyte cell is selected from the group consisting of naïve CD8+ T cells, central memory CD8+ T cells, effector memory CD8+ T cells or bulk CD8+ T cells. In some embodiments, the CD8+ cytotoxic T lymphocyte cell is a central memory T cell wherein the central memory T cell comprises a CD45RO+, CD62L+, CD8+ T cell. In yet other embodiments, the CD8+ cytotoxic T lymphocyte cell is a central memory T cell and the CD4+ helper T lymphocyte cell is a naïve or central memory CD4+ T cell.

Methods

The disclosure provides methods of making adoptive immunotherapy compositions and uses or methods of using these compositions for performing cellular immunotherapy in a subject having a disease or disorder. In embodiments, the chimeric receptor modified T cells as described herein are able to persist in vivo for at least 3 days, or at least 10 days. In embodiments, the chimeric receptor modified T cells as described herein can proliferate in vivo through at least 2, or at least 3 generations as determined by CFSE dye dilution. Proliferation and persistence of the chimeric receptor modified T cells can be determined by using an animal model of the disease or disorder and administering the cells and determining persistence and/or proliferative capacity of the transferred cells. In other embodiments, proliferation and activation can be tested in vitro by going through multiple cycles of activation with antigen bearing cells.

In embodiments, a method of manufacturing the compositions comprises obtaining a modified naïve CD4+ T helper cell, wherein the modified helper T lymphocyte cell preparation comprises CD4+ T cells that have a chimeric receptor comprising a ligand binding domain specific for a tumor cell surface molecule, a customized spacer domain, a transmembrane domain, and an intracellular signaling domain as described herein.

In another embodiment, a method further comprises obtaining a modified CD8+ cytotoxic T cell, wherein the modified cytotoxic T lymphocyte cell preparation comprises CD8+ cells that have a chimeric receptor comprising a ligand binding domain specific for a tumor cell surface molecule, a customized spacer domain, a transmembrane domain, and an intracellular signaling domain as described herein.

In another embodiment, a method comprises obtaining a modified CD8+ cytotoxic T cell, wherein the modified cytotoxic T lymphocyte cell preparation comprises CD8+ T cells that have a chimeric receptor comprising a ligand binding domain specific for a tumor cell surface molecule, a customized spacer domain, a transmembrane domain, and an intracellular signaling domain as described herein, and further comprising combining the modified CD8+ cytotoxic T cells with a CD4+ helper cell lymphocyte cell preparation.

The preparation of the CD4+ and CD8+ cells that are modified with a chimeric receptor has been described above as well as in the examples. Antigen specific T lymphocytes can be obtained from a patient having the disease or disorder or can be prepared by in vitro stimulation of T lymphocytes in the presence of antigen. Subpopulations of CD4+ and CD8+ T lymphocytes that are not selected for antigen specificity can also be isolated as described herein and combined in the methods of manufacturing. In embodiments, the combination of cell populations can be evaluated for uniformity of cell surface makers, the ability to proliferate through at least two generations, to have a uniform cell differentiation status. Quality control can be performed by co-culturing a cell line expressing the target ligand with chimeric receptor modified T cells to determine if the chimeric receptor modified T cells recognize the cell line using cytotoxicity, proliferation, or cytokine production assays that are known in the field. Cell differentiation status and cell surface markers on the chimeric receptor modified T cells can be determined by flow cytometry. In embodiments, the markers and cell differentiation status on the CD8+ cells include CD3, CD8, CD62L, CD28, CD27, CD69, CD25, PD-1, CTLA-4, CD45RO, and CD45RA. In embodiments, the markers and the cell differentiation status on the CD4+ cells include CD3, CD4, CD62L, CD28, CD27, CD69, CD25, PD-1, CTLA-4 CD45RO, and CD45RA.

In embodiments, a method of selecting a spacer region for a chimeric receptor is provided herein. Surprisingly some chimeric receptor constructs, although effective to activate T cells in vitro, were not effective in vivo. In embodiments, a method comprises providing a plurality of chimeric receptor nucleic acids, wherein the chimeric receptor nucleic acids differ only in the spacer region; introducing each of the chimeric receptor nucleic acids into a separate T lymphocyte population; expanding each separate lymphocyte population in vitro, and introducing each lymphocyte population into an animal bearing a tumor to determine the anti-tumor efficacy of each of the chimeric receptor modified T cells, and selecting a chimeric receptor that provides anti-tumor efficacy as compared to each of the other separate lymphocyte populations modified with each of the other chimeric receptor modified T cells.

Animal models of different tumors are known. Anti-tumor efficacy can be measured by identifying a decrease in tumor volume, by determining animal death, persistence of the genetically modified T cells in vivo, activation of genetically modified T cells (for example, by detecting an increase in expression of CD25 and/CD69), and/or proliferation of genetically modified T cells in vivo. In an embodiment, a chimeric receptor is selected that provides for the best anti-tumor efficacy in vivo as determined by one or more of these parameters. Lack of anti-tumor efficacy can be determined by lack of persistence of the genetically modified lymphocytes in vivo, animal death, an increase in apoptosis as measured by an increase in induction of caspase −3, and/or a decrease in proliferation of genetically modified lymphocytes.

In embodiments, providing a plurality of chimeric receptor nucleic acids, wherein the chimeric receptor nucleic acids differ only in the spacer region comprises providing a chimeric receptor construct comprising a polynucleotide coding for a ligand binding domain, wherein the ligand is a tumor specific antigen, viral antigen, or any other molecule expressed on a target cell population that is suitable to mediate recognition and elimination by a lymphocyte; a polynucleotide coding for a first polypeptide spacer having a defined restriction site at the 5' and 3' end of the coding sequence for the first polypeptide spacer; a polynucleotide coding for a transmembrane domain; and a polynucleotide coding for an intracellular signaling domain.

The disclosure also provides methods of performing cellular immunotherapy in a subject having a disease or disorder comprising: administering a composition of lymphocytes expressing a chimeric receptor as described herein. In other embodiments, a method comprises administering to the subject a genetically modified cytotoxic T lymphocyte cell preparation that provides a cellular immune response, wherein the cytotoxic T lymphocyte cell preparation comprises CD8+ T cells that have a chimeric receptor comprising a ligand binding domain specific for a tumor cell surface molecule, a customized spacer domain, a transmembrane domain, and an intracellular signaling domain as described herein, and a genetically modified helper T lymphocyte cell preparation that elicits direct tumor recognition and augments the genetically modified cytotoxic T lymphocyte cell preparations ability to mediate a cellular immune response, wherein the helper T lymphocyte cell preparation comprises CD4+ T cells that have a chimeric receptor comprising a ligand binding domain specific for a tumor cell surface molecule, a customized spacer domain, a transmembrane domain, and an intracellular signaling domain as described herein.

While not limiting the scope of the disclosure, it is believed by selecting the chimeric receptor modified T cell population that can persist and proliferate in vivo prior to administration may result in the ability to use a lower dose of T cells and provide more uniform therapeutic activity. In embodiments, the dose of T cells can be reduced at least 10%, 20%, or 30% or greater. Reduction in the dose of T cells may be beneficial to reduce the risk or tumor lysis syndrome and cytokine storm.

In another embodiment, a method of performing cellular immunotherapy in subject having a disease or disorder comprises: administering to the subject a genetically modified helper T lymphocyte cell preparation, wherein the modified helper T lymphocyte cell preparation comprises CD4+ T cells that have a chimeric receptor comprising a ligand binding domain specific for a tumor cell surface molecule, a customized spacer domain, a transmembrane domain, and an intracellular signaling domain as described herein. In an embodiments, the method further comprises administering to the subject a genetically modified cytotoxic T lymphocyte cell preparation, wherein the modified cytotoxic T lymphocyte cell preparation comprises CD8+ cells that have a chimeric receptor comprising a ligand binding domain specific for a tumor cell surface molecule, a customized spacer domain, a transmembrane domain, and an intracellular signaling domain as described herein.

Another embodiment describes a method of performing cellular immunotherapy in a subject having a disease or disorder comprising: analyzing a biological sample of the subject for the presence of a target molecule associated with the disease or disorder and administering the adoptive immunotherapy compositions described herein, wherein the chimeric receptor specifically binds to the target molecule.

In some embodiments, the CD4+ T helper lymphocyte cell is selected prior to introduction of the chimeric receptor from the group consisting of naïve CD4+ T cells, central memory CD4+ T cells, effector memory CD4+ T cells or bulk CD4+ T cells. In a specific embodiment, CD4+ helper lymphocyte cell is a naïve CD4+ T cell, wherein the naïve CD4+ T cell comprises a CD45RO−, CD45RA+, CD62L+ CD4+ T cell. In yet other embodiments, the CD8+ T cytotoxic lymphocyte cell is selected prior to introduction of the chimeric receptor from the group consisting of naïve CD8+ T cells, central memory CD8+ T cells, effector memory CD8+ T cells or bulk CD8+ T cells. In a specific embodiment, the CD8+ cytotoxic T lymphocyte cell is a central memory T cell wherein the central memory T cell comprises a CD45RO+, CD62L+, CD8+ T cell. In a specific embodiment, the CD8+ cytotoxic T lymphocyte cell is a central memory T cell and the CD4+ helper T lymphocyte cell is a naïve CD4+ T cell.

In embodiments, the CD8+ T cell and the CD4+ T cell are both genetically modified with a chimeric receptor comprising an antibody heavy chain domain that specifically binds a tumor-specific cell surface molecule. In other embodiments, the intracellular signaling domain of the CD8 cytotoxic T cells is the same as the intracellular signaling domain of the CD4 helper T cells. In yet other embodiments, the intracellular signaling domain of the CD8 cytotoxic T cells is different than the intracellular signaling domain of the CD4 helper T cells.

Subjects that can be treated by the present invention are, in general, human and other primate subjects, such as monkeys and apes for veterinary medicine purposes. The subjects can be male or female and can be any suitable age, including infant, juvenile, adolescent, adult, and geriatric subjects.

The methods are useful in the treatment of, for example, hematologic malignancy, melanoma, breast cancer, and other epithelial malignancies or solid tumors. In some embodiments, the molecule associated with the disease or disorder is selected from the group consisting of orphan tyrosine kinase receptor ROR1, Her2, CD19, CD20, CD22, mesothelin, CEA, and hepatitis B surface antigen.

Subjects that can be treated include subjects afflicted with cancer, including but not limited to colon, lung, liver, breast, renal, prostate, ovarian, skin (including melanoma), bone, and brain cancer, etc. In some embodiments the tumor associated antigens or molecules are known, such as melanoma, breast cancer, squamous cell carcinoma, colon cancer, leukemia, myeloma, and prostate cancer. In other embodiments the tumor associated molecules can be targeted with genetically modified T cells expressing an engineered chimeric receptor. Examples include but are not limited to B cell lymphoma, breast cancer, prostate cancer, and leukemia.

Cells prepared as described above can be utilized in methods and compositions for adoptive immunotherapy in accordance with known techniques, or variations thereof that will be apparent to those skilled in the art based on the instant disclosure.

In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin, fetal bovine serum or other human serum components.

A treatment effective amount of cells in the composition is at least 2 cell subsets (for example, 1 CD8+ central memory T cell subset and 1 CD4+ helper T cell subset) or is more typically greater than $10^2$ cells, and up to $10^6$, up to and including $10^8$ or $10^9$ cells and can be more than $10^{10}$ cells. The number of cells will depend upon the ultimate use for which the composition is intended as will the type of cells included therein. For example, if cells that are specific for a particular antigen are desired, then the population will contain greater than 70%, generally greater than 80%, 85% and 90-95% of such cells. For uses provided herein, the cells are generally in a volume of a liter or less, can be 500 mls or less, even 250 mls or 100 mls or less. Hence the density of the desired cells is typically greater than $10^4$ cells/ml and generally is greater than $10^7$ cells/ml, generally $10^8$ cells/ml or greater. The clinically relevant number of immune cells can be apportioned into multiple infusions that cumulatively equal or exceed $10^6$, $10^7$, $\mathbf{10^8}$, $10^8$, $10^9$, $10^{10}$ or $10^{11}$ cells.

In some embodiments, the lymphocytes of the invention may be used to confer immunity to individuals. By "immunity" is meant a lessening of one or more physical symptoms associated with a response to infection by a pathogen, or to a tumor, to which the lymphocyte response is directed. The amount of cells administered is usually in the range present in normal individuals with immunity to the pathogen. Thus, the cells are usually administered by infusion, with each infusion in a range of from 2 cells, up to at least $10^6$ to $3\times10^{10}$ cells, preferably in the range of at least $10^7$ to $10^9$ cells. The T cells may be administered by a single infusion, or by multiple infusions over a range of time. However, since different individuals are expected to vary in responsiveness, the type and amount of cells infused, as well as the number of infusions and the time range over which multiple infusions are given are determined by the attending physician, and can be determined by routine examination. The generation of sufficient levels of T lymphocytes (including cytotoxic T lymphocytes and/or helper T lymphocytes) is readily achievable using the rapid expansion method of the present invention, as exemplified herein. See, e.g., U.S. Pat. No. 6,040,177 to Riddell et al. at column 17.

In embodiments, the composition as described herein are administered intravenously, intraperitoneally, intratumorly, into the bone marrow, into the lymph node, and/or into cerebrospinal fluid. In embodiments, the chimeric receptor engineered compositions are delivered to the site of the tumor. Alternatively, the compositions as described herein can be combined with a compound that targets the cells to the tumor or the immune system compartments and avoid sites such as the lung.

In embodiments, the compositions as described herein are administered with chemotherapeutic agents and/or immunosuppressants. In an embodiment, a patient is first treated with a chemotherapeutic agent that inhibits or destroys other immune cells followed by the compositions described herein. In some cases, chemotherapy may be avoided entirely.

The present invention is illustrated further in the examples set forth below.

EXPERIMENTAL

Example I. Customizing Spacer Domain Length and scFv Affinity for Optimal Recognition of ROR1 with Chimeric Receptor Modified T Cells We constructed chimeric receptors specific for the ROR1 molecule that is expressed on a large number of human malignancies including chronic lymphocytic leukemia, mantle cell lymphoma, acute lymphoblastic leukemia, and breast, lung prostate, pancreas and ovarian cancer. The ROR1 chimeric receptors were designed from ROR1 specific scFVs with different affinities and containing extracellular IgG4-Fc spacer domains of different lengths. The ability of T-cells expressing each ROR-1 specific chimeric receptor to recognize $ROR1^+$ hematopoietic and epithelial tumors in vitro, and to eliminate human mantle cell lymphoma engrafted into immunodeficient mice was analyzed.

Materials and Methods

Human Subjects

Peripheral blood mononuclear cells (PBMC) were obtained from healthy donors and patients after written informed consent on research protocols approved by the Institutional Review Board of the Fred Hutchinson Cancer Research Center (FHCRC).

Cell Lines

The K562, Raji, JeKo-1, MDA-MB-231, MDA-MB-468, and 293T cell lines were obtained from the American Type Culture Collection. Dr. Edus H. Warren (FHCRC) kindly provided the renal cell cancer lines FARP, TREP and RWL. K562/ROR1 and Raji/ROR1 were generated by lentiviral transduction with the full-length ROR1-gene. To derive JeKo-1/ffluc, native JeKo-1 cells were transduced with a lentiviral vector encoding the firefly luciferase (ffluc)-gene upstream of a T2A sequence and eGFP. The transduced JeKo-1 cells were sorted for eGFP expression, and expanded for in vivo experiments.

Immunophenotyping

PBMC and cell lines were stained with the following conjugated mAbs: CD3, CD4, CD5, CD8, CD19, CD28, CD45RO, CD62L, CD314 (NKG2D), MICAS and matched isotype controls (BD Biosciences). Propidium iodide (PI) staining was performed for live/dead cell discrimination. Cell surface expression of ROR1 was analyzed using a polyclonal goat anti-human-ROR1 antibody (R&D Systems).

Surface expression of 2A2 ROR1chimeric receptor was analyzed using a polyclonal goat anti-mouse-IgG antibody (Fab-specific) (Jackson ImmunoResearch). Flow analyses were done on a FACSCanto®, sort-purifications on a FACSAriaII® (Becton Dickinson) and data analyzed using FlowJo® software (Treestar).

Vector Construction and Preparation of Chimeric Receptor Encoding Lentivirus

Figure 1:
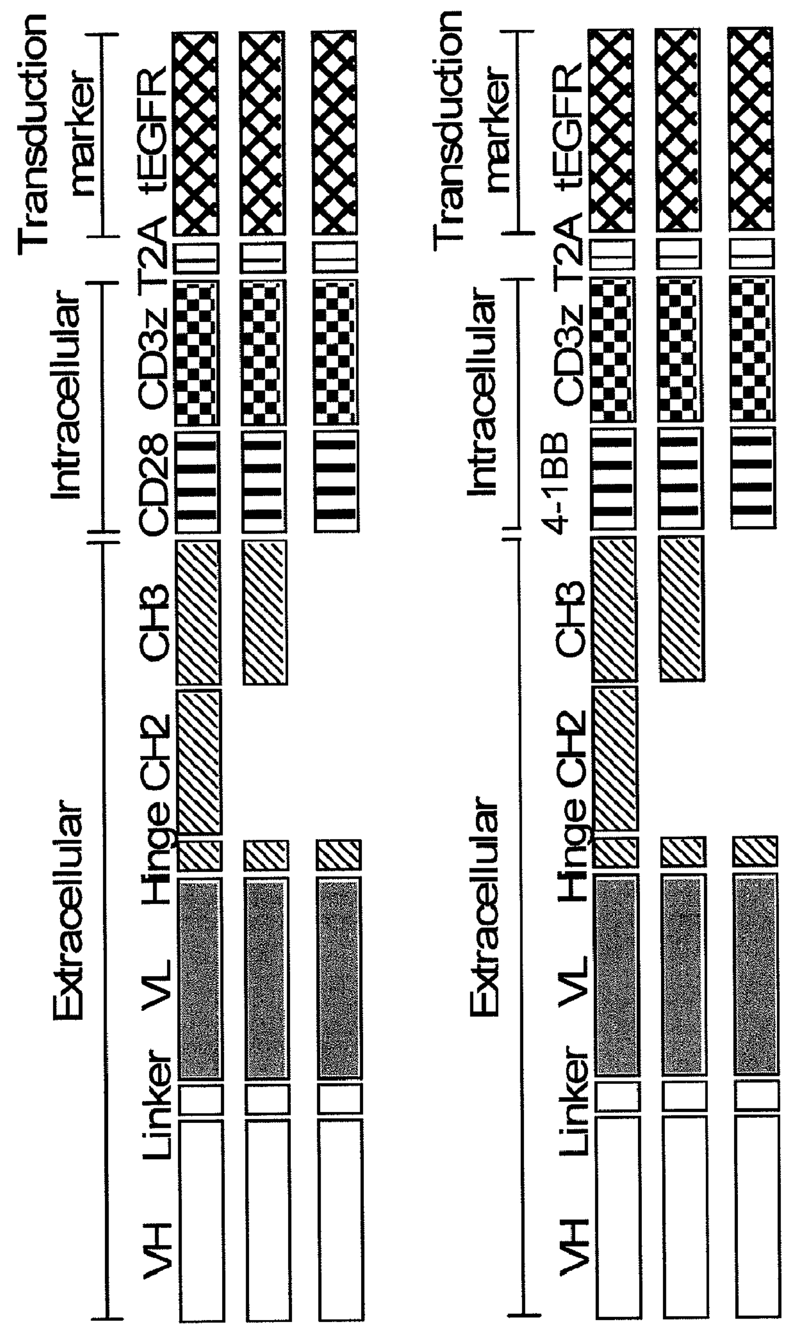
FIG. 1 Library of spacer sequences. We constructed a plasmid library that contain codon optimized DNA sequences that encode extracellular components including of the IgG4 hinge alone, IgG4 hinge linked to CH2 and CH3 domains, or IgG4 hinge linked to the CH3 domain. Any scFV sequence (VH and VL) can be cloned 5' to the sequences encoding this library of variable spacer domains. The spacer domains are in turn linked to CD28 transmembrane and intracellular signaling domains and to CD3 zeta. A T2A sequence in the vector separates the chimeric receptor from a selectable marker encoding a truncated human epidermal growth factor receptor (tEGFR).

ROR1-specific and CD19-specific chimeric receptors were constructed using VL and VH chain segments of the 2A2, R12, and R11 mAbs (ROR1) and FMC63 mAb (CD19). (Variable region sequences for R11 and R12 are provided in Yang et al, Plos One 6(6):e21018, Jun. 15, 2011) Each scFV was linked by a $(G_4S)_3$ (SEQ ID NO:12) peptide to a spacer domain derived from IgG4-Fc (Uniprot Database: P01861, SEQ ID NO:13) comprising either 'Hinge-CH2-CH3' (229 AA, SEQ ID NO:), 'Hinge-CH3' (119 AA, SEQ ID NO:) or 'Hinge' only (12 AA, SEQ. ID NO:4) sequences (FIG. 1). All spacers contained a S→P substitution within the 'Hinge' domain located at position 108 of the native IgG4-Fc protein, and were linked to the 27 AA transmembrane domain of human CD28 (Uniprot: P10747, SEQ ID NO:14) and to a signaling module comprising either (i) the 41 AA cytoplasmic domain of human CD28 with an LL→GG substitution located at positions 186-187 of the native CD28 protein (SEQ ID NO:14) or (ii) the 42 AA cytoplasmic domain of human 4-1BB (Uniprot: Q07011, SEQ ID NO:15), each of which was linked to the 112 AA cytoplasmic domain of isoform 3 of human CD3 (Uniprot: P20963, SEQ ID NO;16). The construct encoded a T2A ribosomal skip element (SEQ ID NO:8)) and a tEGFR sequence (SEQ ID NO:9) downstream of the chimeric receptor. Codon-optimized nucleotide sequences encoding each transgene were synthesized (Life Technologies) and cloned into the epHIV7 lentiviral vector ROR1-chimeric receptor, CD19-chimeric receptor or tEGFR-encoding lentiviruses were produced in 293T cells using the packaging vectors pCHGP-2, pCMV-Rev2 and pCMV-G, and Calphos® transfection reagent (Clontech).

Generation of T-Cell Lines Expressing ROR1 and CD19-Chimeric Receptors $CD8^+$ $CD45RO^+$ $CD62L^+$ central memory T-cells ($T_{CM}$) or bulk $CD4^+$ T-cells were sorted from PBMC of normal donors, activated with anti-CD3/CD28 beads (Life Technologies), and transduced on day 3 after activation by centrifugation at 800 g for 45 min at 32° C. with lentiviral supernatant (MOI=3) supplemented with 1 μg/mL polybrene (Millipore). T-cells were expanded in RPMI with 10% human serum, 2 mM L-glutamine and 1% penicillin-streptomycin (CTL medium), supplemented with recombinant human IL-2 to a final concentration of 50 U/mL. The $tEGFR^+$ subset of each T-cell line was enriched by immunomagnetic selection with biotin-conjugated anti-EGFR mAb (ImClone Systems) and streptavidin-beads (Miltenyi). ROR1-chimeric receptor and tEGFR control T-cells were expanded using a rapid expansion protocol (Riddell S R, Greenberg P D, The use of anti-CD3 and anti-CD28 monoclonal antibodies to clone and expand human antigen-specific T cells J Immunol Methods. 1990; 128(2):189-201. Epub 1990/04/17.), and CD19-chimeric receptor modified T-cells were expanded by stimulation with irradiated (8,000 rad) B-LCL at a T-cell:LCL ratio of 1:7. T-cells were cultured in CTL medium with 50 U/mL IL-2.

Cytotoxicity, Cytokine Secretion and Proliferation Assays

Target cells were labeled with $^{51}Cr$ (PerkinElmer), washed and incubated in triplicate at $1\text{-}2\times10^3$ cells/well with effector chimeric receptor modified T-cells at various effector to target (E:T) ratios. Supernatants were harvested for γ-counting after a 4-hour incubation and specific lysis calculated using the standard formula. For analysis of cytokine secretion, $5\times10^4$ T-cells were plated in triplicate with target cells at an E:T ratio of 1:1 (primary CLL), 2:1 (Raji/ROR1; JeKo-1), 4:1 (K562/ROR1, K562/CD19 and K562) or 10:1 (MDA-MB-231), and IFN-γ, TNF-α and IL-2 measured by ELISA or multiplex cytokine immunoassay (Luminex) in supernatant removed after 24-h incubation. In experiments blocking NKG2D signaling, anti-NKG2D (clone 1D11), anti-MICAS (clone 6D4, all from BD) and anti-ULBP (kindly provided by Dr. Veronika Groh, FHCRC) were used at saturating concentrations. For analysis of proliferation, T-cells were labeled with 0.2 μM carboxyfluorescein succinimidyl ester (CFSE, Invitrogen), washed and plated in triplicate with stimulator cells in medium without exogenous cytokines. After 72-h incubation, cells were labeled with anti-CD8 mAb and PI, and analyzed by flow cytometry to assess cell division of live $CD8^+$ T-cells.

Experiments in NOD/SCID/$\gamma c^{-/-}$ (NSG) Mice

The Institutional Animal Chimeric receptor and Use Committee approved all mouse experiments. Six- to 8-week old female NOD.Cg-$Prkdc^{scid}$ $Il2rg^{tmlWjl}$/SzJ (NSG) mice were obtained from the Jackson Laboratory or bred in-house. Mice were injected with $0.5\times10^6$ JeKo-1/ffluc tumor cells via tail vein and received a subsequent tail vein injection of chimeric receptor-modified or control T-cells.

For bioluminescence imaging of tumor growth, mice received intraperitoneal injections of luciferin substrate (Caliper Life Sciences) resuspended in PBS (15 μg/g body weight). Mice were anesthetized with isoflurane and imaged using an Xenogen IVIS Imaging System (Caliper) 10, 12 and 14 minutes after the injection of luciferin in small binning mode at an acquisition time of 1 s to 1 min to obtain unsaturated images. Luciferase activity was analyzed using Living Image Software (Caliper) and the photon flux analyzed within regions of interest that encompassed the entire body or the thorax of each individual mouse.

Statistical Analyses

Statistical analyses were performed using Prism Software (GraphPad®). Student's t-test was performed as a two-sided paired test with a confidence interval of 95% and results with a p-value of $p<0.05$ were considered significant. Statistical analysis of survival were done by log-rank testing and results with a p-value of $p<0.05$ considered significant.

Results

Truncating the Spacer Domain of the 2A2 ROR1-Chimeric Receptor Confers Superior Recognition of $ROR1^+$ Tumors We previously reported the design of a ROR1-specific chimeric receptor using the 2A2 scFV, which binds to an epitope in the NH2-terminal, membrane distal Ig-like/Frizzled portion of ROR1-1. The initial 2A2 ROR1-chimeric receptor had a long 229 AA spacer that included the 'Hinge-CH2-CH3' region of IgG4-Fc, and incorporated CD28 costimulatory and CD3ζ signaling domains (Hudecek M et al. Blood, 2010). This chimeric receptor conferred specific recognition of $ROR1^+$ tumors, but we hypothesized that because of the membrane distal location of the ROR1 epitope, truncating the spacer domain might enhance tumor recognition and T-cell signaling. Therefore, we constructed 2 additional chimeric receptors in which the IgG4-Fc spacer domain was sequentially deleted to derive 'Hinge-CH3' (119 AA, intermediate), and 'Hinge-only' (12 AA, short) variants. Each of the new receptors contained the identical 2A2 scFV, and CD28 and CD3t signaling modules. The transgene cassette included a truncated EGFR (tEGFR) to serve as a transduction, selection and in vivo tracking marker for chimeric receptor-modified T-cells.

We transduced purified $CD8^+$ $T_{CM}$ with the 2A2 ROR1-chimeric receptors containing full length or truncated IgG4-Fc spacers, and with a tEGFR control vector. The mean transduction efficiency was 15% (range 9-22%), and transgene-positive T-cells were enriched to uniform purity (>90%) on day 10 by selection for tEGFR expression, and expanded (FIG. 2A). Surface expression of each of the chimeric receptors was confirmed by staining with F(ab)-specific antibodies (FIG. 2A).

Analysis of the in vitro function of $CD8^+$ T-cells modified to express each of the 2A2 ROR1-chimeric receptors demonstrated that each receptor conferred specific lysis of JeKo-1 MCL and primary CLL cells that naturally express ROR1, and of K562 cells that had been transduced with ROR1, but did not confer recognition of control $ROR1^-$ targets (FIG. 2B). T-cells expressing the short 'Hinge-only' 2A2 ROR1-chimeric receptor had maximum cytolytic activity, and a hierarchy (short>intermediate>>long) of tumor lysis was clearly evident against all $ROR1^+$ tumor targets (FIG. 2B), illustrating the importance of spacer domain length on the recognition of $ROR1^+$ tumor cells.

Anti-tumor efficacy of adoptive T-cell therapy correlates with proliferation and survival of transferred T-cells, which could be altered by signaling through the chimeric receptor. We used CFSE dilution assays to analyze proliferation of T-cells modified with each of the 2A2 ROR1-chimeric receptors after engagement of Raji/ROR1 or CLL, and found that the short spacer construct promoted the greatest T-cell proliferation following stimulation (FIG. 2C). To ensure that the enhanced proliferation was not associated with greater activation induced cell death (AICD), we also analyzed the proportion of 2A2 ROR 1 chimeric receptor modified T-cells that stained with propidium iodide (PI) after stimulation with Raji/ROR1 and JeKo-1 tumor cells. We detected a much lower frequency of $PI^+$ $CD8^+$ T-cells in the T-cell line modified with the short (Raji/ROR1: 17.2%/JeKo-1: 20.2%) compared to the intermediate (41.6%/42.4%) and long (44.5%/48.5%) spacers.

Quantitative analysis of cytokine production in response to stimulation with Raji/ROR1 and primary CLL cells showed production of IFN-γ, TNF-α and IL-2 by T-cells expressing each of the 2A2 ROR1 chimeric receptors. As observed in cytotoxicity assays, the short spacer construct was superior in mediating cytokine secretion after tumor recognition (FIG. 2D). Thus, this analysis shows that truncating the extracellular IgG4-Fc spacer domain of the 2A2 ROR1-chimeric receptor leads to a significant increase in cytotoxicity, proliferation and in vitro effector functions after tumor recognition.

The R11 scFv that is Specific for a Membrane Proximal Epitope in the ROR1 Kringle Domain Requires a Long Extracellular Spacer Domain.

Figure 3:
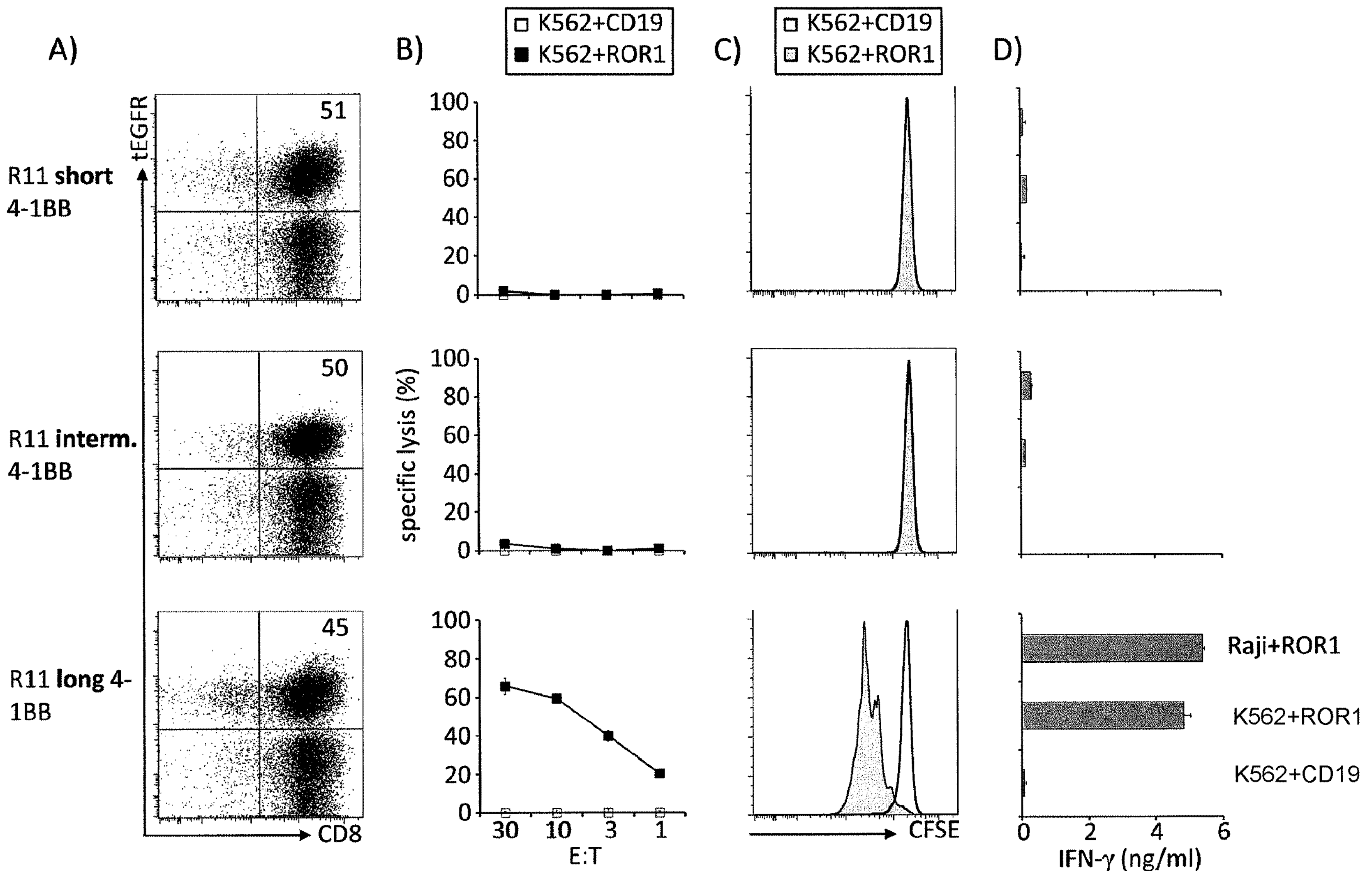
FIG. 3. R11 chimeric receptor requires a long spacer for recognition of ROR1$^+$ tumor cells. The sequences encoding the scFV from the R11 monoclonal antibody that is specific for an epitope in the membrane proximal Kringle domain of the orphan tyrosine kinase receptor ROR1 were cloned upstream of IgG4 hinge only (short), IgG4 hinge/CH3 (intermediate), and IgG4 hinge/CH2/CH3 sequences in our chimeric receptor library containing the 4-1BB costimulatory domains and prepared as lentiviral vectors. A). Human CD8$^+$ T cells were transduced and the transduction efficiency with each of the short, intermediate and long chimeric receptors was determined by staining for the tEGFR marker. B). Transduced T cells expressing the short (top), intermediate (middle), and long (bottom) were assayed for lysis of K562 leukemia cells alone or transfected to express ROR1. Only the T cells expressing the long spacer chimeric receptor efficiently killed ROR1+K562 cells. C). Transduced T cells expressing the short (top), intermediate (middle), and long (bottom) were labeled with CFSE, stimulated with K562 cells expressing ROR1 or CD19 (control) and assayed for cell proliferation over 72 hours. The T cells expressing the long spacer chimeric receptor proliferated specifically to the ROR1+K562 cells. D). Transduced T cells expressing the short (top), intermediate (middle), and long (bottom) were stimulated with Raji lymphoma cells and K562 cells that expressed ROR1 or CD19 (control) and assayed for the secretion of interferon gamma into the supernatant over 24 hours. The T cells expressing the long spacer chimeric receptor proliferated and produced the highest levels of interferon gamma in response to ROR1 positive target cells.

We transduced purified $CD8^+$ T cells with ROR1-chimeric receptors containing the R11 scFv that is specific for the Kringle domain of ROR1 and containing full length or truncated IgG4-Fc spacers (CH3 and hinge only). The transduction efficiency with each of the short (IgG4 hinge only), intermediate (IgG4 hinge/CH3), and long (IgG4 hinge/CH2/CH3) vectors was comparable (45-51%) as measured by EGFR expression. (FIG. 3A). T cells transduced with each of the vectors were assayed for cytolysis (FIG. 3 B), proliferation (FIG. 3C), and cytokine production (FIG. 3D) in response to leukemia or lymphoma cells that did or did not express ROR1. As shown, only T cells transduced with the R11 chimeric receptor containing a long spacer sequence were able to efficiently recognize ROR1+ tumors and mediate effector functions.

ROR1 Chimeric Receptors Derived from a mAb R12 with Higher Affinity than 2A2 Mediate Superior Anti-Tumor Reactivity We next examined whether increasing the affinity of the scFV used to construct the ROR1 chimeric receptor might influence tumor recognition and T-cell function. We generated ROR1-specific chimeric receptors from the mAb R12 that like 2A2, binds to an epitope in the NH2-terminal Ig/Frizzled domain of ROR1 but with >50-fold higher monovalent binding affinity.

R12 ROR1 chimeric receptors were constructed with both long and short IgG4-Fc spacers to determine whether the optimal spacer design for this higher affinity scFV differed from that for a lower affinity scFV. We found that similar to 2A2, the short spacer R12 ROR1 chimeric receptor conferred improved cytolytic activity, cytokine secretion and proliferation (data not shown), suggesting that the shorter spacer length provides superior spatial engagement of the T-cell and $ROR1^+$ target cell for T-cell activation.

Figure 4:
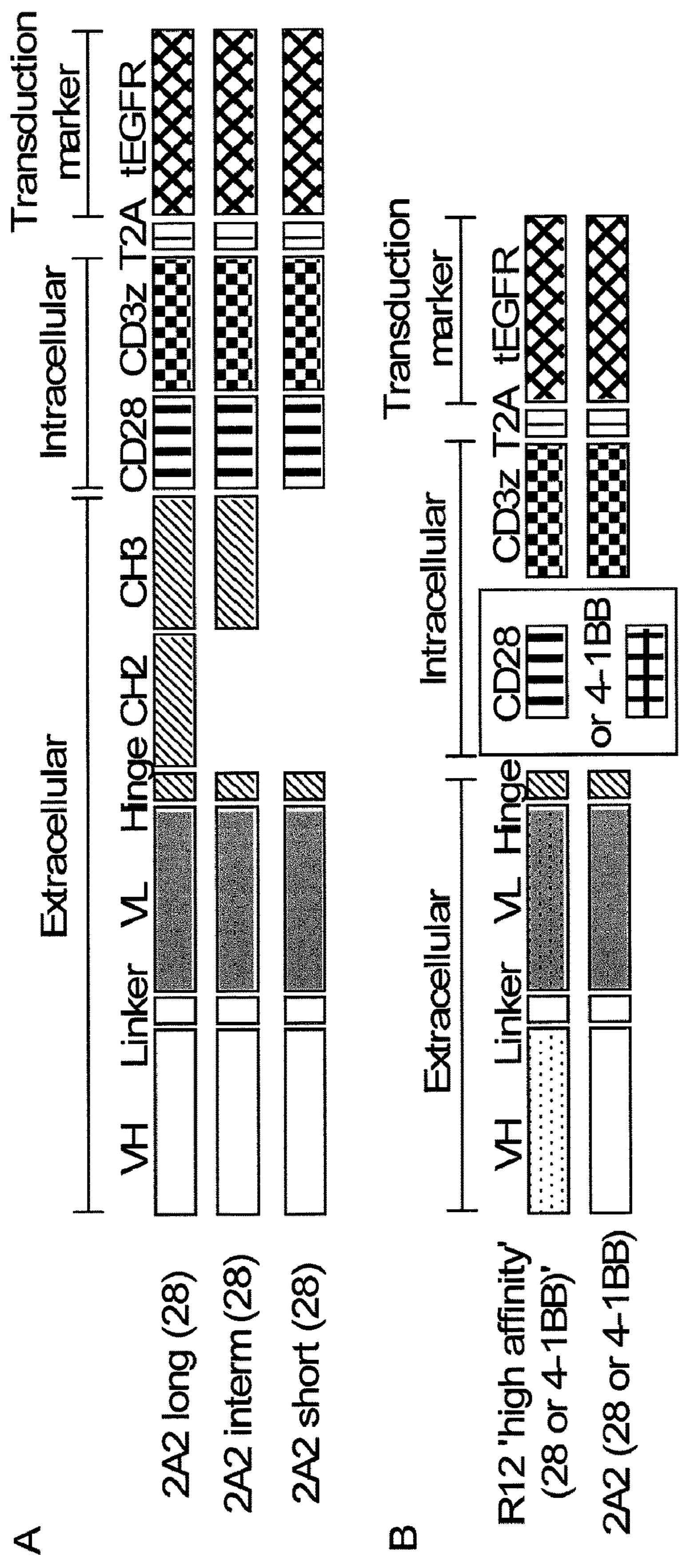
FIG. 4: Design of ROR1 chimeric receptors with modified spacer length and derived from the 2A2 and R12 scFV with different affinity. (A) Design of lentiviral transgene inserts encoding a panel of ROR1 chimeric receptors containing the 2A2 scFV, an IgG4-Fc derived spacer of 'Hinge-CH2-CH3' (long spacer, 229 AA), 'Hinge-CH3' (intermediate, 119 AA), or 'Hinge' only (short, 12 AA), and a signaling module with CD3t and CD28. Each chimeric receptor cassette contains a truncated EGFR marker encoded downstream of a T2A element. (B) Lentiviral transgene inserts encoding ROR1-specific chimeric receptors derived from the R12 and 2A2 scFV with short IgG4-Fc 'Hinge' spacer (12 AA), and a signaling module containing CD28 or 4-1BB and CD3t respectively (total: 4 constructs).
Figure 5:
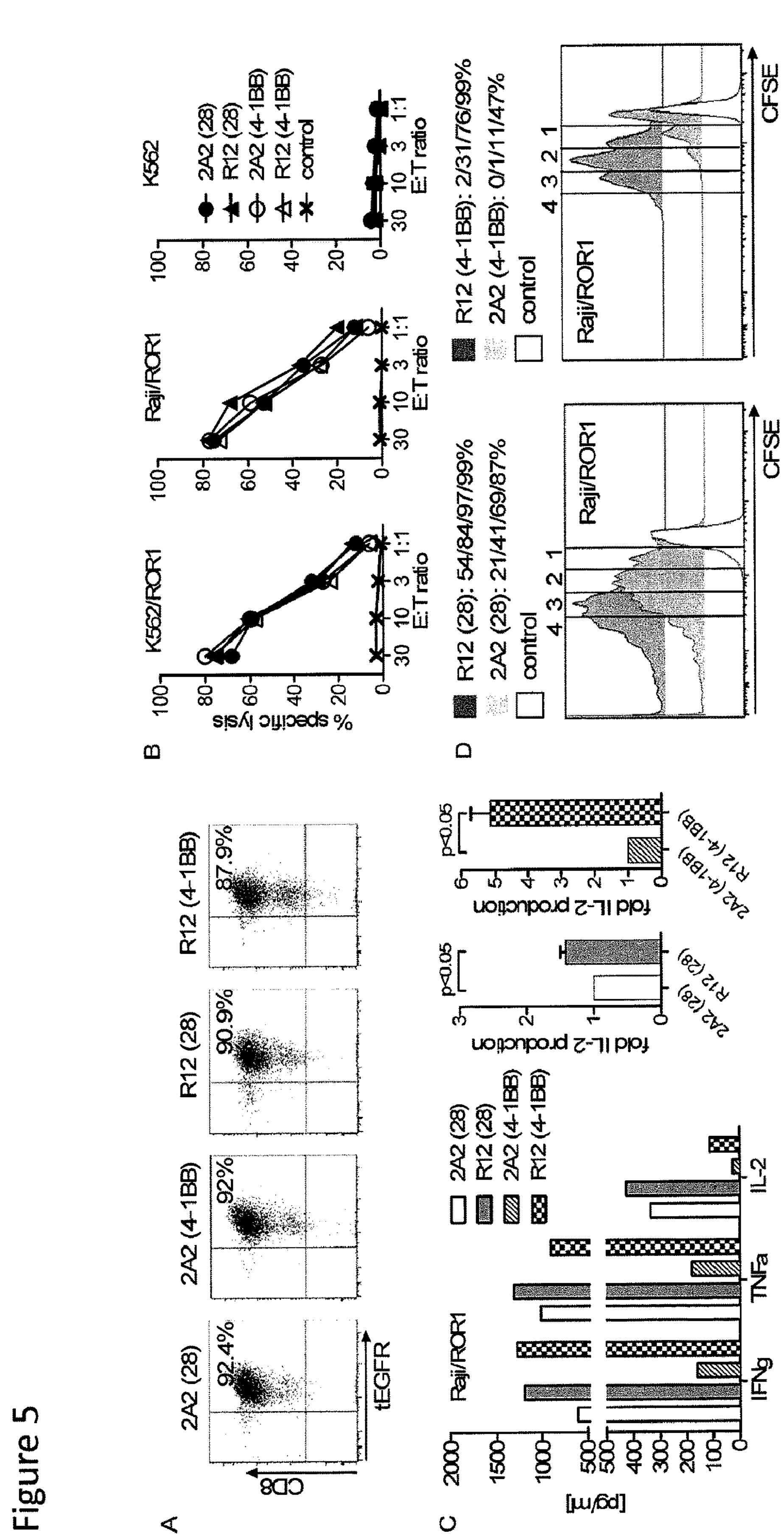
FIG. 5: Anti-tumor reactivity of T-cells modified with ROR1 chimeric receptors derived from mAb R12 with higher affinity than 2A2. (A) tEGFR expression on purified polyclonal CD8$^+$ $T_{CM}$-derived T-cell lines modified with each of the R12 and 2A2 ROR1 chimeric receptors with short IgG4-Fc 'Hinge' spacer, and CD28 or 4-1BB costimulatory domain. (B) Cytotoxicity against ROR1$^+$ and control target cells by T-cells expressing R12(28-▲; 4-1BB-Δ) and 2A2 ROR1 chimeric receptors (28-●; 4-1BB○) or a tEGFR control vector (x). (C) Multiplex cytokine assay of supernatants obtained after 24 hours from co-cultures of $5\times10^4$ T-cells expressing the various ROR1 chimeric receptors with Raji/ROR1 tumor cells. The middle/right bar diagrams show normalized multiplex data from 3 independent experiments (cytokine release by ROR1 chimeric receptor 2A2=1) analyzed by Student's t-test. (D) Proliferation of ROR1 chimeric receptor T-cells and tEGFR control T-cells 72 hours after stimulation with Raji/ROR1 cells and without addition of exogenous cytokines was assessed by CFSE dye dilution. Numbers above each histogram indicate the number of cell divisions the proliferating subset underwent, and the fraction of T-cells in each gate that underwent ≥4/3/2/1 cell divisions is provided above each plot.

We then designed R12 and 2A2 ROR1 chimeric receptors that contained an optimal (short) extracellular spacer, and either a CD28 or 4-1BB costimulatory domain in tandem with CD3ζ (4 constructs) for comparison (FIG. 4A.B). These ROR1-chimeric receptor constructs were expressed in purified $CD8^+$ $T_{CM}$ of healthy donors, and we confirmed equivalent transgene expression by tEGFR staining (FIG. 5A). T-cells modified with each of the 2A2 and R12 ROR1-chimeric receptors specifically lysed K562/ROR1 and Raji/ROR1 tumor cells with approximately equivalent efficiency (FIG. 5B). However, analysis of cytokine production showed that the high affinity R12 ROR1 chimeric receptors that contained CD28 or 4-1BB conferred significantly higher IFN-γ, TNF-α and IL-2 production compared to the corresponding 2A2 constructs (FIG. 5C). We found that T-cells expressing chimeric receptors with a CD28 costimulatory domain produced more IFN-γ, TNF-α and IL-2 compared to those with 4-1BB.

Experiments to analyze the proliferation of ROR1 chimeric receptor T-cells showed a higher percentage of proliferating T-cells and a higher number of cell divisions in T-cells expressing the high affinity R12 ROR1 chimeric receptors with CD28 and 4-1BB domain compared to T-cells expressing the respective 2A2 counterparts (FIG. 4D). There was more vigorous proliferation in T-cells that expressed chimeric receptors with a CD28 domain, consistent with higher IL-2 production induced by these receptors. There was a lower frequency of AICD as measured by PI staining in T-cell lines modified with R12 compared to 2A2 ROR1-chimeric receptors after stimulation with Raji/ROR1 and JeKo-1 tumor cells respectively (R12: 5.6%/6.9% vs. 2A2: 10%/9.65%). T-cell lines that expressed chimeric receptors with a CD28 domain also had lower AICD compared to 4-1BB in response to Raji/ROR1 and JeKo-1 tumor cells respectively (R12: 16.4%/18.4% vs. 2A2 38.1%/39.6%).

To determine if the enhanced function observed with R12 ROR1 chimeric receptors in $CD8^+$ T-cells extended to $CD4^+$ T-cells, we transduced bulk $CD4^+$ T-cells with the 2A2 and R12 ROR1 chimeric receptors containing the short spacer and CD28 costimulatory domain. In response to Raji/$ROR1^+$ tumor cells, $CD4^+$ T-cells that expressed the high affinity R12 scFV produced higher levels of IFN-γ, TNF-α, IL-2, IL-4, and IL-10, and underwent greater proliferation than $CD4^+$ T-cells that expressed 2A2 (FIG. 5A,B). Both cytokine production and proliferation was superior in $CD4^+$ compared to $CD8^+$ T-cells modified with the same ROR1 chimeric receptors. In summary, our data demonstrate that tailoring both the length of the non-signaling extracellular chimeric receptor spacer domain and scFV affinity are independent parameters that affect the function of ROR1-chimeric receptor T-cells.

$CD8^+$ T-Cells Modified with a High Affinity ROR1 Chimeric Receptor have Comparable Activity to a CD19 Chimeric Receptor Against Primary CLL In Vitro ROR1 and CD19 are both uniformly expressed on all primary CLL (FIG. 6A), however the absolute number of ROR1-molecules per tumor cell is estimated to be 10-fold lower than that of CD19, which has been successfully targeted in clinical trials with CD19 chimeric receptor T-cells. We compared recognition of primary CLL by $CD8^+$ T-cells expressing the optimized R12 and 2A2 ROR1 chimeric receptors, and a CD19 chimeric receptor derived from the FMC63 scFV.

We used purified $CD8^+$ $T_{CM}$ for chimeric receptor-modification to provide a uniform cell product and each chimeric receptor contained a short IgG4-Fc 'Hinge-only' spacer and 4-1BB costimulatory domain. We confirmed our CD19 chimeric receptor (IgG4 Hinge) was at least as and more effective in recognizing $CD19^+$ tumors as a CD19 chimeric receptor with CD8a Hinge spacer and 4-1BB costimulatory domain that is being used in ongoing clinical trials. (FIG. 20). T cells expressing CD19 chimeric receptors with 4-1BB and CD3zeta and a modified IgG4-Fc hinge exhibit superior in vitro and in vivo function compared to T cells expressing CD19 chimeric receptors with 4-1BB and CD3zeta and a CD8 alpha hinge. In FIG. 20D, in vivo antitumor activity of T cells expressing a CD19 chimeric receptor with an IgG4 Fc hinge (group 1) or CD8 alpha hinge (group 2) and T cells that express tEGFR alone (group 3) in NSG mice inoculated with Raji tumor cells expressing firefly luciferase (ffluc) were compared. Mice were imaged 17 days after tumor inoculation and 10 days after T cell inoculation. The data shows greater tumor burden in mice treated with control tEGFR T cells (group 3) or with CD19 chimeric receptor CD8 alpha hinge T cells (group 2) compared with mice treated with CD19 chimeric receptor IgG4 Fc hinge T cells (group 1).

Figure 6:
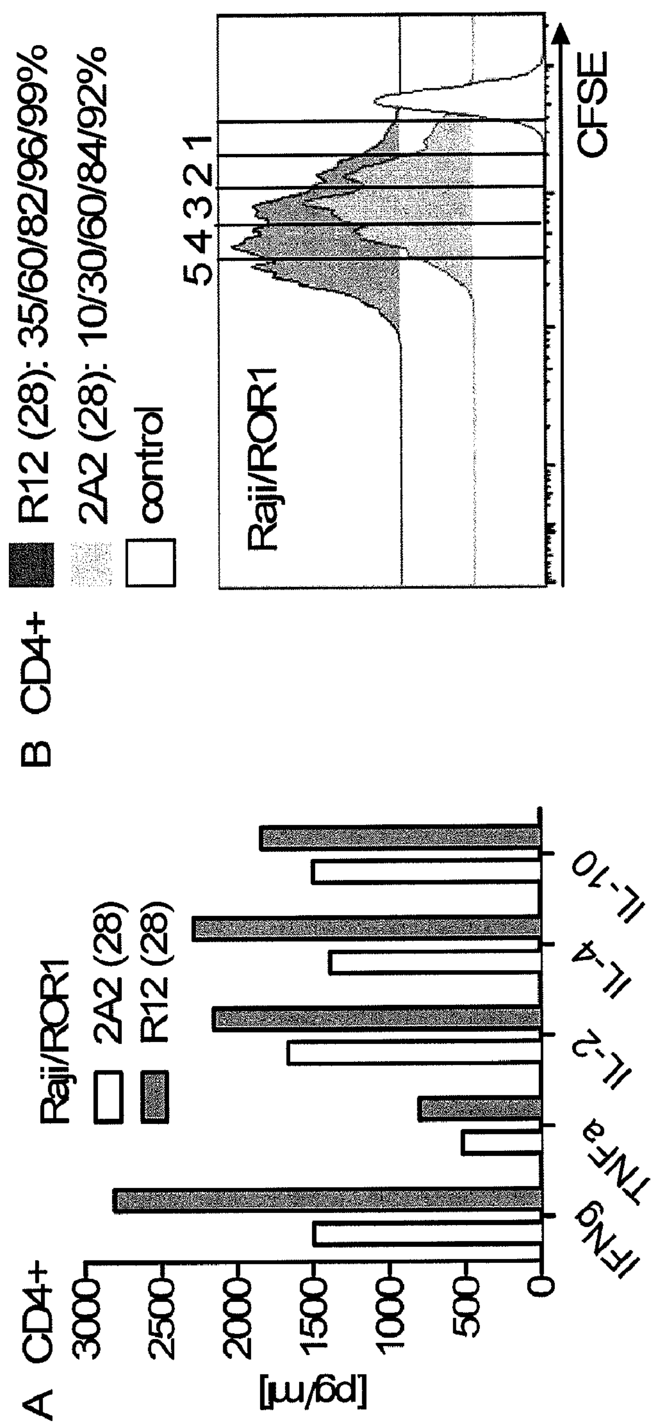
FIG. 6: Analysis of cytokine production and proliferation of CD4$^+$ T-cells lines modified with a ROR1 chimeric receptor derived from mAb R12 with higher affinity than 2A2. (A-B) The 2A2 and R12 ROR1 chimeric receptors had the short spacer and a CD28 costimulatory domain. (A) Multiplex cytokine analysis from supernatants obtained 24 hours after stimulation of $5\times10^4$ CD4$^+$ T-cells expressing the 2A2 and R12 ROR1 chimeric receptor with Raji/ROR1 tumor cells. (B) Proliferation of CD4$^+$ R12 and 2A2 ROR1 chimeric receptor T-cells and tEGFR control T-cells 72 hours after stimulation with Raji/ROR1 cells and without addition of exogenous cytokines was assessed by CFSE dye dilution. Numbers above each histogram indicate the number of cell divisions the proliferating subset underwent, and the fraction of T-cells in each gate that underwent ≥5/4/3/2/1 cell divisions is provided above the histograms.
Figure 7:
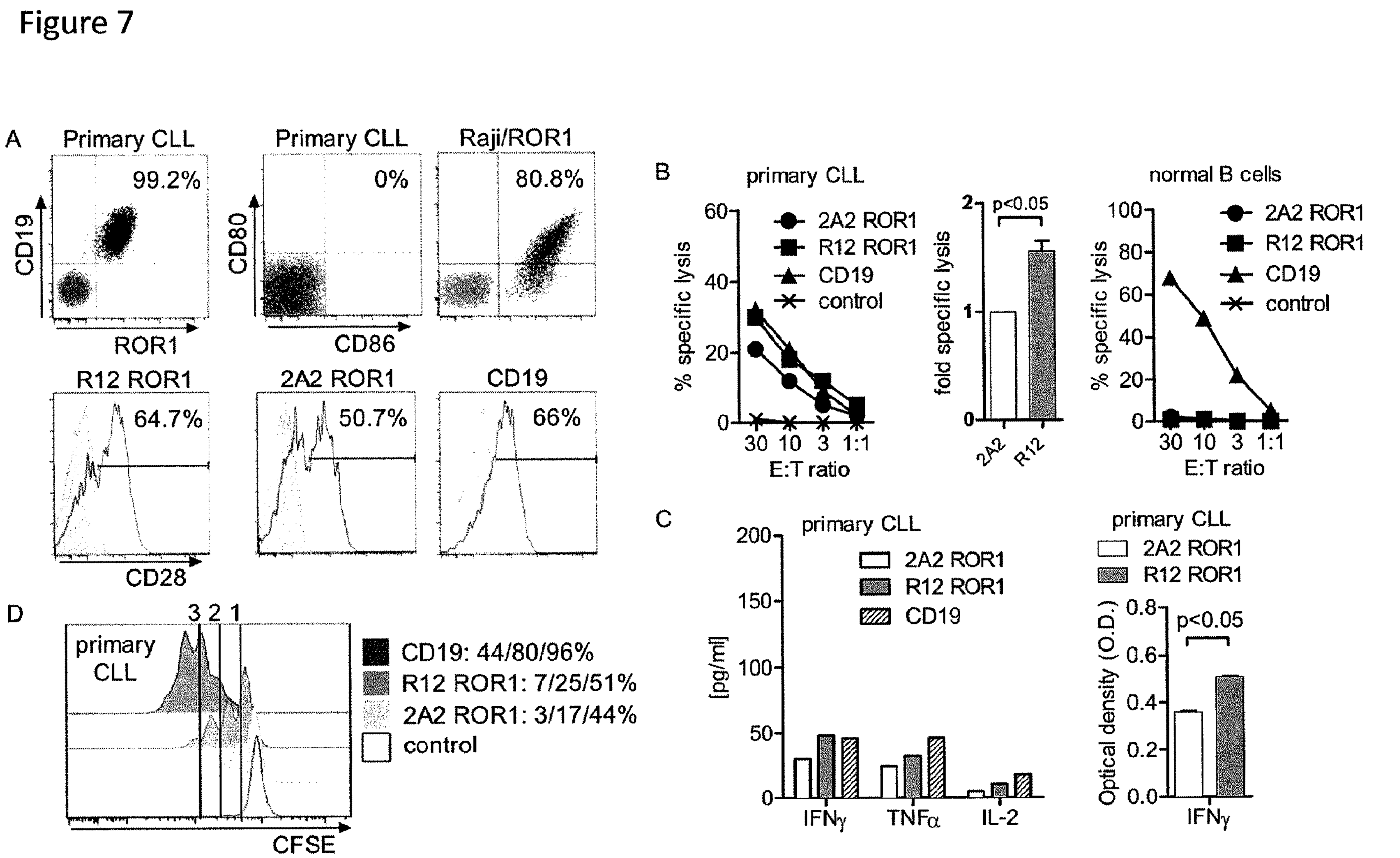
FIG. 7: Recognition of primary CLL by T-cells modified with 2A2 and R12 ROR1 chimeric receptors with optimal short spacer and 4-1BB costimulatory domain or with a CD19-specific chimeric receptor. (A) Expression of ROR1/CD19 on primary CLL, and CD80/86 on primary CLL and Raji/ROR1 tumor cells (black dot plots) that can engage CD28 on chimeric receptor T-cells (white histograms). Staining with matched isotype control mAbs is shown as grey dot plots/histograms. (B) Cytolytic activity of T-cells expressing the 2A2(●) and R12 ROR1 chimeric receptor (■), a CD19-specific chimeric receptor (▲) and T-cells modified with a tEGFR control vector (x) against primary CLL (left diagram) and normal B cells (right diagram) analyzed by chromium release assay. Cytotoxicity data against primary CLL from 4 independent experiments (E:T=30:1) were normalized (cytolytic activity by ROR1 chimeric receptor 2A2=1) and analyzed by Student's t-test (bar diagram). (C) Multiplex cytokine analysis after a 24-hour stimulation of $5\times10^4$ chimeric receptor T-cells with primary CLL cells. Cytokine release of unstimulated chimeric receptor T-cells was below 3.6 pg/ml (detection limit) (left bar diagram). ELISA for IFN-γ production by $5\times10^4$ 2 A2 and R12 ROR1 chimeric receptor T-cells after a 24-hour co-culture with primary CLL. O.D. of 1 corresponds to approximately 250 pg/ml (right bar diagram). (D) Proliferation of CD8$^+$ T-cells modified with the 2A2 ROR1, R12

The cytolytic activity of R12 ROR1 chimeric receptor T-cells against primary tumor cells from multiple CLL patients (n=4) was higher compared to T-cells modified with the lower affinity 2A2 ROR1 chimeric receptor, and equivalent to the lysis observed with CD19 chimeric receptor T-cells (FIG. 6B). Multiplex cytokine analysis showed nearly equivalent production of IFN-γ and TNF-α, but less IL-2 production by $CD8^+$ T-cells expressing the R12 ROR1 compared with those expressing the CD19-chimeric receptor after co-culture with primary CLL (FIG. 6C). 2A2 ROR1 chimeric receptor T-cells produced lower amounts of all cytokines than R12 ROR1 chimeric receptor T-cells as noted previously. Cytokine production by all of the chimeric receptor-transduced T-cells after stimulation with CLL was substantially less than with Raji/ROR1, which unlike CLL expresses both CD80 and CD86 that can engage CD28 expressed on chimeric receptor T-cells (FIG. 6A, C).

We observed less proliferation of T-cells expressing the R12 and 2A2 ROR1 chimeric receptor compared to the CD19 chimeric receptor after stimulation with CLL (CD19>R12>2A2) (FIG. 6D). We hypothesized that proliferation of $CD8^+$ ROR1 chimeric receptor T-cells in response to CLL may be augmented in the presence of chimeric receptor-modified $CD4^+$ T-cells because of their higher secretion of IL-2 compared to $CD8^+$ $T_{CM}$ (FIG. 4A; FIG. 8A). To test this possibility, we performed in vitro co-culture experiments where $CD4^+$ and CD8 $T_{CM}$ were separately modified with the R12 ROR1, 2A2 ROR1 and CD19 chimeric receptors respectively, enriched for chimeric receptor expression, and combined at a 1:1 ratio to ensure equivalent proportions of $CD8^+$ and $CD4^+$ T-cells modified with each of the vectors. These cells were CFSE-labeled and stimulated with primary CLL. We observed a dramatic increase in proliferation of CD8+ R12 ROR1 chimeric receptor T-cells after addition of chimeric receptor-transduced, but not untransduced CD4+ T-cells (FIG. 8B). Notably, when provided with CD4-help, we observed equivalent proliferation of R12 ROR1 and CD19 chimeric receptor CD8+ T-cells in response to CLL, whereas proliferation of CD8+ T-cells expressing the lower affinity 2A2 ROR1 chimeric receptor remained less. Collectively, our data show that the high affinity R12 ROR1 chimeric receptor confers superior reactivity compared to 2A2 against primary CLL cells in vitro.

ROR1-Chimeric Receptor T-Cells Mediate In Vivo Anti-Tumor Activity in a Mouse Model of Systemic Mantle Cell Lymphoma It remained uncertain whether the superior in vitro activity of T-cells modified with the higher affinity R12 chimeric receptor would translate into improved anti-tumor activity in vivo, and how targeting ROR1 would compare to targeting CD19. To address these questions, we inoculated cohorts of immunodeficient NSG mice with the human MCL line JeKo-1/ffluc by tail vein injection, and seven days later when tumor was disseminated, treated the mice with a single intravenous dose of R12 ROR1, 2A2 ROR1 or CD19 chimeric receptor CD8+ T-cells. Control mice were treated with tEGFR T-cells or untreated. All chimeric receptors had the optimal short spacer and the 4-1BB costimulatory domain. Untreated NSG/JeKo-1 mice developed a rapidly progressive systemic lymphoma necessitating euthanasia approximately 4 weeks after tumor inoculation (FIG. 9A-C).

We observed tumor regression and improved survival in all mice treated with R12 ROR1, 2A2 ROR1 and CD19 chimeric receptor T-cells. Mice treated with R12 ROR1 chimeric receptor T-cells had a superior anti-tumor response and survival compared to mice treated with 2A2 ROR1 chimeric receptor T-cells ($p<0.01$), and comparable anti-tumor activity to mice treated with CD19 chimeric receptor T-cells (FIG. 9A-C).

We analyzed the frequency of chimeric receptor T-cells in the peripheral blood following adoptive transfer and detected higher numbers of tEGFR+ T-cells in mice treated with the R12 ROR1 chimeric receptor compared to the 2A2 ROR1 chimeric receptor, suggesting more vigorous proliferation in vivo improved tumor control. To confirm this, we administered CFSE-labeled CD19 chimeric receptor, R12 and 2A2 ROR1 chimeric receptor T-cells to cohorts of NSG mice bearing JeKo-1/ffluc, and analyzed T-cell proliferation in the peripheral blood, bone marrow and spleen 72 hours after transfer. A higher percentage of the R12 and CD19 chimeric receptor T-cells proliferated and underwent a greater number of cell divisions compared to 2A2 ROR1 chimeric receptor T-cells (FIG. 9D). The JeKo-1 tumor eventually recurred in all mice treated with ROR1 or CD19 chimeric receptor T-cells (FIG. 9A-C). Tumor recurrence was not a result of the selection of ROR1 or CD19 loss variants, as recurrent tumors were positive for both molecules.

For comparison, we analyzed anti-tumor efficacy of CD19 chimeric receptor T-cells in NSG mice engrafted with Raji tumors and observed complete tumor eradication, indicating the recurrence of JeKo-1 reflects difficulty eradicating this tumor (data not shown). In summary, this data is the first to show that ROR1 chimeric receptor T-cells have anti-tumor efficacy in vivo, and suggest that for B-cell malignancies, an optimized ROR1 chimeric receptor such as R12 may be effective and spare normal CD19+ B-cells that lack ROR1 expression.

T-Cells Expressing the R12 ROR1 Chimeric Receptor have Superior Reactivity Compared to 2A2 Against ROR1+ Epithelial Tumor Cells ROR1 has been detected on many epithelial tumors, although it is unknown whether ROR1 expression is sufficient for recognition by ROR1 chimeric receptor T-cells. Using flow cytometry, we confirmed ROR1 expression on breast cancer lines MDA-MB-231 and 468, and on the renal cell carcinoma lines FARP, TREP, and RWL (FIG. 10A). We then analyzed tumor recognition by CD8+ T-cells transduced with the R12 ROR1 chimeric receptors with the optimal short spacer and 4-1BB domain, and observed efficient recognition of MDA-MB-231, MDA-MB-468, FARP, TREP and RWL (FIG. 11A). We analyzed cytokine secretion and proliferation of T-cells modified with the R12 and 2A2 ROR1-chimeric receptors after co-culture with MDA-MB-231, and observed greater cytokine production and proliferation with the R12 ROR1 chimeric receptor (FIG. 11 B, C). Similar to what we observed with ROR1+ B cell malignancies, the superior activation of R12 ROR1 chimeric receptor T cells after stimulation with MDA-MB-231 was not associated with increased AICD (R12: 9.8% vs. 2A2: 10.9%).

Discussion

ROR1 has attracted interest as a potential target for cancer immunotherapy due to its expression on the surface of many B-lymphoid and epithelial cancers, including subsets of lung, colorectal and renal cell cancer. We previously showed that CLL and MCL were specifically recognized by T-cells modified to express a ROR1-specific chimeric receptor (Hudecek M, et al. Blood. 2010; 116(22):4532-41. Epub 2010/08/13). The design and function of ROR1-chimeric receptors has been improved through modification of the extracellular spacer domain and deriving the chimeric receptor from a scFV of higher affinity, and demonstrate that T-cells modified with designed ROR1 chimeric receptors have in vivo activity against ROR1+ B-cell lymphoma and in vitro activity against a wide range of epithelial tumors.

We compared the function of T-cells modified with ROR1 chimeric receptors derived from the 2A2 mAb that contained either the original long IgG4-Fc 'Hinge-CH2-CH3' spacer that we have shown enables high level cell surface expression, or truncated intermediate 'Hinge-CH3' and short 'Hinge-only' spacer variants. We preserved the 12 AA Hinge domain in our short spacer construct based on prior data that a flexible spacer was required for separating the scFV from the T-cell membrane and allowing antigen recognition on tumor cells (Fitzer-Attas C J, et al., Harnessing Syk family tyrosine kinases as signaling domains for chimeric single chain of the variable domain receptors: optimal design for T cell activation. J Immunol. 1998; 160(1):145-54. Epub 1998/04/29.)

Our studies with the 2A2 ROR1 chimeric receptor show that T-cell cytokine secretion and proliferation after tumor cell recognition are superior with the intermediate and short spacer constructs compared to the long spacer construct. Staining with anti-F(ab) Abs showed equivalent chimeric receptor expression of all three receptors, demonstrating the improved T-cell function with the short spacer chimeric receptor was not due to differences in chimeric receptor density. This data supports the principle that the design of extracellular spacers should be tailored for each target molecule and epitope.

The affinity of the scFV selected for designing a chimeric receptor is an additional parameter that could affect T-cell recognition. We generated and characterized a panel of ROR1-specific mAbs of different affinities and selected the R12 mAb, which recognizes an epitope in the Ig-like/Frizzled region as 2A2. R12 has a higher affinity for ROR1-protein due to a much slower dissociation. The R12 chimeric receptor, like the 2A2 chimeric receptor conferred optimal T-cell recognition and function when designed with a short extracellular spacer. A direct comparison of proliferation and cytokine production after tumor engagement by T-cells modified with the 2A2 and R12 chimeric receptors demonstrated that the R12 chimeric receptor derived from the higher affinity mAb was superior. We were concerned that the slower dissociation of R12 from ROR1 could prolong T-cell activation and confer an increased susceptibility to AICD. However, we detected a lower rate of AICD in T-cells modified with the R12 ROR1-chimeric receptor compared to 2A2, demonstrating that the increased affinity of R12 had no detrimental effect on T-cell survival in our preclinical models.

ROR1 has a potential advantage over CD19 as a target for CLL and MCL since it is not expressed on normal mature naïve and memory B-cells. However, there is a lower number of ROR1 molecules on B-cell tumors compared with CD19 and it is uncertain if an optimized ROR1 chimeric receptor would be as effective as a CD19 chimeric receptor similar in design to those being used in the clinic. Unfortunately, B-cell tumor xenograft models used previously in NSG mice to evaluate the function of CD19 chimeric receptor T-cells including Raji, Daudi and Nalm-6, are not derived from CLL or MCL and do not constitutively express ROR1. Thus, to compare targeting CD19 and ROR1 in vivo, we used the JeKo-1 MCL cell line, which naturally expresses both CD19 and ROR1 and engrafts in NSG mice. To make our model clinically relevant, we inoculated JeKo-1 lymphoma cells intravenously to generate systemic tumors, and treated mice with T-cell products of uniform consistency once tumors were established. We found that T-cells expressing the high affinity R12 chimeric receptor conferred equivalent anti-tumor activity in vivo as CD19 chimeric receptor T-cells. Consistent with our in vitro analysis, the R12 ROR1 chimeric receptor also mediated superior activity in vivo compared to the optimal 2A2 ROR1-chimeric receptor. These results should be interpreted cautiously since murine tumor models may not predict the efficacy of adoptive therapy in clinical settings. However, the results suggest that ROR1 warrants consideration as an alternative to CD19, or to provide an additional target to minimize the potential for CD19 loss variants to emerge.

ROR1 appears to play a decisive role in survival of some epithelial tumors. Thus, an advantage of targeting ROR1 is that a single chimeric receptor may be useful to treat patients with a large number of hematopoietic and non-hematopoietic tumors.

Our data shows for the first time that T-cells that express a designed ROR1 chimeric receptor efficiently recognize epithelial cancers in vitro. Cytokine secretion and T-cell proliferation induced by ROR1$^+$ breast cancer cells were higher than that induced by leukemia cells, despite the absence of the CD80/86 costimulatory ligand. The studies reported here demonstrate that the design of the extracellular spacer domain and chimeric receptor affinity are parameters that can be modulated to enhance the recognition of ROR1$^+$ hematologic and epithelial tumors in vitro and in vivo by ROR1-chimeric receptor modified T-cells. The development of ROR1-chimeric receptors with enhanced tumor reactivity provides the opportunity for clinical applications in a variety of human cancers.

Example 2. Effect of Extracellular Spacer Domain Length on Triggering of Tumor Cell Lysis with a Her2-Specific Chimeric Receptor that Recognizes an Epitope Located Proximal to the Tumor Cell Membrane The effect of CAR spacer length on recognition and triggering of tumor cell recognition by CD8+ human T lymphocytes that expressed a HER2-specific chimeric receptor was examined using similar methods to those described above for ROR1. HER2-specific chimeric receptors were constructed using VL and VH chain segments of a HER2-specific mAb that recognized a membrane proximal epitope on HER2 (FIG. 12A), and the scFVs were linked to IgG4 hinge/CH2/CH3, IgG4 hinge/CH3, and IgG4 hinge only extracellular spacer domains and to the CD28 transmembrane domain, 4-1BB and CD3 zeta signaling domains (FIG. 12B). Primary CD8+ T cells were transduced with each of the HER2 chimeric receptors and selected for expression of the EGFR transducton marker (FIG. 12D). Expression of the HER 2 chimeric receptors and the size of each receptor was confirmed by Western Blot (FIG. 12C). The T cells were then expanded with anti CD3 mAb and feeder cells and examined for their ability to recognize HER2+ tumor cells. As observed with the R11 ROR 1 specific chimeric receptor, the HER2 chimeric receptor that contained a long extracellular spacer domain conferred superior T cell recognition of HER2+ tumor cells (FIG. 12E).

Discussion

This example of the effect of extracellular spacer length on chimeric receptor modified T cell recognition of tumor cells used a chimeric receptor comprising a scFv built from the $V_{H+L}$ sequences of the Herceptin chimeric mAb. Studies by Cho et al (Nature 421:756, 2003) localized to epitope location of Herceptin to a membrane proximal location on the HER2 (ERRB2) extracellular domain (FIG. 12A). Based on our understanding of the structure of human IgG4 hinge: Fc variants (FIG. 12B), we hypothesize that a membrane proximal location of the targeting epitope on an extracellular tumor cell antigen would best recognized by effector T cells that express a chimeric receptor encoding a long spacer. Our data demonstrating a gradient of cytolytic activity from near back ground activity by T cells expressing a short spacer Herceptin chimeric receptor, to intermediate activity by T cells expressing a medium length spacer chimeric receptor, and maximal lysis by T cells that expressed the long spacer chimeric receptor. Thus, the extracellular spacer has definitive effects on tumor recognition by T cells, and this data provides further support for the need to tailor chimeric receptor design based on epitope location of tumor expressed target molecules.

Example 3. Customizing Spacer Length and Sequence for Optimal Recognition and In Vivo Efficacy of CD19 with Chimeric Receptor Modified T Cells Materials and Methods Human Subjects Blood samples were obtained from healthy donors who provided written informed consent to participate in research protocols approved by the Institutional Review Board of the Fred Hutchinson Cancer Research Center (FHCRC). Peripheral blood mononuclear cells (PBMC) were isolated by centrifugation over Ficoll-Hypaque (Sigma, St. Louis, Mo.), and cryopreserved in RPMI, 20% human serum and 10% dimethyl sulfoxide.

Cell Lines

The K562, Raji, JeKo-1 and 293T cell lines were obtained from the American Type Culture Collection (Manassas, Va.) and cultured as directed. A lentivirus encoding the ffluc-gene upstream of a T2A sequence and eGFP was produced in 293T cells and used to transduce Raji and JeKo-1 tumor cells. Raji, and JeKo-1 cells were expanded after lentiviral transduction and the eGFP positive subset sort-purified.

Immunophenotyping

PBMC and T-cell lines were stained with one or more of the following conjugated monoclonal antibodies: CD3, CD4, CD8, CD25, CD45RA, CD45RO, CD62L, CD69 and matched isotype controls (BD Biosciences). Staining with propidium iodide (PI, BD Biosciences) was performed for live/dead cell discrimination as directed by the manufacturer. Flow analyses were done on a FACSCanto, sort-purifications on a FACSAriaII (Becton Dickinson) and data analyzed using FlowJo software (Treestar).

Vector Construction and Preparation of CD19 Chimeric Receptor Encoding Lentivirus CD19 specific chimeric receptors were constructed using: (1) the VL and VH chain segments of the CD19-specific mAb FMC63 (SEQ ID NO:3), linked by a $(G_4S)_3$ linker (SEQ ID NO: 12) peptide (VL-linker-VH); (2) a spacer domain derived from IgG4-Fc (Uniprot Database: P01861, (SEQ ID NO: 13)) comprising either the Hinge-CH2-CH3 portion (229 AA, (SEQ ID NO:)) or Hinge only (12 AA; (SEQ ID NO:4)). Both spacers contained a S→P substitution within the Hinge domain located at position 108 of the native IgG4-Fc protein; the 27 AA transmembrane domain of human CD28 (Uniprot Database: P10747, (SEQ ID NO: 14)); (4) a signaling module comprising either (i) the 41 AA cytoplasmic domain of human CD28 with an LL→GG substitution located at position 186-187 of the native CD28 protein (SEQ ID NO:14); and/or (ii) the 42 AA cytoplasmic domain of human 4-1BB (Uniprot Database: Q07011, (SEQ ID NO:15)); linked to (iii) the 112 AA cytoplasmic domain of isoform 3 of human CD3 (Uniprot Database: P20963, (SEQ ID NO:16)); the self cleaving T2A sequence (SEQ ID NO:8); and (6) a truncated epidermal growth factor receptor (EGFR) sequence (SEQ ID NO:9)

Codon-optimized nucleotide sequences encoding each trans gene were synthesized (LifeTechnologies, Carlsbad, Calif.) and cloned into the epHIV7 lentiviral vector using NheI and Not1 restriction sites. The epHIV7 lentiviral vector had been derived from the pHIV7 vector by replacing the cytomegalovirus promoter of pHIV7 with an EF-1 promoter.

CD19 chimeric receptor or tEGFR-encoding lentivirus was produced in 293T cells co-transfected with the lentiviral vector and the packaging vectors pCHGP-2, pCMV-Rev2 and pCMV-G using Calphos transfection reagent (Clontech). Medium was changed 16 h after transfection, and lentivirus collected after 24, 48 and 72 h.

Generation of T-Cell Lines Expressing the CD19 Chimeric Receptors Sort-purified $CD8^+$ $CD45RA^-$ $CD45RO^+$ $CD62L^+$ central memory T-cells ($T_{CM}$) of normal donors were activated with anti-CD3/CD28 beads (Life Technologies) according to the manufacturer's instructions, and transduced with lentiviral supernatant (MOI=3) supplemented with 1 μg/mL polybrene (Millipore) on day 3 after activation by centrifugation at 2,100 rpm for 45 min at 32° C. T cells were expanded in RPMI, 10% human serum, 2 mM L-glutamine and 1% penicillin-streptomycin (CTL medium), supplemented with recombinant human (rh) IL-2 to a final concentration of 50 U/mL every 48 h. After expansion, an aliquot of each transduced T cell line was stained with biotin-conjugated anti-EGFR (epithelial growth factor receptor) antibody and streptavidin-beads (Miltenyi), and tEGFR+ T cells isolated by immunomagnetic selection.

The tEGFR+ T-cell subset was then stimulated with irradiated (8,000 rad) TM EBV-LCL at a T cell: LCL ratio of 1:7, and expanded for 8 days in CTL medium with addition of 50 U/mL rh IL-2 every 48 h.

Chromium Release, Cytokine Secretion and CFSE Proliferation Assays

Target cells were labeled with $^{51}Cr$ (PerkinElmer) overnight, washed and incubated in triplicate at $1\text{-}2\times10^3$ cells/well with effector T cells at various effector to target (E:T) ratios Supernatants were harvested for γ counting after a 4-hour incubation and specific lysis calculated using the standard formula. For analyses of cytokine secretion, target and effector cells were plated in triplicate wells at an E:T ratio of 2:1 (Raji) or 4:1 (K562/CDI9 and K562), and INF-γ, TNF-α, IL-2, IL-4, IL-6 and IL-10 measured by multiplex cytokine immunoassay (Luminex) in supernatant removed after a 24-hour incubation.

For analysis of proliferation, T cells were labeled with 0.2 μM carboxyfluorescein succinimidyl ester (CFSE, Invitrogen), washed and plated in triplicate wells with stimulator cells at a ratio of 2:1 (Raji) or 4:1 (K562/CD19 and K562) in CTL medium without exogenous cytokines. After 72 h of incubation, cells were labeled with anti-CD3 mAb and propidium iodide (PI) to exclude dead cells from analysis. Samples were analyzed by flow cytometry and cell division of live CD3+ T-cells assessed by CFSE dilution.

Experiments in NOD/SCID and NOD/SCID/$\gamma c^{-/-}$ (NSG) Mice

All mouse experiments were approved by the FRCRC Institutional Animal Chimeric receptore and Use Committee. Six- to 8-week old female NOD.CBI7-$Prkdc^{scid}$/J (NOD/SCID) and NOD.Cg-$Prkdc^{scid}$ $Il2rg^{tmlWjl}$/SzJ (NSG) mice were obtained from the Jackson Laboratory or bred in-house (FRCRC. Mice were injected intravenously (i. v.) with $0.5\times10^6$ Raji-ffluc tumor cells via tail vein injection, and received injections of chimeric receptor-modified T cells, control T cells, or PBS via tail vein injection as indicated.

For bioluminescence imaging, mice received intraperitoneal (i.p.) injections of freshly prepared luciferin substrate (Caliper Life Sciences, MA) resuspended in PBS (15 μg/g body weight) and were then anesthetized with isoflurane in an induction chamber. After induction of deep anesthesia, mice were imaged using an Xenogen IVIS In Vivo Imaging System (Caliper Life Sciences, MA) at 10, 12 and 14 minutes post i.p. injection of luciferin at an acquisition time of 1 second to 1 minute in small binning mode to obtain unsaturated images. Luciferase activity was analyzed using Living Image Software (Caliper Life Sciences, MA) and the photon flux analyzed within regions of interest that encompassed the entire body of each individual mouse.

Statistical Analyses

Statistical analyses were performed using Prism Software (GraphPad, CA). Student's t-test was performed as a two-sided test with a confidence interval of 95% and results considered significant with a p-value of $p<0.05$. Statistical analysis of survival were done by Log-rank testing and results considered significant with a p-value of $p<0.05$.

Results

Preparation of Polyclonal CD8+ $T_{CM}$-Derived Cell Lines that Express CD19 Chimeric Receptors with Long and Short Extracellular Spacers We constructed individual lentiviral vectors encoding a panel of codon-optimized CD 19 chimeric receptor genes to examine the influence of extracellular spacer length on the in vitro function and in vivo antitumor activity of CD19 chimeric receptor-modified T cells. Each chimeric receptor was comprised of a single chain variable fragment corresponding to the sequence of the CD19-specific mAb FMC63 (scFv: VL-VH), a spacer derived from IgG4-Fc including either the 'Hinge-CH2-CH3' domain (229 AA, long spacer) or the 'Hinge' domain only (12 AA, short spacer), and a signaling module of CD35 with membrane proximal CD28 or 4-1 BB costimulatory domains, either alone or in tandem (FIG. 13A). The transgene cassette included a truncated EGFR (tEGFR) downstream from the chimeric receptor gene and separated by a cleavable T2A element, to serve as a transduction, selection and in vivo tracking marker for chimeric receptor-modified T cells.

We isolated a CD8+ CD45RO+ CD62L+ central memory T cell ($T_{CM}$) cell population by cell sorting from the blood of normal donors for transduction and expansion, because of the superior ability of $T_{CM}$, to persist in vivo after adoptive transfer. CD8+ T cells were stimulated with anti CD3/28 beads, transduced with each of the lentiviral vectors, and expanded in culture for 18 days before being used for in vitro and in vivo experiments. (FIG. 13B) Similar transduction efficiencies were achieved with each of the lentiviral vectors (mean 25%) and transgene-positive T cells were enriched to uniform purity by immunomagnetic selection using a biotinylated anti-EGFR mAb and streptavidin beads. Following tEGFR-enrichment, each of the CD19 chimeric receptor T cell lines were expanded by a single stimulation with CD19+B-LCL, without apparent differences in in vitro growth kinetics between T cell lines expressing the various CD 19 chimeric receptor constructs. After expansion, the tEGFR marker was expressed at equivalent levels on >90% of the T cells transduced with each of the vectors (FIG. 13C).

CD19 Chimeric Receptors with Long and Short Extracellular Spacer Domain Confer Specific Anti-Tumor Reactivity In Vitro We compared the effector function of $T_{CM}$-derived T cell lines modified to express CD19 chimeric receptors with CD28 and 4-1BB costimulatory signaling moieties, and either a short ('short/CD28'; 'short/4-1 BB') or long ('long/CD28'; 'long/4-1BB') extracellular spacer domain respectively. T cells expressing each of the 4 CD19 chimeric receptor constructs conferred specific cytolytic activity against $CD19^+$ Raji and JeKo-1 lymphoma cells, and against K562 cells that had been stably transfected with CD19, but not native $CD19^-$ K562 cells (FIG. 14A). Quantitative analyses of cytokine production in response to stimulation with K562/CD19 or Raji tumor cells by multiplex cytokine assay (Luminex) showed production of IFN-γ, TNF-α, IL-2, IL-4, 11-6, and IL-10 by T cells expressing each of the CD19 chimeric receptors (FIG. 14B). T cells expressing CD19 chimeric receptors with a CD28 costimulatory domain produced significantly higher levels of IFN-γ, TNF-α, IL-2 and IL-10 compared to the corresponding constructs with a 4-1BB costimulatory domain (FIG. 14B, C). There was significantly higher IFN-γ production and significantly less IL-4 production by T cells expressing the CD19 'long/CD28' chimeric receptor compared with those expressing the 'short/CD28' chimeric receptor. Amongst the CD19 chimeric receptors with 4-1BB costimulatory signaling module, we detected significantly higher levels of IFN-γ, TNF-α, IL-2, IL-4, and IL-10 secretion in T cells expressing the construct with the short spacer domain (FIG. 14B, C).

We used CFSE dye dilution to analyze proliferation of T cells modified with each of the CD 19 chimeric receptors after engagement of CD 19+ tumor cells. Specific and vigorous proliferation of each of the CD19 chimeric receptor T cell lines was observed 72 hours following stimulation with either K562/CD19 or Raji. The average number of cell divisions was higher for CD19 chimeric receptor T cells with a CD28 costimulatory domain compared to those with 4-1BB, consistent with greater IL-2 production by T cells expressing a CD28 containing chimeric receptor (FIG. 14B-D). We also analyzed the proportion of chimeric receptor T cells that underwent activation induced cell death after stimulation with K562/CD19 and Raji tumor cells at the end of the 72-hours by costaining the culture with CD3+ and PI. We detected a higher frequency of $CD3^+$ $CD8^+$ $PI^+$ T cells in the CD 19 chimeric receptor cell line 'long/4-1 BB', but few PI+ cells were observed with the other CD19 chimeric receptors. (FIG. 14E).

This analysis of in vitro effector functions was consistent with prior studies that have compared CD28 and 4-1BB costimulatory domains, and did not reveal differences in T cell function that would suggest that a particular CD19 chimeric receptor construct from this panel would lack anti-tumor efficacy in vivo.

T Cells Expressing CD19 Chimeric Receptors with Short Extracellular Spacer Domains but not Long Extracellular Spacer Domains Eradicate Raji Tumors in Immunodeficient Mouse Models We next evaluated the in vivo antitumor efficacy of T cells modified with each of the CD19 chimeric receptors in immunodeficient (NOD/SCID) mice engrafted with firefly luciferase transfected Raji cells (Raji-ffluc), which enables sequential quantitative analyses of tumor burden and distribution using bioluminescence imaging. NOD/SCID mice inoculated with $0.5\times10^6$ Raji-ffluc cells via tail vein injection developed disseminated lymphoma, which if untreated led to hind limb paralysis after approximately 3.5 weeks, necessitating euthanasia. Tumor bearing mice were treated with 2 doses of CD8+ $T_{CM}$-derived T cells modified with each of the CD19 chimeric receptors or with a tEGFR control vector administered on day 2 and day 9 after tumor inoculation (FIG. 15A).

Surprisingly, only T cells modified to express CD19 chimeric receptors with short extracellular spacer domain ('short/CD28' and 'short/4-1BB') eradicated Raji tumors in this model, whereas mice treated with T cells expressing CD19 chimeric receptors with long spacer ('long/CD28' and 'long/4-1BB') developed systemic lymphoma and hind limb paralysis with nearly identical kinetics as untreated mice or mice treated with control tEGFR+ T cells (FIG. 15B, C). The striking difference in antitumor activity between CD19 chimeric receptors with short and long spacer domains was highly significant and reproducible in multiple experiments with chimeric receptor T cell lines generated from 3 different normal donors.

The NOD/SCID lymphoma model may be suboptimal for predicting anti-tumor activity in a clinical setting because of the short interval between tumor inoculation and T cell administration and the greater resistance to engraftment of human cells compared to more immunodeficient mouse strains such as NOD/SCID/$\gamma c^{-/-}$ (NSG). Thus, we evaluated antitumor activity of adoptive therapy in a more clinically relevant model in which Raji-ffluc lymphoma was established in NSG mice, and the CD19 chimeric receptor T cells were administered after 7 days when the tumor was readily detectable in the bone marrow by bioluminescence imaging (FIG. 16A). We performed initial dose titration experiments to determine the minimal dose of T cells transduced with the CD19 'short/4-1BB' chimeric receptor that was required for eradication of established Raji tumors. A single dose of $2.5\times10^6$ T cells expressing CD19-chimeric receptor 'short/4-1BB' promoted complete regression of established Raji tumors and resulted in long-term tumor-free survival in 100% of mice (FIG. 16B,C). At the $2.5\times10^6$ dose level, the T-cells were easily detected in the peripheral blood of NSG mice for at least 3 weeks following adoptive transfer and tumor eradication. Thus, this model enabled comparative studies both of antitumor activity and persistence of T cells modified with each of the CD19-chimeric receptors in our panel (FIG. 16D).

We then treated cohorts of NSG mice that were engrafted with Raji lymphoma with PBS alone, with a single dose of $2.5\times10^6$ T cells expressing each of the CD19 chimeric receptors or with T cells modified with a tEGFR encoding control vector (FIG. 17A). In this model of established lymphoma, T cells expressing CD19 chimeric receptors with a short extracellular spacer domain and either 4-1BB or CD28 costimulatory domains ('short/CD28' and 'short/4-1BB') mediated complete tumor regression over 7-10 days and all mice survived tumor free for >56 days. By contrast, mice treated with T cells modified to express CD19 chimeric receptors with a long spacer domain ('long/CD28' and 'long/4-1BB') exhibited tumor progression and had to be sacrificed at a similar time as mice that had received control tEGFR T cells (FIG. 17B, C). The lack of in vivo antitumor activity of the chimeric receptor constructs with long spacers was unexpected given the ability of T cells expressing these constructs to lyse tumor cells in vitro, and the enhanced IL-2 production and proliferation after engagement of T cells expressing the 'long/CD28' CD19 chimeric receptor compared to the 4-1BB constructs.

To provide insight into the basis for the lack of efficacy, we performed sequential flow cytometry on peripheral blood samples of mice at intervals after the T cell infusion. All mice treated with T cells expressing the 'short/CD28' and 'short/4-1BB' CD19 chimeric receptors had significantly higher levels of transferred T cells in the blood at all time points after adoptive transfer, compared to mice treated with T cells that expressed corresponding CD19 chimeric receptors with long extracellular spacer ($p<0.01$) (FIG. 17D). We did not observe significant differences in T-cell persistence in the peripheral blood of mice that had received T cells expressing CD19 chimeric receptors with CD28 or 4-1BB co-stimulatory domains and short spacer domains (FIG. 17D).

The In Vivo Anti-Tumor Efficacy of CD19 Chimeric Receptors with Long Spacers is not Improved by Increasing T Cell Dose or Providing an Additional Costimulatory Domain The lack of in vivo anti-tumor efficacy and the lower level of persisting chimeric receptor T cells in mice treated with T cells modified with CD19 chimeric receptors with long spacer domains suggested that efficacy might be improved by increasing the chimeric receptor T cell dose or by including both CD28 and 4-IBB domains into the chimeric receptor to augment costimulatory signaling. To evaluate this possibility we modified CD8+ $T_{CM}$ with 'long/CD28', 'short CD28', and 'long/CD28_4-1BB' CD19 chimeric receptor vectors and confirmed that the long/CD28_4-1BB' CD19 chimeric receptor conferred specific lysis and cytokine production in vitro after recognition of CD19+ target cells (FIG. 18A-C).

Consistent with previous studies of CD19 chimeric receptors, the level of cytokine production and proliferation in vitro in T cells expressing the CD28_4-IBB' CD19 chimeric receptor was inferior compared to the identical construct with CD28 alone, and superior to T cells expressing the 'long 4-IBB' CD19 chimeric receptor (FIG. 18B, C).

Groups of NSG mice with established Raji tumors were then treated with a high dose of T cells ($10\times10^6$) T cells expressing the 'long/CD28' CD19 chimeric receptor, the 'long/CD28_4-IBB' CD19 chimeric receptor, the 'short/CD28' CD19-chimeric receptor, and tEGFR alone. Tumor burden was measured by bioluminescence imaging and serial flow cytometric analyses of peripheral blood samples performed to determine the frequency of transferred T cells. Consistent with the results of our prior experiments using much lower doses of T cells, Raji tumors were completely eradicated in mice treated with T cells expressing the 'short/CD28' CD19-chimeric receptor. However, even with a 4-fold higher T cell dose, treatment with T cells expressing the 'long/CD28' CD19 chimeric receptor or the 'long/CD28_4-1BB' CD19 chimeric receptor did not provide a discernible antitumor effect (FIG. 18D,E).

Thus, increasing the chimeric receptor T cell dose and adding a 4-1BB costimulatory domain to CD19 chimeric receptors failed to overcome the negative impact of the longer spacer domain on antitumor activity in vivo. Thus, in this model, anti-tumor reactivity of CD19 chimeric receptors is dictated to a great extent by the length of the extracellular spacer domain, and not by the intracellular costimulatory signaling modules.

T Cells Modified with CD19 Chimeric Receptors that Possess Long Extracellular Spacers Undergo Activation Induced Cell Death In Vivo We sought to determine potential mechanisms underlying the inferior in vivo antitumor activity of T cells that express CD19 chimeric receptors with long spacer domains. Because lower numbers of transferred T cells modified to express CD19 chimeric receptors with long spacer domains were present in the blood, we considered the possibility that the T cells were not efficiently activated by tumor cells in vivo or conversely, that they underwent activation induced T cell death in vivo. Therefore, we labeled CD19 chimeric receptor modified and corresponding control T cells with CFSE and administered these T cells to tumor bearing NSG/Raji mice to examine activation, proliferation and survival of T cells modified with each of the CD19 chimeric receptor constructs at tumor sites in vivo (FIG. 19A). At the end of their in vitro expansion and immediately prior to CFSE labeling and infusion into NSG mice bearing established Raji tumors, T cells transduced with each of the CD19 chimeric receptors expressed low levels of the activation markers CD69 and CD25 (FIG. 19B).

Bone marrow was obtained from subgroups of mice 24 and 72 hours after the T cell infusion to examine the frequency, activation and proliferation of transferred T cells. At 24 hours, tumor cells (CD45+CD3−) were present in the bone marrow in all treatment groups and a large fraction of chimeric receptor T cells, but not control T cells, had upregulated CD69 and CD25. There was no measurable dilution of CFSE in the transferred chimeric receptor T cells. (FIG. 19C) Both CD69 and CD25 were expressed in a higher proportion of T cells modified with 'long spacer' CD19 chimeric receptors, suggesting these cells may have received a stronger stimulus compared to T cells with 'short spacer' CD19 chimeric receptors (FIG. C). Despite evidence of T cell activation at 24 hours there were significantly lower numbers of chimeric receptor T cells in the bone marrow of mice treated with T cells modified with the CD28 and 4-IBB 'long spacer' constructs compared to those modified with the CD28 and 4-IBB 'short spacer' constructs, or with the control tEGFR 10 vector (FIG. 19C, E).

At 72 hours after T cell transfer, T cells expressing the 'short/CD28' and 'short/4-1BB' CD19 chimeric receptors had increased 3 to >10 fold in frequency in the bone marrow and spleen, and had undergone several cell divisions (FIG. 19D,E). Control tEGFR+ T cells remained present in the bone marrow and spleen at 72 hours at a level similar to that observed at 24 hours, and had not divided as measured by CFSE dilution. By contrast, the numbers of T cells expressing the 'long/CD28' and 'long/4-IBB' CD19 chimeric receptors had not increased in the bone marrow and spleen. (FIG. 19D, E) Consistent with lower cell numbers, analysis of CFSE staining in viable PI− 'long/CD28' and 'long/4-IBB' CD19 chimeric receptor T cells demonstrated these cells had undergone a much lower number of cell divisions compared with 'short/CD28' and 'short/4-IBB' CD19 chimeric receptor T cells. (FIG. 19D) When the flow data was analyzed to include PI+ T cells, we detected a much higher frequency of PI+ CD3+ T cells in bone marrow and spleen of mice that received CD19 chimeric receptor T cells with 'long spacer' domains, demonstrating that a significant proportion of T cells, despite being activated by tumor in vivo had undergone cell death (FIG. 19F). Consistent with the bioluminescence imaging, CD45+CD3− Raji tumor cells were present in greater numbers in the bone marrow of mice treated with T cells expressing CD19 chimeric receptors with long spacer domains or expressing tEGFR only compared to mice treated with CD19 chimeric receptors with short spacer domains (FIG. 19D,E, G).

Collectively, the data provides evidence that CD19 chimeric receptors with long extracellular spacer domain, despite mediating equivalent or superior effector function in vitro and recognizing tumor in vivo, induce a high level of activation induced cell death in vivo and fail to eradicate established lymphoma.

Discussion

Chimeric receptors are artificial receptors that include an extracellular antigen-binding scFv, a spacer domain that provides separation of the scFv from the cell membrane and an intracellular signaling module that mediates T cell activation. Chimeric receptors that contain a scFv derived from the CD19-specific FMC63 mAb studied here, have advanced to testing in clinical trials in patients with B-cell malignancies. Antitumor activity and T cell persistence have varied substantially in different trials. Each of these clinical trials differed in potentially critical variables, including different gene transfer vectors, cell culture methodologies, and conditioning regimens prior to CD19 chimeric receptor T cell transfer.

We examined the possibility that the extracellular spacer domain of CD19 chimeric receptors may be an important determinant of anti-tumor activity in vivo, independent of the costimulatory signaling provided by the chimeric receptor. We derived spacer domains from IgG4-Fc, which enables high levels of chimeric receptor cell surface expression and is less likely to provoke recognition by innate immune cells compared to other IgG isotypes. We used the IgG4 'Hinge-CH2-CH3' in the design of the long (229 AA) spacer constructs and the IgG4 'Hinge' domain in our short (12 AA) spacer chimeric receptors. To compare the individual chimeric receptor constructs, we used purified (>90%) chimeric receptor positive $CD8^+$ $T_{CM}$-derived T cells to remove differences in the cellular composition and transduction frequency as a potential source of bias in the analysis of in vitro and in vivo function. $CD8^+$ $T_{CM}$ have been shown to have superior traits for adoptive immunotherapy, compared with other more prevalent T cell subsets in blood that persist poorly and are ineffective in tumor therapy. The CD19 chimeric receptor T cells were generated using a standardized culture protocol that is similar to that used to derive chimeric receptor T cells for clinical trials. Our data show that CD19 chimeric receptors with a short IgG4 'Hinge' spacer conferred potent anti-tumor reactivity in vitro and in vivo, whereas corresponding CD19 chimeric receptors with a long spacer of IgG4 'Hinge-CH2-CH3', despite equivalent or superior reactivity in vitro, failed to confer significant anti-tumor effects in murine lymphoma models. Surprisingly, the length of the spacer domain proved to be a decisive element for in vivo antitumor activity, and the lack of efficacy of the 'long spacer' chimeric receptor could not be overcome by increasing the T cell dose.

We also observed major differences in cytokine secretion and proliferation in vitro between T cells expressing CD19 chimeric receptors containing CD28 and 4-1BB costimulatory domains, with CD28 augmenting secretion of IFN-γ, IL-2, and TNF-α compared with 4-1BB. CD19 chimeric receptors that possessed a tandem CD28_4-1BB also produced higher levels of these cytokines compared to chimeric receptors encoding 4-1BB only. However, our data shows that these differences in in vitro function were not predictive of in vivo anti-tumor efficacy, since CD19 chimeric receptors with either CD28 or 4-1BB costimulatory domain and a short spacer were similarly effective at eradicating advanced established Raji tumors in NSG mice. In contrast, CD19 chimeric receptors with suboptimal spacer length and CD28, 4-1BB, or both costimulatory domains, despite conferring similar in vitro function as the identical chimeric receptor construct with a short spacer domain, lacked significant anti-tumor activity in vivo, demonstrating the contribution of spacer length to in vivo function of chimeric receptor T cells.

Our studies provide insight into the mechanism responsible for the lack of in vivo efficacy of CD19 chimeric receptors with long spacer domains. T cells expressing CD19 chimeric receptors with both long and short spacer domains could be detected in the bone marrow and spleen after adoptive transfer into NSG mice bearing established Raji lymphoma, and the majority were activated as demonstrated by upregulation of CD25 and CD69. However, T cells modified to express a CD19 chimeric receptor with a long spacer domain exhibited a steep decline in cell number, in contrast to the marked in vivo expansion of T cells expressing CD19 chimeric receptors with a short spacer domain. The decline in T cell number was a consequence of much higher levels of cell death in the first 72 hours after adoptive transfer compared with T cells with short spacer domains, and control T cells that did not express a CD19 chimeric receptor. Collectively, these data indicate that recognition of tumor cells in vivo resulted in death of T cells expressing CD19-chimeric receptors with long spacer domains. A similar mechanism may explain the short duration and low levels of T cell persistence in the clinical trials that employed long spacer CD19-chimeric receptors (14).

The studies reported here are the first to show that the spacer domains of CD19 chimeric receptors that lack intrinsic signaling properties have dramatic effects on in vivo antitumor activity independent of costimulatory signaling, and identify the importance of analyzing the optimal composition of this region in the design of chimeric receptors for clinical applications.

The foregoing is illustrative of the present invention, and is not to be construed as limiting thereof. The invention is defined by the following claims, with equivalents of the claims to be included therein. All references and documents referred to herein are hereby incorporated by reference.

TABLE 1

| Sequence of anti-CD19 short spacer chimeric receptor |
|---|
| GMCSFRss-CD19scFv-IgG4hinge-CD28tm-41BB-Zeta-T2A-EGFRt<br>***Atg*ctgctgctggtgaccagcctgctgctgtgcgagctgccccaccccgcctttctgctgatcccc** (GMCSFRss)<br>(SEQ ID NO: 2) |
| **Gacatccagatgacccagaccacctccagcctgagcgccagcctgggcgaccgggtgaccatcagctgccgggccagcca<br>ggacatcagcaagtacctgaactggtatcagcagaagcccgacggcaccgtcaagctgctgatctaccacaccagccggctg<br>cacagcggcgtgcccagccggtttagcggcagcggctccggcaccgactacagcctgaccatctccaacctggaacaggaa<br>gatatcgccacctacttttgccagcagggcaacacactgccctacacctttggcggcggaacaaagctggaaatcaccggca<br>gcacctccggcagcggcaagcctggcagcggcgagggcagcaccaagggcgaggtgaagctgcaggaaagcggccctgg<br>cctggtggccccagccagagcctgagcgtgacctgcaccgtgagcggcgtgagcctgcccgactacggcgtgagctggatc<br>cggcagccccccaggaagggcctggaatggctgggcgtgatctggggcagcgagaccacctactacaacagcgccctgaa<br>gagccggctgaccatcatcaaggacaacagcaagagccaggtgttcctgaagatgaacagcctgcagaccgacgacaccg<br>ccatctactactgcgccaagcactactactacggcggcagctacgccatggactactggggccagggcaccagcgtgaccgt<br>gagcagc** (CD19scFv) (SEQ ID NO: 3) |
| **Gaatctaagtacggaccgccctgccccccttgccct** (IgG4hinge) (SEQ ID NO: 4) |
| **Atgttctgggtgctggtggtggtcggaggcgtgctggcctgctacagcctgctggtcaccgtggccttcatcatcttttgggtg**<br>(CD28tm-)(SEQ ID NO: 5) |
| **Aaacggggcagaaagaaactcctgtatatattcaaacaaccatttatgagaccagtacaaactactcaagaggaagatggc<br>tgtagctgccgatttccagaagaagaagaaggaggatgtgaactg** (41BB) (SEQ ID NO: 6) |
| **Cgggtgaagttcagcagaagcgccgacgcccctgcctaccagcagggccagaatcagctgtacaacgagctgaacctggg<br>cagaagggaagagtacgacgtcctggataagcggagaggccgggaccctgagatgggcggcaagcctcggcggaagaac<br>cccaggaaggcctgtataacgaactgcagaaagacaagatggccgaggcctacagcgagatcggcatgaagggcgagc<br>ggaggcggggcaagggccacgacggcctgtatcagggcctgtccaccgccaccaaggatacctacgacgccctgcacatgc<br>aggccctgcccccaagg** (CD3Zeta)-(SEQ ID NO: 7) |
| **Ctcgagggcggcggagagggcagaggaagtcttctaacatgcggtgacgtggaggagaatcccggccctagg** (T2A)<br>(SEQ ID NO: 9) |
| **Atgcttctcctggtgacaagccttctgctctgtgagttaccacacccagcattcctcctgatcccacgcaaagtgtgtaacgga<br>ataggtattggtgaatttaaagactcactctccataaatgctacgaatattaaacacttcaaaaactgcacctccatcagtggc<br>gatctccacatcctgccggtggcatttaggggtgactccttcacacatactcctcctctggatccacaggaactggatattctga<br>aaaccgtaaaggaaatcacagggtttttgctgattcaggcttggcctgaaaacaggacggacctccatgcctttgagaaccta<br>gaaatcatacgcggcaggaccaagcaacatggtcagttttctcttgcagtcgtcagcctgaacataacatccttgggattacgc<br>tccctcaaggagataagtgatggagatgtgataatttcaggaaacaaaaatttgtgctatgcaaatacaataaactggaaaa<br>aactgtttgggacctccggtcagaaaaccaaaattataagcaacagaggtgaaaacagctgcaaggccacaggccaggtct<br>gccatgccttgtgctcccccgagggctgctggggcccggagcccagggactgcgtctcttgccggaatgtcagccgaggcag<br>ggaatgcgtggacaagtgcaaccttctggagggtgagccaagggagtttgtggagaactctgagtgcatacagtgccaccca<br>gagtgcctgcctcaggccatgaacatcacctgcacaggacggggaccagacaactgtatccagtgtgcccactacattgacg<br>gcccccactgcgtcaagacctgcccggcaggagtcatgggagaaaacaacaccctggtctggaagtacgcagacgccggcc<br>atgtgtgccacctgtgccatccaaactgcacctacggatgcactgggccaggtcttgaaggctgtccaacgaatggcctaag<br>atcccgtccatcgccactgggatggtgggggccctcctcttgctgctggtggtggccctggggatcggcctcttcatg*tga*** <br>(EGFRt) (SEQ ID NO: 8) |

TABLE 2

```
        GMCSFRss
DNA: ATGCTGCTGCTGGTGACCAGCCTGCTGCTGTGCGAGCTGCCCCACCCCGCC
AA:  M  L  L  L  V  T  S  L  L  L  C  E  L  P  H  P  A

                     CD19scFv
DNA: TTTCTGCTGATCCCC:GACATCCAGATGACCCAGACCACCTCCAGCCTGAGC
AA:  F  L  L  I  P   D  I  Q  M  T  Q  T  T  S  S  L  S

DNA: GCCAGCCTGGGCGACCGGGTGACCATCAGCTGCCGGGCCAGCCAGGACATC
AA:  A  S  L  G  D  R  V  T  I  S  C  R  A  S  Q  D  I

DNA: AGCAAGTACCTGAACTGGTATCAGCAGAAGCCCGACGGCACCGTCAAGCTG
AA:  S  K  Y  L  N  W  Y  Q  Q  K  P  D  G  T  V  K  L

DNA: CTGATCTACCACACCAGCCGGCTGCACAGCGGCGTGCCCAGCCGGTTTAGC
AA:  L  I  Y  H  T  S  R  L  H  S  G  V  P  S  R  F  S

DNA: GGCAGCGGCTCCGGCACCGACTACAGCCTGACCATCTCCAACCTGGAACAG
AA:  G  S  G  S  G  T  D  Y  S  L  T  I  S  N  L  E  Q

DNA: GAAGATATCGCCACCTACTTTTGCCAGCAGGGCAACACACTGCCCTACACC
AA:  E  D  I  A  T  Y  F  C  Q  Q  G  N  T  L  P  Y  T

DNA: TTTGGCGGCGGAACAAAGCTGGAAATCACCGGCAGCACCTCCGGCAGCGGC
AA:  F  G  G  G  T  K  L  E  I  T  G  S  T  S  G  S  G
```

TABLE 2-continued

| | |
|---|---|
| DNA: | AAGCCTGGCAGCGGCGAGGGCAGCACCAAGGGCGAGGTGAAGCTGCAGGAA |
| AA: | K P G S G E G S T K G E V K L Q E |
| DNA: | AGCGGCCCTGGCCTGGTGGCCCCCAGCCAGAGCCTGAGCGTGACCTGCACC |
| AA: | S G P G L V A P S Q S L S V T C T |
| DNA: | GTGAGCGGCGTGAGCCTGCCCGACTACGGCGTGAGCTGGATCCGGCAGCCC |
| AA: | V S G V S L P D Y G V S W I R Q P |
| DNA: | CCCAGGAAGGGCCTGGAATGGCTGGGCGTGATCTGGGGCAGCGAGACCACC |
| AA: | P R K G L E W L G V I W G S E T T |
| DNA: | TACTACAACAGCGCCCTGAAGAGCCGGCTGACCATCATCAAGGACAACAGC |
| AA: | Y Y N S A L K S R L T I I K D N S |
| DNA: | AAGAGCCAGGTGTTCCTGAAGATGAACAGCCTGCAGACCGACGACACCGCC |
| AA: | K S Q V F L K M N S L Q T D D T A |
| DNA: | ATCTACTACTGCGCCAAGCACTACTACTACGGCGGCAGCTACGCCATGGAC |
| AA: | I Y Y C A K H Y Y Y G G S Y A M D |
| | IgG4hinge |
| DNA: | TACTGGGGCCAGGGCACCAGCGTGACCGTGAGCAGC:GAGAGCAAGTACGGA |
| AA: | Y W G Q G T S V T V S S E S K Y G |
| | CD28tm |
| DNA: | CCGCCCTGCCCCCCTTGCCCT:ATGTTCTGGGTGCTGGTGGTGGTCGGAGGC |
| AA: | P P C P P C P M F W V L V V V G G |
| DNA: | GTGCTGGCCTGCTACAGCCTGCTGGTCACCGTGGCCTTCATCATCTTTTGG |
| AA: | V L A C Y S L L V T V A F I I F W |
| | 41BB |
| DNA: | GTG:AAACGGGGCAGAAAGAAACTCCTGTATATATTCAAACAACCATTTATG |
| AA: | V K R G R K K L L Y I F K Q P F M |
| DNA: | AGACCAGTACAAACTACTCAAGAGGAAGATGGCTGTAGCTGCCGATTTCCA |
| AA: | R P V Q T T Q E E D G C S C R F P |
| | cD3Zeta |
| DNA: | GAAGAAGAAGAAGGAGGATGTGAACTGCGGGTGAAG:TTCAGCAGAAGCGCC |
| AA: | E E E E G G C E L R V K F S R S A |
| DNA: | GACGCCCCTGCCTACCAGCAGGGCCAGAATCAGCTGTACAACGAGCTGAAC |
| AA: | D A P A Y Q Q G Q N Q L Y N E L N |
| DNA: | CTGGGCAGAAGGGAAGAGTACGACGTCCTGGATAAGCGGAGAGGCCGGGAC |
| AA: | L G R R E E Y D V L D K R R G R D |
| DNA: | CCTGAGATGGGCGGCAAGCCTCGGCGGAAGAACCCCCAGGAAGGCCTGTAT |
| AA: | P E M G G K P R R K N P Q E G L Y |
| DNA: | AACGAACTGCAGAAAGACAAGATGGCCGAGGCCTACAGCGAGATCGGCATG |
| AA: | N E L Q K D K M A E A Y S E I G M |
| DNA: | AAGGGCGAGCGGAGGCGGGGCAAGGGCCACGACGGCCTGTATCAGGGCCTG |
| AA: | K G E R R R G K G H D G L Y Q G L |
| DNA: | TCCACCGCCACCAAGGATACCTACGACGCCCTGCACATGCAGGCCCTGCCC |
| AA: | S T A T K D T Y D A L H M Q A L P |
| | T2A |
| DNA: | CCAAGG:CTCGAGGGCGGCGGAGAGGGCAGAGGAAGTCTTCTAACATGCGGT |
| AA: | P R L E G G G E G R G S L L T C G |
| | **EGFRt** |
| DNA: | GACGTGGAGGAGAATCCCGGCCCTAGG:**ATGCTTCTCCTGGTGACAAGCCTT** |
| AA: | D V E E N P G P R M L L L V T S L |
| DNA: | **CTGCTCTGTGAGTTACCACACCCAGCATTCCTCCTGATCCCACGCAAAGTG** |
| AA: | L L C E L P H P A F L L I P R K V |
| DNA: | **TGTAACGGAATAGGTATTGGTGAATTTAAAGACTCACTCTCCATAAATGCT** |
| AA: | C N G I G I G E F K D S L S I N A |
| DNA: | **ACGAATATTAAACACTTCAAAAACTGCACCTCCATCAGTGGCGATCTCCAC** |
| AA: | T N I K H F K N C T S I S G D L H |
| DNA: | **ATCCTGCCGGTGGCATTTAGGGGTGACTCCTTCACACATACTCCTCCTCTG** |
| AA: | I L P V A F R G D S F T H T P P L |

TABLE 2-continued

DNA: GATCCACAGGAACTGGATATTCTGAAAACCGTAAAGGAAATCACAGGGTTT

AA: D P Q E L D I L K T V K E I T G F

DNA: TTGCTGATTCAGGCTTGGCCTGAAAACAGGACGGACCTCCATGCCTTTGAG

AA: L L I Q A W P E N R T D L H A F E

DNA: AACCTAGAAATCATACGCGGCAGGACCAAGCAACATGGTCAGTTTTCTCTT

AA: N L E I I R G R T K Q H G Q F S L

DNA: GCAGTCGTCAGCCTGAACATAACATCCTTGGGATTACGCTCCCTCAAGGAG

AA: A V V S L N I T S L G L R S L K E

DNA: ATAAGTGATGGAGATGTGATAATTTCAGGAAACAAAAATTTGTGCTATGCA

AA: I S D G D V I I S G N K N L C Y A

DNA: AATACAATAAACTGGAAAAAACTGTTTGGGACCTCCGGTCAGAAAACCAAA

AA: N T I N W K K L F G T S G Q K T K

DNA: ATTATAAGCAACAGAGGTGAAAACAGCTGCAAGGCCACAGGCCAGGTCTGC

AA: I I S N R G E N S C K A T G Q V C

DNA: CATGCCTTGTGCTCCCCCGAGGGCTGCTGGGGCCCGGAGCCCAGGGACTGC

AA: H A L C S P E G C W G P E P R D C

DNA: GTCTCTTGCCGGAATGTCAGCCGAGGCAGGGAATGCGTGGACAAGTGCAAC

AA: V S C R N V S R G R E C V D K C N

DNA: CTTCTGGAGGGTGAGCCAAGGGAGTTTGTGGAGAACTCTGAGTGCATACAG

AA: L L E G E P R E F V E N S E C I Q

DNA: TGCCACCCAGAGTGCCTGCCTCAGGCCATGAACATCACCTGCACAGGACGG

AA: C H P E C L P Q A M N I T C T G R

DNA: GGACCAGACAACTGTATCCAGTGTGCCCACTACATTGACGGCCCCCACTGC

AA: G P D N C I Q C A H Y I D G P H C

DNA: GTCAAGACCTGCCCGGCAGGAGTCATGGGAGAAAACAACACCCTGGTCTGG

AA: V K T C P A G V M G E N N T L V W

DNA: AAGTACGCAGACGCCGGCCATGTGTGCCACCTGTGCCATCCAAACTGCACC

AA: K Y A D A G H V C H L C H P N C T

DNA: TACGGATGCACTGGGCCAGGTCTTGAAGGCTGTCCAACGAATGGGCCTAAG

AA: Y G C T G P G L E G C P T N G P K

DNA: ATCCCGTCCATCGCCACTGGGATGGTGGGGGCCCTCCTCTTGCTGCTGGTG

AA: I P S I A T G M V G A L L L L L V

DNA: **GTGGCCCTGGGGATCGGCCTCTTCATG*<u>TGA</u>*** (SEQ ID NO: 10)

AA: V A L G I G L F M * (SEQ ID NO: 11)

TABLE 3

| ZXR-014 Nucleotide and amino acid sequences (map of sections) | |
|---|---|
| GMCSFRss: | nt2084-2149 |
| CD19scFv: | nt2150-2884 |
| Igg4Hinge: | nt2885-2920 |
| CD28tm: | nt2921-3004 |
| 41BB: | nt3005-3130 |
| Zeta: | nt3131-3466 |
| T2A: | nt3467-3538 |
| EGFRt: | nt3539-4612 |

Primers for sequencing:

| Oligo name | Sequence | Region |
|---|---|---|
| oJ02649 | ATCAAAAGAATAGACCGAGATAGGGT | pre-U5(SEQ ID NO: 22) |
| oJ02648 | CCGTACCTTTAAGACCAATGACTTAC | delU3(SEQ ID NO: 23) |
| oJ02650 | TTGAGAGTTTTCGCCCCG | mid-Ampr(SEQ ID NO: 24) |
| oJ02651 | AATAGACAGATCGCTGAGATAGGT | post-Ampr(SEQ ID NO: 25) |

TABLE 3-continued

| | | |
|---|---|---|
| oJ02652 | CAGGTATCCGGTAAGCGG | CoE1 ori(SEQ ID NO: 26) |
| oJ02653 | CGACCAGCAACCATAGTCC | SV40(SEQ ID NO: 27) |
| oJ02654 | TAGCGGTTTGACTCACGG | CMV(SEQ ID NO: 28) |
| oJ02655 | GCAGGGAGCTAGAACGATTC | psi(SEQ ID NO: 29) |
| oJ02656 | ATTGTCTGGTATAGTGCAGCAG | RRE(SEQ ID NO: 30) |
| oJ02657 | TCGCAACGGGTTTGCC | EF1p(SEQ ID NO: 31) |
| oJ02658 | AGGAAGATATCGCCACCTACT | CD19Rop(SEQ ID NO: 32) |
| oJ02601 | CGGGTGAAGTTCAGCAGAAG | Zeta(SEQ ID NO: 33) |
| oJ02735 | ACTGTGTTTGCTGACGCAAC | WPRE(SEQ ID NO: 34) |
| oJ02715 | ATGCTTCTCCTGGTGACAAG | EGFRt(SEQ ID NO: 35) |

TABLE 4

| UniprotP0861 IgG4-Fc (SEQ ID NO: 13) | | | |
|---|---|---|---|
| 10 | 20 | 30 | 40 |
| ASTKGPSVFP | LAPCSRSTSE | STAALGCLVK | DYFPEPVTVS |
| 50 | 60 | 70 | 80 |
| WNSGALTSGV | HTFPAVLQSS | GLYSLSSVVT | VPSSSLGTKT |
| 90 | 100 | 110 | 120 |
| YTCNVDHKPS | NTKVDKRVES | KYGPPCPSCP | APEFLGGPSV |
| 130 | 140 | 150 | 160 |
| FLFPPKPKDT | LMISRTPEVT | CVVVDVSQED | PEVQFNWYVD |
| 170 | 180 | 190 | 200 |
| GVEVHNAKTK | PREEQFNSTY | RVVSVLTVLH | QDWLNGKEYK |
| 210 | 220 | 230 | 240 |
| CKVSNKGLPS | SIEKTISKAK | GQPREPQVYT | LPPSQEEMTK |
| 250 | 260 | 270 | 280 |
| NQVSLTCLVK | GFYPSDIAVE | WESNGQPENN | YKTTPPVLDS |
| 290 | 300 | 310 | 320 |
| DGSFFLYSRL | TVDKSRWQEG | NVFSCSVMHE | ALHNHYTQKS |
| LSLSLGK | | | |

1-98 CH1
99-110 Hinge
111-220 CH2
221-327 CH3
Position 108 S→P

TABLE 5

| Uniprot P10747 CD28 (SEQ ID NO: 14) | | | |
|---|---|---|---|
| 10 | 20 | 30 | 40 |
| MLRLLLALNL | FPSIQVTGNK | ILVKQSPMLV | AYDNAVNLSC |
| 50 | 60 | 70 | 80 |
| KYSYNLFSRE | FRASLHKGLD | SAVEVCVVYG | NYSQQLQVYS |
| 90 | 100 | 110 | 120 |
| KTGFNCDGKL | GNESVTFYLQ | NLYVNQTDIY | FCKIEVMYPP |
| 130 | 140 | 150 | 160 |
| PYLDNEKSNG | TIIHVKGKHL | CPSPLFPGPS | KPFWVLVVVG |
| 170 | 180 | 190 | 200 |
| GVLACYSLLV | TVAFIIFWVR | SKRSR**LL**HSD | YMNMTPRRPG |

TABLE 5-continued

| Uniprot P10747 CD28 (SEQ ID NO: 14) | |
|---|---|
| 210 | 220 |
| PTRKHYQPYA | PPRDFAAYRS |

1-18 signal peptide
19-152 extracellular domain
153-179 transmembrane domain
180-220 intracellular domain
Position 186-187 LL→GG

TABLE 6

| Uniprot Q07011 4-1BB (SEQ ID NO: 15) | | | |
|---|---|---|---|
| 10 | 20 | 30 | 40 |
| MGNSCYNIVA | TLLLVLNFER | TRSLQDPCSN | CPAGTFCDNN |
| 50 | 60 | 70 | 80 |
| RNQICSPCPP | NSFSSAGGQR | TCDICRQCKG | VFRTRKECSS |
| 90 | 100 | 110 | 120 |
| TSNAECDCTP | GFHCLGAGCS | MCEQDCKQGQ | ELTKKGCKDC |
| 130 | 140 | 150 | 160 |
| CFGTFNDQKR | GICRPWTNCS | LDGKSVLVNG | TKERDVVCGP |
| 170 | 180 | 190 | 200 |
| SPADLSPGAS | SVTPPAPARE | PGHSPQIISF | FLALTSTALL |
| 210 | 220 | 230 | 240 |
| FLLFFLTLRF | SVVKRGRKKL | LYIFKQPFMR | PVQTTQEEDG |
| 250 | | | |
| CSCRFPEEEE | GGCEL | | |

1-23 signal peptide
24-186 extracellular domain
187-213 transmembrane domain
214-255 intracellular domain

TABLE 7

| Uniprot P20963 human CD3ζ isoform 3 (SEQ ID NO: 16) |
|---|

```
        10         20         30         40
MKWKALFTAA ILQAQLPITE AQSFGLLDPK LCYLLDGILF

        50         60         70         80
IYGVILTALF LRVKFSRSAD APAYQQGQNQ LYNELNLGRR

        90        100        110        120
EEYDVLDKRR GRDPEMGGKP QRRKNPQEGL YNELQKDKMA
```

TABLE 7-continued

| Uniprot P20963 human CD3ζ isoform 3 (SEQ ID NO: 16) |
|---|

```
       130        140        150        160
EAYSEIGMKG ERRRGKGHDG LYQGLSTATK DTYDALHMQA

LPPR
```

1-21 signal peptide
22-30 extracellular
31-51 transmembrane
52-164 intracellular domain
61-89 ITAM1
100-128 ITAM2
131-159 ITAM3

TABLE 8

| Exemplary Hinge region Sequences | | |
|---|---|---|
| Human IgG1 | EPKSCDKTHTCPPCP | (SEQ ID NO: 17) |
| Human IgG2 | ERKCCVECPPCP | (SEQ ID NO: 18) |
| Human IgG3 | ELKTPLGDTHTCPRCP $(EPKSCDTPPPCPRCP)_3$ | (SEQ ID NO: 19) |
| Human IgG4 | ESKYGPPCPSCP | (SEQ ID NO: 20) |
| Modified Human IgG4 | ESKYGPPCPPCP | (SEQ ID NO: 21) |
| Modified Human IgG4 | YGPPCPPCP | (SEQ ID NO: 51) |
| Modified Human IgG4 | KYGPPCPPCP | (SEQ ID NO: 52) |
| Modified Human IgG4 | EVVKYGPPCPPCP | (SEQ ID NO: 53) |

TABLE 9

| R12 long spacer CAR: PJ_R12-CH2-CH3-41BB-Z-T2A-tEGFR (SEQ ID NO: 37) |
|---|

```
GTTAGACCAGATCTGAGCCTGGGAGCTCTCTGGCTAACTAGGGAACCCACTGCTTAAGC
CTCAATAAAGCTTGCCTTGAGTGCTTCAAGTAGTGTGTGCCCGTCTGTTGTGTGACTCTG
GTAACTAGAGATCCCTCAGACCCTTTTAGTCAGTGTGGAAAATCTCTAGCAGTGGCGCCC
GAACAGGGACTTGAAAGCGAAAGGGAAACCAGAGGAGCTCTCTCGACGCAGGACTCGG
CTTGCTGAAGCGCGCACGGCAAGAGGCGAGGGGCGGCGACTGGTGAGTACGCCAAAAA
TTTTGACTAGCGGAGGCTAGAAGGAGAGAGATGGGTGCGAGAGCGTCAGTATTAAGCGG
GGGAGAATTAGATCGATGGGAAAAAATTCGGTTAAGGCCAGGGGGAAAGAAAAAATAT
AAATTAAAACATATAGTATGGGCAAGCAGGGAGCTAGAACGATTCGCAGTTAATCCTGG
CCTGTTAGAAACATCAGAAGGCTGTAGACAAATACTGGGACAGCTACAACCATCCCTTC
AGACAGGATCAGAAGAACTTAGATCATTATATAATACAGTAGCAACCCTCTATTGTGTG
CATCAAAGGATAGAGATAAAAGACACCAAGGAAGCTTTAGACAAGATAGAGGAAGAGC
AAAACAAAAGTAAGAAAAAAGCACAGCAAGCAGCAGCTGACACAGGACACAGCAATCA
GGTCAGCCAAAATTACCCTATAGTGCAGAACATCCAGGGGCAAATGGTACATCAGGCCA
TATCACCTAGAACTTTAAATGCATGGGTAAAAGTAGTAGAAGAGAAGGCTTTCAGCCCA
GAAGTGATACCCATGTTTTCAGCATTATCAGAAGGAGCCACCCCACAAGATTTAAACAC
CATGCTAAACACAGTGGGGGGACATCAAGCAGCCATGCAAATGTTAAAAGAGACCATCA
ATGAGGAAGCTGCAGGCAAAGAGAAGAGTGGTGCAGAGAGAAAAAAGAGCAGTGGGA
ATAGGAGCTTTGTTCCTTGGGTTCTTGGGAGCAGCAGGAAGCACTATGGGCGCAGCGTC
AATGACGCTGACGGTACAGGCCAGACAATTATTGTCTGGTATAGTGCAGCAGCAGAACA
ATTTGCTGAGGGCTATTGAGGCGCAACAGCATCTGTTGCAACTCACAGTCTGGGGCATCA
AGCAGCTCCAGGCAAGAATCCTGGCTGTGGAAAGATACCTAAAGGATCAACAGCTCCTG
GGGATTTGGGGTTGCTCTGGAAAACTCATTTGCACCACTGCTGTGCCTTGGATCTACAAA
TGGCAGTATTCATCCACAATTTTAAAAGAAAAGGGGGGATTGGGGGGTACAGTGCAGGG
GAAAGAATAGTAGACATAATAGCAACAGACATACAAACTAAAGAATTACAAAAACAAA
TTACAAAAATTCAAAATTTTCGGGTTTATTACAGGGACAGCAGAGATCCAGTTTGGGGAT
CAATTGCATGAAGAATCTGCTTAGGGTTAGGCGTTTTGCGCTGCTTCGCGAGGATCTGCG
ATCGCTCCGGTGCCCGTCAGTGGGCAGAGCGCACATCGCCCACAGTCCCCGAGAAGTTG
GGGGGAGGGGTCGGCAATTGAACCGGTGCCTAGAGAAGGTGGCGCGGGGTAAACTGGG
AAAGTGATGTCGTGTACTGGCTCCGCCTTTTTCCCGAGGGTGGGGGAGAACCGTATATAA
GTGCAGTAGTCGCCGTGAACGTTCTTTTTCGCAACGGGTTTGCCGCCAGAACACAGCTGA
AGCTTCGAGGGGCTCGCATCTCTCCTTCACGCGCCCGCCGCCCTACCTGAGGCCGCCATC
CACGCCGGTTGAGTCGCGTTCTGCCGCCTCCCGCCTGTGGTGCCTCCTGAACTGCGTCCG
CCGTCTAGGTAAGTTTAAAGCTCAGGTCGAGACCGGGCCTTTGTCCGGCGCTCCCTTGGA
```

TABLE 9-continued

| R12 long spacer CAR: PJ_R12-CH2-CH3-41BB-Z-T2A-tEGFR (SEQ ID NO: 37) |
|---|

GCCTACCTAGACTCAGCCGGCTCTCCACGCTTTGCCTGACCCTGCTTGCTCAACTCTACGT
CTTTGTTTCGTTTTCTGTTCTGCGCCGTTACAGATCCAAGCTGTGACCGGCGCCTACG

[illegible]GAATTCCTCGAGGCCACCATGCTGCTGCTGGTGACAAGCCTGCTGCTGTGCGA

GCTGCCCCACCCCGCCTTTCTGCTGATCCCCCAGGAACAGCTCGTCGAAAGCGGCGGCA
GACTGGTGACACCTGGCGGCAGCCTGACCCTGAGCTGCAAGGCCAGCGGCTTCGACTTC
AGCGCCTACTACATGAGCTGGGTCCGCCAGGCCCCTGGCAAGGGACTGGAATGGATCGC
CACCATCTACCCCAGCAGCGGCAAGACCTACTACGCCACCTGGGTGAACGGACGGTTCA
CCATCTCCAGCGACAACGCCCAGAACACCGTGGACCTGCAGATGAACAGCCTGACAGCC
GCCGACCGGGCCACCTACTTTTGCGCCAGAGACAGCTACGCCGACGACGGCGCCCTGTT
CAACATCTGGGGCCCTGGCACCCTGGTGACAATCTCTAGCGGCGGAGGCGGATCTGGTG
GCGGAGGAAGTGGCGGCGGAGGATCTGAGCTGGTGCTGACCCAGAGCCCCTCTGTGTCT
GCTGCCCTGGGAAGCCCTGCCAAGATCACCTGTACCCTGAGCAGCGCCCACAAGACCGA
CACCATCGACTGGTATCAGCAGCTGCAGGGCGAGGCCCCCAGATACCTGATGCAGGTGC
AGAGCGACGGCAGCTACACCAAGAGGCCAGGCGTGCCCGACCGGTTCAGCGGATCTAGC
TCTGGCGCCGACCGCTACCTGATCATCCCCAGCGTGCAGGCCGATGACGAGGCCGATTA
CTACTGTGGCGCCGACTACATCGGCGGCTACGTGTTCGGCGGAGGCACCCAGCTGACCG
TGACCGGCGAGTCTAAG

IgG4 spacer

TACGGACCGCCCTGCCCCCCTTGCCCT

CH2
GCCCCCGAGTTCCTGGGCGGACCCAGCGTGTTCCTGTTCCCCCCCAAGCCCAAGGACACC
CTGATGATCAGCCGGACCCCCGAGGTGACCTGCGTGGTGGTGGACGTGAGCCAGGAAGA
TCCCGAGGTCCAGTTCAATTGGTACGTGGACGGCGTGGAAGTGCACAACGCCAAGACCA
AGCCCAGAGAGGAACAGTTCAACAGCACCTACCGGGTGGTGTCTGTGCTGACCGTGCTG
CACCAGGACTGGCTGAACGGCAAAGAATACAAGTGCAAGGTGTCCAACAAGGGCCTGC
CCAGCAGCATCGAAAAGACCATCAGCAAGGCCAAG

CH3
GGCCAGCCTCGCGAGCCCCAGGTGTACACCCTGCCTCCCTCCCAGGAAGAGATGACCAA
GAACCAGGTGTCCCTGACCTGCCTGGTGAAGGGCTTCTACCCCAGCGACATCGCCGTGG
AGTGGGAGAGCAACGGCCAGCCTGAGAACAACTACAAGACCACCCCTCCCGTGCTGGAC
AGCGACGGCAGCTTCTTCCTGTACAGCCGGCTGACCGTGGACAAGAGCCGGTGGCAGGA
AGGCAACGTCTTTAGCTGCAGCGTGATGCACGAGGCCCTGCACAACCACTACACCCAGA
AGAGCCTGAGCCTGTCCCTGGGCAAG 4-1BB
ATGTTCTGGGTGCTGGTGGTGGTGGGCGGGGTGCTGGCCTGCTACAGCCTGCTGGTGACA
GTGGCCTTCATCATCTTTTGGGTGAAACGGGGCAGAAAGAAACTCCTGTATATATTCAAA
CAACCATTTATGAGACCAGTACAAACTACTCAAGAGGAAGATGGCTGTAGCTGCCGATT
TCCAGAAGAAGAAGAAGGAGGATGTGAACTG

CD3 zeta
CGGGTGAAGTTCAGCAGAAGCGCCGACGCCCCTGCCTACCAGCAGGGCCAGAATCAGCT
GTACAACGAGCTGAACCTGGGCAGAAGGGAAGAGTACGACGTCCTGGATAAGCGGAGA
GGCCGGGACCCTGAGATGGGCGGCAAGCCTCGGCGGAAGAACCCCCAGGAAGGCCTGT
ATAACGAACTGCAGAAAGACAAGATGGCCGAGGCCTACAGCGAGATCGGCATGAAGGG
CGAGCGGAGGCGGGGCAAGGGCCACGACGGCCTGTATCAGGGCCTGTCCACCGCCACCA
AGGATACCTACGACGCCCTGCACATGCAGGCCCTGCCCCCAAGG

T2A

CTCGAGGGCGGCGGAGAGGGCAGAGGAAGTCTTCTAACATGCGGTGACGTGGAGGAGA

ATCCCGGCCCTAGG tEGFR
ATGCTTCTCCTGGTGACAAGCCTTCTGCTCTGTGAGTTACCACACCCAGCATTCCTCCTGA
TCCCACGCAAAGTGTGTAACGGAATAGGTATTGGTGAATTTAAAGACTCACTCTCCATAA
ATGCTACGAATATTAAACACTTCAAAAACTGCACCTCCATCAGTGGCGATCTCCACATCC

TGCCGGTGGCATTTAGGGGTGACTCCTTCACACATACTCCTCCTCTGGATCCACAGGAAC

TGGATATTCTGAAAACCGTAAAGGAAATCACAGGGTTTTTGCTGATTCAGGCTTGGCCTG
AAAACAGGACGGACCTCCATGCCTTTGAGAACCTAGAAATCATACGCGGCAGGACCAAG
CAACATGGTCAGTTTTCTCTTGCAGTCGTCAGCCTGAACATAACATCCTTGGGATTACGC
TCCCTCAAGGAGATAAGTGATGGAGATGTGATAATTTCAGGAAACAAAAATTTGTGCTA
TGCAAATACAATAAACTGGAAAAAACTGTTTGGGACCTCCGGTCAGAAAACCAAAATTA
TAAGCAACAGAGGTGAAAACAGCTGCAAGGCCACAGGCCAGGTCTGCCATGCCTTGTGC
TCCCCCGAGGGCTGCTGGGGCCCGGAGCCCAGGGACTGCGTCTCTTGCCGGAATGTCAG

TABLE 9-continued

| R12 long spacer CAR: PJ_R12-CH2-CH3-41BB-Z-T2A-tEGFR (SEQ ID NO: 37) |
|---|

CCGAGGCAGGGAATGCGTGGACAAGTGCAACCTTCTGGAGGGTGAGCCAAGGGAGTTTG
TGGAGAACTCTGAGTGCATACAGTGCCACCCAGAGTGCCTGCCTCAGGCCATGAACATC
ACCTGCACAGGACGGGGACCAGACAACTGTATCCAGTGTGCCCACTACATTGACGGCCC
CCACTGCGTCAAGACCTGCCCGGCAGGAGTCATGGGAGAAAACAACACCCTGGTCTGGA
AGTACGCAGACGCCGGCCATGTGTGCCACCTGTGCCATCCAAACTGCACCTACGGATGC
ACTGGGCCAGGTCTTGAAGGCTGTCCAACGAATGGGCCTAAGATCCCGTCCATCGCCAC
TGGGATGGTGGGGGCCCTCCTCTTGCTGCTGGTGGTGGCCCTGGGGATCGGCCTCTTCAT

GTGAGCGGCCGCTCTAGACCCGGGCTGCAGGAATTCGATATCAAGCTTATCGATAATCA

ACCTCTGGATTACAAAATTTGTGAAAGATTGACTGGTATTCTTAACTATGTTGCTCCTTTT
ACGCTATGTGGATACGCTGCTTTAATGCCTTTGTATCATGCTATTGCTTCCCGTATGGCTT
TCATTTTCTCCTCCTTGTATAAATCCTGGTTGCTGTCTCTTTATGAGGAGTTGTGGCCCGT
TGTCAGGCAACGTGGCGTGGTGTGCACTGTGTTTGCTGACGCAACCCCCACTGGTTGGGG
CATTGCCACCACCTGTCAGCTCCTTTCCGGGACTTTCGCTTTCCCCCTCCCTATTGCCACG
GCGGAACTCATCGCCGCCTGCCTTGCCCGCTGCTGGACAGGGGCTCGGCTGTTGGGCACT
GACAATTCCGTGGTGTTGTCGGGGAAATCATCGTCCTTTCCTTGGCTGCTCGCCTGTGTTG
CCACCTGGATTCTGCGCGGGACGTCCTTCTGCTACGTCCCTTCGGCCCTCAATCCAGCGG
ACCTTCCTTCCCGCGGCCTGCTGCCGGCTCTGCGGCCTCTTCCGCGTCTTCGCCTTCGCCC
TCAGACGAGTCGGATCTCCCTTTGGGCCGCCTCCCCGCATCGATACCGTCGACTAGCCGT
ACCTTTAAGACCAATGACTTACAAGGCAGCTGTAGATCTTAGCCACTTTTTAAAAGAAAA
GGGGGGACTGGAAGGGCTAATTCACTCCCAAAGAAGACAAGATCTGCTTTTTGCCTGTA
CTGGGTCTCTCTGGTTAGACCAGATCTGAGCCTGGGAGCTCTCTGGCTAACTAGGGAACC
CACTGCTTAAGCCTCAATAAAGCTTGCCTTGAGTGCTTCAAGTAGTGTGTGCCCGTCTGT
TGTGTGACTCTGGTAACTAGAGATCCCTCAGACCCTTTTAGTCAGTGTGGAAAATCTCTA

GCAGAATTCGATATCAAGCTTATCGATACCGTCGACCTCGAGGGGGGGCCCGGTACCCA

ATTCGCCCTATAGTGAGTCGTATTACAATTCACTGGCCGTCGTTTTACAACGTCGTGACT
GGGAAAACCCTGGCGTTACCCAACTTAATCGCCTTGCAGCACATCCCCCTTTCGCCAGCT
GGCGTAATAGCGAAGAGGCCCGCACCGATCGCCCTTCCCAACAGTTGCGCAGCCTGAAT
GGCGAATGGAAATTGTAAGCGTTAATATTTTGTTAAAATTCGCGTTAAATTTTTGTTAAA
TCAGCTCATTTTTTAACCAATAGGCCGAAATCGGCAAAATCCCTTATAAATCAAAAGAAT
AGACCGAGATAGGGTTGAGTGTTGTTCCAGTTTGGAACAAGAGTCCACTATTAAAGAAC
GTGGACTCCAACGTCAAAGGGCGAAAAACCGTCTATCAGGGCGATGGCCCACTACGTGA
ACCATCACCCTAATCAAGTTTTTTGGGGTCGAGGTGCCGTAAAGCACTAAATCGGAACCC
TAAAGGGAGCCCCCGATTTAGAGCTTGACGGGGAAAGCCGGCGAACGTGGCGAGAAAG
GAAGGGAAGAAAGCGAAAGGAGCGGGCGCTAGGGCGCTGGCAAGTGTAGCGGTCACGC
TGCGCGTAACCACCACACCCGCCGCGCTTAATGCGCCGCTACAGGGCGCGTCAGGTGGC
ACTTTTCGGGGAAATGTGCGCGGAACCCCTATTTGTTTATTTTTCTAAATACATTCAAATA
TGTATCCGCTCATGAGACAATAACCCTGATAAATGCTTCAATAATATTGAAAAAGGAAG
AGTATGAGTATTCAACATTTCCGTGTCGCCCTTATTCCCTTTTTTGCGGCATTTTGCCTTC
CTGTTTTTGCTCACCCAGAAACGCTGGTGAAAGTAAAAGATGCTGAAGATCAGTTGGGT
GCACGAGTGGGTTACATCGAACTGGATCTCAACAGCGGTAAGATCCTTGAGAGTTTTCG
CCCCGAAGAACGTTTTCCAATGATGAGCACTTTTAAAGTTCTGCTATGTGGCGCGGTATT
ATCCCGTATTGACGCCGGGCAAGAGCAACTCGGTCGCCGCATACACTATTCTCAGAATG
ACTTGGTTGAGTACTCACCAGTCACAGAAAAGCATCTTACGGATGGCATGACAGTAAGA
GAATTATGCAGTGCTGCCATAACCATGAGTGATAACACTGCGGCCAACTTACTTCTGACA
ACGATCGGAGGACCGAAGGAGCTAACCGCTTTTTTGCACAACATGGGGGATCATGTAAC
TCGCCTTGATCGTTGGGAACCGGAGCTGAATGAAGCCATACCAAACGACGAGCGTGACA
CCACGATGCCTGTAGCAATGGCAACAACGTTGCGCAAACTATTAACTGGCGAACTACTT
ACTCTAGCTTCCCGGCAACAATTAATAGACTGGATGGAGGCGGATAAAGTTGCAGGACC
ACTTCTGCGCTCGGCCCTTCCGGCTGGCTGGTTTATTGCTGATAAATCTGGAGCCGGTGA
GCGTGGGTCTCGCGGTATCATTGCAGCACTGGGGCCAGATGGTAAGCCCTCCCGTATCGT
AGTTATCTACACGACGGGGAGTCAGGCAACTATGGATGAACGAAATAGACAGATCGCTG
AGATAGGTGCCTCACTGATTAAGCATTGGTAACTGTCAGACCAAGTTTACTCATATATAC
TTTAGATTGATTTAAAACTTCATTTTTAATTTAAAAGGATCTAGGTGAAGATCCTTTTTGA
TAATCTCATGACCAAAATCCCTTAACGTGAGTTTTCGTTCCACTGAGCGTCAGACCCCGT
AGAAAAGATCAAAGGATCTTCTTGAGATCCTTTTTTTCTGCGCGTAATCTGCTGCTTGCA
AACAAAAAAACCACCGCTACCAGCGGTGGTTTGTTTGCCGGATCAAGAGCTACCAACTC
TTTTTCCGAAGGTAACTGGCTTCAGCAGAGCGCAGATACCAAATACTGTTCTTCTAGTGT
AGCCGTAGTTAGGCCACCACTTCAAGAACTCTGTAGCACCGCCTACATACCTCGCTCTGC
TAATCCTGTTACCAGTGGCTGCTGCCAGTGGCGATAAGTCGTGTCTTACCGGGTTGGACT
CAAGACGATAGTTACCGGATAAGGCGCAGCGGTCGGGCTGAACGGGGGGTTCGTGCACA
CAGCCCAGCTTGGAGCGAACGACCTACACCGAACTGAGATACCTACAGCGTGAGCTATG
AGAAAGCGCCACGCTTCCCGAAGGGAGAAAGGCGGACAGGTATCCGGTAAGCGGCAGG
GTCGGAACAGGAGAGCGCACGAGGGAGCTTCCAGGGGGAAACGCCTGGTATCTTTATAG
TCCTGTCGGGTTTCGCCACCTCTGACTTGAGCGTCGATTTTTGTGATGCTCGTCAGGGGG
GCGGAGCCTATGGAAAAACGCCAGCAACGCGGCCTTTTTACGGTTCCTGGCCTTTTGCTG
GCCTTTTGCTCACATGTTCTTTCCTGCGTTATCCCCTGATTCTGTGGATAACCGTATTACC
GCCTTTGAGTGAGCTGATACCGCTCGCCGCAGCCGAACGACCGAGCGCAGCGAGTCAGT
GAGCGAGGAAGCGGAAGAGCGCCCAATACGCAAACCGCCTCTCCCCGCGCGTTGGCCGA
TTCATTAATGCAGCTGGCACGACAGGTTTCCCGACTGGAAAGCGGGCAGTGAGCGCAAC
GCAATTAATGTGAGTTAGCTCACTCATTAGGCACCCCAGGCTTTACACTTTATGCTTCCG

TABLE 9-continued

| R12 long spacer CAR: PJ_R12-CH2-CH3-41BB-Z-T2A-tEGFR (SEQ ID NO: 37) |
|---|
| GCTCGTATGTTGTGTGGAATTGTGAGCGGATAACAATTTCACACAGGAAACAGCTATGA<br>CCATGATTACGCCAAGCTCGAAATTAACCCTCACTAAAGGGAACAAAAGCTGGAGCTCC<br><br>ACCGCGGTGGCGGCCTCGAGGTCGAGATCCGGTCGACCAGCAACCATAGTCCCGCCCCT<br><br>AACTCCGCCCATCCCGCCCCTAACTCCGCCCAGTTCCGCCCATTCTCCGCCCCATGGCTG<br>ACTAATTTTTTTTATTTATGCAGAGGCCGAGGCCGCCTCGGCCTCTGAGCTATTCCAGAA<br>GTAGTGAGGAGGCTTTTTTGGAGGCCTAGGCTTTTGCAAAAAGCTTCGACGGTATCGATT<br>GGCTCATGTCCAACATTACCGCCATGTTGACATTGATTATTGACTAGTTATTAATAGTAA<br>TCAATTACGGGGTCATTAGTTCATAGCCCATATATGGAGTTCCGCGTTACATAACTTACG<br>GTAAATGGCCCGCCTGGCTGACCGCCCAACGACCCCCGCCCATTGACGTCAATAATGAC<br>GTATGTTCCCATAGTAACGCCAATAGGGACTTTCCATTGACGTCAATGGGTGGAGTATTT<br>ACGGTAAACTGCCCACTTGGCAGTACATCAAGTGTATCATATGCCAAGTACGCCCCCTAT<br>TGACGTCAATGACGGTAAATGGCCCGCCTGGCATTATGCCCAGTACATGACCTTATGGG<br>ACTTTCCTACTTGGCAGTACATCTACGTATTAGTCATCGCTATTACCATGGTGATGCGGTT<br>TTGGCAGTACATCAATGGGCGTGGATAGCGGTTTGACTCACGGGGATTTCCAAGTCTCCA<br>CCCCATTGACGTCAATGGGAGTTTGTTTTGGCACCAAAATCAACGGGACTTTCCAAAATG<br>TCGTAACAACTCCGCCCCATTGACGCAAATGGGCGGTAGGCGTGTACGGAATTCGGAGT<br>GGCGAGCCCTCAGATCCTGCATATAAGCAGCTGCTTTTTGCCTGTACTGGGTCTCTCTG |

TABLE 10

| Leader _R12-Hinge-CH2-CH3-CD28tm/41BB-Z-T2A-tEGFR (SEQ ID NO: 38) |
|---|
| Leader: MLLLVTSLLLCELPHPAFLLIP<br><br>R12 scFv<br>QEQLVESGGRLVTPGGSLTLSCKASGFDFSAYYMSWVRQAPGKGLEWIATIYPSSGKTYYAT<br>WVNGRFTISSDNAQNTVDLQMNSLTAADRATYFCARDSYADDGALFNIWGPGTLVTISSGG<br>GGSGGGGSGGGGSELVLTQSPSVSAALGSPAKITCTLSSAHKTDTIDWYQQLQGEAPRYLMQ<br>VQSDGSYTKRPGVPDRFSGSSSGADRYLIIPSVQADDEADYYCGADYIGGYVFGGGTQLTVT<br>G<br><br>Hinge Spacer: ESKYGPPCPPCP<br><br>CH2<br><br>APEFLGGPSVFLFPPKPKDTLMISRTPEVTCVVVDVSQEDPEVQFNWYVDGVEVHNAKTKPR<br><br>EEQFNSTYRVVSVLTVLHQDWLNGKEYKCKVSNKGLPSSIEKTISKAK<br><br>CH3<br><br>GQPREPQVYTLPPSQEEMTKNQVSLTCLVKGFYPSDIAVEWESNGQPENNYKTTPPVLDSDG<br><br>SFFLYSRLTVDKSRWQEGNVFSCSVMHEALHNHYTQKSLSLSLGK<br><br>CD28: MFWVLVVVGGVLACYSLLVTVAFIIFWV<br><br>4-1BB: KRGRKKLLYIFKQPFMRPVQTTQEEDGCSCRFPEEEEGGCEL<br><br>CD3 zeta<br>RVKFSRSADAPAYQQGQNQLYNELNLGRREEYDVLDKRRGRDPEMGGKPRRKNPQEGLYN<br>ELQKDKMAEAYSEIGMKGERRRGKGHDGLYQGLSTATKDTYDALHMQALPPR<br><br>T2A<br>LEGGGEGRGSLLTCGDVEENPGPR<br><br>tEGFR<br>MLLLVTSLLLCELPHPAFLLIPRKVCNGIGIGEFKDSLSINATNIKHFKNCTSISGDLHILPVAFR<br>GDSFTHTPPLDPQELDILKTVKEITGFLLIQAWPENRTDLHAFENLEIIRGRTKQHGQFSLAVV<br>SLNITSLGLRSLKEISDGDVIISGNKNLCYANTINWKKLFGTSGQKTKIISNRGENSCKATGQV<br>CHALCSPEGCWGPEPRDCVSCRNVSRGRECVDKCNLLEGEPREFVENSECIQCHPECLPQAM<br>NITCTGRGPDNCIQCAHYIDGPHCVKTCPAGVMGENNTLVWKYADAGHVCHLCHPNCTYG<br>CTGPGLEGCPTNGPKIPSIATGMVGALLLLLVVALGIGLFM |

TABLE 11

| R12 intermediate spacer CAR: PJ_R12-CH3-41BB-Z-T2A-tEGFR(SEQ ID NO: 39) |
|---|

GTTAGACCAGATCTGAGCCTGGGAGCTCTCTGGCTAACTAGGGAACCCACTGCTTAAGC
CTCAATAAAGCTTGCCTTGAGTGCTTCAAGTAGTGTGTGCCCGTCTGTTGTGTGACTCTG
GTAACTAGAGATCCCTCAGACCCTTTTAGTCAGTGTGGAAAATCTCTAGCAGTGGCGCCC
GAACAGGGACTTGAAAGCGAAAGGGAAACCAGAGGAGCTCTCTCGACGCAGGACTCGG
CTTGCTGAAGCGCGCACGGCAAGAGGCGAGGGGCGGCGACTGGTGAGTACGCCAAAAA
TTTTGACTAGCGGAGGCTAGAAGGAGAGAGATGGGTGCGAGAGCGTCAGTATTAAGCGG
GGGAGAATTAGATCGATGGGAAAAAATTCGGTTAAGGCCAGGGGGAAAGAAAAAATAT
AAATTAAAACATATAGTATGGGCAAGCAGGGAGCTAGAACGATTCGCAGTTAATCCTGG
CCTGTTAGAAACATCAGAAGGCTGTAGACAAATACTGGGACAGCTACAACCATCCCTTC
AGACAGGATCAGAAGAACTTAGATCATTATATAATACAGTAGCAACCCTCTATTGTGTG
CATCAAAGGATAGAGATAAAAGACACCAAGGAAGCTTTAGACAAGATAGAGGAAGAGC
AAAACAAAAGTAAGAAAAAAGCACAGCAAGCAGCAGCTGACACAGGACACAGCAATCA
GGTCAGCCAAAATTACCCTATAGTGCAGAACATCCAGGGGCAAATGGTACATCAGGCCA
TATCACCTAGAACTTTAAATGCATGGGTAAAAGTAGTAGAAGAGAAGGCTTTCAGCCCA
GAAGTGATACCCATGTTTTCAGCATTATCAGAAGGAGCCACCCCACAAGATTTAAACAC
CATGCTAAACACAGTGGGGGGACATCAAGCAGCCATGCAAATGTTAAAAGAGACCATCA
ATGAGGAAGCTGCAGGCAAAGAGAAGAGTGGTGCAGAGAGAAAAAAGAGCAGTGGGA
ATAGGAGCTTTGTTCCTTGGGTTCTTGGGAGCAGCAGGAAGCACTATGGGCGCAGCGTC
AATGACGCTGACGGTACAGGCCAGACAATTATTGTCTGGTATAGTGCAGCAGCAGAACA
ATTTGCTGAGGGCTATTGAGGCGCAACAGCATCTGTTGCAACTCACAGTCTGGGGCATCA
AGCAGCTCCAGGCAAGAATCCTGGCTGTGGAAAGATACCTAAAGGATCAACAGCTCCTG
GGGATTTGGGGTTGCTCTGGAAAACTCATTTGCACCACTGCTGTGCCTTGGATCTACAAA
TGGCAGTATTCATCCACAATTTTAAAAGAAAAGGGGGGATTGGGGGGTACAGTGCAGGG
GAAAGAATAGTAGACATAATAGCAACAGACATACAAACTAAAGAATTACAAAAACAAA
TTACAAAAATTCAAAATTTTCGGGTTTATTACAGGGACAGCAGAGATCCAGTTTGGGGAT
CAATTGCATGAAGAATCTGCTTAGGGTTAGGCGTTTTGCGCTGCTTCGCGAGGATCTGCG
ATCGCTCCGGTGCCCGTCAGTGGGCAGAGCGCACATCGCCCACAGTCCCCGAGAAGTTG
GGGGGAGGGGTCGGCAATTGAACCGGTGCCTAGAGAAGGTGGCGCGGGGTAAACTGGG
AAAGTGATGTCGTGTACTGGCTCCGCCTTTTTCCCGAGGGTGGGGGAGAACCGTATATAA
GTGCAGTAGTCGCCGTGAACGTTCTTTTTCGCAACGGGTTTGCCGCCAGAACACAGCTGA
AGCTTCGAGGGGCTCGCATCTCTCCTTCACGCGCCCGCCGCCCTACCTGAGGCCGCCATC
CACGCCGGTTGAGTCGCGTTCTGCCGCCTCCCGCCTGTGGTGCCTCCTGAACTGCGTCCG
CCGTCTAGGTAAGTTTAAAGCTCAGGTCGAGACCGGGCCTTTGTCCGGCGCTCCCTTGGA
GCCTACCTAGACTCAGCCGGCTCTCCACGCTTTGCCTGACCCTGCTTGCTCAACTCTACGT
CTTTGTTTCGTTTTCTGTTCTGCGCCGTTACAGATCCAAGCTGTGACCGGCGCCTACG

GCTAGCGAATTCCTCGAGGCC

R12 ScFv

ACCATGCTGCTGCTGGTGACAAGCCTGCTGCTGTGCGAGCTGCCCCACCCCGCCTTTCTG

CTGATCCCCCAGGAACAGCTCGTCGAAAGCGGCGGCAGACTGGTGACACCTGGCGGCAG
CCTGACCCTGAGCTGCAAGGCCAGCGGCTTCGACTTCAGCGCCTACTACATGAGCTGGGT
CCGCCAGGCCCCTGGCAAGGGACTGGAATGGATCGCCACCATCTACCCCAGCAGCGGCA
AGACCTACTACGCCACCTGGGTGAACGGACGGTTCACCATCTCCAGCGACAACGCCCAG
AACACCGTGGACCTGCAGATGAACAGCCTGACAGCCGCCGACCGGGCCACCTACTTTTG
CGCCAGAGACAGCTACGCCGACGACGGCGCCCTGTTCAACATCTGGGGCCCTGGCACCC
TGGTGACAATCTCTAGCGGCGGAGGCGGATCTGGTGGCGGAGGAAGTGGCGGCGGAGG
ATCTGAGCTGGTGCTGACCCAGAGCCCCTCTGTGTCTGCTGCCCTGGGAAGCCCTGCCAA
GATCACCTGTACCCTGAGCAGCGCCCACAAGACCGACACCATCGACTGGTATCAGCAGC
TGCAGGGCGAGGCCCCCAGATACCTGATGCAGGTGCAGAGCGACGGCAGCTACACCAA
GAGGCCAGGCGTGCCCGACCGGTTCAGCGGATCTAGCTCTGGCGCCGACCGCTACCTGA
TCATCCCCAGCGTGCAGGCCGATGACGAGGCCGATTACTACTGTGGCGCCGACTACATC
GGCGGCTACGTGTTCGGCGGAGGCACCCAGCTGACCGTGACCGGCGAGTCTAAG

Hinge Spacer

TACGGACCGCCCTGCCCCCCTTGCCCT

CH3
GGCCAGCCTCGCGAGCCCCAGGTGTACACCCTGCCTCCCTCCCAGGAAGAGATGACCAA
GAACCAGGTGTCCCTGACCTGCCTGGTGAAGGGCTTCTACCCCAGCGACATCGCCGTGG
AGTGGGAGAGCAACGGCCAGCCTGAGAACAACTACAAGACCACCCCTCCCGTGCTGGAC
AGCGACGGCAGCTTCTTCCTGTACAGCCGGCTGACCGTGGACAAGAGCCGGTGGCAGGA
AGGCAACGTCTTTAGCTGCAGCGTGATGCACGAGGCCCTGCACAACCACTACACCCAGA
AGAGCCTGAGCCTGTCCCTGGGCAAG 4-1BB
ATGTTCTGGGTGCTGGTGGTGGTGGGCGGGGTGCTGGCCTGCTACAGCCTGCTGGTGACA
GTGGCCTTCATCATCTTTTGGGTGAAACGGGGCAGAAAGAAACTCCTGTATATATTCAAA
CAACCATTTATGAGACCAGTACAAACTACTCAAGAGGAAGATGGCTGTAGCTGCCGATT
TCCAGAAGAAGAAGAAGGAGGATGTGAACTG

TABLE 11-continued

| R12 intermediate spacer CAR: PJ_R12-CH3-41BB-Z-T2A-tEGFR(SEQ ID NO: 39) |
|---|

CD3zeta
CGGGTGAAGTTCAGCAGAAGCGCCGACGCCCCTGCCTACCAGCAGGGCCAGAATCAGCT
GTACAACGAGCTGAACCTGGGCAGAAGGGAAGAGTACGACGTCCTGGATAAGCGGAGA
GGCCGGGACCCTGAGATGGGCGGCAAGCCTCGGCGGAAGAACCCCCAGGAAGGCCTGT
ATAACGAACTGCAGAAAGACAAGATGGCCGAGGCCTACAGCGAGATCGGCATGAAGGG
CGAGCGGAGGCGGGGCAAGGGCCACGACGGCCTGTATCAGGGCCTGTCCACCGCCACCA
AGGATACCTACGACGCCCTGCACATGCAGGCCCTGCCCCCAAGG

T2A

CTCGAGGGCGGCGGAGAGGGCAGAGGAAGTCTTCTAACATGCGGTGACGTGGAGGAGA

ATCCCGGCCCTAGG tEGFR
ATGCTTCTCCTGGTGACAAGCCTTCTGCTCTGTGAGTTACCACACCCAGCATTCCTCCTGA
TCCCACGCAAAGTGTGTAACGGAATAGGTATTGGTGAATTTAAAGACTCACTCTCCATAA
ATGCTACGAATATTAAACACTTCAAAAACTGCACCTCCATCAGTGGCGATCTCCACATCC

TGCCGGTGGCATTTAGGGGTGACTCCTTCACACATACTCCTCCTCTGGATCCACAGGAAC

TGGATATTCTGAAAACCGTAAAGGAAATCACAGGGTTTTTGCTGATTCAGGCTTGGCCTG
AAAACAGGACGGACCTCCATGCCTTTGAGAACCTAGAAATCATACGCGGCAGGACCAAG
CAACATGGTCAGTTTTCTCTTGCAGTCGTCAGCCTGAACATAACATCCTTGGGATTACGC
TCCCTCAAGGAGATAAGTGATGGAGATGTGATAATTTCAGGAAACAAAAATTTGTGCTA
TGCAAATACAATAAACTGGAAAAAACTGTTTGGGACCTCCGGTCAGAAAACCAAAATTA
TAAGCAACAGAGGTGAAAACAGCTGCAAGGCCACAGGCCAGGTCTGCCATGCCTTGTGC
TCCCCCGAGGGCTGCTGGGGCCCGGAGCCCAGGGACTGCGTCTCTTGCCGGAATGTCAG
CCGAGGCAGGGAATGCGTGGACAAGTGCAACCTTCTGGAGGGTGAGCCAAGGGAGTTTG
TGGAGAACTCTGAGTGCATACAGTGCCACCCAGAGTGCCTGCCTCAGGCCATGAACATC
ACCTGCACAGGACGGGGACCAGACAACTGTATCCAGTGTGCCCACTACATTGACGGCCC
CCACTGCGTCAAGACCTGCCCGGCAGGAGTCATGGGAGAAAACAACACCCTGGTCTGGA
AGTACGCAGACGCCGGCCATGTGTGCCACCTGTGCCATCCAAACTGCACCTACGGATGC
ACTGGGCCAGGTCTTGAAGGCTGTCCAACGAATGGGCCTAAGATCCCGTCCATCGCCAC
TGGGATGGTGGGGGCCCTCCTCTTGCTGCTGGTGGTGGCCCTGGGGATCGGCCTCTTCAT
GTGA

GCGGCCGCTCTAGACCCGGGCTGCAGGAATTCGATATCAAGCTTATCGATAATCAACCT

CTGGATTACAAAATTTGTGAAAGATTGACTGGTATTCTTAACTATGTTGCTCCTTTTACGC
TATGTGGATACGCTGCTTTAATGCCTTTGTATCATGCTATTGCTTCCCGTATGGCTTTCAT
TTTCTCCTCCTTGTATAAATCCTGGTTGCTGTCTCTTTATGAGGAGTTGTGGCCCGTTGTC
AGGCAACGTGGCGTGGTGTGCACTGTGTTTGCTGACGCAACCCCCACTGGTTGGGGCATT
GCCACCACCTGTCAGCTCCTTTCCGGGACTTTCGCTTTCCCCCTCCCTATTGCCACGGCGG
AACTCATCGCCGCCTGCCTTGCCCGCTGCTGGACAGGGGCTCGGCTGTTGGGCACTGACA
ATTCCGTGGTGTTGTCGGGGAAATCATCGTCCTTTCCTTGGCTGCTCGCCTGTGTTGCCAC
CTGGATTCTGCGCGGGACGTCCTTCTGCTACGTCCCTTCGGCCCTCAATCCAGCGGACCT
TCCTTCCCGCGGCCTGCTGCCGGCTCTGCGGCCTCTTCCGCGTCTTCGCCTTCGCCCTCAG
ACGAGTCGGATCTCCCTTTGGGCCGCCTCCCCGCATCGATACCGTCGACTAGCCGTACCT
TTAAGACCAATGACTTACAAGGCAGCTGTAGATCTTAGCCACTTTTTAAAAGAAAAGGG
GGGACTGGAAGGGCTAATTCACTCCCAAAGAAGACAAGATCTGCTTTTTGCCTGTACTG
GGTCTCTCTGGTTAGACCAGATCTGAGCCTGGGAGCTCTCTGGCTAACTAGGGAACCCAC
TGCTTAAGCCTCAATAAAGCTTGCCTTGAGTGCTTCAAGTAGTGTGTGCCCGTCTGTTGT
GTGACTCTGGTAACTAGAGATCCCTCAGACCCTTTTAGTCAGTGTGGAAAATCTCTAGCA

GAATTCGATATCAAGCTTATCGATACCGTCGACCTCGAGGGGGGGCCCGGTACCCAATT

CGCCCTATAGTGAGTCGTATTACAATTCACTGGCCGTCGTTTTACAACGTCGTGACTGGG
AAAACCCTGGCGTTACCCAACTTAATCGCCTTGCAGCACATCCCCCTTTCGCCAGCTGGC
GTAATAGCGAAGAGGCCCGCACCGATCGCCCTTCCCAACAGTTGCGCAGCCTGAATGGC
GAATGGAAATTGTAAGCGTTAATATTTTGTTAAAATTCGCGTTAAATTTTTGTTAAATCA
GCTCATTTTTTAACCAATAGGCCGAAATCGGCAAAATCCCTTATAAATCAAAAGAATAG
ACCGAGATAGGGTTGAGTGTTGTTCCAGTTTGGAACAAGAGTCCACTATTAAAGAACGT
GGACTCCAACGTCAAAGGGCGAAAAACCGTCTATCAGGGCGATGGCCCACTACGTGAAC
CATCACCCTAATCAAGTTTTTTGGGGTCGAGGTGCCGTAAAGCACTAAATCGGAACCCTA
AAGGGAGCCCCCGATTTAGAGCTTGACGGGGAAAGCCGGCGAACGTGGCGAGAAAGGA
AGGGAAGAAAGCGAAAGGAGCGGGCGCTAGGGCGCTGGCAAGTGTAGCGGTCACGCTG
CGCGTAACCACCACACCCGCCGCGCTTAATGCGCCGCTACAGGGCGCGTCAGGTGGCAC
TTTTCGGGGAAATGTGCGCGGAACCCCTATTTGTTTATTTTTCTAAATACATTCAAATATG
TATCCGCTCATGAGACAATAACCCTGATAAATGCTTCAATAATATTGAAAAAGGAAGAG
TATGAGTATTCAACATTTCCGTGTCGCCCTTATTCCCTTTTTTGCGGCATTTTGCCTTCCTG
TTTTTGCTCACCCAGAAACGCTGGTGAAAGTAAAAGATGCTGAAGATCAGTTGGGTGCA
CGAGTGGGTTACATCGAACTGGATCTCAACAGCGGTAAGATCCTTGAGAGTTTTCGCCCC

TABLE 11-continued

| R12 intermediate spacer CAR: PJ_R12-CH3-41BB-Z-T2A-tEGFR(SEQ ID NO: 39) |
|---|
| GAAGAACGTTTTCCAATGATGAGCACTTTTAAAGTTCTGCTATGTGGCGCGGTATTATCC<br>CGTATTGACGCCGGGCAAGAGCAACTCGGTCGCCGCATACACTATTCTCAGAATGACTT<br>GGTTGAGTACTCACCAGTCACAGAAAAGCATCTTACGGATGGCATGACAGTAAGAGAAT<br>TATGCAGTGCTGCCATAACCATGAGTGATAACACTGCGGCCAACTTACTTCTGACAACGA<br>TCGGAGGACCGAAGGAGCTAACCGCTTTTTTGCACAACATGGGGGATCATGTAACTCGC<br>CTTGATCGTTGGGAACCGGAGCTGAATGAAGCCATACCAAACGACGAGCGTGACACCAC<br>GATGCCTGTAGCAATGGCAACAACGTTGCGCAAACTATTAACTGGCGAACTACTTACTCT<br>AGCTTCCCGGCAACAATTAATAGACTGGATGGAGGCGGATAAAGTTGCAGGACCACTTC<br>TGCGCTCGGCCCTTCCGGCTGGCTGGTTTATTGCTGATAAATCTGGAGCCGGTGAGCGTG<br>GGTCTCGCGGTATCATTGCAGCACTGGGGCCAGATGGTAAGCCCTCCCGTATCGTAGTTA<br>TCTACACGACGGGGAGTCAGGCAACTATGGATGAACGAAATAGACAGATCGCTGAGATA<br>GGTGCCTCACTGATTAAGCATTGGTAACTGTCAGACCAAGTTTACTCATATATACTTTAG<br>ATTGATTTAAAACTTCATTTTTAATTTAAAAGGATCTAGGTGAAGATCCTTTTTGATAATC<br>TCATGACCAAAATCCCTTAACGTGAGTTTTCGTTCCACTGAGCGTCAGACCCCGTAGAAA<br>AGATCAAAGGATCTTCTTGAGATCCTTTTTTTCTGCGCGTAATCTGCTGCTTGCAAACAA<br>AAAAACCACCGCTACCAGCGGTGGTTTGTTTGCCGGATCAAGAGCTACCAACTCTTTTTC<br>CGAAGGTAACTGGCTTCAGCAGAGCGCAGATACCAAATACTGTTCTTCTAGTGTAGCCGT<br>AGTTAGGCCACCACTTCAAGAACTCTGTAGCACCGCCTACATACCTCGCTCTGCTAATCC<br>TGTTACCAGTGGCTGCTGCCAGTGGCGATAAGTCGTGTCTTACCGGGTTGGACTCAAGAC<br>GATAGTTACCGGATAAGGCGCAGCGGTCGGGCTGAACGGGGGGTTCGTGCACACAGCCC<br>AGCTTGGAGCGAACGACCTACACCGAACTGAGATACCTACAGCGTGAGCTATGAGAAAG<br>CGCCACGCTTCCCGAAGGGAGAAAGGCGGACAGGTATCCGGTAAGCGGCAGGGTCGGA<br>ACAGGAGAGCGCACGAGGGAGCTTCCAGGGGGAAACGCCTGGTATCTTTATAGTCCTGT<br>CGGGTTTCGCCACCTCTGACTTGAGCGTCGATTTTTGTGATGCTCGTCAGGGGGGCGGAG<br>CCTATGGAAAAACGCCAGCAACGCGGCCTTTTTACGGTTCCTGGCCTTTTGCTGGCCTTT<br>TGCTCACATGTTCTTTCCTGCGTTATCCCCTGATTCTGTGGATAACCGTATTACCGCCTTT<br>GAGTGAGCTGATACCGCTCGCCGCAGCCGAACGACCGAGCGCAGCGAGTCAGTGAGCG<br>AGGAAGCGGAAGAGCGCCCAATACGCAAACCGCCTCTCCCCGCGCGTTGGCCGATTCAT<br>TAATGCAGCTGGCACGACAGGTTTCCCGACTGGAAAGCGGGCAGTGAGCGCAACGCAAT<br>TAATGTGAGTTAGCTCACTCATTAGGCACCCCAGGCTTTACACTTTATGCTTCCGGCTCGT<br>ATGTTGTGTGGAATTGTGAGCGGATAACAATTTCACACAGGAAACAGCTATGACCATGA<br>TTACGCCAAGCTCGAAATTAACCCTCACTAAAGGGAACAAAAGCTGGAGCTCCACCGCG |
| GTGGCGGCCTCGAGGTCGAGATCCGGTCGACCAGCAACCATAGTCCCGCCCCTAACTCC |
| GCCCATCCCGCCCCTAACTCCGCCCAGTTCCGCCCATTCTCCGCCCCATGGCTGACTAAT<br>TTTTTTATTTATGCAGAGGCCGAGGCCGCCTCGGCCTCTGAGCTATTCCAGAAGTAGTG<br>AGGAGGCTTTTTTGGAGGCCTAGGCTTTTGCAAAAAGCTTCGACGGTATCGATTGGCTCA<br>TGTCCAACATTACCGCCATGTTGACATTGATTATTGACTAGTTATTAATAGTAATCAATT<br>ACGGGGTCATTAGTTCATAGCCCATATATGGAGTTCCGCGTTACATAACTTACGGTAAAT<br>GGCCCGCCTGGCTGACCGCCCAACGACCCCCGCCCATTGACGTCAATAATGACGTATGTT<br>CCCATAGTAACGCCAATAGGGACTTTCCATTGACGTCAATGGGTGGAGTATTTACGGTAA<br>ACTGCCCACTTGGCAGTACATCAAGTGTATCATATGCCAAGTACGCCCCCTATTGACGTC<br>AATGACGGTAAATGGCCCGCCTGGCATTATGCCCAGTACATGACCTTATGGGACTTTCCT<br>ACTTGGCAGTACATCTACGTATTAGTCATCGCTATTACCATGGTGATGCGGTTTTGGCAG<br>TACATCAATGGGCGTGGATAGCGGTTTGACTCACGGGGATTTCCAAGTCTCCACCCCATT<br>GACGTCAATGGGAGTTTGTTTTGGCACCAAAATCAACGGGACTTTCCAAAATGTCGTAAC<br>AACTCCGCCCCATTGACGCAAATGGGCGGTAGGCGTGTACGGAATTCGGAGTGGCGAGC<br>CCTCAGATCCTGCATATAAGCAGCTGCTTTTTGCCTGTACTGGGTCTCTCTG |

TABLE 12

| Leader _R12- Hinge- CH3- CD28tm/41BB-Z-T2A-tEGFR (SEQ ID NO:40) |
|---|
| Leader |
| MLLLVTSLLLCELPHPAFLLIP |
| R12 scFV |
| QEQLVESGGRLVTPGGSLTLSCKASGFDFSAYYMSWVRQAPGKGLEWIATIYPSSGKTYYAT<br>WVNGRFTISSDNAQNTVDLQMNSLTAADRATYFCARDSYADDGALFNIWGPGTLVTISSGG |

TABLE 12 -continued

| Leader _R12- Hinge- CH3- CD28tm/41BB-Z-T2A-tEGFR (SEQ ID NO:40) |
|---|
| GGSGGGGSGGGGSELVLTQSPSVSAALGSPAKITCTLSSAHKTDTIDWYQQLQGEAPRYLMQ |
| VQSDGSYTKRPGVPDRFSGSSSGADRYLIIPSVQADDEADYYCGADYIGGYVFGGGTQLTVT |
| G |
| |
| Hinge Spacer |
| ESKYGPPCPPCP |
| |
| CH3 |
| |
| GQPREPQVYTLPPSQEEMTKNQVSLTCLVKGFYPSDIAVEWESNGQPENNYKTTPPVLDSDG |
| |
| SFFLYSRLTVDKSRWQEGNVFSCSVMHEALHNHYTQKSLSLSLGK |
| |
| CD28tm |
| MFWVLVVVGGVLACYSLLVTVAFIIFWV |
| |
| 4-1BB |
| KRGRKKLLYIFKQPFMRPVQTTQEEDGCSCRFPEEEEGGCEL |
| |
| CD3 zeta |
| RVKFSRSADAPAYQQGQNQLYNELNLGRREEYDVLDKRRGRDPEMGGKPRRKNPQEGLYN |
| ELQKDKMAEAYSEIGMKGERRRGKGHDGLYQGLSTATKDTYDALHMQALPPR |
| |
| T2A |
| LEGGGEGRGSLLTCGDVEENPGPR |
| |
| tEGFR |
| MLLLVTSLLLCELPHPAFLLIPRKVCNGIGIGEFKDSLSINATNIKHFKNCTSISGDLHILPVAFR |
| GDSFTHTPPLDPQELDILKTVKEITGFLLIQAWPENRTDLHAFENLEIIRGRTKQHGQFSLAVV |
| SLNITSLGLRSLKEISDGDVIISGNKNLCYANTINWKKLFGTSGQKTKIISNRGENSCKATGQV |
| CHALCSPEGCWGPEPRDCVSCRNVSRGRECVDKCNLLEGEPREFVENSECIQCHPECLPQAM |
| NITCTGRGPDNCIQCAHVIDGPHCVKTCPAGVMGENNTLVWKYADAGHVCHLCHPNCTYG |
| CTGPGLEGCPTNGPKIPSIATGMVGALLLLLVVALGIGLFM |

TABLE 13

| R12 short spacer CAR: PJ_R12-Hinge-41BB-Z-T2A-tEGFR (SEQ ID NO:41) |
|---|
| GTTAGACCAGATCTGAGCCTGGGAGCTCTCTGGCTAACTAGGGAACCCACTGCTTAAGC |
| CTCAATAAAGCTTGCCTTGAGTGCTTCAAGTAGTGTGTGCCCGTCTGTTGTGTGACTCTG |
| GTAACTAGAGATCCCTCAGACCCTTTTAGTCAGTGTGGAAAATCTCTAGCAGTGGCGCCC |
| GAACAGGGACTTGAAAGCGAAAGGGAAACCAGAGGAGCTCTCTCGACGCAGGACTCGG |
| CTTGCTGAAGCGCGCACGGCAAGAGGCGAGGGGCGGCGACTGGTGAGTACGCCAAAAA |
| TTTTGACTAGCGGAGGCTAGAAGGAGAGAGATGGGTGCGAGAGCGTCAGTATTAAGCGG |
| GGGAGAATTAGATCGATGGGAAAAAATTCGGTTAAGGCCAGGGGGAAAGAAAAAATAT |
| AAATTAAAACATATAGTATGGGCAAGCAGGGAGCTAGAACGATTCGCAGTTAATCCTGG |
| CCTGTTAGAAACATCAGAAGGCTGTAGACAAATACTGGGACAGCTACAACCATCCCTTC |
| AGACAGGATCAGAAGAACTTAGATCATTATATAATACAGTAGCAACCCTCTATTGTGTG |
| CATCAAAGGATAGAGATAAAAGACACCAAGGAAGCTTTAGACAAGATAGAGGAAGAGC |
| AAAACAAAAGTAAGAAAAAAGCACAGCAAGCAGCAGCTGACACAGGACACAGCAATCA |
| GGTCAGCCAAAATTACCCTATAGTGCAGAACATCCAGGGGCAAATGGTACATCAGGCCA |
| TATCACCTAGAACTTTAAATGCATGGGTAAAAGTAGTAGAAGAGAAGGCTTTCAGCCCA |
| GAAGTGATACCCATGTTTTCAGCATTATCAGAAGGAGCCACCCCACAAGATTTAAACAC |
| CATGCTAAACACAGTGGGGGGACATCAAGCAGCCATGCAAATGTTAAAAGAGACCATCA |
| ATGAGGAAGCTGCAGGCAAAGAGAAGAGTGGTGCAGAGAGAAAAAAGAGCAGTGGGA |
| ATAGGAGCTTTGTTCCTTGGGTTCTTGGGAGCAGCAGGAAGCACTATGGGCGCAGCGTC |
| AATGACGCTGACGGTACAGGCCAGACAATTATTGTCTGGTATAGTGCAGCAGCAGAACA |
| ATTTGCTGAGGGCTATTGAGGCGCAACAGCATCTGTTGCAACTCACAGTCTGGGGCATCA |
| AGCAGCTCCAGGCAAGAATCCTGGCTGTGGAAAGATACCTAAAGGATCAACAGCTCCTG |
| GGGATTTGGGGTTGCTCTGGAAAACTCATTTGCACCACTGCTGTGCCTTGGATCTACAAA |
| TGGCAGTATTCATCCACAATTTTAAAAGAAAAGGGGGGATTGGGGGGTACAGTGCAGGG |
| GAAAGAATAGTAGACATAATAGCAACAGACATACAAACTAAAGAATTACAAAAACAAA |
| TTACAAAAATTCAAAATTTTCGGGTTTATTACAGGGACAGCAGAGATCCAGTTTGGGGAT |
| CAATTGCATGAAGAATCTGCTTAGGGTTAGGCGTTTTGCGCTGCTTCGCGAGGATCTGCG |
| ATCGCTCCGGTGCCCGTCAGTGGGCAGAGCGCACATCGCCCACAGTCCCCGAGAAGTTG |
| GGGGGAGGGGTCGGCAATTGAACCGGTGCCTAGAGAAGGTGGCGCGGGGTAAACTGGG |
| AAAGTGATGTCGTGTACTGGCTCCGCCTTTTTCCCGAGGGTGGGGGAGAACCGTATATAA |
| GTGCAGTAGTCGCCGTGAACGTTCTTTTTCGCAACGGGTTTGCCGCCAGAACACAGCTGA |
| AGCTTCGAGGGGCTCGCATCTCTCCTTCACGCGCCCGCCGCCCTACCTGAGGCCGCCATC |
| CACGCCGGTTGAGTCGCGTTCTGCCGCCTCCCGCCTGTGGTGCCTCCTGAACTGCGTCCG |
| CCGTCTAGGTAAGTTTAAAGCTCAGGTCGAGACCGGGCCTTTGTCCGGCGCTCCCTTGGA |

TABLE 13-continued

| R12 short spacer CAR: PJ_R12-Hinge-41BB-Z-T2A-tEGFR (SEQ ID NO:41) |
|---|

GCCTACCTAGACTCAGCCGGCTCTCCACGCTTTGCCTGACCCTGCTTGCTCAACTCTACGT
CTTTGTTTCGTTTTCTGTTCTGCGCCGTTACAGATCCAAGCTGTGACCGGCGCCTACG

GCTAGF

R12 scFV

ACCATGCTGCTGCTGGTGACAAGCCTGCTGCTGTGCGAGCTGCCCCACCCCGCCTTTCTG

CTGATCCCCCAGGAACAGCTCGTCGAAAGCGGCGGCAGACTGGTGACACCTGGCGGCAG
CCTGACCCTGAGCTGCAAGGCCAGCGGCTTCGACTTCAGCGCCTACTACATGAGCTGGGT
CCGCCAGGCCCCTGGCAAGGGACTGGAATGGATCGCCACCATCTACCCCAGCAGCGGCA
AGACCTACTACGCCACCTGGGTGAACGGACGGTTCACCATCTCCAGCGACAACGCCCAG
AACACCGTGGACCTGCAGATGAACAGCCTGACAGCCGCCGACCGGGCCACCTACTTTTG
CGCCAGAGACAGCTACGCCGACGACGGCGCCCTGTTCAACATCTGGGGCCCTGGCACCC
TGGTGACAATCTCTAGCGGCGGAGGCGGATCTGGTGGCGGAGGAAGTGGCGGCGGAGG
ATCTGAGCTGGTGCTGACCCAGAGCCCCTCTGTGTCTGCTGCCCTGGGAAGCCCTGCCAA
GATCACCTGTACCCTGAGCAGCGCCCACAAGACCGACACCATCGACTGGTATCAGCAGC
TGCAGGGCGAGGCCCCCAGATACCTGATGCAGGTGCAGAGCGACGGCAGCTACACCAA
GAGGCCAGGCGTGCCCGACCGGTTCAGCGGATCTAGCTCTGGCGCCGACCGCTACCTGA
TCATCCCCAGCGTGCAGGCCGATGACGAGGCCGATTACTACTGTGGCGCCGACTACATC
GGCGGCTACGTGTTCGGCGGAGGCACCCAGCTGACCGTGACCGGCGAGTCTAAG

Hinge/Spacer

TA CGGACCGCCCTGCCCCCCTTGCCCT 4-1BB
ATGTTCTGGGTGCTGGTGGTGGTGGGCGGGGTGCTGGCCTGCTACAGCCTGCTGGTGACA
GTGGCCTTCATCATCTTTTGGGTGAAACGGGGCAGAAAGAAACTCCTGTATATATTCAAA
CAACCATTTATGAGACCAGTACAAACTACTCAAGAGGAAGATGGCTGTAGCTGCCGATT
TCCAGAAGAAGAAGAAGGAGGATGTGAACTG

CD3 zeta
CGGGTGAAGTTCAGCAGAAGCGCCGACGCCCCTGCCTACCAGCAGGGCCAGAATCAGCT
GTACAACGAGCTGAACCTGGGCAGAAGGGAAGAGTACGACGTCCTGGATAAGCGGAGA
GGCCGGGACCCTGAGATGGGCGGCAAGCCTCGGCGGAAGAACCCCCAGGAAGGCCTGT
ATAACGAACTGCAGAAAGACAAGATGGCCGAGGCCTACAGCGAGATCGGCATGAAGGG
CGAGCGGAGGCGGGGCAAGGGCCACGACGGCCTGTATCAGGGCCTGTCCACCGCCACCA
AGGATACCTACGACGCCCTGCACATGCAGGCCCTGCCCCCAAGG

T2A

CTCGAGGGCGGCGGAGAGGGCAGAGGAAGTCTTCTAACATGCGGTGACGTGGAGGAGA

ATCCCGGCCCTAGG tEGFR
ATGCTTCTCCTGGTGACAAGCCTTCTGCTCTGTGAGTTACCACACCCAGCATTCCTCCTGA
TCCCACGCAAAGTGTGTAACGGAATAGGTATTGGTGAATTTAAAGACTCACTCTCCATAA
ATGCTACGAATATTAAACACTTCAAAAACTGCACCTCCATCAGTGGCGATCTCCACATCC

TGCCGGTGGCATTTAGGGGTGACTCCTTCACACATACTCCTCCTCTGGATCCACAGGAAC

TGGATATTCTGAAAACCGTAAAGGAAATCACAGGGTTTTTGCTGATTCAGGCTTGGCCTG
AAAACAGGACGGACCTCCATGCCTTTGAGAACCTAGAAATCATACGCGGCAGGACCAAG
CAACATGGTCAGTTTTCTCTTGCAGTCGTCAGCCTGAACATAACATCCTTGGGATTACGC
TCCCTCAAGGAGATAAGTGATGGAGATGTGATAATTTCAGGAAACAAAAATTTGTGCTA
TGCAAATACAATAAACTGGAAAAAACTGTTTGGGACCTCCGGTCAGAAAACCAAAATTA
TAAGCAACAGAGGTGAAAACAGCTGCAAGGCCACAGGCCAGGTCTGCCATGCCTTGTGC
TCCCCCGAGGGCTGCTGGGGCCCGGAGCCCAGGGACTGCGTCTCTTGCCGGAATGTCAG
CCGAGGCAGGGAATGCGTGGACAAGTGCAACCTTCTGGAGGGTGAGCCAAGGGAGTTTG
TGGAGAACTCTGAGTGCATACAGTGCCCACCCAGAGTGCCTGCCTCAGGCCATGAACATC
ACCTGCACAGGACGGGGACCAGACAACTGTATCCAGTGTGCCCACTACATTGACGGCCC
CCACTGCGTCAAGACCTGCCCGGCAGGAGTCATGGGAGAAAACAACACCCTGGTCTGGA
AGTACGCAGACGCCGGCCATGTGTGCCACCTGTGCCATCCAAACTGCACCTACGGATGC
ACTGGGCCAGGTCTTGAAGGCTGTCCAACGAATGGGCCTAAGATCCCGTCCATCGCCAC

TABLE 13-continued

| R12 short spacer CAR: PJ_R12-Hinge-41BB-Z-T2A-tEGFR (SEQ ID NO:41) |
|---|

TGGGATGGTGGGGGCCCTCCTCTTGCTGCTGGTGGTGGCCCTGGGGATCGGCCTCTTCAT
GTGA

GCGGCCGCTCTAGACCCGGGCTGCAGGAATTCGATATCAAGCTTATCGATAATCAACCT

CTGGATTACAAAATTTGTGAAAGATTGACTGGTATTCTTAACTATGTTGCTCCTTTTACGC
TATGTGGATACGCTGCTTTAATGCCTTTGTATCATGCTATTGCTTCCCGTATGGCTTTCAT
TTTCTCCTCCTTGTATAAATCCTGGTTGCTGTCTCTTTATGAGGAGTTGTGGCCCGTTGTC
AGGCAACGTGGCGTGGTGTGCACTGTGTTTGCTGACGCAACCCCCACTGGTTGGGGCATT
GCCACCACCTGTCAGCTCCTTTCCGGGACTTTCGCTTTCCCCCTCCCTATTGCCACGGCGG
AACTCATCGCCGCCTGCCTTGCCCGCTGCTGGACAGGGGCTCGGCTGTTGGGCACTGACA
ATTCCGTGGTGTTGTCGGGGAAATCATCGTCCTTTCCTTGGCTGCTCGCCTGTGTTGCCAC
CTGGATTCTGCGCGGGACGTCCTTCTGCTACGTCCCTTCGGCCCTCAATCCAGCGGACCT
TCCTTCCCGCGGCCTGCTGCCGGCTCTGCGGCCTCTTCCGCGTCTTCGCCTTCGCCCTCAG
ACGAGTCGGATCTCCCTTTGGGCCGCCTCCCCGCATCGATACCGTCGACTAGCCGTACCT
TTAAGACCAATGACTTACAAGGCAGCTGTAGATCTTAGCCACTTTTTAAAAGAAAAGGG
GGGACTGGAAGGGCTAATTCACTCCCAAAGAAGACAAGATCTGCTTTTTGCCTGTACTG
GGTCTCTCTGGTTAGACCAGATCTGAGCCTGGGAGCTCTCTGGCTAACTAGGGAACCCAC
TGCTTAAGCCTCAATAAAGCTTGCCTTGAGTGCTTCAAGTAGTGTGTGCCCGTCTGTTGT
GTGACTCTGGTAACTAGAGATCCCTCAGACCCTTTTAGTCAGTGTGGAAAATCTCTAGCA

GAATTCGATATCAAGCTTATCGATACCGTCGACCTCGAGGGGGGGCCCGGTACCCAATT

CGCCCTATAGTGAGTCGTATTACAATTCACTGGCCGTCGTTTTACAACGTCGTGACTGGG
AAAACCCTGGCGTTACCCAACTTAATCGCCTTGCAGCACATCCCCCTTTCGCCAGCTGGC
GTAATAGCGAAGAGGCCCGCACCGATCGCCCTTCCCAACAGTTGCGCAGCCTGAATGGC
GAATGGAAATTGTAAGCGTTAATATTTTGTTAAAATTCGCGTTAAATTTTTGTTAAATCA
GCTCATTTTTTAACCAATAGGCCGAAATCGGCAAAATCCCTTATAAATCAAAAGAATAG
ACCGAGATAGGGTTGAGTGTTGTTCCAGTTTGGAACAAGAGTCCACTATTAAAGAACGT
GGACTCCAACGTCAAAGGGCGAAAAACCGTCTATCAGGGCGATGGCCCACTACGTGAAC
CATCACCCTAATCAAGTTTTTTGGGGTCGAGGTGCCGTAAAGCACTAAATCGGAACCCTA
AAGGGAGCCCCCGATTTAGAGCTTGACGGGGAAAGCCGGCGAACGTGGCGAGAAAGGA
AGGGAAGAAAGCGAAAGGAGCGGGCGCTAGGGCGCTGGCAAGTGTAGCGGTCACGCTG
CGCGTAACCACCACACCCGCCGCGCTTAATGCGCCGCTACAGGGCGCGTCAGGTGGCAC
TTTTCGGGGAAATGTGCGCGGAACCCCTATTTGTTTATTTTTCTAAATACATTCAAATATG
TATCCGCTCATGAGACAATAACCCTGATAAATGCTTCAATAATATTGAAAAAGGAAGAG
TATGAGTATTCAACATTTCCGTGTCGCCCTTATTCCCTTTTTTGCGGCATTTTGCCTTCCTG
TTTTTGCTCACCCAGAAACGCTGGTGAAAGTAAAAGATGCTGAAGATCAGTTGGGTGCA
CGAGTGGGTTACATCGAACTGGATCTCAACAGCGGTAAGATCCTTGAGAGTTTTCGCCCC
GAAGAACGTTTTCCAATGATGAGCACTTTTAAAGTTCTGCTATGTGGCGCGGTATTATCC
CGTATTGACGCCGGGCAAGAGCAACTCGGTCGCCGCATACACTATTCTCAGAATGACTT
GGTTGAGTACTCACCAGTCACAGAAAAGCATCTTACGGATGGCATGACAGTAAGAGAAT
TATGCAGTGCTGCCATAACCATGAGTGATAACACTGCGGCCAACTTACTTCTGACAACGA
TCGGAGGACCGAAGGAGCTAACCGCTTTTTTGCACAACATGGGGGATCATGTAACTCGC
CTTGATCGTTGGGAACCGGAGCTGAATGAAGCCATACCAAACGACGAGCGTGACACCAC
GATGCCTGTAGCAATGGCAACAACGTTGCGCAAACTATTAACTGGCGAACTACTTACTCT
AGCTTCCCGGCAACAATTAATAGACTGGATGGAGGCGGATAAAGTTGCAGGACCACTTC
TGCGCTCGGCCCTTCCGGCTGGCTGGTTTATTGCTGATAAATCTGGAGCCGGTGAGCGTG
GGTCTCGCGGTATCATTGCAGCACTGGGGCCAGATGGTAAGCCCTCCCGTATCGTAGTTA
TCTACACGACGGGGAGTCAGGCAACTATGGATGAACGAAATAGACAGATCGCTGAGATA
GGTGCCTCACTGATTAAGCATTGGTAACTGTCAGACCAAGTTTACTCATATATACTTTAG
ATTGATTTAAAACTTCATTTTTAATTTAAAAGGATCTAGGTGAAGATCCTTTTTGATAATC
TCATGACCAAAATCCCTTAACGTGAGTTTTCGTTCCACTGAGCGTCAGACCCCGTAGAAA
AGATCAAAGGATCTTCTTGAGATCCTTTTTTTCTGCGCGTAATCTGCTGCTTGCAAACAA
AAAAACCACCGCTACCAGCGGTGGTTTGTTTGCCGGATCAAGAGCTACCAACTCTTTTTC
CGAAGGTAACTGGCTTCAGCAGAGCGCAGATACCAAATACTGTTCTTCTAGTGTAGCCGT
AGTTAGGCCACCACTTCAAGAACTCTGTAGCACCGCCTACATACCTCGCTCTGCTAATCC
TGTTACCAGTGGCTGCTGCCAGTGGCGATAAGTCGTGTCTTACCGGGTTGGACTCAAGAC
GATAGTTACCGGATAAGGCGCAGCGGTCGGGCTGAACGGGGGGTTCGTGCACACAGCCC
AGCTTGGAGCGAACGACCTACACCGAACTGAGATACCTACAGCGTGAGCTATGAGAAAG
CGCCACGCTTCCCGAAGGGAGAAAGGCGGACAGGTATCCGGTAAGCGGCAGGGTCGGA
ACAGGAGAGCGCACGAGGGAGCTTCCAGGGGGAAACGCCTGGTATCTTTATAGTCCTGT
CGGGTTTCGCCACCTCTGACTTGAGCGTCGATTTTTGTGATGCTCGTCAGGGGGGCGGAG
CCTATGGAAAAACGCCAGCAACGCGGCCTTTTTACGGTTCCTGGCCTTTTGCTGGCCTTT
TGCTCACATGTTCTTTCCTGCGTTATCCCCTGATTCTGTGGATAACCGTATTACCGCCTTT
GAGTGAGCTGATACCGCTCGCCGCAGCCGAACGACCGAGCGCAGCGAGTCAGTGAGCG
AGGAAGCGGAAGAGCGCCCAATACGCAAACCGCCTCTCCCCGCGCGTTGGCCGATTCAT
TAATGCAGCTGGCACGACAGGTTTCCCGACTGGAAAGCGGGCAGTGAGCGCAACGCAAT
TAATGTGAGTTAGCTCACTCATTAGGCACCCCAGGCTTTACACTTTATGCTTCCGGCTCGT

TABLE 13-continued

| R12 short spacer CAR: PJ_R12-Hinge-41BB-Z-T2A-tEGFR (SEQ ID NO:41) |
|---|
| ATGTTGTGTGGAATTGTGAGCGGATAACAATTTCACACAGGAAACAGCTATGACCATGA |
| TTACGCCAAGCTCGAAATTAACCCTCACTAAAGGGAACAAAAGCTGGAGCTCCACCGCG |
| |
| GTGGCGGCCTCGAGGTCGAGATCCGGTCGACCAGCAACCATAGTCCCGCCCCTAACTCC |
| |
| GCCCATCCCGCCCCTAACTCCGCCCAGTTCCGCCCATTCTCCGCCCCATGGCTGACTAAT |
| TTTTTTTATTTATGCAGAGGCCGAGGCCGCCTCGGCCTCTGAGCTATTCCAGAAGTAGTG |
| AGGAGGCTTTTTTGGAGGCCTAGGCTTTTGCAAAAAGCTTCGACGGTATCGATTGGCTCA |
| TGTCCAACATTACCGCCATGTTGACATTGATTATTGACTAGTTATTAATAGTAATCAATT |
| ACGGGGTCATTAGTTCATAGCCCATATATGGAGTTCCGCGTTACATAACTTACGGTAAAT |
| GGCCCGCCTGGCTGACCGCCCAACGACCCCCGCCCATTGACGTCAATAATGACGTATGTT |
| CCCATAGTAACGCCAATAGGGACTTTCCATTGACGTCAATGGGTGGAGTATTTACGGTAA |
| ACTGCCCACTTGGCAGTACATCAAGTGTATCATATGCCAAGTACGCCCCCTATTGACGTC |
| AATGACGGTAAATGGCCCGCCTGGCATTATGCCCAGTACATGACCTTATGGGACTTTCCT |
| ACTTGGCAGTACATCTACGTATTAGTCATCGCTATTACCATGGTGATGCGGTTTTGGCAG |
| TACATCAATGGGCGTGGATAGCGGTTTGACTCACGGGGATTTCCAAGTCTCCACCCCATT |
| GACGTCAATGGGAGTTTGTTTTGGCACCAAAATCAACGGGACTTTCCAAAATGTCGTAAC |
| AACTCCGCCCCATTGACGCAAATGGGCGGTAGGCGTGTACGGAATTCGGAGTGGCGAGC |
| CCTCAGATCCTGCATATAAGCAGCTGCTTTTTGCCTGTACTGGGTCTCTCTG |

TABLE 14

| Leader _R12 - CD28tm/41BB-Z-T2A-tEGFR (SEQ ID NO: 42) |
|---|
| Leader |
| MLLLVTSLLLCELPHPAFLLIP |
| |
| scFv R12 |
| QEQLVESGGRLVTPGGSLTLSCKASGFDFSAYYMSWVRQAPGKGLEWIAT |
| IYPSSGKTYYATWVNGRFTISSDNAQNTVDLQMNSLTAADRATYFCARDS |
| YADDGALFNIWGPGTLVTISSGGGGSGGGGSGGGGSELVLTQSPSVSAAL |
| GSPAKITCTLSSAHKTDTIDWYQQLQGEAPRYLMQVQSDGSYTKRPGVPD |
| RFSGSSSGADRYLIIPSVQADDEADYYCGADYIGGYVFGGGTQLTVTG |
| |
| Hinge/spacer |
| ESKYGPPCPPCP |
| |
| CD28tm |
| MFWVLVVVGGVLACYSLLVTVAFIIFWV |
| |
| 4-1BB |
| KRGRKKLLYIFKQPFMRPVQTTQEEDGCSCRFPEEEEGGCEL |

TABLE 14-continued

| Leader _R12 - CD28tm/41BB-Z-T2A-tEGFR (SEQ ID NO: 42) |
|---|
| CD3zeta |
| RVKFSRSADAPAYQQGQNQLYNELNLGRREEYDVLDKRRGRDPEMGGKPR |
| RKNPQEGLYNELQKDKMAEAYSEIGMKGERRRGKGHDGLYQGLSTATKDT |
| YDALHMQALPPR |
| |
| T2A |
| LEGGGEGRGSLLTCGDVEENPGPR |
| |
| tEGFR |
| MLLLVTSLLLCELPHPAFLLIPRKVCNGIGIGEFKDSLSINATNIKHFKN |
| CTSISGDLHILPVAFRGDSFTHTPPLDPQELDILKTVKEITGFLLIQAWP |
| ENRTDLHAFENLEIIRGRTKQHGQFSLAVVSLNITSLGLRSLKEISDGDV |
| IISGNKNLCYANTINWKKLFGTSGQKTKIISNRGENSCKATGQVCHALCS |
| PEGCWGPEPRDCVSCRNVSRGRECVDKCNLLEGEPREFVENSECIQCHPE |
| CLPQAMNITCTGRGPDNCIQCAHYIDGPHCVKTCPAGVMGENNTLVWKYA |
| DAGHVCHLCHPNCTYGCTGPGLEGCPTNGPKIPSIATGMVGALLLLLVVA |
| LGIGLFM |

TABLE 15

| R11 long spacer CAR: PJ_R11-CH2-CH3-41BB-Z-T2A-tEGFR (SEQ ID NO: 43) |
|---|
| GTTAGACCAGATCTGAGCCTGGGAGCTCTCTGGCTAACTAGGGAACCCACTGCTTAAGC |
| CTCAATAAAGCTTGCCTTGAGTGCTTCAAGTAGTGTGTGCCCGTCTGTTGTGTGACTCTG |
| GTAACTAGAGATCCCTCAGACCCTTTTAGTCAGTGTGGAAAATCTCTAGCAGTGGCGCCC |
| GAACAGGGACTTGAAAGCGAAAGGGAAACCAGAGGAGCTCTCTCGACGCAGGACTCGG |
| CTTGCTGAAGCGCGCACGGCAAGAGGCGAGGGGCGGCGACTGGTGAGTACGCCAAAAA |
| TTTTGACTAGCGGAGGCTAGAAGGAGAGAGATGGGTGCGAGAGCGTCAGTATTAAGCGG |
| GGGAGAATTAGATCGATGGGAAAAAATTCGGTTAAGGCCAGGGGGAAAGAAAAAATAT |
| AAATTAAAACATATAGTATGGGCAAGCAGGGAGCTAGAACGATTCGCAGTTAATCCTGG |
| CCTGTTAGAAACATCAGAAGGCTGTAGACAAATACTGGGACAGCTACAACCATCCCTTC |
| AGACAGGATCAGAAGAACTTAGATCATTATATAATACAGTAGCAACCCTCTATTGTGTG |
| CATCAAAGGATAGAGATAAAAGACACCAAGGAAGCTTTAGACAAGATAGAGGAAGAGC |
| AAAACAAAAGTAAGAAAAAAGCACAGCAAGCAGCAGCTGACACAGGACACAGCAATCA |
| GGTCAGCCAAAATTACCCTATAGTGCAGAACATCCAGGGGCAAATGGTACATCAGGCCA |
| TATCACCTAGAACTTTAAATGCATGGGTAAAAGTAGTAGAAGAGAAGGCTTTCAGCCCA |
| GAAGTGATACCCATGTTTTCAGCATTATCAGAAGGAGCCACCCCACAAGATTTAAACAC |
| CATGCTAAACACAGTGGGGGGACATCAAGCAGCCATGCAAATGTTAAAAGAGACCATCA |
| ATGAGGAAGCTGCAGGCAAAGAGAAGAGTGGTGCAGAGAGAAAAAAGAGCAGTGGGA |
| ATAGGAGCTTTGTTCCTTGGGTTCTTGGGAGCAGCAGGAAGCACTATGGGCGCAGCGTC |
| AATGACGCTGACGGTACAGGCCAGACAATTATTGTCTGGTATAGTGCAGCAGCAGAACA |
| ATTTGCTGAGGGCTATTGAGGCGCAACAGCATCTGTTGCAACTCACAGTCTGGGGCATCA |
| AGCAGCTCCAGGCAAGAATCCTGGCTGTGGAAAGATACCTAAAGGATCAACAGCTCCTG |
| GGGATTTGGGGTTGCTCTGGAAAACTCATTTGCACCACTGCTGTGCCTTGGATCTACAAA |
| TGGCAGTATTCATCCACAATTTTAAAAGAAAAGGGGGGATTGGGGGGTACAGTGCAGGG |

TABLE 15 -continued

R11 long spacer CAR: PJ_R11-CH2-CH3-41BB-Z-T2A-tEGFR (SEQ ID NO: 43)

GAAAGAATAGTAGACATAATAGCAACAGACATACAAACTAAAGAATTACAAAAACAAA
TTACAAAAATTCAAAATTTTCGGGTTTATTACAGGGACAGCAGAGATCCAGTTTGGGGAT
CAATTGCATGAAGAATCTGCTTAGGGTTAGGCGTTTTGCGCTGCTTCGCGAGGATCTGCG
ATCGCTCCGGTGCCCGTCAGTGGGCAGAGCGCACATCGCCCACAGTCCCCGAGAAGTTG
GGGGGAGGGGTCGGCAATTGAACCGGTGCCTAGAGAAGGTGGCGCGGGGTAAACTGGG
AAAGTGATGTCGTGTACTGGCTCCGCCTTTTTCCCGAGGGTGGGGGAGAACCGTATATAA
GTGCAGTAGTCGCCGTGAACGTTCTTTTTCGCAACGGGTTTGCCGCCAGAACACAGCTGA
AGCTTCGAGGGGCTCGCATCTCTCCTTCACGCGCCCGCCGCCCTACCTGAGGCCGCCATC
CACGCCGGTTGAGTCGCGTTCTGCCGCCTCCCGCCTGTGGTGCCTCCTGAACTGCGTCCG
CCGTCTAGGTAAGTTTAAAGCTCAGGTCGAGACCGGGCCTTTGTCCGGCGCTCCCTTGGA
GCCTACCTAGACTCAGCCGGCTCTCCACGCTTTGCCTGACCCTGCTTGCTCAACTCTACGT
CTTTGTTTCGTTTTCTGTTCTGCGCCGTTACAGATCCAAGCTGTGACCGGCGCCTACG

GCTAGC scFv R12

GAATTCGCCACCATGCTGCTGCTGGTGACAAGCCTGCTGCTGTGCGAGCTGCCCCACCCC

GCCTTTCTGCTGATCCCCCAGAGCGTGAAAGAGTCCGAGGGCGACCTGGTCACACCAGC
CGGCAACCTGACCCTGACCTGTACCGCCAGCGGCAGCGACATCAACGACTACCCCATCT
CTTGGGTCCGCCAGGCTCCTGGCAAGGGACTGGAATGGATCGGCTTCATCAACAGCGGC
GGCAGCACTTGGTACGCCAGCTGGGTCAAAGGCCGGTTCACCATCAGCCGGACCAGCAC
CACCGTGGACCTGAAGATGACAAGCCTGACCACCGACGACACCGCCACCTACTTTTGCG
CCAGAGGCTACAGCACCTACTACGGCGACTTCAACATCTGGGGCCCTGGCACCCTGGTC
ACAATCTCTAGCGGCGGAGGCGGCAGCGGAGGTGGAGGAAGTGGCGGCGGAGGATCCG
AGCTGGTCATGACCCAGACCCCCAGCAGCACATCTGGCGCCGTGGGCGGCACCGTGACC
ATCAATTGCCAGGCCAGCCAGAGCATCGACAGCAACCTGGCCTGGTTCCAGCAGAAGCC
CGGCCAGCCCCCCACCCTGCTGATCTACAGAGCCTCCAACCTGGCCAGCGGCGTGCCAA
GCAGATTCAGCGGCAGCAGATCTGGCACCGAGTACACCCTGACCATCTCCGGCGTGCAG
AGAGAGGACGCCGCTACCTATTACTGCCTGGGCGGCGTGGGCAACGTGTCCTACAGAAC
CAGCTTCGGCGGAGGTACTGAGGTGGTCGTCAAA

Hinge/Spacer

TA CGGACCGCCCTGCCCCCCTTGCCCT

CH2
GCCCCCGAGTTCCTGGGCGGACCCAGCGTGTTCCTGTTCCCCCCCAAGCCCAAGGACACC
CTGATGATCAGCCGGACCCCCGAGGTGACCTGCGTGGTGGTGGACGTGAGCCAGGAAGA
TCCCGAGGTCCAGTTCAATTGGTACGTGGACGGCGTGGAAGTGCACAACGCCAAGACCA
AGCCCAGAGAGGAACAGTTCAACAGCACCTACCGGGTGGTGTCTGTGCTGACCGTGCTG
CACCAGGACTGGCTGAACGGCAAAGAATACAAGTGCAAGGTGTCCAACAAGGGCCTGC
CCAGCAGCATCGAAAAGACCATCAGCAAGGCCAAG

CH3
GGCCAGCCTCGCGAGCCCCAGGTGTACACCCTGCCTCCCTCCCAGGAAGAGATGACCAA
GAACCAGGTGTCCCTGACCTGCCTGGTGAAGGGCTTCTACCCCAGCGACATCGCCGTGG
AGTGGGAGAGCAACGGCCAGCCTGAGAACAACTACAAGACCACCCCTCCCGTGCTGGAC
AGCGACGGCAGCTTCTTCCTGTACAGCCGGCTGACCGTGGACAAGAGCCGGTGGCAGGA
AGGCAACGTCTTTAGCTGCAGCGTGATGCACGAGGCCCTGCACAACCACTACACCCAGA
AGAGCCTGAGCCTGTCCCTGGGCAAG 4-1BB
ATGTTCTGGGTGCTGGTGGTGGTGGGCGGGGTGCTGGCCTGCTACAGCCTGCTGGTGACA
GTGGCCTTCATCATCTTTTGGGTGAAACGGGGCAGAAAGAAACTCCTGTATATATTCAAA
CAACCATTTATGAGACCAGTACAAACTACTCAAGAGGAAGATGGCTGTAGCTGCCGATT
TCCAGAAGAAGAAGAAGGAGGATGTGAACTG

CD3zeta
CGGGTGAAGTTCAGCAGAAGCGCCGACGCCCCTGCCTACCAGCAGGGCCAGAATCAGCT
GTACAACGAGCTGAACCTGGGCAGAAGGGAAGAGTACGACGTCCTGGATAAGCGGAGA
GGCCGGGACCCTGAGATGGGCGGCAAGCCTCGGCGGAAGAACCCCCAGGAAGGCCTGT
ATAACGAACTGCAGAAAGACAAGATGGCCGAGGCCTACAGCGAGATCGGCATGAAGGG TABLE 15 -continued

| R11 long spacer CAR: PJ_R11-CH2-CH3-41BB-Z-T2A-tEGFR (SEQ ID NO: 43) |
|---|

CGAGCGGAGGCGGGGCAAGGGCCACGACGGCCTGTATCAGGGCCTGTCCACCGCCACCA
AGGATACCTACGACGCCCTGCACATGCAGGCCCTGCCCCCAAGG

T2A

CTCGAGGGCGGCGGAGAGGGCAGAGGAAGTCTTCTAACATGCGGTGACGTGGAGGAGA

ATCCCGGCCCTAGG tEGFR
ATGCTTCTCCTGGTGACAAGCCTTCTGCTCTGTGAGTTACCACACCCAGCATTCCTCCTGA
TCCCACGCAAAGTGTGTAACGGAATAGGTATTGGTGAATTTAAAGACTCACTCTCCATAA
ATGCTACGAATATTAAACACTTCAAAAACTGCACCTCCATCAGTGGCGATCTCCACATCC

TGCCGGTGGCATTTAGGGGTGACTCCTTCACACATACTCCTCCTCTGGATCCACAGGAAC

TGGATATTCTGAAAACCGTAAAGGAAATCACAGGGTTTTTGCTGATTCAGGCTTGGCCTG
AAAACAGGACGGACCTCCATGCCTTTGAGAACCTAGAAATCATACGCGGCAGGACCAAG
CAACATGGTCAGTTTTCTCTTGCAGTCGTCAGCCTGAACATAACATCCTTGGGATTACGC
TCCCTCAAGGAGATAAGTGATGGAGATGTGATAATTTCAGGAAACAAAAATTTGTGCTA
TGCAAATACAATAAACTGGAAAAAACTGTTTGGGACCTCCGGTCAGAAAACCAAAATTA
TAAGCAACAGAGGTGAAAACAGCTGCAAGGCCACAGGCCAGGTCTGCCATGCCTTGTGC
TCCCCCGAGGGCTGCTGGGGCCCGGAGCCCAGGGACTGCGTCTCTTGCCGGAATGTCAG
CCGAGGCAGGGAATGCGTGGACAAGTGCAACCTTCTGGAGGGTGAGCCAAGGGAGTTTG
TGGAGAACTCTGAGTGCATACAGTGCCACCCAGAGTGCCTGCCTCAGGCCATGAACATC
ACCTGCACAGGACGGGGACCAGACAACTGTATCCAGTGTGCCCACTACATTGACGGCCC
CCACTGCGTCAAGACCTGCCCGGCAGGAGTCATGGGAGAAAACAACACCCTGGTCTGGA
AGTACGCAGACGCCGGCCATGTGTGCCACCTGTGCCATCCAAACTGCACCTACGGATGC
ACTGGGCCAGGTCTTGAAGGCTGTCCAACGAATGGGCCTAAGATCCCGTCCATCGCCAC
TGGGATGGTGGGGGCCCTCCTCTTGCTGCTGGTGGTGGCCCTGGGGATCGGCCTCTTCAT
GTGA

GCGGCCGCTCTAGACCCGGGCTGCAGGAATTCGATATCAAGCTTATCGATAATCAACCT

CTGGATTACAAAATTTGTGAAAGATTGACTGGTATTCTTAACTATGTTGCTCCTTTTACGC
TATGTGGATACGCTGCTTTAATGCCTTTGTATCATGCTATTGCTTCCCGTATGGCTTTCAT
TTTCTCCTCCTTGTATAAATCCTGGTTGCTGTCTCTTTATGAGGAGTTGTGGCCCGTTGTC
AGGCAACGTGGCGTGGTGTGCACTGTGTTTGCTGACGCAACCCCCACTGGTTGGGGCATT
GCCACCACCTGTCAGCTCCTTTCCGGGACTTTCGCTTTCCCCCTCCCTATTGCCACGGCGG
AACTCATCGCCGCCTGCCTTGCCCGCTGCTGGACAGGGGCTCGGCTGTTGGGCACTGACA
ATTCCGTGGTGTTGTCGGGGAAATCATCGTCCTTTCCTTGGCTGCTCGCCTGTGTTGCCAC
CTGGATTCTGCGCGGGACGTCCTTCTGCTACGTCCCTTCGGCCCTCAATCCAGCGGACCT
TCCTTCCCGCGGCCTGCTGCCGGCTCTGCGGCCTCTTCCGCGTCTTCGCCTTCGCCCTCAG
ACGAGTCGGATCTCCCTTTGGGCCGCCTCCCCGCATCGATACCGTCGACTAGCCGTACCT
TTAAGACCAATGACTTACAAGGCAGCTGTAGATCTTAGCCACTTTTTAAAAGAAAAGGG
GGGACTGGAAGGGCTAATTCACTCCCAAAGAAGACAAGATCTGCTTTTTGCCTGTACTG
GGTCTCTCTGGTTAGACCAGATCTGAGCCTGGGAGCTCTCTGGCTAACTAGGGAACCCAC
TGCTTAAGCCTCAATAAAGCTTGCCTTGAGTGCTTCAAGTAGTGTGTGCCCGTCTGTTGT
GTGACTCTGGTAACTAGAGATCCCTCAGACCCTTTTAGTCAGTGTGGAAAATCTCTAGCA

GAATTCGATATCAAGCTTATCGATACCGTCGACCTCGAGGGGGGGCCCGGTACCCAATT

CGCCCTATAGTGAGTCGTATTACAATTCACTGGCCGTCGTTTTACAACGTCGTGACTGGG
AAAACCCTGGCGTTACCCAACTTAATCGCCTTGCAGCACATCCCCCTTTCGCCAGCTGGC
GTAATAGCGAAGAGGCCCGCACCGATCGCCCTTCCCAACAGTTGCGCAGCCTGAATGGC
GAATGGAAATTGTAAGCGTTAATATTTTGTTAAAATTCGCGTTAAATTTTTGTTAAATCA
GCTCATTTTTTAACCAATAGGCCGAAATCGGCAAAATCCCTTATAAATCAAAAGAATAG
ACCGAGATAGGGTTGAGTGTTGTTCCAGTTTGGAACAAGAGTCCACTATTAAAGAACGT
GGACTCCAACGTCAAAGGGCGAAAAACCGTCTATCAGGGCGATGGCCCACTACGTGAAC
CATCACCCTAATCAAGTTTTTTGGGGTCGAGGTGCCGTAAAGCACTAAATCGGAACCCTA
AAGGGAGCCCCCGATTTAGAGCTTGACGGGGAAAGCCGGCGAACGTGGCGAGAAAGGA
AGGGAAGAAAGCGAAAGGAGCGGGCGCTAGGGCGCTGGCAAGTGTAGCGGTCACGCTG
CGCGTAACCACCACACCCGCCGCGCTTAATGCGCCGCTACAGGGCGCGTCAGGTGGCAC
TTTTCGGGGAAATGTGCGCGGAACCCCTATTTGTTTATTTTTCTAAATACATTCAAATATG
TATCCGCTCATGAGACAATAACCCTGATAAATGCTTCAATAATATTGAAAAAGGAAGAG
TATGAGTATTCAACATTTCCGTGTCGCCCTTATTCCCTTTTTTGCGGCATTTTGCCTTCCTG
TTTTTGCTCACCCAGAAACGCTGGTGAAAGTAAAAGATGCTGAAGATCAGTTGGGTGCA
CGAGTGGGTTACATCGAACTGGATCTCAACAGCGGTAAGATCCTTGAGAGTTTTCGCCCC
GAAGAACGTTTTCCAATGATGAGCACTTTTAAAGTTCTGCTATGTGGCGCGGTATTATCC
CGTATTGACGCCGGGCAAGAGCAACTCGGTCGCCGCATACACTATTCTCAGAATGACTT
GGTTGAGTACTCACCAGTCACAGAAAAGCATCTTACGGATGGCATGACAGTAAGAGAAT
TATGCAGTGCTGCCATAACCATGAGTGATAACACTGCGGCCAACTTACTTCTGACAACGA
TCGGAGGACCGAAGGAGCTAACCGCTTTTTTGCACAACATGGGGGATCATGTAACTCGC

TABLE 15 -continued

| R11 long spacer CAR: PJ_R11-CH2-CH3-41BB-Z-T2A-tEGFR (SEQ ID NO: 43) |
|---|
| CTTGATCGTTGGGAACCGGAGCTGAATGAAGCCATACCAAACGACGAGCGTGACACCAC<br>GATGCCTGTAGCAATGGCAACAACGTTGCGCAAACTATTAACTGGCGAACTACTTACTCT<br>AGCTTCCCGGCAACAATTAATAGACTGGATGGAGGCGGATAAAGTTGCAGGACCACTTC<br>TGCGCTCGGCCCTTCCGGCTGGCTGGTTTATTGCTGATAAATCTGGAGCCGGTGAGCGTG<br>GGTCTCGCGGTATCATTGCAGCACTGGGGCCAGATGGTAAGCCCTCCCGTATCGTAGTTA<br>TCTACACGACGGGGAGTCAGGCAACTATGGATGAACGAAATAGACAGATCGCTGAGATA<br>GGTGCCTCACTGATTAAGCATTGGTAACTGTCAGACCAAGTTTACTCATATATACTTTAG<br>ATTGATTTAAAACTTCATTTTTAATTTAAAAGGATCTAGGTGAAGATCCTTTTTGATAATC<br>TCATGACCAAAATCCCTTAACGTGAGTTTTCGTTCCACTGAGCGTCAGACCCCGTAGAAA<br>AGATCAAAGGATCTTCTTGAGATCCTTTTTTTCTGCGCGTAATCTGCTGCTTGCAAACAA<br>AAAAACCACCGCTACCAGCGGTGGTTTGTTTGCCGGATCAAGAGCTACCAACTCTTTTTC<br>CGAAGGTAACTGGCTTCAGCAGAGCGCAGATACCAAATACTGTTCTTCTAGTGTAGCCGT<br>AGTTAGGCCACCACTTCAAGAACTCTGTAGCACCGCCTACATACCTCGCTCTGCTAATCC<br>TGTTACCAGTGGCTGCTGCCAGTGGCGATAAGTCGTGTCTTACCGGGTTGGACTCAAGAC<br>GATAGTTACCGGATAAGGCGCAGCGGTCGGGCTGAACGGGGGGTTCGTGCACACAGCCC<br>AGCTTGGAGCGAACGACCTACACCGAACTGAGATACCTACAGCGTGAGCTATGAGAAAG<br>CGCCACGCTTCCCGAAGGGAGAAAGGCGGACAGGTATCCGGTAAGCGGCAGGGTCGGA<br>ACAGGAGAGCGCACGAGGGAGCTTCCAGGGGGAAACGCCTGGTATCTTTATAGTCCTGT<br>CGGGTTTCGCCACCTCTGACTTGAGCGTCGATTTTTGTGATGCTCGTCAGGGGGGCGGAG<br>CCTATGGAAAAACGCCAGCAACGCGGCCTTTTTACGGTTCCTGGCCTTTTGCTGGCCTTT<br>TGCTCACATGTTCTTTCCTGCGTTATCCCCTGATTCTGTGGATAACCGTATTACCGCCTTT<br>GAGTGAGCTGATACCGCTCGCCGCAGCCGAACGACCGAGCGCAGCGAGTCAGTGAGCG<br>AGGAAGCGGAAGAGCGCCCAATACGCAAACCGCCTCTCCCCGCGCGTTGGCCGATTCAT<br>TAATGCAGCTGGCACGACAGGTTTCCCGACTGGAAAGCGGGCAGTGAGCGCAACGCAAT<br>TAATGTGAGTTAGCTCACTCATTAGGCACCCCAGGCTTTACACTTTATGCTTCCGGCTCGT<br>ATGTTGTGTGGAATTGTGAGCGGATAACAATTTCACACAGGAAACAGCTATGACCATGA<br>TTACGCCAAGCTCGAAATTAACCCTCACTAAAGGGAACAAAAGCTGGAGCTCCACCGCG<br><br>GTGGCGGCCTCGAGGTCGAGATCCGGTCGACCAGCAACCATAGTCCCGCCCCTAACTCC<br><br>GCCCATCCCGCCCCTAACTCCGCCCAGTTCCGCCCATTCTCCGCCCCATGGCTGACTAAT<br>TTTTTTTATTTATGCAGAGGCCGAGGCCGCCTCGGCCTCTGAGCTATTCCAGAAGTAGTG<br>AGGAGGCTTTTTTGGAGGCCTAGGCTTTTGCAAAAAGCTTCGACGGTATCGATTGGCTCA<br>TGTCCAACATTACCGCCATGTTGACATTGATTATTGACTAGTTATTAATAGTAATCAATT<br>ACGGGGTCATTAGTTCATAGCCCATATATGGAGTTCCGCGTTACATAACTTACGGTAAAT<br>GGCCCGCCTGGCTGACCGCCCAACGACCCCCGCCCATTGACGTCAATAATGACGTATGTT<br>CCCATAGTAACGCCAATAGGGACTTTCCATTGACGTCAATGGGTGGAGTATTTACGGTAA<br>ACTGCCCACTTGGCAGTACATCAAGTGTATCATATGCCAAGTACGCCCCCTATTGACGTC<br>AATGACGGTAAATGGCCCGCCTGGCATTATGCCCAGTACATGACCTTATGGGACTTTCCT<br>ACTTGGCAGTACATCTACGTATTAGTCATCGCTATTACCATGGTGATGCGGTTTTGGCAG<br>TACATCAATGGGCGTGGATAGCGGTTTGACTCACGGGGATTTCCAAGTCTCCACCCCATT<br>GACGTCAATGGGAGTTTGTTTTGGCACCAAAATCAACGGGACTTTCCAAAATGTCGTAAC<br>AACTCCGCCCCATTGACGCAAATGGGCGGTAGGCGTGTACGGAATTCGGAGTGGCGAGC<br>CCTCAGATCCTGCATATAAGCAGCTGCTTTTTGCCTGTACTGGGTCTCTCTG |

TABLE 16

| Leader _R11- Hinge-CH2-CH3- CD28tm/41BB-Z-T2A-tEGFR (SEQ ID NO:44) |
|---|
| Leader: MLLLVTSLLLCELPHPAFLLIP<br><br>R11 scFv<br>QSVKESEGDLVTPAGNLTLTCTASGSDINDYPISWVRQAPGKGLEWIGFINSGGSTWYASWV<br>KGRFTISRTSTTVDLKMTSLTTDDTATYFCARGYSTYYGDFNIWGPGTLVTISSGGGGSGGG<br>GSGGGGSELVMTQTPSSTSGAVGGTVTINCQASQSIDSNLAWFQQKPGQPPTLLIYRASNLAS<br>GVPSRFSGSRSGTEYTLTISGVQREDAATYYCLGGVGNVSYRTSFGGGTEVVVK<br><br>Hinge/Spacer: ESKYGPPCPPCP<br><br>CH2<br><br>APEFLGGPSVFLFPPKPKDTLMISRTPEVTCVVVDVSQEDPEVQFNWYVDGVEVHNAKTKPR<br><br>EEQFNSTYRVVSVLTVLHQDWLNGKEYKCKVSNKGLPSSIEKTISKAK<br><br>CH3<br><br>GQPREPQVYTLPPSQEEMTKNQVSLTCLVKGFYPSDIAVEWESNGQPENNYKTTPPVLDSDG |

TABLE 16 -continued

| Leader _R11- Hinge-CH2-CH3- CD28tm/41BB-Z-T2A-tEGFR (SEQ ID NO:44) |
| --- |
| SFFLYSRLTVDKSRWQEGNVFSCSVMHEALHNHYTQKSLSLSLGK |
| CD28tm: MFWVLVVVGGVLACYSLLVTVAFIIFWV |
| 4-1BB: KRGRKKLLYIFKQPFMRPVQTTQEEDGCSCRFPEEEEGGCEL |
| CD3zeta<br>RVKFSRSADAPAYQQGQNQLYNELNLGRREEYDVLDKRRGRDPEMGGKPRRKNPQEGLYN<br>ELQKDKMAEAYSEIGMKGERRRGKGHDGLYQGLSTATKDTYDALHMQALPPR |
| T2A: LEGGGEGRGSLLTCGDVEENPGPR |
| tEGFR<br>MLLLVTSLLLCELPHPAFLLIPRKVCNGIGIGEFKDSLSINATNIKHFKNCTSISGDLHILPVAFR<br>GDSFTHTPPLDPQELDILKTVKEITGFLLIQAWPENRTDLHAFENLEIIRGRTKQHGQFSLAVV<br>SLNITSLGLRSLKEISDGDVIISGNKNLCYANTINWKKLFGTSGQKTKIISNRGENSCKATGQV<br>CHALCSPEGCWGPEPRDCVSCRNVSRGRECVDKCNLLEGEPREFVENSECIQCHPECLPQAM<br>NITCTGRGPDNCIQCAHYIDGPHCVKTCPAGVMGENNTLVWKYADAGHVCHLCHPNCTYG<br>CTGPGLEGCPTNGPKIPSIATGMVGALLLLLVVALGIGLFM |

TABLE 17

| R11 intermediate spacer CAR: PJ_R11-CH3-41BB-Z-T2A-tEGFR (SEQ ID NO:45) |
| --- |
| GTTAGACCAGATCTGAGCCTGGGAGCTCTCTGGCTAACTAGGGAACCCACTGCTTAAGC<br>CTCAATAAAGCTTGCCTTGAGTGCTTCAAGTAGTGTGTGCCCGTCTGTTGTGTGACTCTG<br>GTAACTAGAGATCCCTCAGACCCTTTTAGTCAGTGTGGAAAATCTCTAGCAGTGGCGCCC<br>GAACAGGGACTTGAAAGCGAAAGGGAAACCAGAGGAGCTCTCTCGACGCAGGACTCGG<br>CTTGCTGAAGCGCGCACGGCAAGAGGCGAGGGGCGGCGACTGGTGAGTACGCCAAAAA<br>TTTTGACTAGCGGAGGCTAGAAGGAGAGAGATGGGTGCGAGAGCGTCAGTATTAAGCGG<br>GGGAGAATTAGATCGATGGGAAAAAATTCGGTTAAGGCCAGGGGGAAAGAAAAAATAT<br>AAATTAAAACATATAGTATGGGCAAGCAGGGAGCTAGAACGATTCGCAGTTAATCCTGG<br>CCTGTTAGAAACATCAGAAGGCTGTAGACAAATACTGGGACAGCTACAACCATCCCTTC<br>AGACAGGATCAGAAGAACTTAGATCATTATATAATACAGTAGCAACCCTCTATTGTGTG<br>CATCAAAGGATAGAGATAAAAGACACCAAGGAAGCTTTAGACAAGATAGAGGAAGAGC<br>AAAACAAAAGTAAGAAAAAAGCACAGCAAGCAGCAGCTGACACAGGACACAGCAATCA<br>GGTCAGCCAAAATTACCCTATAGTGCAGAACATCCAGGGGCAAATGGTACATCAGGCCA<br>TATCACCTAGAACTTTAAATGCATGGGTAAAAGTAGTAGAAGAGAAGGCTTTCAGCCCA<br>GAAGTGATACCCATGTTTTCAGCATTATCAGAAGGAGCCACCCCACAAGATTTAAACAC<br>CATGCTAAACACAGTGGGGGGACATCAAGCAGCCATGCAAATGTTAAAAGAGACCATCA<br>ATGAGGAAGCTGCAGGCAAAGAGAAGAGTGGTGCAGAGAGAAAAAAGAGCAGTGGGA<br>ATAGGAGCTTTGTTCCTTGGGTTCTTGGGAGCAGCAGGAAGCACTATGGGCGCAGCGTC<br>AATGACGCTGACGGTACAGGCCAGACAATTATTGTCTGGTATAGTGCAGCAGCAGAACA<br>ATTTGCTGAGGGCTATTGAGGCGCAACAGCATCTGTTGCAACTCACAGTCTGGGGCATCA<br>AGCAGCTCCAGGCAAGAATCCTGGCTGTGGAAAGATACCTAAAGGATCAACAGCTCCTG<br>GGGATTTGGGGTTGCTCTGGAAAACTCATTTGCACCACTGCTGTGCCTTGGATCTACAAA<br>TGGCAGTATTCATCCACAATTTTAAAAGAAAAGGGGGGATTGGGGGGTACAGTGCAGGG<br>GAAAGAATAGTAGACATAATAGCAACAGACATACAAACTAAAGAATTACAAAAACAAA<br>TTACAAAAATTCAAAATTTTCGGGTTTATTACAGGGACAGCAGAGATCCAGTTTGGGGAT<br>CAATTGCATGAAGAATCTGCTTAGGGTTAGGCGTTTTGCGCTGCTTCGCGAGGATCTGCG<br>ATCGCTCCGGTGCCCGTCAGTGGGCAGAGCGCACATCGCCCACAGTCCCCGAGAAGTTG<br>GGGGGAGGGGTCGGCAATTGAACCGGTGCCTAGAGAAGGTGGCGCGGGGTAAACTGGG<br>AAAGTGATGTCGTGTACTGGCTCCGCCTTTTTCCCGAGGGTGGGGGAGAACCGTATATAA<br>GTGCAGTAGTCGCCGTGAACGTTCTTTTTCGCAACGGGTTTGCCGCCAGAACACAGCTGA<br>AGCTTCGAGGGGCTCGCATCTCTCCTTCACGCGCCCGCCGCCCTACCTGAGGCCGCCATC<br>CACGCCGGTTGAGTCGCGTTCTGCCGCCTCCCGCCTGTGGTGCCTCCTGAACTGCGTCCG<br>CCGTCTAGGTAAGTTTAAAGCTCAGGTCGAGACCGGGCCTTTGTCCGGCGCTCCCTTGGA<br>GCCTACCTAGACTCAGCCGGCTCTCCACGCTTTGCCTGACCCTGCTTGCTCAACTCTACGT<br>CTTTGTTTCGTTTTCTGTTCTGCGCCGTTACAGATCCAAGCTGTGACCGGCGCCTACG |
| GCTAGC |
| R11 scFV |
| GAATTCGCCACCATGCTGCTGCTGGTGACAAGCCTGCTGCTGTGCGAGCTGCCCCACCCC |
| GCCTTTCTGCTGATCCCCCAGAGCGTGAAAGAGTCCGAGGGCGACCTGGTCACACCAGC<br>CGGCAACCTGACCCTGACCTGTACCGCCAGCGGCAGCGACATCAACGACTACCCCATCT<br>CTTGGGTCCGCCAGGCTCCTGGCAAGGGACTGGAATGGATCGGCTTCATCAACAGCGGC |

TABLE 17-continued

| R11 intermediate spacer CAR: PJ_R11-CH3-41BB-Z-T2A-tEGFR (SEQ ID NO:45) |
|---|

GGCAGCACTTGGTACGCCAGCTGGGTCAAAGGCCGGTTCACCATCAGCCGGACCAGCAC
CACCGTGGACCTGAAGATGACAAGCCTGACCACCGACGACACCGCCACCTACTTTTGCG
CCAGAGGCTACAGCACCTACTACGGCGACTTCAACATCTGGGGCCCTGGCACCCTGGTC
ACAATCTCTAGCGGCGGAGGCGGCAGCGGAGGTGGAGGAAGTGGCGGCGGAGGATCCG
AGCTGGTCATGACCCAGACCCCCAGCAGCACATCTGGCGCCGTGGGCGGCACCGTGACC
ATCAATTGCCAGGCCAGCCAGAGCATCGACAGCAACCTGGCCTGGTTCCAGCAGAAGCC
CGGCCAGCCCCCCACCCTGCTGATCTACAGAGCCTCCAACCTGGCCAGCGGCGTGCCAA
GCAGATTCAGCGGCAGCAGATCTGGCACCGAGTACACCCTGACCATCTCCGGCGTGCAG
AGAGAGGACGCCGCTACCTATTACTGCCTGGGCGGCGTGGGCAACGTGTCCTACAGAAC
CAGCTTCGGCGGAGGTACTGAGGTGGTCGTCAAA

Hinge/Spacer

TAGGACCGCCCTGCCCCCCTTGCCCT

CH2
GCCCCCGAGTTCCTGGGCGGACCCAGCGTGTTCCTGTTCCCCCCCAAGCCCAAGGACACC
CTGATGATCAGCCGGACCCCCGAGGTGACCTGCGTGGTGGTGGACGTGAGCCAGGAAGA
TCCCGAGGTCCAGTTCAATTGGTACGTGGACGGCGTGGAAGTGCACAACGCCAAGACCA
AGCCCAGAGAGGAACAGTTCAACAGCACCTACCGGGTGGTGTCTGTGCTGACCGTGCTG
CACCAGGACTGGCTGAACGGCAAAGAATACAAGTGCAAGGTGTCCAACAAGGGCCTGC
CCAGCAGCATCGAAAAGACCATCAGCAAGGCCAAG

CH3
GGCCAGCCTCGCGAGCCCCAGGTGTACACCCTGCCTCCCTCCCAGGAAGAGATGACCAA
GAACCAGGTGTCCCTGACCTGCCTGGTGAAGGGCTTCTACCCCAGCGACATCGCCGTGG
AGTGGGAGAGCAACGGCCAGCCTGAGAACAACTACAAGACCACCCCTCCCGTGCTGGAC
AGCGACGGCAGCTTCTTCCTGTACAGCCGGCTGACCGTGGACAAGAGCCGGTGGCAGGA
AGGCAACGTCTTTAGCTGCAGCGTGATGCACGAGGCCCTGCACAACCACTACACCCAGA
AGAGCCTGAGCCTGTCCCTGGGCAAG 4-1BB
ATGTTCTGGGTGCTGGTGGTGGTGGGCGGGGTGCTGGCCTGCTACAGCCTGCTGGTGACA
GTGGCCTTCATCATCTTTTGGGTGAAACGGGGCAGAAAGAAACTCCTGTATATATTCAAA
CAACCATTTATGAGACCAGTACAAACTACTCAAGAGGAAGATGGCTGTAGCTGCCGATT
TCCAGAAGAAGAAGAAGGAGGATGTGAACTG

CD3zeta
CGGGTGAAGTTCAGCAGAAGCGCCGACGCCCCTGCCTACCAGCAGGGCCAGAATCAGCT
GTACAACGAGCTGAACCTGGGCAGAAGGGAAGAGTACGACGTCCTGGATAAGCGGAGA
GGCCGGGACCCTGAGATGGGCGGCAAGCCTCGGCGGAAGAACCCCCAGGAAGGCCTGT
ATAACGAACTGCAGAAAGACAAGATGGCCGAGGCCTACAGCGAGATCGGCATGAAGGG
CGAGCGGAGGCGGGGCAAGGGCCACGACGGCCTGTATCAGGGCCTGTCCACCGCCACCA
AGGATACCTACGACGCCCTGCACATGCAGGCCCTGCCCCCAAGG

T2A

CTCGAGGGCGGCGGAGAGGGCAGAGGAAGTCTTCTAACATGCGGTGACGTGGAGGAGA

ATCCCGGCCCTAGG tEGFR
ATGCTTCTCCTGGTGACAAGCCTTCTGCTCTGTGAGTTACCACACCCAGCATTCCTCCTGA
TCCCACGCAAAGTGTGTAACGGAATAGGTATTGGTGAATTTAAAGACTCACTCTCCATAA
ATGCTACGAATATTAAACACTTCAAAAACTGCACCTCCATCAGTGGCGATCTCCACATCC

TGCCGGTGGCATTTAGGGGTGACTCCTTCACACATACTCCTCCTCTGGATCCACAGGAAC

TGGATATTCTGAAAACCGTAAAGGAAATCACAGGGTTTTTGCTGATTCAGGCTTGGCCTG
AAAACAGGACGGACCTCCATGCCTTTGAGAACCTAGAAATCATACGCGGCAGGACCAAG
CAACATGGTCAGTTTTCTCTTGCAGTCGTCAGCCTGAACATAACATCCTTGGGATTACGC
TCCCTCAAGGAGATAAGTGATGGAGATGTGATAATTTCAGGAAACAAAAATTTGTGCTA
TGCAAATACAATAAACTGGAAAAAACTGTTTGGGACCTCCGGTCAGAAAACCAAAATTA
TAAGCAACAGAGGTGAAAACAGCTGCAAGGCCACAGGCCAGGTCTGCCATGCCTTGTGC
TCCCCCGAGGGCTGCTGGGGCCCGGAGCCCAGGGACTGCGTCTCTTGCCGGAATGTCAG
CCGAGGCAGGGAATGCGTGGACAAGTGCAACCTTCTGGAGGGTGAGCCAAGGGAGTTTG
TGGAGAACTCTGAGTGCATACAGTGCCCACCCAGAGTGCCTGCCTCAGGCCATGAACATC
ACCTGCACAGGACGGGGACCAGACAACTGTATCCAGTGTGCCCACTACATTGACGGCCC
CCACTGCGTCAAGACCTGCCCGGCAGGAGTCATGGGAGAAAACAACACCCTGGTCTGGA
AGTACGCAGACGCCGGCCATGTGTGCCACCTGTGCCATCCAAACTGCACCTACGGATGC

TABLE 17-continued

| R11 intermediate spacer CAR: PJ_R11-CH3-41BB-Z-T2A-tEGFR (SEQ ID NO:45) |
|---|

ACTGGGCCAGGTCTTGAAGGCTGTCCAACGAATGGGCCTAAGATCCCGTCCATCGCCAC
TGGGATGGTGGGGGCCCTCCTCTTGCTGCTGGTGGTGGCCCTGGGGATCGGCCTCTTCAT

GTGAGCGGCCGCTCTAGACCCGGGCTGCAGGAATTCGATATCAAGCTTATCGATAATCA

ACCTCTGGATTACAAAATTTGTGAAAGATTGACTGGTATTCTTAACTATGTTGCTCCTTTT
ACGCTATGTGGATACGCTGCTTTAATGCCTTTGTATCATGCTATTGCTTCCCGTATGGCTT
TCATTTTCTCCTCCTTGTATAAATCCTGGTTGCTGTCTCTTTATGAGGAGTTGTGGCCCGT
TGTCAGGCAACGTGGCGTGGTGTGCACTGTGTTTGCTGACGCAACCCCCACTGGTTGGGG
CATTGCCACCACCTGTCAGCTCCTTTCCGGGACTTTCGCTTTCCCCCTCCCTATTGCCACG
GCGGAACTCATCGCCGCCTGCCTTGCCCGCTGCTGGACAGGGGCTCGGCTGTTGGGCACT
GACAATTCCGTGGTGTTGTCGGGGAAATCATCGTCCTTTCCTTGGCTGCTCGCCTGTGTTG
CCACCTGGATTCTGCGCGGGACGTCCTTCTGCTACGTCCCTTCGGCCCTCAATCCAGCGG
ACCTTCCTTCCCGCGGCCTGCTGCCGGCTCTGCGGCCTCTTCCGCGTCTTCGCCTTCGCCC
TCAGACGAGTCGGATCTCCCTTTGGGCCGCCTCCCCGCATCGATACCGTCGACTAGCCGT
ACCTTTAAGACCAATGACTTACAAGGCAGCTGTAGATCTTAGCCACTTTTTAAAAGAAAA
GGGGGGACTGGAAGGGCTAATTCACTCCCAAAGAAGACAAGATCTGCTTTTTGCCTGTA
CTGGGTCTCTCTGGTTAGACCAGATCTGAGCCTGGGAGCTCTCTGGCTAACTAGGGAACC
CACTGCTTAAGCCTCAATAAAGCTTGCCTTGAGTGCTTCAAGTAGTGTGTGCCCGTCTGT
TGTGTGACTCTGGTAACTAGAGATCCCTCAGACCCTTTTAGTCAGTGTGGAAAATCTCTA

GCAGAATTCGATATCAAGCTTATCGATACCGTCGACCTCGAGGGGGGGCCCGGTACCCA

ATTCGCCCTATAGTGAGTCGTATTACAATTCACTGGCCGTCGTTTTACAACGTCGTGACT
GGGAAAACCCTGGCGTTACCCAACTTAATCGCCTTGCAGCACATCCCCCTTTCGCCAGCT
GGCGTAATAGCGAAGAGGCCCGCACCGATCGCCCTTCCCAACAGTTGCGCAGCCTGAAT
GGCGAATGGAAATTGTAAGCGTTAATATTTTGTTAAAATTCGCGTTAAATTTTTGTTAAA
TCAGCTCATTTTTTAACCAATAGGCCGAAATCGGCAAAATCCCTTATAAATCAAAAGAAT
AGACCGAGATAGGGTTGAGTGTTGTTCCAGTTTGGAACAAGAGTCCACTATTAAAGAAC
GTGGACTCCAACGTCAAAGGGCGAAAAACCGTCTATCAGGGCGATGGCCCACTACGTGA
ACCATCACCCTAATCAAGTTTTTTGGGGTCGAGGTGCCGTAAAGCACTAAATCGGAACCC
TAAAGGGAGCCCCCGATTTAGAGCTTGACGGGGAAAGCCGGCGAACGTGGCGAGAAAG
GAAGGGAAGAAAGCGAAAGGAGCGGGCGCTAGGGCGCTGGCAAGTGTAGCGGTCACGC
TGCGCGTAACCACCACACCCGCCGCGCTTAATGCGCCGCTACAGGGCGCGTCAGGTGGC
ACTTTTCGGGGAAATGTGCGCGGAACCCCTATTTGTTTATTTTTCTAAATACATTCAAATA
TGTATCCGCTCATGAGACAATAACCCTGATAAATGCTTCAATAATATTGAAAAAGGAAG
AGTATGAGTATTCAACATTTCCGTGTCGCCCTTATTCCCTTTTTTGCGGCATTTTGCCTTC
CTGTTTTTGCTCACCCAGAAACGCTGGTGAAAGTAAAAGATGCTGAAGATCAGTTGGGT
GCACGAGTGGGTTACATCGAACTGGATCTCAACAGCGGTAAGATCCTTGAGAGTTTTCG
CCCCGAAGAACGTTTTCCAATGATGAGCACTTTTAAAGTTCTGCTATGTGGCGCGGTATT
ATCCCGTATTGACGCCGGGCAAGAGCAACTCGGTCGCCGCATACACTATTCTCAGAATG
ACTTGGTTGAGTACTCACCAGTCACAGAAAAGCATCTTACGGATGGCATGACAGTAAGA
GAATTATGCAGTGCTGCCATAACCATGAGTGATAACACTGCGGCCAACTTACTTCTGACA
ACGATCGGAGGACCGAAGGAGCTAACCGCTTTTTTGCACAACATGGGGGATCATGTAAC
TCGCCTTGATCGTTGGGAACCGGAGCTGAATGAAGCCATACCAAACGACGAGCGTGACA
CCACGATGCCTGTAGCAATGGCAACAACGTTGCGCAAACTATTAACTGGCGAACTACTT
ACTCTAGCTTCCCGGCAACAATTAATAGACTGGATGGAGGCGGATAAAGTTGCAGGACC
ACTTCTGCGCTCGGCCCTTCCGGCTGGCTGGTTTATTGCTGATAAATCTGGAGCCGGTGA
GCGTGGGTCTCGCGGTATCATTGCAGCACTGGGGCCAGATGGTAAGCCCTCCCGTATCGT
AGTTATCTACACGACGGGGAGTCAGGCAACTATGGATGAACGAAATAGACAGATCGCTG
AGATAGGTGCCTCACTGATTAAGCATTGGTAACTGTCAGACCAAGTTTACTCATATATAC
TTTAGATTGATTTAAAACTTCATTTTTAATTTAAAAGGATCTAGGTGAAGATCCTTTTTGA
TAATCTCATGACCAAAATCCCTTAACGTGAGTTTTCGTTCCACTGAGCGTCAGACCCCGT
AGAAAAGATCAAAGGATCTTCTTGAGATCCTTTTTTTCTGCGCGTAATCTGCTGCTTGCA
AACAAAAAAACCACCGCTACCAGCGGTGGTTTGTTTGCCGGATCAAGAGCTACCAACTC
TTTTTCCGAAGGTAACTGGCTTCAGCAGAGCGCAGATACCAAATACTGTTCTTCTAGTGT
AGCCGTAGTTAGGCCACCACTTCAAGAACTCTGTAGCACCGCCTACATACCTCGCTCTGC
TAATCCTGTTACCAGTGGCTGCTGCCAGTGGCGATAAGTCGTGTCTTACCGGGTTGGACT
CAAGACGATAGTTACCGGATAAGGCGCAGCGGTCGGGCTGAACGGGGGGTTCGTGCACA
CAGCCCAGCTTGGAGCGAACGACCTACACCGAACTGAGATACCTACAGCGTGAGCTATG
AGAAAGCGCCACGCTTCCCGAAGGGAGAAAGGCGGACAGGTATCCGGTAAGCGGCAGG
GTCGGAACAGGAGAGCGCACGAGGGAGCTTCCAGGGGGAAACGCCTGGTATCTTTATAG
TCCTGTCGGGTTTCGCCACCTCTGACTTGAGCGTCGATTTTTGTGATGCTCGTCAGGGGG
GCGGAGCCTATGGAAAAACGCCAGCAACGCGGCCTTTTTACGGTTCCTGGCCTTTTGCTG
GCCTTTTGCTCACATGTTCTTTCCTGCGTTATCCCCTGATTCTGTGGATAACCGTATTACC
GCCTTTGAGTGAGCTGATACCGCTCGCCGCAGCCGAACGACCGAGCGCAGCGAGTCAGT
GAGCGAGGAAGCGGAAGAGCGCCCAATACGCAAACCGCCTCTCCCCGCGCGTTGGCCGA
TTCATTAATGCAGCTGGCACGACAGGTTTCCCGACTGGAAAGCGGGCAGTGAGCGCAAC
GCAATTAATGTGAGTTAGCTCACTCATTAGGCACCCCAGGCTTTACACTTTATGCTTCCG

TABLE 17-continued

| R11 intermediate spacer CAR: PJ_R11-CH3-41BB-Z-T2A-tEGFR (SEQ ID NO:45) |
|---|
| GCTCGTATGTTGTGTGGAATTGTGAGCGGATAACAATTTCACACAGGAAACAGCTATGA |
| CCATGATTACGCCAAGCTCGAAATTAACCCTCACTAAAGGGAACAAAAGCTGGAGCTCC |
| ACCGCGGTGGCGGCCTCGAGGTCGAGATCCGGTCGACCAGCAACCATAGTCCCGCCCCT |
| AACTCCGCCCATCCCGCCCCTAACTCCGCCCAGTTCCGCCCATTCTCCGCCCCATGGCTG |
| ACTAATTTTTTTTATTTATGCAGAGGCCGAGGCCGCCTCGGCCTCTGAGCTATTCCAGAA |
| GTAGTGAGGAGGCTTTTTTGGAGGCCTAGGCTTTTGCAAAAAGCTTCGACGGTATCGATT |
| GGCTCATGTCCAACATTACCGCCATGTTGACATTGATTATTGACTAGTTATTAATAGTAA |
| TCAATTACGGGGTCATTAGTTCATAGCCCATATATGGAGTTCCGCGTTACATAACTTACG |
| GTAAATGGCCCGCCTGGCTGACCGCCCAACGACCCCCGCCCATTGACGTCAATAATGAC |
| GTATGTTCCCATAGTAACGCCAATAGGGACTTTCCATTGACGTCAATGGGTGGAGTATTT |
| ACGGTAAACTGCCCACTTGGCAGTACATCAAGTGTATCATATGCCAAGTACGCCCCCTAT |
| TGACGTCAATGACGGTAAATGGCCCGCCTGGCATTATGCCCAGTACATGACCTTATGGG |
| ACTTTCCTACTTGGCAGTACATCTACGTATTAGTCATCGCTATTACCATGGTGATGCGGTT |
| TTGGCAGTACATCAATGGGCGTGGATAGCGGTTTGACTCACGGGGATTTCCAAGTCTCCA |
| CCCCATTGACGTCAATGGGAGTTTGTTTTGGCACCAAAATCAACGGGACTTTCCAAAATG |
| TCGTAACAACTCCGCCCCATTGACGCAAATGGGCGGTAGGCGTGTACGGAATTCGGAGT |
| GGCGAGCCCTCAGATCCTGCATATAAGCAGCTGCTTTTTGCCTGTACTGGGTCTCTCTG |

TABLE 18

| Leader _R11- Hinge-CH3- CD28tm/41BB-Z-T2A-tEGFR (SEQ ID NO:46) |
|---|
| Leader: MLLLVTSLLLCELPHPAFLLIP |
| scFV R11 |
| QSVKESEGDLVTPAGNLTLTCTASGSDINDYPISWVRQAPGKGLEWIGFINSGGSTWYASWV |
| KGRFTISRTSTTVDLKMTSLTTDDTATYFCARGYSTYYGDFNIWGPGTLVTISSGGGGSGGG |
| GSGGGGSELVMTQTPSSTSGAVGGTVTINCQASQSIDSNLAWFQQKPGQPPTLLIYRASNLAS |
| GVPSRFSGSRSGTEYTLTISGVQREDAATYYCLGGVGNVSYRTSFGGGTEVVVK |
| Hinge/Spacer: ESKYGPPCPPCP |
| CH3 |
| GQPREPQVYTLPPSQEEMTKNQVSLTCLVKGFYPSDIAVEWESNGQPENNYKTTPPVLDSDG |
| SFFLYSRLTVDKSRWQEGNVFSCSVMHEALHNHYTQKSLSLSLGK |
| CD28tm:MFWVLVVVGGVLACYSLLVTVAFIIFWV |
| 4-1BB: KRGRKKLLYIFKQPFMRPVQTTQEEDGCSCRFPEEEEGGCEL |
| CD3zeta |
| RVKFSRSADAPAYQQGQNQLYNELNLGRREEYDVLDKRRGRDPEMGGKPRRKNPQEGLYN |
| ELQKDKMAEAYSEIGMKGERRRGKGHDGLYQGLSTATKDTYDALHMQALPPR |
| T2A: LEGGGEGRGSLLTCGDVEENPGPRM |
| tEGFR |
| LLLVTSLLLCELPHPAFLLIPRKVCNGIGIGEFKDSLSINATNIKHFKNCTSISGDLHILPVAFRG |
| DSFTHTPPLDPQELDILKTVKEITGFLLIQAWPENRTDLHAFENLEIIRGRTKQHGQFSLAVVS |
| LNITSLGLRSLKEISDGDVIISGNKNLCYANTINWKKLFGTSGQKTKIISNRGENSCKATGQVC |
| HALCSPEGCWGPEPRDCVSCRNVSRGRECVDKCNLLEGEPREFVENSECIQCHPECLPQAMN |
| ITCTGRGPDNCIQCAHYIDGPHCVKTCPAGVMGENNTLVWKYADAGHVCHLCHPNCTYGC |
| TGPGLEGCPTNGPKIPSIATGMVGALLLLLVVALGIGLFM |

TABLE 19

| R11 short spacer CAR: PJ_R11- 41BB-Z-T2A-tEGFR(SEQ ID NO:47) |
|---|

GTTAGACCAGATCTGAGCCTGGGAGCTCTCTGGCTAACTAGGGAACCCACTGCTTAAGC
CTCAATAAAGCTTGCCTTGAGTGCTTCAAGTAGTGTGTGCCCGTCTGTTGTGTGACTCTG
GTAACTAGAGATCCCTCAGACCCTTTTAGTCAGTGTGGAAAATCTCTAGCAGTGGCGCCC
GAACAGGGACTTGAAAGCGAAAGGGAAACCAGAGGAGCTCTCTCGACGCAGGACTCGG
CTTGCTGAAGCGCGCACGGCAAGAGGCGAGGGGCGGCGACTGGTGAGTACGCCAAAAA
TTTTGACTAGCGGAGGCTAGAAGGAGAGAGATGGGTGCGAGAGCGTCAGTATTAAGCGG
GGGAGAATTAGATCGATGGGAAAAAATTCGGTTAAGGCCAGGGGGAAAGAAAAAATAT
AAATTAAAACATATAGTATGGGCAAGCAGGGAGCTAGAACGATTCGCAGTTAATCCTGG
CCTGTTAGAAACATCAGAAGGCTGTAGACAAATACTGGGACAGCTACAACCATCCCTTC
AGACAGGATCAGAAGAACTTAGATCATTATATAATACAGTAGCAACCCTCTATTGTGTG
CATCAAAGGATAGAGATAAAAGACACCAAGGAAGCTTTAGACAAGATAGAGGAAGAGC
AAAACAAAAGTAAGAAAAAAGCACAGCAAGCAGCAGCTGACACAGGACACAGCAATCA
GGTCAGCCAAAATTACCCTATAGTGCAGAACATCCAGGGGCAAATGGTACATCAGGCCA
TATCACCTAGAACTTTAAATGCATGGGTAAAAGTAGTAGAAGAGAAGGCTTTCAGCCCA
GAAGTGATACCCATGTTTTCAGCATTATCAGAAGGAGCCACCCCACAAGATTTAAACAC
CATGCTAAACACAGTGGGGGGACATCAAGCAGCCATGCAAATGTTAAAAGAGACCATCA
ATGAGGAAGCTGCAGGCAAAGAGAAGAGTGGTGCAGAGAGAAAAAAGAGCAGTGGGA
ATAGGAGCTTTGTTCCTTGGGTTCTTGGGAGCAGCAGGAAGCACTATGGGCGCAGCGTC
AATGACGCTGACGGTACAGGCCAGACAATTATTGTCTGGTATAGTGCAGCAGCAGAACA
ATTTGCTGAGGGCTATTGAGGCGCAACAGCATCTGTTGCAACTCACAGTCTGGGGCATCA
AGCAGCTCCAGGCAAGAATCCTGGCTGTGGAAAGATACCTAAAGGATCAACAGCTCCTG
GGGATTTGGGGTTGCTCTGGAAAACTCATTTGCACCACTGCTGTGCCTTGGATCTACAAA
TGGCAGTATTCATCCACAATTTTAAAAGAAAAGGGGGGATTGGGGGGTACAGTGCAGGG
GAAAGAATAGTAGACATAATAGCAACAGACATACAAACTAAAGAATTACAAAAACAAA
TTACAAAAATTCAAAATTTTCGGGTTTATTACAGGGACAGCAGAGATCCAGTTTGGGGAT
CAATTGCATGAAGAATCTGCTTAGGGTTAGGCGTTTTGCGCTGCTTCGCGAGGATCTGCG
ATCGCTCCGGTGCCCGTCAGTGGGCAGAGCGCACATCGCCCACAGTCCCCGAGAAGTTG
GGGGGAGGGGTCGGCAATTGAACCGGTGCCTAGAGAAGGTGGCGCGGGGTAAACTGGG
AAAGTGATGTCGTGTACTGGCTCCGCCTTTTTCCCGAGGGTGGGGGAGAACCGTATATAA
GTGCAGTAGTCGCCGTGAACGTTCTTTTTCGCAACGGGTTTGCCGCCAGAACACAGCTGA
AGCTTCGAGGGGCTCGCATCTCTCCTTCACGCGCCCGCCGCCCTACCTGAGGCCGCCATC
CACGCCGGTTGAGTCGCGTTCTGCCGCCTCCCGCCTGTGGTGCCTCCTGAACTGCGTCCG
CCGTCTAGGTAAGTTTAAAGCTCAGGTCGAGACCGGGCCTTTGTCCGGCGCTCCCTTGGA
GCCTACCTAGACTCAGCCGGCTCTCCACGCTTTGCCTGACCCTGCTTGCTCAACTCTACGT
CTTTGTTTCGTTTTCTGTTCTGCGCCGTTACAGATCCAAGCTGTGACCGGCGCCTACG

GCTAGC scFV R11

GAATTCGCCACCATGCTGCTGCTGGTGACAAGCCTGCTGCTGTGCGAGCTGCCCCACCCC

GCCTTTCTGCTGATCCCCCAGAGCGTGAAAGAGTCCGAGGGCGACCTGGTCACACCAGC
CGGCAACCTGACCCTGACCTGTACCGCCAGCGGCAGCGACATCAACGACTACCCCATCT
CTTGGGTCCGCCAGGCTCCTGGCAAGGGACTGGAATGGATCGGCTTCATCAACAGCGGC
GGCAGCACTTGGTACGCCAGCTGGGTCAAAGGCCGGTTCACCATCAGCCGGACCAGCAC
CACCGTGGACCTGAAGATGACAAGCCTGACCACCGACGACACCGCCACCTACTTTTGCG
CCAGAGGCTACAGCACCTACTACGGCGACTTCAACATCTGGGGCCCTGGCACCCTGGTC
ACAATCTCTAGCGGCGGAGGCGGCAGCGGAGGTGGAGGAAGTGGCGGCGGAGGATCCG
AGCTGGTCATGACCCAGACCCCCAGCAGCACATCTGGCGCCGTGGGCGGCACCGTGACC
ATCAATTGCCAGGCCAGCCAGAGCATCGACAGCAACCTGGCCTGGTTCCAGCAGAAGCC
CGGCCAGCCCCCCACCCTGCTGATCTACAGAGCCTCCAACCTGGCCAGCGGCGTGCCAA
GCAGATTCAGCGGCAGCAGATCTGGCACCGAGTACACCCTGACCATCTCCGGCGTGCAG
AGAGAGGACGCCGCTACCTATTACTGCCTGGGCGGCGTGGGCAACGTGTCCTACAGAAC
CAGCTTCGGCGGAGGTACTGAGGTGGTCGTCAAA

Hinge/spacer

TACGGACCGCCCTGCCCCCCTTGCCCT

CH3
GGCCAGCCTCGCGAGCCCCAGGTGTACACCCTGCCTCCCTCCCAGGAAGAGATGACCAA
GAACCAGGTGTCCCTGACCTGCCTGGTGAAGGGCTTCTACCCCAGCGACATCGCCGTGG
AGTGGGAGAGCAACGGCCAGCCTGAGAACAACTACAAGACCACCCCTCCCGTGCTGGAC
AGCGACGGCAGCTTCTTCCTGTACAGCCGGCTGACCGTGGACAAGAGCCGGTGGCAGGA
AGGCAACGTCTTTAGCTGCAGCGTGATGCACGAGGCCCTGCACAACCACTACACCCAGA
AGAGCCTGAGCCTGTCCCTGGGCAAG 4-1BB
ATGTTCTGGGTGCTGGTGGTGGTGGGCGGGGTGCTGGCCTGCTACAGCCTGCTGGTGACA
GTGGCCTTCATCATCTTTTGGGTGAAACGGGGCAGAAAGAAACTCCTGTATATATTCAAA
CAACCATTTATGAGACCAGTACAAACTACTCAAGAGGAAGATGGCTGTAGCTGCCGATT
TCCAGAAGAAGAAGAAGGAGGATGTGAACTG

TABLE 19 -continued

| R11 short spacer CAR: PJ_R11- 41BB-Z-T2A-tEGFR(SEQ ID NO:47) |
|---|

CD3zeta
CGGGTGAAGTTCAGCAGAAGCGCCGACGCCCCTGCCTACCAGCAGGGCCAGAATCAGCT
GTACAACGAGCTGAACCTGGGCAGAAGGGAAGAGTACGACGTCCTGGATAAGCGGAGA
GGCCGGGACCCTGAGATGGGCGGCAAGCCTCGGCGGAAGAACCCCCAGGAAGGCCTGT
ATAACGAACTGCAGAAAGACAAGATGGCCGAGGCCTACAGCGAGATCGGCATGAAGGG
CGAGCGGAGGCGGGGCAAGGGCCACGACGGCCTGTATCAGGGCCTGTCCACCGCCACCA
AGGATACCTACGACGCCCTGCACATGCAGGCCCTGCCCCCAAGG

T2A

CTCGAGGGCGGCGGAGAGGGCAGAGGAAGTCTTCTAACATGCGGTGACGTGGAGGAGA

ATCCCGGCCCTAGG tEGFR
ATGCTTCTCCTGGTGACAAGCCTTCTGCTCTGTGAGTTACCACACCCAGCATTCCTCCTGA
TCCCACGCAAAGTGTGTAACGGAATAGGTATTGGTGAATTTAAAGACTCACTCTCCATAA
ATGCTACGAATATTAAACACTTCAAAAACTGCACCTCCATCAGTGGCGATCTCCACATCC

TGCCGGTGGCATTTAGGGGTGACTCCTTCACACATACTCCTCCTCTGGATCCACAGGAAC

TGGATATTCTGAAAACCGTAAAGGAAATCACAGGGTTTTTGCTGATTCAGGCTTGGCCTG
AAAACAGGACGGACCTCCATGCCTTTGAGAACCTAGAAATCATACGCGGCAGGACCAAG
CAACATGGTCAGTTTTCTCTTGCAGTCGTCAGCCTGAACATAACATCCTTGGGATTACGC
TCCCTCAAGGAGATAAGTGATGGAGATGTGATAATTTCAGGAAACAAAAATTTGTGCTA
TGCAAATACAATAAACTGGAAAAAACTGTTTGGGACCTCCGGTCAGAAAACCAAAATTA
TAAGCAACAGAGGTGAAAACAGCTGCAAGGCCACAGGCCAGGTCTGCCATGCCTTGTGC
TCCCCCGAGGGCTGCTGGGGCCCGGAGCCCAGGGACTGCGTCTCTTGCCGGAATGTCAG
CCGAGGCAGGGAATGCGTGGACAAGTGCAACCTTCTGGAGGGTGAGCCAAGGGAGTTTG
TGGAGAACTCTGAGTGCATACAGTGCCACCCAGAGTGCCTGCCTCAGGCCATGAACATC
ACCTGCACAGGACGGGGACCAGACAACTGTATCCAGTGTGCCCACTACATTGACGGCCC
CCACTGCGTCAAGACCTGCCCGGCAGGAGTCATGGGAGAAAACAACACCCTGGTCTGGA
AGTACGCAGACGCCGGCCATGTGTGCCACCTGTGCCATCCAAACTGCACCTACGGATGC
ACTGGGCCAGGTCTTGAAGGCTGTCCAACGAATGGGCCTAAGATCCCGTCCATCGCCAC
TGGGATGGTGGGGGCCCTCCTCTTGCTGCTGGTGGTGGCCCTGGGGATCGGCCTCTTCAT

GTGAGCGGCCGCTCTAGACCCGGGCTGCAGGAATTCGATATCAAGCTTATCGATAATCA

ACCTCTGGATTACAAAATTTGTGAAAGATTGACTGGTATTCTTAACTATGTTGCTCCTTTT
ACGCTATGTGGATACGCTGCTTTAATGCCTTTGTATCATGCTATTGCTTCCCGTATGGCTT
TCATTTTCTCCTCCTTGTATAAATCCTGGTTGCTGTCTCTTTATGAGGAGTTGTGGCCCGT
TGTCAGGCAACGTGGCGTGGTGTGCACTGTGTTTGCTGACGCAACCCCCACTGGTTGGGG
CATTGCCACCACCTGTCAGCTCCTTTCCGGGACTTTCGCTTTCCCCCTCCCTATTGCCACG
GCGGAACTCATCGCCGCCTGCCTTGCCCGCTGCTGGACAGGGGCTCGGCTGTTGGGCACT
GACAATTCCGTGGTGTTGTCGGGGAAATCATCGTCCTTTCCTTGGCTGCTCGCCTGTGTTG
CCACCTGGATTCTGCGCGGGACGTCCTTCTGCTACGTCCCTTCGGCCCTCAATCCAGCGG
ACCTTCCTTCCCGCGGCCTGCTGCCGGCTCTGCGGCCTCTTCCGCGTCTTCGCCTTCGCCC
TCAGACGAGTCGGATCTCCCTTTGGGCCGCCTCCCCGCATCGATACCGTCGACTAGCCGT
ACCTTTAAGACCAATGACTTACAAGGCAGCTGTAGATCTTAGCCACTTTTTAAAAGAAAA
GGGGGGACTGGAAGGGCTAATTCACTCCCAAAGAAGACAAGATCTGCTTTTTGCCTGTA
CTGGGTCTCTCTGGTTAGACCAGATCTGAGCCTGGGAGCTCTCTGGCTAACTAGGGAACC
CACTGCTTAAGCCTCAATAAAGCTTGCCTTGAGTGCTTCAAGTAGTGTGTGCCCGTCTGT
TGTGTGACTCTGGTAACTAGAGATCCCTCAGACCCTTTTAGTCAGTGTGGAAAATCTCTA

GCAGAATTCGATATCAAGCTTATCGATACCGTCGACCTCGAGGGGGGGCCCGGTACCCA

ATTCGCCCTATAGTGAGTCGTATTACAATTCACTGGCCGTCGTTTTACAACGTCGTGACT
GGGAAAACCCTGGCGTTACCCAACTTAATCGCCTTGCAGCACATCCCCCTTTCGCCAGCT
GGCGTAATAGCGAAGAGGCCCGCACCGATCGCCCTTCCCAACAGTTGCGCAGCCTGAAT
GGCGAATGGAAATTGTAAGCGTTAATATTTTGTTAAAATTCGCGTTAAATTTTTGTTAAA
TCAGCTCATTTTTTAACCAATAGGCCGAAATCGGCAAAATCCCTTATAAATCAAAAGAAT
AGACCGAGATAGGGTTGAGTGTTGTTCCAGTTTGGAACAAGAGTCCACTATTAAAGAAC
GTGGACTCCAACGTCAAAGGGCGAAAAACCGTCTATCAGGGCGATGGCCCACTACGTGA
ACCATCACCCTAATCAAGTTTTTTGGGGTCGAGGTGCCGTAAAGCACTAAATCGGAACCC
TAAAGGGAGCCCCCGATTTAGAGCTTGACGGGGAAAGCCGGCGAACGTGGCGAGAAAG
GAAGGGAAGAAAGCGAAAGGAGCGGGCGCTAGGGCGCTGGCAAGTGTAGCGGTCACGC

TABLE 19 -continued

| R11 short spacer CAR: PJ_R11- 41BB-Z-T2A-tEGFR(SEQ ID NO:47) |
|---|

TGCGCGTAACCACCACACCCGCCGCGCTTAATGCGCCGCTACAGGGCGCGTCAGGTGGC
ACTTTTCGGGGAAATGTGCGCGGAACCCCTATTTGTTTATTTTTCTAAATACATTCAAATA
TGTATCCGCTCATGAGACAATAACCCTGATAAATGCTTCAATAATATTGAAAAAGGAAG
AGTATGAGTATTCAACATTTCCGTGTCGCCCTTATTCCCTTTTTTGCGGCATTTTGCCTTC
CTGTTTTTGCTCACCCAGAAACGCTGGTGAAAGTAAAAGATGCTGAAGATCAGTTGGGT
GCACGAGTGGGTTACATCGAACTGGATCTCAACAGCGGTAAGATCCTTGAGAGTTTTCG
CCCCGAAGAACGTTTTCCAATGATGAGCACTTTTAAAGTTCTGCTATGTGGCGCGGTATT
ATCCCGTATTGACGCCGGGCAAGAGCAACTCGGTCGCCGCATACACTATTCTCAGAATG
ACTTGGTTGAGTACTCACCAGTCACAGAAAAGCATCTTACGGATGGCATGACAGTAAGA
GAATTATGCAGTGCTGCCATAACCATGAGTGATAACACTGCGGCCAACTTACTTCTGACA
ACGATCGGAGGACCGAAGGAGCTAACCGCTTYTTTGCACAACATGGGGGATCATGTAAC
TCGCCTTGATCGTTGGGAACCGGAGCTGAATGAAGCCATACCAAACGACGAGCGTGACA
CCACGATGCCTGTAGCAATGGCAACAACGTTGCGCAAACTATTAACTGGCGAACTACTT
ACTCTAGCTTCCCGGCAACAATTAATAGACTGGATGGAGGCGGATAAAGTTGCAGGACC
ACTTCTGCGCTCGGCCCTTCCGGCTGGCTGGTTTATTGCTGATAAATCTGGAGCCGGTGA
GCGTGGGTCTCGCGGTATCATTGCAGCACTGGGGCCAGATGGTAAGCCCTCCCGTATCGT
AGTTATCTACACGACGGGGAGTCAGGCAACTATGGATGAACGAAATAGACAGATCGCTG
AGATAGGTGCCTCACTGATTAAGCATTGGTAACTGTCAGACCAAGTTTACTCATATATAC
TTTAGATTGATTTAAAACTTCATTTTTAATTTAAAAGGATCTAGGTGAAGATCCTTTTTGA
TAATCTCATGACCAAAATCCCTTAACGTGAGTTTTCGTTCCACTGAGCGTCAGACCCCGT
AGAAAAGATCAAAGGATCTTCTTGAGATCCTTTTTTTCTGCGCGTAATCTGCTGCTTGCA
AACAAAAAAACCACCGCTACCAGCGGTGGTTTGTTTGCCGGATCAAGAGCTACCAACTC
TTTTTCCGAAGGTAACTGGCTTCAGCAGAGCGCAGATACCAAATACTGTTCTTCTAGTGT
AGCCGTAGTTAGGCCACCACTTCAAGAACTCTGTAGCACCGCCTACATACCTCGCTCTGC
TAATCCTGTTACCAGTGGCTGCTGCCAGTGGCGATAAGTCGTGTCTTACCGGGTTGGACT
CAAGACGATAGTTACCGGATAAGGCGCAGCGGTCGGGCTGAACGGGGGGTTCGTGCACA
CAGCCCAGCTTGGAGCGAACGACCTACACCGAACTGAGATACCTACAGCGTGAGCTATG
AGAAAGCGCCACGCTTCCCGAAGGGAGAAAGGCGGACAGGTATCCGGTAAGCGGCAGG
GTCGGAACAGGAGAGCGCACGAGGGAGCTTCCAGGGGGAAACGCCTGGTATCTTTATAG
TCCTGTCGGGTTTCGCCACCTCTGACTTGAGCGTCGATTTTTGTGATGCTCGTCAGGGGG
GCGGAGCCTATGGAAAAACGCCAGCAACGCGGCCTTTTTACGGTTCCTGGCCTTTTGCTG
GCCTTTTGCTCACATGTTCTTTCCTGCGTTATCCCCTGATTCTGTGGATAACCGTATTACC
GCCTTTGAGTGAGCTGATACCGCTCGCCGCAGCCGAACGACCGAGCGCAGCGAGTCAGT
GAGCGAGGAAGCGGAAGAGCGCCCAATACGCAAACCGCCTCTCCCCGCGCGTTGGCCGA
TTCATTAATGCAGCTGGCACGACAGGTTTCCCGACTGGAAAGCGGGCAGTGAGCGCAAC
GCAATTAATGTGAGTTAGCTCACTCATTAGGCACCCCAGGCTTTACACTTTATGCTTCCG
GCTCGTATGTTGTGTGGAATTGTGAGCGGATAACAATTTCACACAGGAAACAGCTATGA
CCATGATTACGCCAAGCTCGAAATTAACCCTCACTAAAGGGAACAAAAGCTGGAGCTCC

ACCGCGGTGGCGGCCTCGAGGTCGAGATCCGGTCGACCAGCAACCATAGTCCCGCCCCT

AACTCCGCCCATCCCGCCCCTAACTCCGCCCAGTTCCGCCCATTCTCCGCCCCATGGCTG
ACTAATTTTTTTTATTTATGCAGAGGCCGAGGCCGCCTCGGCCTCTGAGCTATTCCAGAA
GTAGTGAGGAGGCTTTTTTGGAGGCCTAGGCTTTTGCAAAAAGCTTCGACGGTATCGATT
GGCTCATGTCCAACATTACCGCCATGTTGACATTGATTATTGACTAGTTATTAATAGTAA
TCAATTACGGGGTCATTAGTTCATAGCCCATATATGGAGTTCCGCGTTACATAACTTACG
GTAAATGGCCCGCCTGGCTGACCGCCCAACGACCCCCGCCCATTGACGTCAATAATGAC
GTATGTTCCCATAGTAACGCCAATAGGGACTTTCCATTGACGTCAATGGGTGGAGTATTT
ACGGTAAACTGCCCACTTGGCAGTACATCAAGTGTATCATATGCCAAGTACGCCCCCTAT
TGACGTCAATGACGGTAAATGGCCCGCCTGGCATTATGCCCAGTACATGACCTTATGGG

TABLE 19 -continued

| R11 short spacer CAR: PJ_R11- 41BB-Z-T2A-tEGFR(SEQ ID NO:47) |
|---|
| ACTTTCCTACTTGGCAGTACATCTACGTATTAGTCATCGCTATTACCATGGTGATGCGGTT<br>TTGGCAGTACATCAATGGGCGTGGATAGCGGTTTGACTCACGGGGATTTCCAAGTCTCCA<br>CCCCATTGACGTCAATGGGAGTTTGTTTTGGCACCAAAATCAACGGGACTTTCCAAAATG<br>TCGTAACAACTCCGCCCCATTGACGCAAATGGGCGGTAGGCGTGTACGGAATTCGGAGT<br>GGCGAGCCCTCAGATCCTGCATATAAGCAGCTGCTTTTTGCCTGTACTGGGTCTCTCTG |

TABLE 20

Leader _R11-Hinge-CD28tm/41BB-Z-T2A-tEGFR (SEQ ID NO: 48)

Leader: MLLLVTSLLLCELPHPAFLLIP

ScFv R11
QSVKESEGDLVTPAGNLTLTCTASGSDINDYPISWVRQAPGKGLEWIGFI
NSGGSTWYASWVKGRFTISRTSTTVDLKMTSLTTDDTATYFCARGYSTYY
GDFNIWGPGTLVTISSGGGGSGGGGSGGGGSELVMTQTPSSTSGAVGGTV
TINCQASQSIDSNLAWFQQKPGQPPTLLIYRASNLASGVPSRFSGSRSGT
EYTLTISGVQREDAATYYCLGGVGNVSYRTSFGGGTEVVVK

Spacer/Hinge: ESKYGPPCPPCP

CD28tm: MFWVLVVVGGVLACYSLLVTVAFIIFWV 4-1BB: KRGRKKLLYIFKQPFMRPVQTTQEEDGCSCRFPEEEEGGCEL

TABLE 20-continued

Leader _R11-Hinge-CD28tm/41BB-Z-T2A-tEGFR (SEQ ID NO: 48)

CD3zeta
RVKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKDT
YDALHMQALPPR

T2A: LEGGGEGRGSLLTCGDVEENPGPR tEGFR
MLLLVTSLLLCELPHPAFLLIPRKVCNGIGIGEFKDSLSINATNIKHFKN
CTSISGDLHILPVAFRGDSFTHTPPLDPQELDILKTVKEITGFLLIQAWP
ENRTDLHAFENLEIIRGRTKQHGQFSLAVVSLNITSLGLRSLKEISDGDV
IISGNKNLCYANTINWKKLFGTSGQKTKIISNRGENSCKATGQVCHALCS
PEGCWGPEPRDCVSCRNVSRGRECVDKCNLLEGEPREFVENSECIQCHPE
CLPQAMNITCTGRGPDNCIQCAHYIDGPHCVKTCPAGVMGENNTLVWKYA
DAGHVCHLCHPNCTYGCTGPGLEGCPTNGPKIPSIATGMVGALLLLLVVA
LGIGLFM

TABLE 21

Intermediate Spacer (SEQ ID NO:49)

Hinge/spacer: ESKYGPPCPPCP

CH3

GQPREPQVYTLPPSQEEMTKNQVSLTCLVKGFYPSDIAVEWESNGQPENNYKTTPPVLDSDG

SFFLYSRLTVDKSRWQEGNVFSCSVMHEALHNHYTQKSLSLSLGK

Long spacer (SEQ ID NO:50)

Hinge: ESKYGPPCPPCP

CH2
APEFLGGPSVFLFPPKPKDTLMISRTPEVTCVVVDVSQEDPEVQFNWYVDGVEVHNAKTKPR

EEQFNSTYRVVSVLTVLHQDWLNGKEYKCKVSNKGLPSSIEKTISKAK

CH3

GQPREPQVYTLPPSQEEMTKNQVSLTCLVKGFYPSDIAVEWESNGQPENNYKTTPPVLDSDG

SFFLYSRLTVDKSRWQEGNVFSCSVMHEALHNHYTQKSLSLSLGK

TABLE 22

| Her 2 Construct - Short Spacer (SEQ ID NO: 54) |
| --- |
| GMCSFss-Her2scFv-IgG4hinge-CD28tm-41BB-<br>Zeta-T2A-EGFRt |
| Leader |
| Atgcttctcctggtgacaagccttctgctctgtgagttaccacacccagc<br>attcctcctgatccca |
| Her2scFV |
| gatatccagatgacccagtccccgagctccctgtccgcctctgtgggcga<br>tagggtcaccatcacctgccgtgccagtcaggatgtgaatactgctgtag<br>cctggtatcaacagaaaccaggaaaagctccgaaactactgatttactcg<br>gcatccttcctctactctggagtcccttctcgcttctctggttccagatc<br>tgggacggatttcactctgaccatcagcagtctgcagccggaagacttcg<br>caacttattactgtcagcaacattatactactcctcccacgttcggacag<br>ggtaccaaggtggagatcaaaggcagtactagcggcggtggctccggggg<br>cggatccggtgggggcggcagcagcgaggttcagctggtggagtctggcg<br>gtggcctggtgcagccaggggctcactccgtttgtcctgtgcagcttct<br>ggcttcaacattaaagacacctatatacactgggtgcgtcaggccccggg<br>taagggcctggaatgggttgcaaggatttatcctacgaatggttatacta<br>gatatgccgatagcgtcaagggccgtttcactataagcgcagacacatcc<br>aaaaacacagcctacctgcagatgaacagcctgcgtgctgaggacactgc<br>cgtctattattgttctagatggggaggggacggcttctatgctatggact<br>actggggtcaaggaaccctggtcaccgtctcgagt |
| Hinge spacer |
| Gagagcaagtacggaccgccctgccccccttgccct |
| CD28tm |
| atgttctgggtgctggtggtggtcggaggcgtgctggcctgctacagcct |
| 4-1BB |
| gctggtcaccgtggccttcatcatcttttgggtgAaacggggcagaaaga<br>aactcctgtatatattcaaacaaccatttatgagaccagtacaaactact<br>caagaggaagatggctgtagctgccgatttccagaagaagaagaaggagg<br>atgtgaactg |
| CD3 zeta |
| Cgggtgaagttcagcagaagcgccgacgcccctgcctaccagcagggcca<br>gaatcagctgtacaacgagctgaacctgggcagaagggaagagtacgacg<br>tcctggataagcggagaggccgggaccctgagatgggcggcaagcctcgg<br>cggaagaaccccaggaaggcctgtataacgaactgcagaaagacaagat<br>ggccgaggcctacagcgagatcggcatgaagggcgagcggaggcggggca<br>agggccacgacggcctgtatcagggcctgtccaccgccaccaaggatacc<br>tacgacgccctgcacatgcaggccctgcccccaagg |
| T2A |
| Ctcgagggcggcggagagggcagaggaagtcttctaacatgcggtgacgt<br>ggaggagaatcccggccctagg |
| tEGFR |
| atgcttctcctggtgacaagccttctgctctgtgagttaccacacccagc<br>attcctcctgatcccacgcaaagtgtgtaacggaataggtattggtgaat<br>ttaaagactcactctccataaatgctacgaatattaaacacttcaaaaac<br>tgcacctccatcagtggcgatctccacatcctgccggtggcatttagggg<br>tgactccttcacacatactcctcctctggatccacaggaactggatattc<br>tgaaaaccgtaaaggaaatcacagggtttttgctgattcaggcttggcct<br>gaaaacaggacggacctccatgcctttgagaacctagaaatcatacgcgg<br>caggaccaagcaacatggtcagttttctcttgcagtcgtcagcctgaaca<br>taacatccttgggattacgctccctcaaggagataagtgatggagatgtg<br>ataatttcaggaaacaaaaatttgtgctatgcaaatacaataaactggaa<br>aaaactgtttgggacctccggtcagaaaaccaaaattataagcaacagag<br>gtgaaaacagctgcaaggccacaggccaggtctgccatgccttgtgctcc<br>cccgagggctgctggggcccggagcccagggactgcgtctcttgccggaa<br>tgtcagccgaggcagggaatgcgtggacaagtgcaaccttctggagggtg<br>agccaagggagtttgtggagaactctgagtgcatacagtgccacccagag<br>tgcctgcctcaggccatgaacatcacctgcacaggacggggaccagacaa<br>ctgtatccagtgtgcccactacattgacggcccccactgcgtcaagacct<br>gcccggcaggagtcatgggagaaaacaacaccctggtctggaagtacgca<br>gacgccggccatgtgtgccacctgtgccatccaaactgcacctacggatg<br>cactgggccaggtcttgaaggctgtccaacgaatgggcctaagatcccgt<br>ccatcgccactgggatggtgggggccctcctcttgctgctggtggtggcc<br>ctggggatcggcctcttcatgtga |

TABLE 23

| Her 2 construct-intermediate spacer (SEQ ID NO: 55) |
| --- |
| Leader |
| Atgcttctcctggtgacaagccttctgctctgtgagttaccacaccca |
| Her2scFv |
| Gcattcctcctgatcccagatatccagatgacccagtccccgagctccct<br>gtccgcctctgtgggcgatagggtcaccatcacctgccgtgccagtcagg<br>atgtgaatactgctgtagcctggtatcaacagaaaccaggaaaagctccg<br>aaactactgatttactcggcatccttcctctactctggagtcccttctcg<br>cttctctggttccagatctgggacggatttcactctgaccatcagcagtc<br>tgcagccggaagacttcgcaacttattactgtcagcaacattatactact<br>cctcccacgttcggacagggtaccaaggtggagatcaaaggcagtactag<br>cggcggtggctccgggggcggatccggtgggggcggcagcagcgaggttc<br>agctggtggagtctggcggtggcctggtgcagccaggggctcactccgt<br>ttgtcctgtgcagcttctggcttcaacattaaagacacctatatacactg<br>ggtgcgtcaggccccgggtaagggcctggaatgggttgcaaggatttatc<br>ctacgaatggttatactagatatgccgatagcgtcaagggccgtttcact<br>ataagcgcagacacatccaaaaacacagcctacctgcagatgaacagcct<br>gcgtgctgaggacactgccgtctattattgttctagatggggaggggacg<br>gcttctatgctatggactactggggtcaaggaaccctggtcaccgtctcg<br>agt |
| Hinge spacer |
| GagagcaagtacggaccgccctgccccccttgccctGgccagcctagaga<br>accccaggtgtacaccctgcctcccagccaggaagagatgaccaagaacc<br>aggtgtccctgacctgcctggtcaaaggcttctaccccagcgatatcgcc<br>gtggaatgggagagcaacggccagcccgagaacaactacaagaccacccc<br>ccctgtgctggacagcgacggcagcttcttcctgtactcccggctgaccg<br>tggacaagagccggtggcaggaaggcaacgtcttcagctgcagcgtgatg<br>cacgaggccctgcacaaccactacacccagaagtccctgagcctgagcct<br>gggcaag |
| CD28tm |
| Atgttctgggtgctggtggtggtcggaggcgtgctggcctgctacagcct<br>gctggtcaccgtggccttcatcatcttttgggtg |
| 4-1BB |
| Aaacggggcagaaagaaactcctgtatatattcaaacaaccatttatgag<br>accagtacaaactactcaagaggaagatggctgtagctgccgatttccag<br>aagaagaagaaggaggatgtgaactg |
| CD3 zeta |
| Cgggtgaagttcagcagaagcgccgacgcccctgcctaccagcagggcca<br>gaatcagctgtacaacgagctgaacctgggcagaagggaagagtacgacg<br>tcctggataagcggagaggccgggaccctgagatgggcggcaagcctcgg<br>cggaagaaccccaggaaggcctgtataacgaactgcagaaagacaagat<br>ggccgaggcctacagcgagatcggcatgaagggcgagcggaggcggggca<br>agggccacgacggcctgtatcagggcctgtccaccgccaccaaggatacc<br>tacgacgccctgcacatgcaggccctgcccccaagg |
| T2A |
| Ctcgagggcggcggagagggcagaggaagtcttctaacatgcggtgacgt<br>ggaggagaatcccggccctagg |
| tEGFR |
| atgcttctcctggtgacaagccttctgctctgtgagttaccacacccagc<br>attcctcctgatcccacgcaaagtgtgtaacggaataggtattggtgaat<br>ttaaagactcactctccataaatgctacgaatattaaacacttcaaaaac<br>tgcacctccatcagtggcgatctccacatcctgccggtggcatttagggg<br>tgactccttcacacatactcctcctctggatccacaggaactggatattc<br>tgaaaaccgtaaaggaaatcacagggtttttgctgattcaggcttggcct<br>gaaaacaggacggacctccatgcctttgagaacctagaaatcatacgcgg<br>caggaccaagcaacatggtcagttttctcttgcagtcgtcagcctgaaca<br>taacatccttgggattacgctccctcaaggagataagtgatggagatgtg<br>ataatttcaggaaacaaaaatttgtgctatgcaaatacaataaactggaa<br>aaaactgtttgggacctccggtcagaaaaccaaaattataagcaacagag<br>gtgaaaacagctgcaaggccacaggccaggtctgccatgccttgtgctcc<br>cccgagggctgctggggcccggagcccagggactgcgtctcttgccggaa<br>tgtcagccgaggcagggaatgcgtggacaagtgcaaccttctggagggtg<br>agccaagggagtttgtggagaactctgagtgcatacagtgccacccagag<br>tgcctgcctcaggccatgaacatcacctgcacaggacggggaccagacaa<br>ctgtatccagtgtgcccactacattgacggcccccactgcgtcaagacct<br>gcccggcaggagtcatgggagaaaacaacaccctggtctggaagtacgca<br>gacgccggccatgtgtgccacctgtgccatccaaactgcacctacggatg<br>cactgggccaggtcttgaaggctgtccaacgaatgggcctaagatcccgt<br>ccatcgccactgggatggtgggggccctcctcttgctgctggtggtggcc<br>ctggggatcggcctcttcatgtga |

TABLE 24

Her 2 construct-long spacer (SEQ ID NO: 56)

Leader:
atgcttctcctggtgacaagccttctgctctgtgagttaccacaccca

Her2 scFv
gcattcctcctgatcccagatatccagatgacccagtccccgagctccct
gtccgcctctgtgggcgatagggtcaccatcacctgccgtgccagtcagg
atgtgaatactgctgtagcctggttttcaacagaaaccaggaaaagctcc
gaaactactgatttactcggcatccttcctctactctggagtcccttctc
gcttctctggttccagatctgggacggatttcactctgaccatcagcagt
ctgcagccggaagacttcgcaacttattactgtcagcaacattatactac
tcctcccacgttcggacagggtaccaaggtggagatcaaaggcagtacta
gcggcggtggctccgggggcggatccggtgggggcggcagcagcgaggtt
cagctggtggagtctggcggtggcctggtgcagccagggggctcactccg
tttgtcctgtgcagcttctggcttcaacattaaagacacctatatacact
gggtgcgtcaggccccgggtaagggcctggaatgggttgcaaggatttat
cctacgaatggttatactagatatgccgatagcgtcaagggccgtttcac
tataagcgcagacacatccaaaaacacagcctacctgcagatgaacagcc
tgcgtgctgaggacactgccgtctattattgttctagatggggaggggac
ggcttctatgctatggactactggggtcaaggaaccctggtcaccgtctc
gagt long spacer
gagagcaagtacggaccgccctgccccccttgccctgcccccgagttcct
gggcggacccagcgtgttcctgttccccccaagcccaaggacaccctga
tgatcagccggacccccgaggtgacctgcgtggtggtggacgtgagccag
gaagatcccgaggtccagttcaattggtacgtggacggcgtggaagtgca
caacgccaagaccaagcccagagaggaacagttcaacagcacctaccggg
tggtgtctgtgctgaccgtgctgcaccaggactggctgaacggcaaagaa
tacaagtgcaaggtgtccaacaagggcctgcccagcagcatcgaaaagac
catcagcaaggccaagggccagcctcgcgagccccaggtgtacaccctgc
ctccctcccaggaagagatgaccaagaaccaggtgtccctgacctgcctg
gtgaagggcttctaccccagcgacatcgccgtggagtgggagagcaacgg
ccagcctgagaacaactacaagaccacccctcccgtgctggacagcgacg
gcagcttcttcctgtacagccggctgaccgtggacaagagccggtggcag
gaaggcaacgtctttagctgcagcgtgatgcacgaggccctgcacaacca
ctacacccagaagagcctgagcctgtccctgggcaag CD28tm:
atgttctgggtgctggtggtggtgggcggggtgctggcctgctacagcc
tgctggtgacagtggccttcatcatcttttgggtg TABLE 24-continued Her 2 construct-long spacer (SEQ ID NO: 56)

4-1BB
aaacggggcagaaagaaactcctgtatatattcaaacaaccatttatgag
accagtacaaactactcaagaggaagatggctgtagctgccgatttcca
gaagaagaagaaggaggatgtgaactg CD3zeta
Cgggtgaagttcagcagaagcgccgacgcccctgcctaccagcagggcca
gaatcagctgtacaacgagctgaacctgggcagaagggaagagtacgacg
tcctggataagcggagaggccgggaccctgagatgggcggcaagcctcgg
cggaagaacccccaggaaggcctgtataacgaactgcagaaagacaagat
ggccgaggcctacagcgagatcggcatgaagggcgagcggaggcggggca
agggccacgacggcctgtatcagggcctgtccaccgccaccaaggatacc
tacgacgccctgcacatgcaggccctgcccccaagg T2A
Ctcgagggcggcggagagggcagaggaagtcttctaacatgcggtgacgt
ggaggagaatcccggccctagg tEGFR
atgcttctcctggtgacaagccttctgctctgtgagttaccacacccagc
attcctcctgatcccacgcaaagtgtgtaacggaataggtattggtgaat
ttaaagactcactctccataaatgctacgaatattaaacacttcaaaaac
tgcacctccatcagtggcgatctccacatcctgccggtggcatttagggg
tgactccttcacacatactcctcctctggatccacaggaactggatattc
tgaaaaccgtaaaggaaatcacagggtttttgctgattcaggcttggcct
gaaaacaggacggacctccatgcctttgagaacctagaaatcatacgcgg
caggaccaagcaacatggtcagttttctcttgcagtcgtcagcctgaaca
taacatccttgggattacgctccctcaaggagataagtgatggagatgtg
ataatttcaggaaacaaaaatttgtgctatgcaaatacaataaactggaa
aaaactgtttgggacctccggtcagaaaaccaaaattataagcaacagag
gtgaaaacagctgcaaggccacaggccaggtctgccatgccttgtgctcc
cccgagggctgctggggcccggagcccagggactgcgtctcttgccggaa
tgtcagccgaggcagggaatgcgtggacaagtgcaaccttctggagggtg
agccaagggagtttgtggagaactctgagtgcatacagtgccacccagag
tgcctgcctcaggccatgaacatcacctgcacaggacggggaccagacaa
ctgtatccagtgtgcccactacattgacggcccccactgcgtcaagacct
gcccggcaggagtcatgggagaaaacaacaccctggtctggaagtacgca
gacgccggccatgtgtgccacctgtgccatccaaactgcacctacggatg
cactgggccaggtcttgaaggctgtccaacgaatgggcctaagatcccgt
ccatcgccactgggatggtgggggccctcctcttgctgctggtggtggcc
ctggggatcggcctcttcatgtga

What is claimed is:

1. A chimeric receptor, the chimeric receptor comprising an extracellular binding region consisting of an scFv and a polypeptide spacer, a transmembrane domain and an intracellular signaling domain, wherein:
   (a) the scFv binds to an epitope in the extracellular region of CD19, wherein the scFv comprises a variable heavy (VH) chain domain comprising the sequences DYGVS (SEQ ID NO:74), VIWGSETTYYNSALKS (SEQ ID NO:60) and YAMDYWG (SEQ ID NO:61), and a variable light (VL) chain domain comprising the sequences RASQDISKYLN (SEQ ID NO:57), SRLHSGV (SEQ ID NO:58) and GNTLPYTFG (SEQ ID NO:59);
   (b) the polypeptide spacer is located between the scFv and the transmembrane domain, wherein the polypeptide spacer consists of the amino acid sequence of SEQ ID NO:21; and
   (c) the intracellular signaling domain comprises the signaling domain of CD3ζ and a costimulatory domain.

2. A chimeric receptor, the chimeric receptor comprising:
   (a) an scFv that binds to an epitope in the extracellular region of CD19, wherein the scFv comprises the variable heavy (VH) chain domain and the variable light (VL) chain domain encoded by SEQ ID NO:3;
   (b) a transmembrane domain;
   (c) a polypeptide spacer located between the scFv and the transmembrane domain, wherein the polypeptide spacer consists of the amino acid sequence of SEQ ID NO:21; and
   (d) an intracellular signaling domain that comprises the signaling domain of CD3ζ and a costimulatory domain.

3. The chimeric receptor of claim 2, wherein the scFv is encoded by SEQ ID NO:3.

4. The chimeric receptor of claim 1, wherein:
   the transmembrane domain consists of the transmembrane domain of CD8 or of CD28; and
   the costimulatory domain comprises the signaling domain of 4-1BB or of CD28.

5. The chimeric receptor of claim 2, wherein:
   the transmembrane domain consists of the transmembrane domain of CD8 or of CD28; and
   the costimulatory domain comprises the signaling domain of 4-1BB or of CD28.

6. The chimeric receptor of claim 1, wherein:
   the transmembrane domain consists of the amino acid sequence encoded by the polynucleotide sequence of SEQ ID NO:5; and
   the intracellular signaling domain comprises the amino acid sequence encoded by the polynucleotide sequence of SEQ ID NO:6 and the amino acid sequence encoded by SEQ ID NO:7.

7. The chimeric receptor of claim 2, wherein:
   the transmembrane domain consists of the amino acid sequence encoded by the polynucleotide sequence of SEQ ID NO:5; and
   the intracellular signaling domain comprises the amino acid sequence encoded by the polynucleotide sequence of SEQ ID NO:6 and the amino acid sequence encoded by SEQ ID NO:7.

8. The chimeric receptor of claim 1, wherein the chimeric receptor comprises:
   the anti-CD19 scFv encoded by SEQ ID NO:3;
   the polypeptide spacer encoded by SEQ ID NO:4;
   the transmembrane domain encoded by SEQ ID NO:5;
   the costimulatory domain encoded by SEQ ID NO:6; and
   the CD3ζ signaling domain encoded by SEQ ID NO:7.

9. A T cell comprising the chimeric receptor of claim 1.

10. A composition, comprising the T cell of claim 9 in a pharmaceutically acceptable excipient.

11. A T cell comprising the chimeric receptor of claim 8.

12. A composition, comprising the T cell of claim 11 in a pharmaceutically acceptable excipient.

13. A T cell comprising the chimeric receptor of claim 2.

14. A composition, comprising the T cell of claim 13 in a pharmaceutically acceptable excipient.

15. A T cell comprising the chimeric receptor of claim 6.

16. A composition, comprising the T cell of claim 15 in a pharmaceutically acceptable excipient.

17. A T cell comprising the chimeric receptor of claim 7.

18. A composition, comprising the T cell of claim 17 in a pharmaceutically acceptable excipient.

* * * * *

UNITED STATES PATENT AND TRADEMARK OFFICE

CERTIFICATE OF CORRECTION

PATENT NO. : 10,869,889 B2
APPLICATION NO. : 16/657666
DATED : December 22, 2020
INVENTOR(S) : Michael C. Jensen et al.

It is certified that error appears in the above-identified patent and that said Letters Patent is hereby corrected as shown below:

In the Specification

At Column 5, Line 63, replace "CD3t" with -- CD3ζ --;

At Column 6, Line 1, replace "CD3t" with -- CD3ζ --;

At Column 7, Line 29, replace "2 A2" with -- 2A2 --;

At Column 7, Line 66, replace "MICAS" with -- MICA/B --;

At Column 8, Line 27, replace "anti-MICAS" with -- anti-MICA/B --;

At Column 9, Line 29, replace "Pt" with -- $PI^-$ --;

At Column 30, Line 47, replace "CD3t" with -- CD3ζ --;

At Column 39, Line 56, replace "MICAS" with -- MICA/B --;

At Column 40, Line 23, replace "CD3" with -- CD3ζ --;

At Column 40, Line 63, replace "y-counting" with -- γ-counting --;

At Column 41, Line 5, replace "anti-MICAS" with -- anti-MICA/B --;

At Column 41, Line 59, replace "CD3t" with -- CD3ζ --;

At Column 49, Line 41, replace "CD3" with -- CD3ζ --;

At Column 51, Line 15, replace "CD35" with -- CD3ζ --;

Signed and Sealed this
Twenty-third Day of March, 2021

Drew Hirshfeld
*Performing the Functions and Duties of the
Under Secretary of Commerce for Intellectual Property and
Director of the United States Patent and Trademark Office*

At Column 51, Line 57, replace “11-6” with -- IL-6 --;

At Column 53, Line 60, replace “4-IBB” with -- 4-1BB --;

At Column 54, Line 3, replace “CD28_4-IBB’” with -- CD28_4-1BB’ --;

At Column 54, Line 6, replace “4-IBB’” with -- 4-1BB’ --;

At Column 54, Line 9, replace “‘long/CD28_4-IBB’” with -- ‘long/CD28_4-1BB’ --;

At Column 54, Line 64, replace “4-IBB” with -- 4-1BB --;

At Column 54, Line 64, replace “4-IBB” with -- 4-1BB --;

At Column 54, Line 67, replace “tEGFR 10 vector” with -- tEGFR vector --;

At Column 55, Line 9, replace “4-IBB’” with -- 4-1BB’ --;

At Column 55, Line 12, replace “4-IBB’” with -- 4-1BB’ --;

At Column 55, Line 15, replace “4-IBB’” with -- 4-1BB’ --.

SEQUENCE LISTING

<160> NUMBER OF SEQ ID NOS: 74

<210> SEQ ID NO 1
<211> LENGTH: 5
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: 1
<223> OTHER INFORMATION: Xaa = glycine, cysteine or arginine
<220> FEATURE:
<221> NAME/KEY: VARIANT
<222> LOCATION: 4
<223> OTHER INFORMATION: Xaa = cysteine or threonine

<400> SEQUENCE: 1

Xaa Pro Pro Xaa Pro
1 5

<210> SEQ ID NO 2
<211> LENGTH: 66
<212> TYPE: DNA
<213> ORGANISM: Artificial Sequence
<220> FEATURE:

<223> OTHER INFORMATION: Synthetic sequence

<400> SEQUENCE: 2
atgctgctgc tggtgaccag cctgctgctg tgcgagctgc cccaccccgc ctttctgctg 60
atcccc 66

<210> SEQ ID NO 3
<211> LENGTH: 735
<212> TYPE: DNA
<213> ORGANISM: Artificial Sequence
<220> FEATURE:
<223> OTHER INFORMATION: Synthetic sequence

<400> SEQUENCE: 3
gacatccaga tgacccagac cacctccagc ctgagcgcca gcctgggcga ccgggtgacc 60
atcagctgcc gggccagcca ggacatcagc aagtacctga actggtatca gcagaagccc 120
gacggcaccg tcaagctgct gatctaccac accagccggc tgcacagcgg cgtgcccagc 180
cggtttagcg gcagcggctc cggcaccgac tacagcctga ccatctccaa cctggaacag 240
gaagatatcg ccacctactt ttgccagcag ggcaacacac tgccctacac ctttggcggc 300
ggaacaaagc tggaaatcac cggcagcacc tccggcagcg gcaagcctgg cagcggcgag 360
ggcagcacca agggcgaggt gaagctgcag gaaagcggcc ctggcctggt ggcccccagc 420
cagagcctga gcgtgacctg caccgtgagc ggcgtgagcc tgcccgacta cggcgtgagc 480
tggatccggc agcccccccag gaagggcctg gaatggctgg gcgtgatctg gggcagcgag 540
accacctact acaacagcgc cctgaagagc cggctgacca tcatcaagga caacagcaag 600
agccaggtgt tcctgaagat gaacagcctg cagaccgacg acaccgccat ctactactgc 660
gccaagcact actactacgg cggcagctac gccatggact actggggcca gggcaccagc 720
gtgaccgtga gcagc 735

<210> SEQ ID NO 4
<211> LENGTH: 36
<212> TYPE: DNA
<213> ORGANISM: Artificial Sequence
<220> FEATURE:
<223> OTHER INFORMATION: Synthetic sequence

<400> SEQUENCE: 4
gaatctaagt acggaccgcc ctgccccccct tgccct 36

<210> SEQ ID NO 5
<211> LENGTH: 84
<212> TYPE: DNA
<213> ORGANISM: Artificial Sequence
<220> FEATURE:
<223> OTHER INFORMATION: Synthetic sequence

<400> SEQUENCE: 5
atgttctggg tgctggtggt ggtcggaggc gtgctggcct gctacagcct gctggtcacc 60
gtggccttca tcatcttttg ggtg 84

<210> SEQ ID NO 6
<211> LENGTH: 126
<212> TYPE: DNA
<213> ORGANISM: Artificial Sequence
<220> FEATURE:
<223> OTHER INFORMATION: Synthetic sequence

<400> SEQUENCE: 6
aaacggggca gaaagaaact cctgtatata ttcaaacaac catttatgag accagtacaa 60
actactcaag aggaagatgg ctgtagctgc cgatttccag aagaagaaga aggaggatgt 120
gaactg 126

<210> SEQ ID NO 7
<211> LENGTH: 336
<212> TYPE: DNA
<213> ORGANISM: Artificial Sequence
<220> FEATURE:
<223> OTHER INFORMATION: Synthetic sequence

<400> SEQUENCE: 7
cgggtgaagt tcagcagaag cgccgacgcc cctgcctacc agcagggcca gaatcagctg 60
tacaacgagc tgaacctggg cagaagggaa gagtacgacg tcctggataa gcggagaggc 120
cgggaccctg agatgggcgg caagcctcgg cggaagaacc cccaggaagg cctgtataac 180
gaactgcaga aagacaagat ggccgaggcc tacagcgaga tcggcatgaa gggcgagcgg 240
aggcggggca agggccacga cggcctgtat cagggcctgt ccaccgccac caaggatacc 300
tacgacgccc tgcacatgca ggccctgccc ccaagg 336

<210> SEQ ID NO 8
<211> LENGTH: 72
<212> TYPE: DNA
<213> ORGANISM: Artificial Sequence
<220> FEATURE:
<223> OTHER INFORMATION: Synthetic sequence

<400> SEQUENCE: 8
ctcgagggcg gcggagaggg cagaggaagt cttctaacat gcggtgacgt ggaggagaat 60
cccggcccta gg 72

<210> SEQ ID NO 9
<211> LENGTH: 1074
<212> TYPE: DNA
<213> ORGANISM: Artificial Sequence
<220> FEATURE:
<223> OTHER INFORMATION: Synthetic sequence

<400> SEQUENCE: 9
atgcttctcc tggtgacaag ccttctgctc tgtgagttac cacacccagc attcctcctg 60
atcccacgca aagtgtgtaa cggaataggt attggtgaat ttaaagactc actctccata 120
aatgctacga atattaaaca cttcaaaaac tgcacctcca tcagtggcga tctccacatc 180
ctgccggtgg catttagggg tgactccttc acacatactc ctcctctgga tccacaggaa 240
ctggatattc tgaaaaccgt aaaggaaatc acagggtttt tgctgattca ggcttggcct 300
gaaaacagga cggacctcca tgcctttgag aacctagaaa tcatacgcgg caggaccaag 360
caacatggtc agttttctct tgcagtcgtc agcctgaaca taacatcctt gggattacgc 420
tccctcaagg agataagtga tggagatgtg ataatttcag gaaacaaaaa tttgtgctat 480
gcaaatacaa taaactggaa aaaactgttt gggacctccg gtcagaaaac caaaattata 540
agcaacagag gtgaaaacag ctgcaaggcc acaggccagg tctgccatgc cttgtgctcc 600
cccgagggct gctggggccc ggagcccagg gactgcgtct cttgccggaa tgtcagccga 660
ggcagggaat gcgtggacaa gtgcaacctt ctggagggtg agccaaggga gtttgtggag 720
aactctgagt gcatacagtg ccacccagag tgcctgcctc aggccatgaa catcacctgc 780

```
acaggacggg gaccagacaa ctgtatccag tgtgcccact acattgacgg cccccactgc    840

gtcaagacct gcccggcagg agtcatggga gaaaacaaca ccctggtctg gaagtacgca    900

gacgccggcc atgtgtgcca cctgtgccat ccaaactgca cctacggatg cactgggcca    960

ggtcttgaag gctgtccaac gaatgggcct aagatcccgt ccatcgccac tgggatggtg   1020

ggggccctcc tcttgctgct ggtggtggcc ctggggatcg gcctcttcat gtga         1074
```

<210> SEQ ID NO 10
<211> LENGTH: 2529
<212> TYPE: DNA
<213> ORGANISM: Artificial Sequence
<220> FEATURE:
<223> OTHER INFORMATION: Synthetic sequence

<400> SEQUENCE: 10

```
atgctgctgc tggtgaccag cctgctgctg tgcgagctgc cccaccccgc ctttctgctg     60

atccccgaca tccagatgac ccagaccacc tccagcctga gcgccagcct gggcgaccgg    120

gtgaccatca gctgccgggc cagccaggac atcagcaagt acctgaactg gtatcagcag    180

aagcccgacg gcaccgtcaa gctgctgatc taccacacca gccggctgca cagcggcgtg    240

cccagccggt ttagcggcag cggctccggc accgactaca gcctgaccat ctccaacctg    300

gaacaggaag atatcgccac ctacttttgc cagcagggca acacactgcc ctacaccttt    360

ggcggcggaa caaagctgga aatcaccggc agcacctccg gcagcggcaa gcctggcagc    420

ggcgagggca gcaccaaggg cgaggtgaag ctgcaggaaa gcggccctgg cctggtggcc    480

cccagccaga gcctgagcgt gacctgcacc gtgagcggcg tgagcctgcc cgactacggc    540

gtgagctgga tccggcagcc ccccaggaag ggcctggaat ggctgggcgt gatctggggc    600

agcgagacca cctactacaa cagcgccctg aagagccggc tgaccatcat caaggacaac    660

agcaagagcc aggtgttcct gaagatgaac agcctgcaga ccgacgacac cgccatctac    720

tactgcgcca agcactacta ctacggcggc agctacgcca tggactactg gggccagggc    780

accagcgtga ccgtgagcag cgagagcaag tacggaccgc cctgcccccc ttgccctatg    840

ttctgggtgc tggtggtggt cggaggcgtg ctggcctgct acagcctgct ggtcaccgtg    900

gccttcatca tcttttgggt gaaacggggc agaaagaaac tcctgtatat attcaaacaa    960

ccatttatga gaccagtaca aactactcaa gaggaagatg gctgtagctg ccgatttcca   1020

gaagaagaag aaggaggatg tgaactgcgg gtgaagttca gcagaagcgc cgacgcccct   1080

gcctaccagc agggccagaa tcagctgtac aacgagctga acctgggcag aagggaagag   1140

tacgacgtcc tggataagcg gagaggccgg gaccctgaga tgggcggcaa gcctcggcgg   1200

aagaaccccc aggaaggcct gtataacgaa ctgcagaaag acaagatggc cgaggcctac   1260

agcgagatcg gcatgaaggg cgagcggagg cggggcaagg gccacgacgg cctgtatcag   1320

ggcctgtcca ccgccaccaa ggatacctac gacgccctgc acatgcaggc cctgccccca   1380

aggctcgagg gcggcggaga gggcagagga agtcttctaa catgcggtga cgtggaggag   1440

aatcccggcc ctaggatgct tctcctggtg acaagccttc tgctctgtga gttaccacac   1500

ccagcattcc tcctgatccc acgcaaagtg tgtaacggaa taggtattgg tgaatttaaa   1560

gactcactct ccataaatgc tacgaatatt aaacacttca aaaactgcac ctccatcagt   1620

ggcgatctcc acatcctgcc ggtggcattt aggggtgact ccttcacaca tactcctcct   1680

ctggatccac aggaactgga tattctgaaa accgtaaagg aaatcacagg gtttttgctg   1740

attcaggctt ggcctgaaaa caggacggac ctccatgcct ttgagaacct agaaatcata   1800
```

cgcggcagga ccaagcaaca tggtcagttt tctcttgcag tcgtcagcct gaacataaca 1860
tccttgggat tacgctccct caaggagata agtgatggag atgtgataat ttcaggaaac 1920
aaaaatttgt gctatgcaaa tacaataaac tggaaaaaac tgtttgggac ctccggtcag 1980
aaaaccaaaa ttataagcaa cagaggtgaa aacagctgca aggccacagg ccaggtctgc 2040
catgccttgt gctcccccga gggctgctgg ggcccggagc ccagggactg cgtctcttgc 2100
cggaatgtca gccgaggcag ggaatgcgtg gacaagtgca accttctgga gggtgagcca 2160
agggagtttg tggagaactc tgagtgcata cagtgccacc cagagtgcct gcctcaggcc 2220
atgaacatca cctgcacagg acggggacca gacaactgta tccagtgtgc ccactacatt 2280
gacggccccc actgcgtcaa gacctgcccg gcaggagtca tgggagaaaa caacaccctg 2340
gtctggaagt acgcagacgc cggccatgtg tgccacctgt gccatccaaa ctgcacctac 2400
ggatgcactg ggccaggtct tgaaggctgt ccaacgaatg ggcctaagat cccgtccatc 2460
gccactggga tggtgggggc cctcctcttg ctgctggtgg tggccctggg gatcggcctc 2520
ttcatgtga 2529

<210> SEQ ID NO 11
<211> LENGTH: 841
<212> TYPE: PRT
<213> ORGANISM: Artificial Sequence
<220> FEATURE:
<223> OTHER INFORMATION: Synthetic sequence

<400> SEQUENCE: 11

Met Leu Leu Leu Val Thr Ser Leu Leu Leu Cys Glu Leu Pro His Pro
1 5 10 15

Ala Phe Leu Leu Ile Pro Asp Ile Gln Met Thr Gln Thr Thr Ser Ser
20 25 30

Leu Ser Ala Ser Leu Gly Asp Arg Val Thr Ile Ser Cys Arg Ala Ser
35 40 45

Gln Asp Ile Ser Lys Tyr Leu Asn Trp Tyr Gln Gln Lys Pro Asp Gly
50 55 60

Thr Val Lys Leu Leu Ile Tyr His Thr Ser Arg Leu His Ser Gly Val
65 70 75 80

Pro Ser Arg Phe Ser Gly Ser Gly Ser Gly Thr Asp Tyr Ser Leu Thr
85 90 95

Ile Ser Asn Leu Glu Gln Glu Asp Ile Ala Thr Tyr Phe Cys Gln Gln
100 105 110

Gly Asn Thr Leu Pro Tyr Thr Phe Gly Gly Gly Thr Lys Leu Glu Ile
115 120 125

Thr Gly Ser Thr Ser Gly Ser Gly Lys Pro Gly Ser Gly Glu Gly Ser
130 135 140

Thr Lys Gly Glu Val Lys Leu Gln Glu Ser Gly Pro Gly Leu Val Ala
145 150 155 160

Pro Ser Gln Ser Leu Ser Val Thr Cys Thr Val Ser Gly Val Ser Leu
165 170 175

Pro Asp Tyr Gly Val Ser Trp Ile Arg Gln Pro Pro Arg Lys Gly Leu
180 185 190

Glu Trp Leu Gly Val Ile Trp Gly Ser Glu Thr Thr Tyr Tyr Asn Ser
195 200 205

Ala Leu Lys Ser Arg Leu Thr Ile Ile Lys Asp Asn Ser Lys Ser Gln
210 215 220

```
Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser Glu Ser Lys Tyr Gly
            260                 265                 270

Pro Pro Cys Pro Pro Cys Pro Met Phe Trp Val Leu Val Val Val Gly
        275                 280                 285

Gly Val Leu Ala Cys Tyr Ser Leu Leu Val Thr Val Ala Phe Ile Ile
    290                 295                 300

Phe Trp Val Lys Arg Gly Arg Lys Lys Leu Leu Tyr Ile Phe Lys Gln
305                 310                 315                 320

Pro Phe Met Arg Pro Val Gln Thr Thr Gln Glu Glu Asp Gly Cys Ser
                325                 330                 335

Cys Arg Phe Glu Glu Glu Glu Gly Gly Cys Glu Leu Arg Val Lys Phe
            340                 345                 350

Ser Arg Ser Ala Asp Ala Pro Ala Tyr Gln Gln Gly Gln Asn Gln Leu
        355                 360                 365

Tyr Asn Glu Leu Asn Leu Gly Arg Arg Glu Glu Tyr Asp Val Leu Asp
    370                 375                 380

Lys Arg Arg Gly Arg Asp Pro Glu Met Gly Gly Lys Pro Arg Arg Lys
385                 390                 395                 400

Asn Pro Gln Glu Gly Leu Tyr Asn Glu Leu Gln Lys Asp Lys Met Ala
                405                 410                 415

Glu Ala Tyr Ser Glu Ile Gly Met Lys Gly Glu Arg Arg Arg Gly Lys
            420                 425                 430

Gly His Asp Gly Leu Tyr Gln Gly Leu Ser Thr Ala Thr Lys Asp Thr
        435                 440                 445

Tyr Asp Ala Leu His Met Gln Ala Leu Pro Pro Arg Leu Glu Gly Gly
    450                 455                 460

Gly Glu Gly Arg Gly Ser Leu Leu Thr Cys Gly Asp Val Glu Glu Asn
465                 470                 475                 480

Pro Gly Pro Arg Met Leu Leu Leu Val Thr Ser Leu Leu Leu Cys Glu
                485                 490                 495

Leu Pro His Pro Ala Phe Leu Leu Ile Pro Arg Lys Val Cys Asn Gly
            500                 505                 510

Ile Gly Ile Gly Glu Phe Lys Asp Ser Leu Ser Ile Asn Ala Thr Asn
        515                 520                 525

Ile Lys His Phe Lys Asn Cys Thr Ser Ile Ser Gly Asp Leu His Ile
    530                 535                 540

Leu Pro Val Ala Phe Arg Gly Asp Ser Phe Thr His Thr Pro Pro Leu
545                 550                 555                 560

Asp Pro Gln Glu Leu Asp Ile Leu Lys Thr Val Lys Glu Ile Thr Gly
                565                 570                 575

Phe Leu Leu Ile Gln Ala Trp Pro Glu Asn Arg Thr Asp Leu His Ala
            580                 585                 590

Phe Glu Asn Leu Glu Ile Ile Arg Gly Arg Thr Lys Gln His Gly Gln
        595                 600                 605

Phe Ser Leu Ala Val Val Ser Leu Asn Ile Thr Ser Leu Gly Leu Arg
    610                 615                 620

Ser Leu Lys Glu Ile Ser Asp Gly Asp Val Ile Ile Ser Gly Asn Lys
625                 630                 635                 640

Asn Leu Cys Tyr Ala Asn Thr Ile Asn Trp Lys Lys Leu Phe Gly Thr
```

```
                645                 650                 655

Ser Gly Gln Lys Thr Lys Ile Ile Ser Asn Arg Gly Glu Asn Ser Cys
            660                 665                 670

Lys Ala Thr Gly Gln Val Cys His Ala Leu Cys Ser Pro Glu Gly Cys
        675                 680                 685

Trp Gly Pro Glu Pro Arg Asp Cys Val Ser Cys Arg Asn Val Ser Arg
    690                 695                 700

Gly Arg Glu Cys Val Asp Lys Cys Asn Leu Leu Glu Gly Glu Pro Arg
705                 710                 715                 720

Glu Phe Val Glu Asn Ser Glu Cys Ile Gln Cys His Pro Glu Cys Leu
                725                 730                 735

Pro Gln Ala Met Asn Ile Thr Cys Thr Gly Arg Gly Pro Asp Asn Cys
            740                 745                 750

Ile Gln Cys Ala His Tyr Ile Asp Gly Pro His Cys Val Lys Thr Cys
        755                 760                 765

Pro Ala Gly Val Met Gly Glu Asn Asn Thr Leu Val Trp Lys Tyr Ala
    770                 775                 780

Asp Ala Gly His Val Cys His Leu Cys His Pro Asn Cys Thr Tyr Gly
785                 790                 795                 800

Cys Thr Gly Pro Gly Leu Glu Gly Cys Pro Thr Asn Gly Pro Lys Ile
                805                 810                 815

Pro Ser Ile Ala Thr Gly Met Val Gly Ala Leu Leu Leu Leu Leu Val
            820                 825                 830

Val Ala Leu Gly Ile Gly Leu Phe Met
        835                 840


<210> SEQ ID NO 12
<211> LENGTH: 15
<212> TYPE: PRT
<213> ORGANISM: Artificial Sequence
<220> FEATURE:
<223> OTHER INFORMATION: Synthetic sequence

<400> SEQUENCE: 12

Gly Gly Gly Gly Ser Gly Gly Gly Gly Ser Gly Gly Gly Gly Ser
1               5                   10                  15


<210> SEQ ID NO 13
<211> LENGTH: 327
<212> TYPE: PRT
<213> ORGANISM: Homo sapiens

<400> SEQUENCE: 13

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110
```

```
Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 14
<211> LENGTH: 220
<212> TYPE: PRT
<213> ORGANISM: Homo sapiens

<400> SEQUENCE: 14

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
```

```
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220


<210> SEQ ID NO 15
<211> LENGTH: 255
<212> TYPE: PRT
<213> ORGANISM: Homo sapiens

<400> SEQUENCE: 15

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255


<210> SEQ ID NO 16
<211> LENGTH: 164
<212> TYPE: PRT
<213> ORGANISM: Homo sapiens

<400> SEQUENCE: 16

Met Lys Trp Lys Ala Leu Phe Thr Ala Ala Ile Leu Gln Ala Gln Leu
```

```
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg


<210> SEQ ID NO 17
<211> LENGTH: 15
<212> TYPE: PRT
<213> ORGANISM: Homo sapiens

<400> SEQUENCE: 17

Glu Pro Lys Ser Cys Asp Lys Thr His Thr Cys Pro Pro Cys Pro
1               5                   10                  15


<210> SEQ ID NO 18
<211> LENGTH: 12
<212> TYPE: PRT
<213> ORGANISM: Artificial Sequence
<220> FEATURE:
<223> OTHER INFORMATION: Synthetic sequence

<400> SEQUENCE: 18

Glu Arg Lys Cys Cys Val Glu Cys Pro Pro Cys Pro
1               5                   10


<210> SEQ ID NO 19
<211> LENGTH: 61
<212> TYPE: PRT
<213> ORGANISM: Homo sapiens

<400> SEQUENCE: 19

Glu Leu Lys Thr Pro Leu Gly Asp Thr His Thr Cys Pro Arg Cys Pro
1               5                   10                  15

Glu Pro Lys Ser Cys Asp Thr Pro Pro Pro Cys Pro Arg Cys Pro Glu
            20                  25                  30

Pro Lys Ser Cys Asp Thr Pro Pro Pro Cys Pro Arg Cys Pro Glu Pro
        35                  40                  45

Lys Ser Cys Asp Thr Pro Pro Pro Cys Pro Arg Cys Pro
    50                  55                  60


<210> SEQ ID NO 20
<211> LENGTH: 12
<212> TYPE: PRT
```

<213> ORGANISM: Homo sapiens

<400> SEQUENCE: 20

Glu Ser Lys Tyr Gly Pro Pro Cys Pro Ser Cys Pro
1 5 10

<210> SEQ ID NO 21
<211> LENGTH: 12
<212> TYPE: PRT
<213> ORGANISM: Artificial Sequence
<220> FEATURE:
<223> OTHER INFORMATION: Synthetic sequence

<400> SEQUENCE: 21

Glu Ser Lys Tyr Gly Pro Pro Cys Pro Pro Cys Pro
1 5 10

<210> SEQ ID NO 22
<211> LENGTH: 26
<212> TYPE: DNA
<213> ORGANISM: Artificial Sequence
<220> FEATURE:
<223> OTHER INFORMATION: Primer sequence

<400> SEQUENCE: 22
atcaaaagaa tagaccgaga tagggt 26

<210> SEQ ID NO 23
<211> LENGTH: 26
<212> TYPE: DNA
<213> ORGANISM: Artificial Sequence
<220> FEATURE:
<223> OTHER INFORMATION: Primer sequence

<400> SEQUENCE: 23
ccgtaccttt aagaccaatg acttac 26

<210> SEQ ID NO 24
<211> LENGTH: 18
<212> TYPE: DNA
<213> ORGANISM: Artificial Sequence
<220> FEATURE:
<223> OTHER INFORMATION: Primer sequence

<400> SEQUENCE: 24
ttgagagttt tcgccccg 18

<210> SEQ ID NO 25
<211> LENGTH: 24
<212> TYPE: DNA
<213> ORGANISM: Artificial Sequence
<220> FEATURE:
<223> OTHER INFORMATION: Primer sequence

<400> SEQUENCE: 25
aatagacaga tcgctgagat aggt 24

<210> SEQ ID NO 26
<211> LENGTH: 18
<212> TYPE: DNA
<213> ORGANISM: Artificial Sequence
<220> FEATURE:
<223> OTHER INFORMATION: Primer sequence

<400> SEQUENCE: 26
caggtatccg gtaagcgg 18

<210> SEQ ID NO 27
<211> LENGTH: 19
<212> TYPE: DNA
<213> ORGANISM: Artificial Sequence
<220> FEATURE:
<223> OTHER INFORMATION: Primer sequence

<400> SEQUENCE: 27
cgaccagcaa ccatagtcc 19

<210> SEQ ID NO 28
<211> LENGTH: 18
<212> TYPE: DNA
<213> ORGANISM: Artificial Sequence
<220> FEATURE:
<223> OTHER INFORMATION: Primer sequence

<400> SEQUENCE: 28
tagcggtttg actcacgg 18

<210> SEQ ID NO 29
<211> LENGTH: 20
<212> TYPE: DNA
<213> ORGANISM: Artificial Sequence
<220> FEATURE:
<223> OTHER INFORMATION: Primer sequence

<400> SEQUENCE: 29
gcagggagct agaacgattc 20

<210> SEQ ID NO 30
<211> LENGTH: 22
<212> TYPE: DNA
<213> ORGANISM: Artificial Sequence
<220> FEATURE:
<223> OTHER INFORMATION: Primer sequence

<400> SEQUENCE: 30
attgtctggt atagtgcagc ag 22

<210> SEQ ID NO 31
<211> LENGTH: 16
<212> TYPE: DNA
<213> ORGANISM: Artificial Sequence
<220> FEATURE:
<223> OTHER INFORMATION: Primer sequence

<400> SEQUENCE: 31
tcgcaacggg tttgcc 16

<210> SEQ ID NO 32
<211> LENGTH: 21
<212> TYPE: DNA
<213> ORGANISM: Artificial Sequence
<220> FEATURE:
<223> OTHER INFORMATION: Primer sequence

<400> SEQUENCE: 32
aggaagatat cgccacctac t 21

<210> SEQ ID NO 33
<211> LENGTH: 20
<212> TYPE: DNA
<213> ORGANISM: Artificial Sequence
<220> FEATURE:

<223> OTHER INFORMATION: Primer sequence

<400> SEQUENCE: 33
cgggtgaagt tcagcagaag 20

<210> SEQ ID NO 34
<211> LENGTH: 20
<212> TYPE: DNA
<213> ORGANISM: Artificial Sequence
<220> FEATURE:
<223> OTHER INFORMATION: Primer sequence

<400> SEQUENCE: 34
actgtgtttg ctgacgcaac 20

<210> SEQ ID NO 35
<211> LENGTH: 20
<212> TYPE: DNA
<213> ORGANISM: Artificial Sequence
<220> FEATURE:
<223> OTHER INFORMATION: Primer sequence

<400> SEQUENCE: 35
atgcttctcc tggtgacaag 20

<210> SEQ ID NO 36
<211> LENGTH: 18
<212> TYPE: PRT
<213> ORGANISM: Artificial Sequence
<220> FEATURE:
<223> OTHER INFORMATION: Synthetic sequence

<400> SEQUENCE: 36

Gly Ser Thr Ser Gly Ser Gly Lys Pro Gly Ser Gly Glu Gly Ser Thr
1 5 10 15

Lys Gly

<210> SEQ ID NO 37
<211> LENGTH: 10051
<212> TYPE: DNA
<213> ORGANISM: Artificial Sequence
<220> FEATURE:
<223> OTHER INFORMATION: Synthetic sequence

<400> SEQUENCE: 37
gttagaccag atctgagcct gggagctctc tggctaacta gggaacccac tgcttaagcc 60
tcaataaagc ttgccttgag tgcttcaagt agtgtgtgcc cgtctgttgt gtgactctgg 120
taactagaga tccctcagac ccttttagtc agtgtggaaa atctctagca gtggcgcccg 180
aacagggact tgaaagcgaa agggaaacca gaggagctct ctcgacgcag gactcggctt 240
gctgaagcgc gcacggcaag aggcgagggg cggcgactgg tgagtacgcc aaaaattttg 300
actagcggag gctagaagga gagagatggg tgcgagagcg tcagtattaa gcgggggaga 360
attagatcga tgggaaaaaa ttcggttaag gccaggggga aagaaaaaat ataaattaaa 420
acatatagta tgggcaagca gggagctaga acgattcgca gttaatcctg gcctgttaga 480
aacatcagaa ggctgtagac aaatactggg acagctacaa ccatcccttc agacaggatc 540
agaagaactt agatcattat ataatacagt agcaaccctc tattgtgtgc atcaaaggat 600
agagataaaa gacaccaagg aagctttaga caagatagag gaagagcaaa acaaaagtaa 660
gaaaaaagca cagcaagcag cagctgacac aggacacagc aatcaggtca gccaaaatta 720

-continued

```
ccctatagtg cagaacatcc aggggcaaat ggtacatcag gccatatcac ctagaacttt    780
aaatgcatgg gtaaaagtag tagaagagaa ggctttcagc ccagaagtga tacccatgtt    840
ttcagcatta tcagaaggag ccaccccaca agatttaaac accatgctaa acacagtggg    900
gggacatcaa gcagccatgc aaatgttaaa agagaccatc aatgaggaag ctgcaggcaa    960
agagaagagt ggtgcagaga gaaaaaagag cagtgggaat aggagctttg ttccttgggt   1020
tcttgggagc agcaggaagc actatgggcg cagcgtcaat gacgctgacg gtacaggcca   1080
gacaattatt gtctggtata gtgcagcagc agaacaattt gctgagggct attgaggcgc   1140
aacagcatct gttgcaactc acagtctggg gcatcaagca gctccaggca agaatcctgg   1200
ctgtggaaag atacctaaag gatcaacagc tcctggggat ttggggttgc tctggaaaac   1260
tcatttgcac cactgctgtg ccttggatct acaaatggca gtattcatcc acaattttaa   1320
aagaaaaggg gggattgggg ggtacagtgc aggggaaaga atagtagaca taatagcaac   1380
agacatacaa actaaagaat tacaaaaaca aattacaaaa attcaaaatt ttcgggttta   1440
ttacagggac agcagagatc cagtttgggg atcaattgca tgaagaatct gcttagggtt   1500
aggcgttttg cgctgcttcg cgaggatctg cgatcgctcc ggtgcccgtc agtgggcaga   1560
gcgcacatcg cccacagtcc ccgagaagtt ggggggaggg gtcggcaatt gaaccggtgc   1620
ctagagaagg tggcgcgggg taaactggga aagtgatgtc gtgtactggc tccgcctttt   1680
tcccgagggt gggggagaac cgtatataag tgcagtagtc gccgtgaacg ttcttttttcg   1740
caacgggttt gccgccagaa cacagctgaa gcttcgaggg gctcgcatct ctccttcacg   1800
cgcccgccgc cctacctgag gccgccatcc acgccggttg agtcgcgttc tgccgcctcc   1860
cgcctgtggt gcctcctgaa ctgcgtccgc cgtctaggta agtttaaagc tcaggtcgag   1920
accgggcctt tgtccggcgc tcccttggag cctacctaga ctcagccggc tctccacgct   1980
ttgcctgacc ctgcttgctc aactctacgt ctttgtttcg ttttctgttc tgcgccgtta   2040
cagatccaag ctgtgaccgg cgcctacggc tagcgaattc ctcgaggcca ccatgctgct   2100
gctggtgaca agcctgctgc tgtgcgagct gccccacccc gcctttctgc tgatccccca   2160
ggaacagctc gtcgaaagcg gcggcagact ggtgacacct ggcggcagcc tgaccctgag   2220
ctgcaaggcc agcggcttcg acttcagcgc ctactacatg agctgggtcc gccaggcccc   2280
tggcaaggga ctggaatgga tcgccaccat ctaccccagc agcggcaaga cctactacgc   2340
cacctgggtg aacggacggt tcaccatctc cagcgacaac gcccagaaca ccgtggacct   2400
gcagatgaac agcctgacag ccgccgaccg ggccacctac ttttgcgcca gagacagcta   2460
cgccgacgac ggcgccctgt tcaacatctg gggccctggc accctggtga caatctctag   2520
cggcggaggc ggatctggtg gcggaggaag tggcggcgga ggatctgagc tggtgctgac   2580
ccagagcccc tctgtgtctg ctgccctggg aagccctgcc aagatcacct gtaccctgag   2640
cagcgcccac aagaccgaca ccatcgactg gtatcagcag ctgcagggcg aggcccccag   2700
atacctgatg caggtgcaga gcgacggcag ctacaccaag aggccaggcg tgcccgaccg   2760
gttcagcgga tctagctctg gcgccgaccg ctacctgatc atccccagcg tgcaggccga   2820
tgacgaggcc gattactact gtggcgccga ctacatcggc ggctacgtgt tcggcggagg   2880
cacccagctg accgtgaccg gcgagtctaa gtacggaccg ccctgccccc cttgccctgc   2940
ccccgagttc ctgggcggac ccagcgtgtt cctgttcccc cccaagccca aggacaccct   3000
gatgatcagc cggacccccg aggtgacctg cgtggtggtg gacgtgagcc aggaagatcc   3060
cgaggtccag ttcaattggt acgtggacgg cgtggaagtg cacaacgcca agaccaagcc   3120
```

```
cagagaggaa cagttcaaca gcacctaccg ggtggtgtct gtgctgaccg tgctgcacca   3180
ggactggctg aacggcaaag aatacaagtg caaggtgtcc aacaagggcc tgcccagcag   3240
catcgaaaag accatcagca aggccaaggg ccagcctcgc gagccccagg tgtacaccct   3300
gcctccctcc caggaagaga tgaccaagaa ccaggtgtcc ctgacctgcc tggtgaaggg   3360
cttctacccc agcgacatcg ccgtggagtg ggagagcaac ggccagcctg agaacaacta   3420
caagaccacc cctcccgtgc tggacagcga cggcagcttc ttcctgtaca gccggctgac   3480
cgtggacaag agccggtggc aggaaggcaa cgtctttagc tgcagcgtga tgcacgaggc   3540
cctgcacaac cactacaccc agaagagcct gagcctgtcc ctgggcaaga tgttctgggt   3600
gctggtggtg gtgggcgggg tgctggcctg ctacagcctg ctggtgacag tggccttcat   3660
catcttttgg gtgaaacggg gcagaaagaa actcctgtat atattcaaac aaccatttat   3720
gagaccagta caaactactc aagaggaaga tggctgtagc tgccgatttc cagaagaaga   3780
agaaggagga tgtgaactgc gggtgaagtt cagcagaagc gccgacgccc ctgcctacca   3840
gcagggccag aatcagctgt acaacgagct gaacctgggc agaagggaag agtacgacgt   3900
cctggataag cggagaggcc gggaccctga gatgggcggc aagcctcggc ggaagaaccc   3960
ccaggaaggc ctgtataacg aactgcagaa agacaagatg gccgaggcct acagcgagat   4020
cggcatgaag ggcgagcgga ggcggggcaa gggccacgac ggcctgtatc agggcctgtc   4080
caccgccacc aaggatacct acgacgccct gcacatgcag gccctgcccc caaggctcga   4140
gggcggcgga gagggcagag gaagtcttct aacatgcggt gacgtggagg agaatcccgg   4200
ccctaggatg cttctcctgg tgacaagcct tctgctctgt gagttaccac acccagcatt   4260
cctcctgatc ccacgcaaag tgtgtaacgg aataggtatt ggtgaattta aagactcact   4320
ctccataaat gctacgaata ttaaacactt caaaaactgc acctccatca gtggcgatct   4380
ccacatcctg ccggtggcat ttaggggtga ctccttcaca catactcctc ctctggatcc   4440
acaggaactg gatattctga aaaccgtaaa ggaaatcaca gggtttttgc tgattcaggc   4500
ttggcctgaa aacaggacgg acctccatgc ctttgagaac ctagaaatca tacgcggcag   4560
gaccaagcaa catggtcagt tttctcttgc agtcgtcagc ctgaacataa catccttggg   4620
attacgctcc ctcaaggaga taagtgatgg agatgtgata atttcaggaa acaaaaattt   4680
gtgctatgca aatacaataa actggaaaaa actgtttggg acctccggtc agaaaaccaa   4740
aattataagc aacagaggtg aaaacagctg caaggccaca ggccaggtct gccatgcctt   4800
gtgctccccc gagggctgct ggggcccgga gcccagggac tgcgtctctt gccggaatgt   4860
cagccgaggc agggaatgcg tggacaagtg caaccttctg gagggtgagc caagggagtt   4920
tgtggagaac tctgagtgca tacagtgcca cccagagtgc ctgcctcagg ccatgaacat   4980
cacctgcaca ggacggggac cagacaactg tatccagtgt gcccactaca ttgacggccc   5040
ccactgcgtc aagacctgcc cggcaggagt catgggagaa aacaacaccc tggtctggaa   5100
gtacgcagac gccggccatg tgtgccacct gtgccatcca aactgcacct acggatgcac   5160
tgggccaggt cttgaaggct gtccaacgaa tgggcctaag atcccgtcca tcgccactgg   5220
gatggtgggg gccctcctct tgctgctggt ggtggccctg gggatcggcc tcttcatgtg   5280
agcggccgct ctagacccgg gctgcaggaa ttcgatatca agcttatcga taatcaacct   5340
ctggattaca aaatttgtga aagattgact ggtattctta actatgttgc tccttttacg   5400
ctatgtggat acgctgcttt aatgcctttg tatcatgcta ttgcttcccg tatggctttc   5460
```

-continued

```
atttctcct ccttgtataa atcctggttg ctgtctcttt atgaggagtt gtggcccgtt   5520
gtcaggcaac gtggcgtggt gtgcactgtg tttgctgacg caacccccac tggttggggc   5580
attgccacca cctgtcagct cctttccggg actttcgctt tccccctccc tattgccacg   5640
gcggaactca tcgccgcctg ccttgcccgc tgctggacag gggctcggct gttgggcact   5700
gacaattccg tggtgttgtc ggggaaatca tcgtcctttc cttggctgct cgcctgtgtt   5760
gccacctgga ttctgcgcgg gacgtccttc tgctacgtcc cttcggccct caatccagcg   5820
gaccttcctt cccgcggcct gctgccggct ctgcggcctc ttccgcgtct tcgccttcgc   5880
cctcagacga gtcggatctc cctttgggcc gcctccccgc atcgataccg tcgactagcc   5940
gtacctttaa gaccaatgac ttacaaggca gctgtagatc ttagccactt tttaaaagaa   6000
aaggggggac tggaagggct aattcactcc caaagaagac aagatctgct tttgcctgt   6060
actgggtctc tctggttaga ccagatctga gcctgggagc tctctggcta actagggaac   6120
ccactgctta agcctcaata aagcttgcct tgagtgcttc aagtagtgtg tgcccgtctg   6180
ttgtgtgact ctggtaacta gagatccctc agaccctttt agtcagtgtg gaaaatctct   6240
agcagaattc gatatcaagc ttatcgatac cgtcgacctc gagggggggc ccggtaccca   6300
attcgcccta tagtgagtcg tattacaatt cactggccgt cgttttacaa cgtcgtgact   6360
gggaaaaccc tggcgttacc caacttaatc gccttgcagc acatccccct ttcgccagct   6420
ggcgtaatag cgaagaggcc cgcaccgatc gcccttccca acagttgcgc agcctgaatg   6480
gcgaatggaa attgtaagcg ttaatatttt gttaaaattc gcgttaaatt tttgttaaat   6540
cagctcattt tttaaccaat aggccgaaat cggcaaaatc ccttataaat caaaagaata   6600
gaccgagata gggttgagtg ttgttccagt ttggaacaag agtccactat taaagaacgt   6660
ggactccaac gtcaaagggc gaaaaaccgt ctatcagggc gatggcccac tacgtgaacc   6720
atcaccctaa tcaagttttt tggggtcgag gtgccgtaaa gcactaaatc ggaaccctaa   6780
agggagcccc cgatttagag cttgacgggg aaagccggcg aacgtggcga gaaaggaagg   6840
gaagaaagcg aaaggagcgg gcgctagggc gctggcaagt gtagcggtca cgctgcgcgt   6900
aaccaccaca cccgccgcgc ttaatgcgcc gctacagggc gcgtcaggtg gcacttttcg   6960
gggaaatgtg cgcggaaccc ctatttgttt atttttctaa atacattcaa atatgtatcc   7020
gctcatgaga caataaccct gataaatgct tcaataatat tgaaaaagga agagtatgag   7080
tattcaacat ttccgtgtcg cccttattcc cttttttgcg gcattttgcc ttcctgtttt   7140
tgctcaccca gaaacgctgg tgaaagtaaa agatgctgaa gatcagttgg gtgcacgagt   7200
gggttacatc gaactggatc tcaacagcgg taagatcctt gagagttttc gccccgaaga   7260
acgttttcca atgatgagca cttttaaagt tctgctatgt ggcgcggtat tatcccgtat   7320
tgacgccggg caagagcaac tcggtcgccg catacactat tctcagaatg acttggttga   7380
gtactcacca gtcacagaaa agcatcttac ggatggcatg acagtaagag aattatgcag   7440
tgctgccata accatgagtg ataacactgc ggccaactta cttctgacaa cgatcggagg   7500
accgaaggag ctaaccgctt ttttgcacaa catgggggat catgtaactc gccttgatcg   7560
ttgggaaccg gagctgaatg aagccatacc aaacgacgag cgtgacacca cgatgcctgt   7620
agcaatggca acaacgttgc gcaaactatt aactggcgaa ctacttactc tagcttcccg   7680
gcaacaatta atagactgga tggaggcgga taaagttgca ggaccacttc tgcgctcggc   7740
ccttccggct ggctggttta ttgctgataa atctggagcc ggtgagcgtg ggtctcgcgg   7800
tatcattgca gcactggggc cagatggtaa gccctcccgt atcgtagtta tctacacgac   7860
```

```
ggggagtcag gcaactatgg atgaacgaaa tagacagatc gctgagatag gtgcctcact   7920
gattaagcat tggtaactgt cagaccaagt ttactcatat atactttaga ttgatttaaa   7980
acttcatttt taatttaaaa ggatctaggt gaagatcctt tttgataatc tcatgaccaa   8040
aatcccttaa cgtgagtttt cgttccactg agcgtcagac cccgtagaaa agatcaaagg   8100
atcttcttga gatccttttt ttctgcgcgt aatctgctgc ttgcaaacaa aaaaaccacc   8160
gctaccagcg gtggtttgtt tgccggatca agagctacca actctttttc cgaaggtaac   8220
tggcttcagc agagcgcaga taccaaatac tgttcttcta gtgtagccgt agttaggcca   8280
ccacttcaag aactctgtag caccgcctac atacctcgct ctgctaatcc tgttaccagt   8340
ggctgctgcc agtggcgata agtcgtgtct taccgggttg gactcaagac gatagttacc   8400
ggataaggcg cagcggtcgg gctgaacggg gggttcgtgc acacagccca gcttggagcg   8460
aacgacctac accgaactga gatacctaca gcgtgagcta tgagaaagcg ccacgcttcc   8520
cgaagggaga aaggcggaca ggtatccggt aagcggcagg gtcggaacag gagagcgcac   8580
gagggagctt ccagggggaa acgcctggta tctttatagt cctgtcgggt ttcgccacct   8640
ctgacttgag cgtcgatttt tgtgatgctc gtcagggggg cggagcctat ggaaaaacgc   8700
cagcaacgcg gcctttttac ggttcctggc cttttgctgg ccttttgctc acatgttctt   8760
tcctgcgtta tcccctgatt ctgtggataa ccgtattacc gcctttgagt gagctgatac   8820
cgctcgccgc agccgaacga ccgagcgcag cgagtcagtg agcgaggaag cggaagagcg   8880
cccaatacgc aaaccgcctc tccccgcgcg ttggccgatt cattaatgca gctggcacga   8940
caggtttccc gactggaaag cgggcagtga gcgcaacgca attaatgtga gttagctcac   9000
tcattaggca ccccaggctt tacactttat gcttccggct cgtatgttgt gtggaattgt   9060
gagcggataa caatttcaca caggaaacag ctatgaccat gattacgcca agctcgaaat   9120
taaccctcac taaagggaac aaaagctgga gctccaccgc ggtggcggcc tcgaggtcga   9180
gatccggtcg accagcaacc atagtcccgc ccctaactcc gcccatcccg cccctaactc   9240
cgcccagttc cgcccattct ccgccccatg gctgactaat tttttttatt tatgcagagg   9300
ccgaggccgc ctcggcctct gagctattcc agaagtagtg aggaggcttt tttggaggcc   9360
taggcttttg caaaaagctt cgacggtatc gattggctca tgtccaacat taccgccatg   9420
ttgacattga ttattgacta gttattaata gtaatcaatt acggggtcat tagttcatag   9480
cccatatatg gagttccgcg ttacataact tacggtaaat ggcccgcctg gctgaccgcc   9540
caacgacccc cgcccattga cgtcaataat gacgtatgtt cccatagtaa cgccaatagg   9600
gactttccat tgacgtcaat gggtggagta tttacggtaa actgcccact tggcagtaca   9660
tcaagtgtat catatgccaa gtacgccccc tattgacgtc aatgacggta aatggcccgc   9720
ctggcattat gcccagtaca tgaccttatg ggactttcct acttggcagt acatctacgt   9780
attagtcatc gctattacca tggtgatgcg gttttggcag tacatcaatg ggcgtggata   9840
gcggtttgac tcacggggat ttccaagtct ccaccccatt gacgtcaatg ggagtttgtt   9900
ttggcaccaa aatcaacggg actttccaaa atgtcgtaac aactccgccc cattgacgca   9960
aatgggcggt aggcgtgtac ggaattcgga gtggcgagcc ctcagatcct gcatataagc  10020
agctgctttt tgcctgtact gggtctctct g                                 10051
```

<210> SEQ ID NO 38
<211> LENGTH: 1062
<212> TYPE: PRT

```
<213> ORGANISM: Artificial Sequence
<220> FEATURE:
<223> OTHER INFORMATION: Synthetic sequence

<400> SEQUENCE: 38

Met Leu Leu Leu Val Thr Ser Leu Leu Leu Cys Glu Leu Pro His Pro
1               5                   10                  15

Ala Phe Leu Leu Ile Pro Gln Glu Gln Leu Val Glu Ser Gly Gly Arg
            20                  25                  30

Leu Val Thr Pro Gly Gly Ser Leu Thr Leu Ser Cys Lys Ala Ser Gly
        35                  40                  45

Phe Asp Phe Ser Ala Tyr Tyr Met Ser Trp Val Arg Gln Ala Pro Gly
    50                  55                  60

Lys Gly Leu Glu Trp Ile Ala Thr Ile Tyr Pro Ser Ser Gly Lys Thr
65                  70                  75                  80

Tyr Tyr Ala Thr Trp Val Asn Gly Arg Phe Thr Ile Ser Ser Asp Asn
                85                  90                  95

Ala Gln Asn Thr Val Asp Leu Gln Met Asn Ser Leu Thr Ala Ala Asp
            100                 105                 110

Arg Ala Thr Tyr Phe Cys Ala Arg Asp Ser Tyr Ala Asp Asp Gly Ala
        115                 120                 125

Leu Phe Asn Ile Trp Gly Pro Gly Thr Leu Val Thr Ile Ser Ser Gly
    130                 135                 140

Gly Gly Gly Ser Gly Gly Gly Gly Ser Gly Gly Gly Gly Ser Glu Leu
145                 150                 155                 160

Val Leu Thr Gln Ser Pro Ser Val Ser Ala Ala Leu Gly Ser Pro Ala
                165                 170                 175

Lys Ile Thr Cys Thr Leu Ser Ser Ala His Lys Thr Asp Thr Ile Asp
            180                 185                 190

Trp Tyr Gln Gln Leu Gln Gly Glu Ala Pro Arg Tyr Leu Met Gln Val
        195                 200                 205

Gln Ser Asp Gly Ser Tyr Thr Lys Arg Pro Gly Val Pro Asp Arg Phe
    210                 215                 220

Ser Gly Ser Ser Ser Gly Ala Asp Arg Tyr Leu Ile Ile Pro Ser Val
225                 230                 235                 240

Gln Ala Asp Asp Glu Ala Asp Tyr Tyr Cys Gly Ala Asp Tyr Ile Gly
                245                 250                 255

Gly Tyr Val Phe Gly Gly Gly Thr Gln Leu Thr Val Thr Gly Glu Ser
            260                 265                 270

Lys Tyr Gly Pro Pro Cys Pro Pro Cys Pro Ala Pro Glu Phe Leu Gly
        275                 280                 285

Gly Pro Ser Val Phe Leu Phe Pro Pro Lys Pro Lys Asp Thr Leu Met
    290                 295                 300

Ile Ser Arg Thr Pro Glu Val Thr Cys Val Val Val Asp Val Ser Gln
305                 310                 315                 320

Glu Asp Pro Glu Val Gln Phe Asn Trp Tyr Val Asp Gly Val Glu Val
                325                 330                 335

His Asn Ala Lys Thr Lys Pro Arg Glu Glu Gln Phe Asn Ser Thr Tyr
            340                 345                 350

Arg Val Val Ser Val Leu Thr Val Leu His Gln Asp Trp Leu Asn Gly
        355                 360                 365

Lys Glu Tyr Lys Cys Lys Val Ser Asn Lys Gly Leu Pro Ser Ser Ile
    370                 375                 380

Glu Lys Thr Ile Ser Lys Ala Lys Gly Gln Pro Arg Glu Pro Gln Val
```

```
385                 390                 395                 400

Tyr Thr Leu Pro Pro Ser Gln Glu Glu Met Thr Lys Asn Gln Val Ser
                405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
        435                 440                 445

Val Leu Asp Ser Asp Gly Ser Phe Phe Leu Tyr Ser Arg Leu Thr Val
    450                 455                 460

Asp Lys Ser Arg Trp Gln Glu Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Leu Gly Lys Met Phe Trp Val Leu Val Val Val Gly Gly Val Leu Ala
            500                 505                 510

Cys Tyr Ser Leu Leu Val Thr Val Ala Phe Ile Ile Phe Trp Val Lys
        515                 520                 525

Arg Gly Arg Lys Lys Leu Leu Tyr Ile Phe Lys Gln Pro Phe Met Arg
    530                 535                 540

Pro Val Gln Thr Thr Gln Glu Glu Asp Gly Cys Ser Cys Arg Phe Pro
545                 550                 555                 560

Glu Glu Glu Glu Gly Gly Cys Glu Leu Arg Val Lys Phe Ser Arg Ser
                565                 570                 575

Ala Asp Ala Pro Ala Tyr Gln Gln Gly Gln Asn Gln Leu Tyr Asn Glu
            580                 585                 590

Leu Asn Leu Gly Arg Arg Glu Glu Tyr Asp Val Leu Asp Lys Arg Arg
        595                 600                 605

Gly Arg Asp Pro Glu Met Gly Gly Lys Pro Arg Arg Lys Asn Pro Gln
    610                 615                 620

Glu Gly Leu Tyr Asn Glu Leu Gln Lys Asp Lys Met Ala Glu Ala Tyr
625                 630                 635                 640

Ser Glu Ile Gly Met Lys Gly Glu Arg Arg Arg Gly Lys Gly His Asp
                645                 650                 655

Gly Leu Tyr Gln Gly Leu Ser Thr Ala Thr Lys Asp Thr Tyr Asp Ala
            660                 665                 670

Leu His Met Gln Ala Leu Pro Pro Arg Leu Glu Gly Gly Gly Glu Gly
        675                 680                 685

Arg Gly Ser Leu Leu Thr Cys Gly Asp Val Glu Glu Asn Pro Gly Pro
    690                 695                 700

Arg Met Leu Leu Leu Val Thr Ser Leu Leu Leu Cys Glu Leu Pro His
705                 710                 715                 720

Pro Ala Phe Leu Leu Ile Pro Arg Lys Val Cys Asn Gly Ile Gly Ile
                725                 730                 735

Gly Glu Phe Lys Asp Ser Leu Ser Ile Asn Ala Thr Asn Ile Lys His
            740                 745                 750

Phe Lys Asn Cys Thr Ser Ile Ser Gly Asp Leu His Ile Leu Pro Val
        755                 760                 765

Ala Phe Arg Gly Asp Ser Phe Thr His Thr Pro Pro Leu Asp Pro Gln
    770                 775                 780

Glu Leu Asp Ile Leu Lys Thr Val Lys Glu Ile Thr Gly Phe Leu Leu
785                 790                 795                 800

Ile Gln Ala Trp Pro Glu Asn Arg Thr Asp Leu His Ala Phe Glu Asn
                805                 810                 815
```

```
Leu Glu Ile Ile Arg Gly Arg Thr Lys Gln His Gly Gln Phe Ser Leu
            820                 825                 830

Ala Val Val Ser Leu Asn Ile Thr Ser Leu Gly Leu Arg Ser Leu Lys
        835                 840                 845

Glu Ile Ser Asp Gly Asp Val Ile Ile Ser Gly Asn Lys Asn Leu Cys
    850                 855                 860

Tyr Ala Asn Thr Ile Asn Trp Lys Lys Leu Phe Gly Thr Ser Gly Gln
865                 870                 875                 880

Lys Thr Lys Ile Ile Ser Asn Arg Gly Glu Asn Ser Cys Lys Ala Thr
                885                 890                 895

Gly Gln Val Cys His Ala Leu Cys Ser Pro Glu Gly Cys Trp Gly Pro
            900                 905                 910

Glu Pro Arg Asp Cys Val Ser Cys Arg Asn Val Ser Arg Gly Arg Glu
        915                 920                 925

Cys Val Asp Lys Cys Asn Leu Leu Glu Gly Glu Pro Arg Glu Phe Val
    930                 935                 940

Glu Asn Ser Glu Cys Ile Gln Cys His Pro Glu Cys Leu Pro Gln Ala
945                 950                 955                 960

Met Asn Ile Thr Cys Thr Gly Arg Gly Pro Asp Asn Cys Ile Gln Cys
                965                 970                 975

Ala His Tyr Ile Asp Gly Pro His Cys Val Lys Thr Cys Pro Ala Gly
            980                 985                 990

Val Met Gly Glu Asn Asn Thr Leu Val Trp Lys Tyr Ala Asp Ala Gly
        995                 1000                1005

His Val Cys His Leu Cys His Pro Asn Cys Thr Tyr Gly Cys Thr Gly
    1010                1015                1020

Pro Gly Leu Glu Gly Cys Pro Thr Asn Gly Pro Lys Ile Pro Ser Ile
1025                1030                1035                1040

Ala Thr Gly Met Val Gly Ala Leu Leu Leu Leu Leu Val Val Ala Leu
                1045                1050                1055

Gly Ile Gly Leu Phe Met
            1060
```

<210> SEQ ID NO 39
<211> LENGTH: 9721
<212> TYPE: DNA
<213> ORGANISM: Artificial Sequence
<220> FEATURE:
<223> OTHER INFORMATION: Synthetic sequence

<400> SEQUENCE: 39

```
gttagaccag atctgagcct gggagctctc tggctaacta gggaacccac tgcttaagcc      60

tcaataaagc ttgccttgag tgcttcaagt agtgtgtgcc cgtctgttgt gtgactctgg     120

taactagaga tccctcagac ccttttagtc agtgtggaaa atctctagca gtggcgcccg     180

aacagggact tgaaagcgaa agggaaacca gaggagctct ctcgacgcag gactcggctt     240

gctgaagcgc gcacggcaag aggcgagggg cggcgactgg tgagtacgcc aaaaattttg     300

actagcggag gctagaagga gagagatggg tgcgagagcg tcagtattaa gcgggggaga     360

attagatcga tgggaaaaaa ttcggttaag gccaggggga aagaaaaaat ataaattaaa     420

acatatagta tgggcaagca gggagctaga acgattcgca gttaatcctg gcctgttaga     480

aacatcagaa ggctgtagac aaatactggg acagctacaa ccatcccttc agacaggatc     540

agaagaactt agatcattat ataatacagt agcaaccctc tattgtgtgc atcaaaggat     600
```

```
agagataaaa gacaccaagg aagctttaga caagatagag gaagagcaaa acaaaagtaa    660
gaaaaaagca cagcaagcag cagctgacac aggacacagc aatcaggtca gccaaaatta    720
ccctatagtg cagaacatcc aggggcaaat ggtacatcag gccatatcac ctagaacttt    780
aaatgcatgg gtaaaagtag tagaagagaa ggctttcagc ccagaagtga tacccatgtt    840
ttcagcatta tcagaaggag ccaccccaca agatttaaac accatgctaa acacagtggg    900
gggacatcaa gcagccatgc aaatgttaaa agagaccatc aatgaggaag ctgcaggcaa    960
agagaagagt ggtgcagaga gaaaaaagag cagtgggaat aggagctttg ttccttgggt   1020
tcttgggagc agcaggaagc actatgggcg cagcgtcaat gacgctgacg gtacaggcca   1080
gacaattatt gtctggtata gtgcagcagc agaacaattt gctgagggct attgaggcgc   1140
aacagcatct gttgcaactc acagtctggg gcatcaagca gctccaggca agaatcctgg   1200
ctgtggaaag atacctaaag gatcaacagc tcctggggat ttggggttgc tctggaaaac   1260
tcatttgcac cactgctgtg ccttggatct acaaatggca gtattcatcc acaattttaa   1320
aagaaaaggg gggattgggg ggtacagtgc aggggaaaga atagtagaca taatagcaac   1380
agacatacaa actaaagaat tacaaaaaca aattacaaaa attcaaaatt ttcgggttta   1440
ttacagggac agcagagatc cagtttgggg atcaattgca tgaagaatct gcttagggtt   1500
aggcgttttg cgctgcttcg cgaggatctg cgatcgctcc ggtgcccgtc agtgggcaga   1560
gcgcacatcg cccacagtcc ccgagaagtt ggggggaggg gtcggcaatt gaaccggtgc   1620
ctagagaagg tggcgcgggg taaactggga aagtgatgtc gtgtactggc tccgcctttt   1680
tcccgagggt gggggagaac cgtatataag tgcagtagtc gccgtgaacg ttcttttccg   1740
caacgggttt gccgccagaa cacagctgaa gcttcgaggg gctcgcatct ctccttcacg   1800
cgcccgccgc cctacctgag gccgccatcc acgccggttg agtcgcgttc tgccgcctcc   1860
cgcctgtggt gcctcctgaa ctgcgtccgc cgtctaggta agtttaaagc tcaggtcgag   1920
accgggcctt tgtccggcgc tcccttggag cctacctaga ctcagccggc tctccacgct   1980
ttgcctgacc ctgcttgctc aactctacgt ctttgtttcg ttttctgttc tgcgccgtta   2040
cagatccaag ctgtgaccgg cgcctacggc tagcgaattc ctcgaggcca ccatgctgct   2100
gctggtgaca agcctgctgc tgtgcgagct gccccacccc gcctttctgc tgatccccca   2160
ggaacagctc gtcgaaagcg gcggcagact ggtgacacct ggcggcagcc tgaccctgag   2220
ctgcaaggcc agcggcttcg acttcagcgc ctactacatg agctgggtcc gccaggcccc   2280
tggcaaggga ctggaatgga tcgccaccat ctaccccagc agcggcaaga cctactacgc   2340
cacctgggtg aacggacggt tcaccatctc cagcgacaac gcccagaaca ccgtggacct   2400
gcagatgaac agcctgacag ccgccgaccg ggccacctac ttttgcgcca gagacagcta   2460
cgccgacgac ggcgccctgt tcaacatctg gggccctggc accctggtga caatctctag   2520
cggcggaggc ggatctggtg gcggaggaag tggcggcgga ggatctgagc tggtgctgac   2580
ccagagcccc tctgtgtctg ctgccctggg aagccctgcc aagatcacct gtaccctgag   2640
cagcgcccac aagaccgaca ccatcgactg gtatcagcag ctgcagggcg aggcccccag   2700
atacctgatg caggtgcaga gcgacggcag ctacaccaag aggccaggcg tgcccgaccg   2760
gttcagcgga tctagctctg gcgccgaccg ctacctgatc atccccagcg tgcaggccga   2820
tgacgaggcc gattactact gtggcgccga ctacatcggc ggctacgtgt tcggcggagg   2880
cacccagctg accgtgaccg gcgagtctaa gtacggaccg ccctgccccc cttgccctgg   2940
ccagcctcgc gagccccagg tgtacaccct gcctccctcc caggaagaga tgaccaagaa   3000
```

```
ccaggtgtcc ctgacctgcc tggtgaaggg cttctacccc agcgacatcg ccgtggagtg   3060
ggagagcaac ggccagcctg agaacaacta caagaccacc cctcccgtgc tggacagcga   3120
cggcagcttc ttcctgtaca gccggctgac cgtggacaag agccggtggc aggaaggcaa   3180
cgtctttagc tgcagcgtga tgcacgaggc cctgcacaac cactacaccc agaagagcct   3240
gagcctgtcc ctgggcaaga tgttctgggt gctggtggtg gtgggcgggg tgctggcctg   3300
ctacagcctg ctggtgacag tggccttcat catcttttgg gtgaaacggg gcagaaagaa   3360
actcctgtat atattcaaac aaccatttat gagaccagta caaactactc aagaggaaga   3420
tggctgtagc tgccgatttc cagaagaaga agaaggagga tgtgaactgc gggtgaagtt   3480
cagcagaagc gccgacgccc ctgcctacca gcagggccag aatcagctgt acaacgagct   3540
gaacctgggc agaagggaag agtacgacgt cctggataag cggagaggcc gggaccctga   3600
gatgggcggc aagcctcggc ggaagaaccc ccaggaaggc ctgtataacg aactgcagaa   3660
agacaagatg gccgaggcct acagcgagat cggcatgaag ggcgagcgga ggcggggcaa   3720
gggccacgac ggcctgtatc agggcctgtc caccgccacc aaggatacct acgacgccct   3780
gcacatgcag gccctgcccc caaggctcga gggcggcgga gagggcagag gaagtcttct   3840
aacatgcggt gacgtggagg agaatcccgg ccctaggatg cttctcctgg tgacaagcct   3900
tctgctctgt gagttaccac acccagcatt cctcctgatc ccacgcaaag tgtgtaacgg   3960
aataggtatt ggtgaattta aagactcact ctccataaat gctacgaata ttaaacactt   4020
caaaaactgc acctccatca gtggcgatct ccacatcctg ccggtggcat ttaggggtga   4080
ctccttcaca catactcctc ctctggatcc acaggaactg gatattctga aaaccgtaaa   4140
ggaaatcaca gggtttttgc tgattcaggc ttggcctgaa aacaggacgg acctccatgc   4200
ctttgagaac ctagaaatca tacgcggcag gaccaagcaa catggtcagt tttctcttgc   4260
agtcgtcagc ctgaacataa catccttggg attacgctcc ctcaaggaga taagtgatgg   4320
agatgtgata atttcaggaa acaaaaattt gtgctatgca aatacaataa actggaaaaa   4380
actgtttggg acctccggtc agaaaaccaa aattataagc aacagaggtg aaaacagctg   4440
caaggccaca ggccaggtct gccatgcctt gtgctccccc gagggctgct ggggcccgga   4500
gcccagggac tgcgtctctt gccggaatgt cagccgaggc agggaatgcg tggacaagtg   4560
caaccttctg gagggtgagc caagggagtt tgtggagaac tctgagtgca tacagtgcca   4620
cccagagtgc ctgcctcagg ccatgaacat cacctgcaca ggacggggac cagacaactg   4680
tatccagtgt gcccactaca ttgacggccc ccactgcgtc aagacctgcc cggcaggagt   4740
catgggagaa aacaacaccc tggtctggaa gtacgcagac gccggccatg tgtgccacct   4800
gtgccatcca aactgcacct acggatgcac tgggccaggt cttgaaggct gtccaacgaa   4860
tgggcctaag atcccgtcca tcgccactgg gatggtgggg gccctcctct tgctgctggt   4920
ggtggccctg gggatcggcc tcttcatgtg agcggccgct ctagacccgg gctgcaggaa   4980
ttcgatatca agcttatcga taatcaacct ctggattaca aaatttgtga aagattgact   5040
ggtattctta actatgttgc tccttttacg ctatgtggat acgctgcttt aatgcctttg   5100
tatcatgcta ttgcttcccg tatggctttc attttctcct ccttgtataa atcctggttg   5160
ctgtctcttt atgaggagtt gtggcccgtt gtcaggcaac gtggcgtggt gtgcactgtg   5220
tttgctgacg caacccccac tggttggggc attgccacca cctgtcagct cctttccggg   5280
actttcgctt tccccctccc tattgccacg gcggaactca tcgccgcctg ccttgcccgc   5340
```

```
tgctggacag gggctcggct gttgggcact gacaattccg tggtgttgtc ggggaaatca   5400
tcgtcctttc cttggctgct cgcctgtgtt gccacctgga ttctgcgcgg gacgtccttc   5460
tgctacgtcc cttcggccct caatccagcg gaccttcctt cccgcggcct gctgccggct   5520
ctgcggcctc ttccgcgtct tcgccttcgc cctcagacga gtcggatctc cctttgggcc   5580
gcctccccgc atcgataccg tcgactagcc gtacctttaa gaccaatgac ttacaaggca   5640
gctgtagatc ttagccactt tttaaaagaa aaggggggac tggaagggct aattcactcc   5700
caaagaagac aagatctgct ttttgcctgt actgggtctc tctggttaga ccagatctga   5760
gcctgggagc tctctggcta actagggaac ccactgctta agcctcaata aagcttgcct   5820
tgagtgcttc aagtagtgtg tgcccgtctg ttgtgtgact ctggtaacta gagatccctc   5880
agaccctttt agtcagtgtg gaaaatctct agcagaattc gatatcaagc ttatcgatac   5940
cgtcgacctc gagggggggc ccggtaccca attcgcccta tagtgagtcg tattacaatt   6000
cactggccgt cgttttacaa cgtcgtgact gggaaaaccc tggcgttacc caacttaatc   6060
gccttgcagc acatccccct ttcgccagct ggcgtaatag cgaagaggcc cgcaccgatc   6120
gcccttccca acagttgcgc agcctgaatg gcgaatggaa attgtaagcg ttaatatttt   6180
gttaaaattc gcgttaaatt tttgttaaat cagctcattt tttaaccaat aggccgaaat   6240
cggcaaaatc ccttataaat caaaagaata gaccgagata gggttgagtg ttgttccagt   6300
ttggaacaag agtccactat taaagaacgt ggactccaac gtcaaagggc gaaaaaccgt   6360
ctatcagggc gatggcccac tacgtgaacc atcaccctaa tcaagttttt tggggtcgag   6420
gtgccgtaaa gcactaaatc ggaaccctaa agggagcccc cgatttagag cttgacgggg   6480
aaagccggcg aacgtggcga gaaaggaagg gaagaaagcg aaaggagcgg gcgctagggc   6540
gctggcaagt gtagcggtca cgctgcgcgt aaccaccaca cccgccgcgc ttaatgcgcc   6600
gctacagggc gcgtcaggtg gcacttttcg gggaaatgtg cgcggaaccc ctatttgttt   6660
atttttctaa atacattcaa atatgtatcc gctcatgaga caataaccct gataaatgct   6720
tcaataatat tgaaaaagga agagtatgag tattcaacat ttccgtgtcg cccttattcc   6780
cttttttgcg gcattttgcc ttcctgtttt tgctcaccca gaaacgctgg tgaaagtaaa   6840
agatgctgaa gatcagttgg gtgcacgagt gggttacatc gaactggatc tcaacagcgg   6900
taagatcctt gagagttttc gccccgaaga acgttttcca atgatgagca cttttaaagt   6960
tctgctatgt ggcgcggtat tatcccgtat tgacgccggg caagagcaac tcggtcgccg   7020
catacactat tctcagaatg acttggttga gtactcacca gtcacagaaa agcatcttac   7080
ggatggcatg acagtaagag aattatgcag tgctgccata accatgagtg ataacactgc   7140
ggccaactta cttctgacaa cgatcggagg accgaaggag ctaaccgctt ttttgcacaa   7200
catgggggat catgtaactc gccttgatcg ttgggaaccg gagctgaatg aagccatacc   7260
aaacgacgag cgtgacacca cgatgcctgt agcaatggca acaacgttgc gcaaactatt   7320
aactggcgaa ctacttactc tagcttcccg gcaacaatta atagactgga tggaggcgga   7380
taaagttgca ggaccacttc tgcgctcggc ccttccggct ggctggttta ttgctgataa   7440
atctggagcc ggtgagcgtg ggtctcgcgg tatcattgca gcactggggc cagatggtaa   7500
gccctcccgt atcgtagtta tctacacgac ggggagtcag gcaactatgg atgaacgaaa   7560
tagacagatc gctgagatag gtgcctcact gattaagcat tggtaactgt cagaccaagt   7620
ttactcatat atactttaga ttgatttaaa acttcatttt taatttaaaa ggatctaggt   7680
gaagatcctt tttgataatc tcatgaccaa aatcccttaa cgtgagtttt cgttccactg   7740
```

```
agcgtcagac cccgtagaaa agatcaaagg atcttcttga gatccttttt ttctgcgcgt   7800

aatctgctgc ttgcaaacaa aaaaaccacc gctaccagcg gtggtttgtt tgccggatca   7860

agagctacca actctttttc cgaaggtaac tggcttcagc agagcgcaga taccaaatac   7920

tgttcttcta gtgtagccgt agttaggcca ccacttcaag aactctgtag caccgcctac   7980

atacctcgct ctgctaatcc tgttaccagt ggctgctgcc agtggcgata agtcgtgtct   8040

taccgggttg gactcaagac gatagttacc ggataaggcg cagcggtcgg gctgaacggg   8100

gggttcgtgc acacagccca gcttggagcg aacgacctac accgaactga gatacctaca   8160

gcgtgagcta tgagaaagcg ccacgcttcc cgaagggaga aaggcggaca ggtatccggt   8220

aagcggcagg gtcggaacag gagagcgcac gagggagctt ccagggggaa acgcctggta   8280

tctttatagt cctgtcgggt ttcgccacct ctgacttgag cgtcgatttt tgtgatgctc   8340

gtcagggggg cggagcctat ggaaaaacgc cagcaacgcg gcctttttac ggttcctggc   8400

cttttgctgg ccttttgctc acatgttctt tcctgcgtta tcccctgatt ctgtggataa   8460

ccgtattacc gcctttgagt gagctgatac cgctcgccgc agccgaacga ccgagcgcag   8520

cgagtcagtg agcgaggaag cggaagagcg cccaatacgc aaaccgcctc tccccgcgcg   8580

ttggccgatt cattaatgca gctggcacga caggtttccc gactggaaag cgggcagtga   8640

gcgcaacgca attaatgtga gttagctcac tcattaggca ccccaggctt tacactttat   8700

gcttccggct cgtatgttgt gtggaattgt gagcggataa caatttcaca caggaaacag   8760

ctatgaccat gattacgcca agctcgaaat taaccctcac taaagggaac aaaagctgga   8820

gctccaccgc ggtggcggcc tcgaggtcga gatccggtcg accagcaacc atagtcccgc   8880

ccctaactcc gcccatcccg cccctaactc cgcccagttc cgcccattct ccgccccatg   8940

gctgactaat tttttttatt tatgcagagg ccgaggccgc ctcggcctct gagctattcc   9000

agaagtagtg aggaggcttt tttggaggcc taggcttttg caaaaagctt cgacggtatc   9060

gattggctca tgtccaacat taccgccatg ttgacattga ttattgacta gttattaata   9120

gtaatcaatt acggggtcat tagttcatag cccatatatg gagttccgcg ttacataact   9180

tacggtaaat ggcccgcctg gctgaccgcc caacgacccc cgcccattga cgtcaataat   9240

gacgtatgtt cccatagtaa cgccaatagg gactttccat tgacgtcaat gggtggagta   9300

tttacggtaa actgcccact tggcagtaca tcaagtgtat catatgccaa gtacgccccc   9360

tattgacgtc aatgacggta aatggcccgc ctggcattat gcccagtaca tgaccttatg   9420

ggactttcct acttggcagt acatctacgt attagtcatc gctattacca tggtgatgcg   9480

gttttggcag tacatcaatg ggcgtggata gcggtttgac tcacggggat ttccaagtct   9540

ccaccccatt gacgtcaatg ggagtttgtt ttggcaccaa aatcaacggg actttccaaa   9600

atgtcgtaac aactccgccc cattgacgca aatgggcggt aggcgtgtac ggaattcgga   9660

gtggcgagcc ctcagatcct gcatataagc agctgctttt tgcctgtact gggtctctct   9720

g                                                                   9721
```

<210> SEQ ID NO 40
<211> LENGTH: 952
<212> TYPE: PRT
<213> ORGANISM: Artificial Sequence
<220> FEATURE:
<223> OTHER INFORMATION: Synthetic sequence

<400> SEQUENCE: 40

```
Met Leu Leu Leu Val Thr Ser Leu Leu Leu Cys Glu Leu Pro His Pro
1               5                   10                  15

Ala Phe Leu Leu Ile Pro Gln Glu Gln Leu Val Glu Ser Gly Gly Arg
            20                  25                  30

Leu Val Thr Pro Gly Gly Ser Leu Thr Leu Ser Cys Lys Ala Ser Gly
        35                  40                  45

Phe Asp Phe Ser Ala Tyr Tyr Met Ser Trp Val Arg Gln Ala Pro Gly
    50                  55                  60

Lys Gly Leu Glu Trp Ile Ala Thr Ile Tyr Pro Ser Ser Gly Lys Thr
65                  70                  75                  80

Tyr Tyr Ala Thr Trp Val Asn Gly Arg Phe Thr Ile Ser Ser Asp Asn
                85                  90                  95

Ala Gln Asn Thr Val Asp Leu Gln Met Asn Ser Leu Thr Ala Ala Asp
            100                 105                 110

Arg Ala Thr Tyr Phe Cys Ala Arg Asp Ser Tyr Ala Asp Asp Gly Ala
        115                 120                 125

Leu Phe Asn Ile Trp Gly Pro Gly Thr Leu Val Thr Ile Ser Ser Gly
    130                 135                 140

Gly Gly Gly Ser Gly Gly Gly Gly Ser Gly Gly Gly Gly Ser Glu Leu
145                 150                 155                 160

Val Leu Thr Gln Ser Pro Ser Val Ser Ala Ala Leu Gly Ser Pro Ala
                165                 170                 175

Lys Ile Thr Cys Thr Leu Ser Ser Ala His Lys Thr Asp Thr Ile Asp
            180                 185                 190

Trp Tyr Gln Gln Leu Gln Gly Glu Ala Pro Arg Tyr Leu Met Gln Val
        195                 200                 205

Gln Ser Asp Gly Ser Tyr Thr Lys Arg Pro Gly Val Pro Asp Arg Phe
    210                 215                 220

Ser Gly Ser Ser Ser Gly Ala Asp Arg Tyr Leu Ile Ile Pro Ser Val
225                 230                 235                 240

Gln Ala Asp Asp Glu Ala Asp Tyr Tyr Cys Gly Ala Asp Tyr Ile Gly
                245                 250                 255

Gly Tyr Val Phe Gly Gly Gly Thr Gln Leu Thr Val Thr Gly Glu Ser
            260                 265                 270

Lys Tyr Gly Pro Pro Cys Pro Pro Cys Pro Gly Gln Pro Arg Glu Pro
        275                 280                 285

Gln Val Tyr Thr Leu Pro Pro Ser Gln Glu Glu Met Thr Lys Asn Gln
    290                 295                 300

Val Ser Leu Thr Cys Leu Val Lys Gly Phe Tyr Pro Ser Asp Ile Ala
305                 310                 315                 320

Val Glu Trp Glu Ser Asn Gly Gln Pro Glu Asn Asn Tyr Lys Thr Thr
                325                 330                 335

Pro Pro Val Leu Asp Ser Asp Gly Ser Phe Phe Leu Tyr Ser Arg Leu
            340                 345                 350

Thr Val Asp Lys Ser Arg Trp Gln Glu Gly Asn Val Phe Ser Cys Ser
        355                 360                 365

Val Met His Glu Ala Leu His Asn His Tyr Thr Gln Lys Ser Leu Ser
    370                 375                 380

Leu Ser Leu Gly Lys Met Phe Trp Val Leu Val Val Val Gly Gly Val
385                 390                 395                 400

Leu Ala Cys Tyr Ser Leu Leu Val Thr Val Ala Phe Ile Ile Phe Trp
                405                 410                 415

Val Lys Arg Gly Arg Lys Lys Leu Leu Tyr Ile Phe Lys Gln Pro Phe
```

```
            420                 425                 430

Met Arg Pro Val Gln Thr Thr Gln Glu Glu Asp Gly Cys Ser Cys Arg
        435                 440                 445

Phe Pro Glu Glu Glu Glu Gly Gly Cys Glu Leu Arg Val Lys Phe Ser
    450                 455                 460

Arg Ser Ala Asp Ala Pro Ala Tyr Gln Gln Gly Gln Asn Gln Leu Tyr
465                 470                 475                 480

Asn Glu Leu Asn Leu Gly Arg Arg Glu Glu Tyr Asp Val Leu Asp Lys
                485                 490                 495

Arg Arg Gly Arg Asp Pro Glu Met Gly Gly Lys Pro Arg Arg Lys Asn
            500                 505                 510

Pro Gln Glu Gly Leu Tyr Asn Glu Leu Gln Lys Asp Lys Met Ala Glu
        515                 520                 525

Ala Tyr Ser Glu Ile Gly Met Lys Gly Glu Arg Arg Arg Gly Lys Gly
    530                 535                 540

His Asp Gly Leu Tyr Gln Gly Leu Ser Thr Ala Thr Lys Asp Thr Tyr
545                 550                 555                 560

Asp Ala Leu His Met Gln Ala Leu Pro Pro Arg Leu Glu Gly Gly Gly
                565                 570                 575

Glu Gly Arg Gly Ser Leu Leu Thr Cys Gly Asp Val Glu Glu Asn Pro
            580                 585                 590

Gly Pro Arg Met Leu Leu Leu Val Thr Ser Leu Leu Leu Cys Glu Leu
        595                 600                 605

Pro His Pro Ala Phe Leu Leu Ile Pro Arg Lys Val Cys Asn Gly Ile
    610                 615                 620

Gly Ile Gly Glu Phe Lys Asp Ser Leu Ser Ile Asn Ala Thr Asn Ile
625                 630                 635                 640

Lys His Phe Lys Asn Cys Thr Ser Ile Ser Gly Asp Leu His Ile Leu
                645                 650                 655

Pro Val Ala Phe Arg Gly Asp Ser Phe Thr His Thr Pro Pro Leu Asp
            660                 665                 670

Pro Gln Glu Leu Asp Ile Leu Lys Thr Val Lys Glu Ile Thr Gly Phe
        675                 680                 685

Leu Leu Ile Gln Ala Trp Pro Glu Asn Arg Thr Asp Leu His Ala Phe
    690                 695                 700

Glu Asn Leu Glu Ile Ile Arg Gly Arg Thr Lys Gln His Gly Gln Phe
705                 710                 715                 720

Ser Leu Ala Val Val Ser Leu Asn Ile Thr Ser Leu Gly Leu Arg Ser
                725                 730                 735

Leu Lys Glu Ile Ser Asp Gly Asp Val Ile Ile Ser Gly Asn Lys Asn
            740                 745                 750

Leu Cys Tyr Ala Asn Thr Ile Asn Trp Lys Lys Leu Phe Gly Thr Ser
        755                 760                 765

Gly Gln Lys Thr Lys Ile Ile Ser Asn Arg Gly Glu Asn Ser Cys Lys
    770                 775                 780

Ala Thr Gly Gln Val Cys His Ala Leu Cys Ser Pro Glu Gly Cys Trp
785                 790                 795                 800

Gly Pro Glu Pro Arg Asp Cys Val Ser Cys Arg Asn Val Ser Arg Gly
                805                 810                 815

Arg Glu Cys Val Asp Lys Cys Asn Leu Leu Glu Gly Glu Pro Arg Glu
            820                 825                 830

Phe Val Glu Asn Ser Glu Cys Ile Gln Cys His Pro Glu Cys Leu Pro
        835                 840                 845
```

```
Gln Ala Met Asn Ile Thr Cys Thr Gly Arg Gly Pro Asp Asn Cys Ile
    850                 855                 860

Gln Cys Ala His Tyr Ile Asp Gly Pro His Cys Val Lys Thr Cys Pro
865                 870                 875                 880

Ala Gly Val Met Gly Glu Asn Asn Thr Leu Val Trp Lys Tyr Ala Asp
                885                 890                 895

Ala Gly His Val Cys His Leu Cys His Pro Asn Cys Thr Tyr Gly Cys
            900                 905                 910

Thr Gly Pro Gly Leu Glu Gly Cys Pro Thr Asn Gly Pro Lys Ile Pro
        915                 920                 925

Ser Ile Ala Thr Gly Met Val Gly Ala Leu Leu Leu Leu Leu Val Val
    930                 935                 940

Ala Leu Gly Ile Gly Leu Phe Met
945                 950


<210> SEQ ID NO 41
<211> LENGTH: 9400
<212> TYPE: DNA
<213> ORGANISM: Artificial Sequence
<220> FEATURE:
<223> OTHER INFORMATION: Synthetic sequence

<400> SEQUENCE: 41

gttagaccag atctgagcct gggagctctc tggctaacta gggaacccac tgcttaagcc      60

tcaataaagc ttgccttgag tgcttcaagt agtgtgtgcc cgtctgttgt gtgactctgg     120

taactagaga tccctcagac ccttttagtc agtgtggaaa atctctagca gtggcgcccg     180

aacagggact tgaaagcgaa agggaaacca gaggagctct ctcgacgcag gactcggctt     240

gctgaagcgc gcacggcaag aggcgagggg cggcgactgg tgagtacgcc aaaaattttg     300

actagcggag gctagaagga gagagatggg tgcgagagcg tcagtattaa gcgggggaga     360

attagatcga tgggaaaaaa ttcggttaag gccaggggga aagaaaaaat ataaattaaa     420

acatatagta tgggcaagca gggagctaga acgattcgca gttaatcctg gcctgttaga     480

aacatcagaa ggctgtagac aaatactggg acagctacaa ccatcccttc agacaggatc     540

agaagaactt agatcattat ataatacagt agcaaccctc tattgtgtgc atcaaaggat     600

agagataaaa gacaccaagg aagctttaga caagatagag gaagagcaaa acaaaagtaa     660

gaaaaaagca cagcaagcag cagctgacac aggacacagc aatcaggtca gccaaaatta     720

ccctatagtg cagaacatcc aggggcaaat ggtacatcag gccatatcac ctagaacttt     780

aaatgcatgg gtaaaagtag tagaagagaa ggctttcagc ccagaagtga tacccatgtt     840

ttcagcatta tcagaaggag ccaccccaca agatttaaac accatgctaa acacagtggg     900

gggacatcaa gcagccatgc aaatgttaaa agagaccatc aatgaggaag ctgcaggcaa     960

agagaagagt ggtgcagaga gaaaaaagag cagtgggaat aggagctttg ttccttgggt    1020

tcttgggagc agcaggaagc actatgggcg cagcgtcaat gacgctgacg gtacaggcca    1080

gacaattatt gtctggtata gtgcagcagc agaacaattt gctgagggct attgaggcgc    1140

aacagcatct gttgcaactc acagtctggg gcatcaagca gctccaggca agaatcctgg    1200

ctgtggaaag atacctaaag gatcaacagc tcctggggat ttggggttgc tctggaaaac    1260

tcatttgcac cactgctgtg ccttggatct acaaatggca gtattcatcc acaattttaa    1320

aagaaaaggg gggattgggg ggtacagtgc aggggaaaga atagtagaca taatagcaac    1380

agacatacaa actaaagaat tacaaaaaca aattacaaaa attcaaaatt ttcgggttta    1440
```

```
ttacagggac agcagagatc cagtttgggg atcaattgca tgaagaatct gcttagggtt   1500
aggcgttttg cgctgcttcg cgaggatctg cgatcgctcc ggtgcccgtc agtgggcaga   1560
gcgcacatcg cccacagtcc ccgagaagtt ggggggaggg gtcggcaatt gaaccggtgc   1620
ctagagaagg tggcgcgggg taaactggga aagtgatgtc gtgtactggc tccgcctttt   1680
tcccgagggt gggggagaac cgtatataag tgcagtagtc gccgtgaacg ttcttttcg    1740
caacgggttt gccgccagaa cacagctgaa gcttcgaggg gctcgcatct ctccttcacg   1800
cgcccgccgc cctacctgag gccgccatcc acgccggttg agtcgcgttc tgccgcctcc   1860
cgcctgtggt gcctcctgaa ctgcgtccgc cgtctaggta agtttaaagc tcaggtcgag   1920
accgggcctt tgtccggcgc tcccttggag cctacctaga ctcagccggc tctccacgct   1980
ttgcctgacc ctgcttgctc aactctacgt ctttgtttcg ttttctgttc tgcgccgtta   2040
cagatccaag ctgtgaccgg cgcctacggc tagcgaattc ctcgaggcca ccatgctgct   2100
gctggtgaca agcctgctgc tgtgcgagct gccccacccc gcctttctgc tgatccccca   2160
ggaacagctc gtcgaaagcg gcggcagact ggtgacacct ggcggcagcc tgaccctgag   2220
ctgcaaggcc agcggcttcg acttcagcgc ctactacatg agctgggtcc gccaggcccc   2280
tggcaaggga ctggaatgga tcgccaccat ctaccccagc agcggcaaga cctactacgc   2340
cacctgggtg aacggacggt tcaccatctc cagcgacaac gcccagaaca ccgtggacct   2400
gcagatgaac agcctgacag ccgccgaccg ggccacctac ttttgcgcca gagacagcta   2460
cgccgacgac ggcgccctgt tcaacatctg ggggccctggc accctggtga caatctctag   2520
cggcggaggc ggatctggtg gcggaggaag tggcggcgga ggatctgagc tggtgctgac   2580
ccagagcccc tctgtgtctg ctgccctggg aagccctgcc aagatcacct gtaccctgag   2640
cagcgcccac aagaccgaca ccatcgactg gtatcagcag ctgcagggcg aggcccccag   2700
atacctgatg caggtgcaga gcgacggcag ctacaccaag aggccaggcg tgcccgaccg   2760
gttcagcgga tctagctctg gcgccgaccg ctacctgatc atccccagcg tgcaggccga   2820
tgacgaggcc gattactact gtggcgccga ctacatcggc ggctacgtgt tcggcggagg   2880
cacccagctg accgtgaccg gcgagtctaa gtacggaccg ccctgccccc cttgccctat   2940
gttctgggtg ctggtggtgg tgggcggggt gctggcctgc tacagcctgc tggtgacagt   3000
ggccttcatc atcttttggg tgaaacgggg cagaaagaaa ctcctgtata tattcaaaca   3060
accatttatg agaccagtac aaactactca agaggaagat ggctgtagct gccgatttcc   3120
agaagaagaa gaaggaggat gtgaactgcg ggtgaagttc agcagaagcg ccgacgcccc   3180
tgcctaccag cagggccaga atcagctgta caacgagctg aacctgggca gaagggaaga   3240
gtacgacgtc ctggataagc ggagaggccg ggaccctgag atgggcggca agcctcggcg   3300
gaagaacccc caggaaggcc tgtataacga actgcagaaa gacaagatgg ccgaggccta   3360
cagcgagatc ggcatgaagg gcgagcggag gcggggcaag ggccacgacg gcctgtatca   3420
gggcctgtcc accgccacca aggataccta cgacgccctg cacatgcagg ccctgccccc   3480
aaggctcgag ggcggcggag agggcagagg aagtcttcta acatgcggtg acgtggagga   3540
gaatcccggc cctaggatgc ttctcctggt gacaagcctt ctgctctgtg agttaccaca   3600
cccagcattc ctcctgatcc cacgcaaagt gtgtaacgga ataggtattg gtgaatttaa   3660
agactcactc tccataaatg ctacgaatat taaacacttc aaaaactgca cctccatcag   3720
tggcgatctc cacatcctgc cggtggcatt taggggtgac tccttcacac atactcctcc   3780
```

```
tctggatcca caggaactgg atattctgaa aaccgtaaag gaaatcacag ggtttttgct   3840
gattcaggct tggcctgaaa acaggacgga cctccatgcc tttgagaacc tagaaatcat   3900
acgcggcagg accaagcaac atggtcagtt ttctcttgca gtcgtcagcc tgaacataac   3960
atccttggga ttacgctccc tcaaggagat aagtgatgga gatgtgataa tttcaggaaa   4020
caaaaatttg tgctatgcaa atacaataaa ctggaaaaaa ctgtttggga cctccggtca   4080
gaaaaccaaa attataagca acagaggtga aaacagctgc aaggccacag gccaggtctg   4140
ccatgccttg tgctcccccg agggctgctg gggcccggag cccagggact gcgtctcttg   4200
ccggaatgtc agccgaggca gggaatgcgt ggacaagtgc aaccttctgg agggtgagcc   4260
aagggagttt gtggagaact ctgagtgcat acagtgccac ccagagtgcc tgcctcaggc   4320
catgaacatc acctgcacag gacggggacc agacaactgt atccagtgtg cccactacat   4380
tgacggcccc cactgcgtca agacctgccc ggcaggagtc atgggagaaa acaacaccct   4440
ggtctggaag tacgcagacg ccggccatgt gtgccacctg tgccatccaa actgcaccta   4500
cggatgcact gggccaggtc ttgaaggctg tccaacgaat gggcctaaga tcccgtccat   4560
cgccactggg atggtggggg ccctcctctt gctgctggtg gtggccctgg ggatcggcct   4620
cttcatgtga gcggccgctc tagacccggg ctgcaggaat tcgatatcaa gcttatcgat   4680
aatcaacctc tggattacaa aatttgtgaa agattgactg gtattcttaa ctatgttgct   4740
ccttttacgc tatgtggata cgctgcttta atgcctttgt atcatgctat tgcttcccgt   4800
atggctttca ttttctcctc cttgtataaa tcctggttgc tgtctcttta tgaggagttg   4860
tggcccgttg tcaggcaacg tggcgtggtg tgcactgtgt ttgctgacgc aacccccact   4920
ggttggggca ttgccaccac ctgtcagctc ctttccggga ctttcgcttt ccccctccct   4980
attgccacgg cggaactcat cgccgcctgc cttgcccgct gctggacagg ggctcggctg   5040
ttgggcactg acaattccgt ggtgttgtcg gggaaatcat cgtcctttcc ttggctgctc   5100
gcctgtgttg ccacctggat tctgcgcggg acgtccttct gctacgtccc ttcggccctc   5160
aatccagcgg accttccttc ccgcggcctg ctgccggctc tgcggcctct tccgcgtctt   5220
cgccttcgcc ctcagacgag tcggatctcc ctttgggccg cctccccgca tcgataccgt   5280
cgactagccg tacctttaag accaatgact tacaaggcag ctgtagatct tagccacttt   5340
ttaaaagaaa aggggggact ggaagggcta attcactccc aaagaagaca agatctgctt   5400
tttgcctgta ctgggtctct ctggttagac cagatctgag cctgggagct ctctggctaa   5460
ctagggaacc cactgcttaa gcctcaataa agcttgcctt gagtgcttca agtagtgtgt   5520
gcccgtctgt tgtgtgactc tggtaactag agatccctca gaccctttta gtcagtgtgg   5580
aaaatctcta gcagaattcg atatcaagct tatcgatacc gtcgacctcg aggggggggcc   5640
cggtacccaa ttcgccctat agtgagtcgt attacaattc actggccgtc gttttacaac   5700
gtcgtgactg ggaaaaccct ggcgttaccc aacttaatcg ccttgcagca catccccctt   5760
tcgccagctg gcgtaatagc gaagaggccc gcaccgatcg cccttcccaa cagttgcgca   5820
gcctgaatgg cgaatggaaa ttgtaagcgt taatattttg ttaaaattcg cgttaaattt   5880
ttgttaaatc agctcatttt ttaaccaata ggccgaaatc ggcaaaatcc cttataaatc   5940
aaaagaatag accgagatag ggttgagtgt tgttccagtt tggaacaaga gtccactatt   6000
aaagaacgtg gactccaacg tcaaagggcg aaaaaccgtc tatcagggcg atggcccact   6060
acgtgaacca tcaccctaat caagtttttt ggggtcgagg tgccgtaaag cactaaatcg   6120
gaaccctaaa gggagccccc gatttagagc ttgacgggga aagccggcga acgtggcgag   6180
```

```
aaaggaaggg aagaaagcga aaggagcggg cgctagggcg ctggcaagtg tagcggtcac   6240
gctgcgcgta accaccacac ccgccgcgct taatgcgccg ctacagggcg cgtcaggtgg   6300
cacttttcgg ggaaatgtgc gcggaacccc tatttgttta tttttctaaa tacattcaaa   6360
tatgtatccg ctcatgagac aataaccctg ataaatgctt caataatatt gaaaaaggaa   6420
gagtatgagt attcaacatt tccgtgtcgc ccttattccc ttttttgcgg cattttgcct   6480
tcctgttttt gctcacccag aaacgctggt gaaagtaaaa gatgctgaag atcagttggg   6540
tgcacgagtg ggttacatcg aactggatct caacagcggt aagatccttg agagttttcg   6600
ccccgaagaa cgttttccaa tgatgagcac ttttaaagtt ctgctatgtg gcgcggtatt   6660
atcccgtatt gacgccgggc aagagcaact cggtcgccgc atacactatt ctcagaatga   6720
cttggttgag tactcaccag tcacagaaaa gcatcttacg gatggcatga cagtaagaga   6780
attatgcagt gctgccataa ccatgagtga taacactgcg gccaacttac ttctgacaac   6840
gatcggagga ccgaaggagc taaccgcttt tttgcacaac atgggggatc atgtaactcg   6900
ccttgatcgt tgggaaccgg agctgaatga agccatacca aacgacgagc gtgacaccac   6960
gatgcctgta gcaatggcaa caacgttgcg caaactatta actggcgaac tacttactct   7020
agcttcccgg caacaattaa tagactggat ggaggcggat aaagttgcag gaccacttct   7080
gcgctcggcc cttccggctg gctggtttat tgctgataaa tctggagccg gtgagcgtgg   7140
gtctcgcggt atcattgcag cactggggcc agatggtaag ccctcccgta tcgtagttat   7200
ctacacgacg gggagtcagg caactatgga tgaacgaaat agacagatcg ctgagatagg   7260
tgcctcactg attaagcatt ggtaactgtc agaccaagtt tactcatata tactttagat   7320
tgatttaaaa cttcattttt aatttaaaag gatctaggtg aagatccttt ttgataatct   7380
catgaccaaa atcccttaac gtgagttttc gttccactga gcgtcagacc ccgtagaaaa   7440
gatcaaagga tcttcttgag atcctttttt tctgcgcgta atctgctgct tgcaaacaaa   7500
aaaaccaccg ctaccagcgg tggtttgttt gccggatcaa gagctaccaa ctctttttcc   7560
gaaggtaact ggcttcagca gagcgcagat accaaatact gttcttctag tgtagccgta   7620
gttaggccac cacttcaaga actctgtagc accgcctaca tacctcgctc tgctaatcct   7680
gttaccagtg gctgctgcca gtggcgataa gtcgtgtctt accgggttgg actcaagacg   7740
atagttaccg gataaggcgc agcggtcggg ctgaacgggg ggttcgtgca cacagcccag   7800
cttggagcga acgacctaca ccgaactgag atacctacag cgtgagctat gagaaagcgc   7860
cacgcttccc gaagggagaa aggcggacag gtatccggta agcggcaggg tcggaacagg   7920
agagcgcacg agggagcttc cagggggaaa cgcctggtat ctttatagtc ctgtcgggtt   7980
tcgccacctc tgacttgagc gtcgattttt gtgatgctcg tcaggggggc ggagcctatg   8040
gaaaaacgcc agcaacgcgg cctttttacg gttcctggcc ttttgctggc cttttgctca   8100
catgttcttt cctgcgttat cccctgattc tgtggataac cgtattaccg cctttgagtg   8160
agctgatacc gctcgccgca gccgaacgac cgagcgcagc gagtcagtga gcgaggaagc   8220
ggaagagcgc ccaatacgca aaccgcctct ccccgcgcgt tggccgattc attaatgcag   8280
ctggcacgac aggtttcccg actggaaagc gggcagtgag cgcaacgcaa ttaatgtgag   8340
ttagctcact cattaggcac cccaggcttt acactttatg cttccggctc gtatgttgtg   8400
tggaattgtg agcggataac aatttcacac aggaaacagc tatgaccatg attacgccaa   8460
gctcgaaatt aaccctcact aaagggaaca aaagctggag ctccaccgcg gtggcggcct   8520
```

```
cgaggtcgag atccggtcga ccagcaacca tagtcccgcc cctaactccg cccatcccgc   8580

ccctaactcc gcccagttcc gcccattctc cgccccatgg ctgactaatt ttttttattt   8640

atgcagaggc cgaggccgcc tcggcctctg agctattcca gaagtagtga ggaggctttt   8700

ttggaggcct aggcttttgc aaaaagcttc gacggtatcg attggctcat gtccaacatt   8760

accgccatgt tgacattgat tattgactag ttattaatag taatcaatta cggggtcatt   8820

agttcatagc ccatatatgg agttccgcgt tacataactt acggtaaatg gcccgcctgg   8880

ctgaccgccc aacgaccccc gcccattgac gtcaataatg acgtatgttc ccatagtaac   8940

gccaataggg actttccatt gacgtcaatg ggtggagtat ttacggtaaa ctgcccactt   9000

ggcagtacat caagtgtatc atatgccaag tacgccccct attgacgtca atgacggtaa   9060

atggcccgcc tggcattatg cccagtacat gaccttatgg gactttccta cttggcagta   9120

catctacgta ttagtcatcg ctattaccat ggtgatgcgg ttttggcagt acatcaatgg   9180

gcgtggatag cggtttgact cacggggatt tccaagtctc caccccattg acgtcaatgg   9240

gagtttgttt tggcaccaaa atcaacggga ctttccaaaa tgtcgtaaca actccgcccc   9300

attgacgcaa atgggcggta ggcgtgtacg gaattcggag tggcgagccc tcagatcctg   9360

catataagca gctgcttttt gcctgtactg ggtctctctg                        9400
```

```
<210> SEQ ID NO 42
<211> LENGTH: 845
<212> TYPE: PRT
<213> ORGANISM: Artificial Sequence
<220> FEATURE:
<223> OTHER INFORMATION: Synthetic sequence

<400> SEQUENCE: 42

Met Leu Leu Leu Val Thr Ser Leu Leu Leu Cys Glu Leu Pro His Pro
1               5                   10                  15

Ala Phe Leu Leu Ile Pro Gln Glu Gln Leu Val Glu Ser Gly Gly Arg
            20                  25                  30

Leu Val Thr Pro Gly Gly Ser Leu Thr Leu Ser Cys Lys Ala Ser Gly
        35                  40                  45

Phe Asp Phe Ser Ala Tyr Tyr Met Ser Trp Val Arg Gln Ala Pro Gly
    50                  55                  60

Lys Gly Leu Glu Trp Ile Ala Thr Ile Tyr Pro Ser Ser Gly Lys Thr
65                  70                  75                  80

Tyr Tyr Ala Thr Trp Val Asn Gly Arg Phe Thr Ile Ser Ser Asp Asn
                85                  90                  95

Ala Gln Asn Thr Val Asp Leu Gln Met Asn Ser Leu Thr Ala Ala Asp
            100                 105                 110

Arg Ala Thr Tyr Phe Cys Ala Arg Asp Ser Tyr Ala Asp Asp Gly Ala
        115                 120                 125

Leu Phe Asn Ile Trp Gly Pro Gly Thr Leu Val Thr Ile Ser Ser Gly
    130                 135                 140

Gly Gly Gly Ser Gly Gly Gly Gly Ser Gly Gly Gly Gly Ser Glu Leu
145                 150                 155                 160

Val Leu Thr Gln Ser Pro Ser Val Ser Ala Ala Leu Gly Ser Pro Ala
                165                 170                 175

Lys Ile Thr Cys Thr Leu Ser Ser Ala His Lys Thr Asp Thr Ile Asp
            180                 185                 190

Trp Tyr Gln Gln Leu Gln Gly Glu Ala Pro Arg Tyr Leu Met Gln Val
        195                 200                 205
```

```
Gln Ser Asp Gly Ser Tyr Thr Lys Arg Pro Gly Val Pro Asp Arg Phe
    210                 215                 220

Ser Gly Ser Ser Ser Gly Ala Asp Arg Tyr Leu Ile Ile Pro Ser Val
225                 230                 235                 240

Gln Ala Asp Asp Glu Ala Asp Tyr Tyr Cys Gly Ala Asp Tyr Ile Gly
                245                 250                 255

Gly Tyr Val Phe Gly Gly Gly Thr Gln Leu Thr Val Thr Gly Glu Ser
            260                 265                 270

Lys Tyr Gly Pro Pro Cys Pro Pro Cys Pro Met Phe Trp Val Leu Val
        275                 280                 285

Val Val Gly Gly Val Leu Ala Cys Tyr Ser Leu Leu Val Thr Val Ala
    290                 295                 300

Phe Ile Ile Phe Trp Val Lys Arg Gly Arg Lys Lys Leu Leu Tyr Ile
305                 310                 315                 320

Phe Lys Gln Pro Phe Met Arg Pro Val Gln Thr Thr Gln Glu Glu Asp
                325                 330                 335

Gly Cys Ser Cys Arg Phe Pro Glu Glu Glu Glu Gly Gly Cys Glu Leu
            340                 345                 350

Arg Val Lys Phe Ser Arg Ser Ala Asp Ala Pro Ala Tyr Gln Gln Gly
        355                 360                 365

Gln Asn Gln Leu Tyr Asn Glu Leu Asn Leu Gly Arg Arg Glu Glu Tyr
    370                 375                 380

Asp Val Leu Asp Lys Arg Arg Gly Arg Asp Pro Glu Met Gly Gly Lys
385                 390                 395                 400

Pro Arg Arg Lys Asn Pro Gln Glu Gly Leu Tyr Asn Glu Leu Gln Lys
                405                 410                 415

Asp Lys Met Ala Glu Ala Tyr Ser Glu Ile Gly Met Lys Gly Glu Arg
            420                 425                 430

Arg Arg Gly Lys Gly His Asp Gly Leu Tyr Gln Gly Leu Ser Thr Ala
        435                 440                 445

Thr Lys Asp Thr Tyr Asp Ala Leu His Met Gln Ala Leu Pro Pro Arg
    450                 455                 460

Leu Glu Gly Gly Gly Glu Gly Arg Gly Ser Leu Leu Thr Cys Gly Asp
465                 470                 475                 480

Val Glu Glu Asn Pro Gly Pro Arg Met Leu Leu Leu Val Thr Ser Leu
                485                 490                 495

Leu Leu Cys Glu Leu Pro His Pro Ala Phe Leu Leu Ile Pro Arg Lys
            500                 505                 510

Val Cys Asn Gly Ile Gly Ile Gly Glu Phe Lys Asp Ser Leu Ser Ile
        515                 520                 525

Asn Ala Thr Asn Ile Lys His Phe Lys Asn Cys Thr Ser Ile Ser Gly
    530                 535                 540

Asp Leu His Ile Leu Pro Val Ala Phe Arg Gly Asp Ser Phe Thr His
545                 550                 555                 560

Thr Pro Pro Leu Asp Pro Gln Glu Leu Asp Ile Leu Lys Thr Val Lys
                565                 570                 575

Glu Ile Thr Gly Phe Leu Leu Ile Gln Ala Trp Pro Glu Asn Arg Thr
            580                 585                 590

Asp Leu His Ala Phe Glu Asn Leu Glu Ile Ile Arg Gly Arg Thr Lys
        595                 600                 605

Gln His Gly Gln Phe Ser Leu Ala Val Val Ser Leu Asn Ile Thr Ser
    610                 615                 620

Leu Gly Leu Arg Ser Leu Lys Glu Ile Ser Asp Gly Asp Val Ile Ile
```

```
625                 630                 635                 640

Ser Gly Asn Lys Asn Leu Cys Tyr Ala Asn Thr Ile Asn Trp Lys Lys
                645                 650                 655

Leu Phe Gly Thr Ser Gly Gln Lys Thr Lys Ile Ile Ser Asn Arg Gly
            660                 665                 670

Glu Asn Ser Cys Lys Ala Thr Gly Gln Val Cys His Ala Leu Cys Ser
        675                 680                 685

Pro Glu Gly Cys Trp Gly Pro Glu Pro Arg Asp Cys Val Ser Cys Arg
    690                 695                 700

Asn Val Ser Arg Gly Arg Glu Cys Val Asp Lys Cys Asn Leu Leu Glu
705                 710                 715                 720

Gly Glu Pro Arg Glu Phe Val Glu Asn Ser Glu Cys Ile Gln Cys His
                725                 730                 735

Pro Glu Cys Leu Pro Gln Ala Met Asn Ile Thr Cys Thr Gly Arg Gly
            740                 745                 750

Pro Asp Asn Cys Ile Gln Cys Ala His Tyr Ile Asp Gly Pro His Cys
        755                 760                 765

Val Lys Thr Cys Pro Ala Gly Val Met Gly Glu Asn Asn Thr Leu Val
    770                 775                 780

Trp Lys Tyr Ala Asp Ala Gly His Val Cys His Leu Cys His Pro Asn
785                 790                 795                 800

Cys Thr Tyr Gly Cys Thr Gly Pro Gly Leu Glu Gly Cys Pro Thr Asn
                805                 810                 815

Gly Pro Lys Ile Pro Ser Ile Ala Thr Gly Met Val Gly Ala Leu Leu
            820                 825                 830

Leu Leu Leu Val Val Ala Leu Gly Ile Gly Leu Phe Met
        835                 840                 845
```

<210> SEQ ID NO 43
<211> LENGTH: 10015
<212> TYPE: DNA
<213> ORGANISM: Artificial Sequence
<220> FEATURE:
<223> OTHER INFORMATION: Synthetic sequence

<400> SEQUENCE: 43

```
gttagaccag atctgagcct gggagctctc tggctaacta gggaacccac tgcttaagcc      60

tcaataaagc ttgccttgag tgcttcaagt agtgtgtgcc cgtctgttgt gtgactctgg     120

taactagaga tccctcagac ccttttagtc agtgtggaaa atctctagca gtggcgcccg     180

aacagggact tgaaagcgaa agggaaacca gaggagctct ctcgacgcag gactcggctt     240

gctgaagcgc gcacggcaag aggcgagggg cggcgactgg tgagtacgcc aaaaattttg     300

actagcggag gctagaagga gagagatggg tgcgagagcg tcagtattaa gcgggggaga     360

attagatcga tgggaaaaaa ttcggttaag gccaggggga aagaaaaaat ataaattaaa     420

acatatagta tgggcaagca gggagctaga acgattcgca gttaatcctg gcctgttaga     480

aacatcagaa ggctgtagac aaatactggg acagctacaa ccatcccttc agacaggatc     540

agaagaactt agatcattat ataatacagt agcaaccctc tattgtgtgc atcaaaggat     600

agagataaaa gacaccaagg aagctttaga caagatagag gaagagcaaa acaaaagtaa     660

gaaaaaagca cagcaagcag cagctgacac aggacacagc aatcaggtca gccaaaatta     720

ccctatagtg cagaacatcc aggggcaaat ggtacatcag gccatatcac ctagaacttt     780

aaatgcatgg gtaaaagtag tagaagagaa ggctttcagc ccagaagtga tacccatgtt     840
```

```
ttcagcatta tcagaaggag ccaccccaca agatttaaac accatgctaa acacagtggg    900
gggacatcaa gcagccatgc aaatgttaaa agagaccatc aatgaggaag ctgcaggcaa    960
agagaagagt ggtgcagaga gaaaaaagag cagtgggaat aggagctttg ttccttgggt   1020
tcttgggagc agcaggaagc actatgggcg cagcgtcaat gacgctgacg gtacaggcca   1080
gacaattatt gtctggtata gtgcagcagc agaacaattt gctgagggct attgaggcgc   1140
aacagcatct gttgcaactc acagtctggg gcatcaagca gctccaggca agaatcctgg   1200
ctgtggaaag atacctaaag gatcaacagc tcctggggat ttggggttgc tctggaaaac   1260
tcatttgcac cactgctgtg ccttggatct acaaatggca gtattcatcc acaattttaa   1320
aagaaaaggg gggattgggg ggtacagtgc aggggaaaga atagtagaca taatagcaac   1380
agacatacaa actaaagaat tacaaaaaca aattacaaaa attcaaaatt ttcgggttta   1440
ttacagggac agcagagatc cagtttgggg atcaattgca tgaagaatct gcttagggtt   1500
aggcgttttg cgctgcttcg cgaggatctg cgatcgctcc ggtgcccgtc agtgggcaga   1560
gcgcacatcg cccacagtcc ccgagaagtt ggggggaggg gtcggcaatt gaaccggtgc   1620
ctagagaagg tggcgcgggg taaactggga aagtgatgtc gtgtactggc tccgcctttt   1680
tcccgagggt gggggagaac cgtatataag tgcagtagtc gccgtgaacg ttctttttcg   1740
caacgggttt gccgccagaa cacagctgaa gcttcgaggg gctcgcatct ctccttcacg   1800
cgcccgccgc cctacctgag gccgccatcc acgccggttg agtcgcgttc tgccgcctcc   1860
cgcctgtggt gcctcctgaa ctgcgtccgc cgtctaggta agtttaaagc tcaggtcgag   1920
accgggcctt tgtccggcgc tcccttggag cctacctaga ctcagccggc tctccacgct   1980
ttgcctgacc ctgcttgctc aactctacgt ctttgtttcg ttttctgttc tgcgccgtta   2040
cagatccaag ctgtgaccgg cgcctacggc tagcgaattc gccaccatgc tgctgctggt   2100
gacaagcctg ctgctgtgcg agctgcccca ccccgccttt ctgctgatcc cccagagcgt   2160
gaaagagtcc gagggcgacc tggtcacacc agccggcaac ctgaccctga cctgtaccgc   2220
cagcggcagc gacatcaacg actaccccat ctcttgggtc cgccaggctc ctggcaaggg   2280
actggaatgg atcggcttca tcaacagcgg cggcagcact tggtacgcca gctgggtcaa   2340
aggccggttc accatcagcc ggaccagcac caccgtggac ctgaagatga caagcctgac   2400
caccgacgac accgccacct acttttgcgc cagaggctac agcacctact acggcgactt   2460
caacatctgg ggccctggca ccctggtcac aatctctagc ggcggaggcg gcagcggagg   2520
tggaggaagt ggcggcggag gatccgagct ggtcatgacc cagaccccca gcagcacatc   2580
tggcgccgtg ggcggcaccg tgaccatcaa ttgccaggcc agccagagca tcgacagcaa   2640
cctggcctgg ttccagcaga agcccggcca gccccccacc ctgctgatct acagagcctc   2700
caacctggcc agcggcgtgc caagcagatt cagcggcagc agatctggca ccgagtacac   2760
cctgaccatc tccggcgtgc agagagagga cgccgctacc tattactgcc tgggcggcgt   2820
gggcaacgtg tcctacagaa ccagcttcgg cggaggtact gaggtggtcg tcaaatacgg   2880
accgccctgc ccccccttgcc ctgcccccga gttcctgggc ggacccagcg tgttcctgtt   2940
ccccccccaag cccaaggaca ccctgatgat cagccggacc cccgaggtga cctgcgtggt   3000
ggtggacgtg agccaggaag atcccgaggt ccagttcaat tggtacgtgg acggcgtgga   3060
agtgcacaac gccaagacca agcccagaga ggaacagttc aacagcacct accgggtggt   3120
gtctgtgctg accgtgctgc accaggactg gctgaacggc aaagaataca agtgcaaggt   3180
gtccaacaag ggcctgccca gcagcatcga aaagaccatc agcaaggcca agggccagcc   3240
```

```
tcgcgagccc caggtgtaca ccctgcctcc ctcccaggaa gagatgacca agaaccaggt   3300
gtccctgacc tgcctggtga agggcttcta ccccagcgac atcgccgtgg agtgggagag   3360
caacggccag cctgagaaca actacaagac cacccctccc gtgctggaca gcgacggcag   3420
cttcttcctg tacagccggc tgaccgtgga caagagccgg tggcaggaag gcaacgtctt   3480
tagctgcagc gtgatgcacg aggccctgca caaccactac acccagaaga gcctgagcct   3540
gtccctgggc aagatgttct gggtgctggt ggtggtgggc ggggtgctgg cctgctacag   3600
cctgctggtg acagtggcct tcatcatctt ttgggtgaaa cggggcagaa agaaactcct   3660
gtatatattc aaacaaccat ttatgagacc agtacaaact actcaagagg aagatggctg   3720
tagctgccga tttccagaag aagaagaagg aggatgtgaa ctgcgggtga agttcagcag   3780
aagcgccgac gcccctgcct accagcaggg ccagaatcag ctgtacaacg agctgaacct   3840
gggcagaagg gaagagtacg acgtcctgga taagcggaga ggccgggacc ctgagatggg   3900
cggcaagcct cggcggaaga acccccagga aggcctgtat aacgaactgc agaaagacaa   3960
gatggccgag gcctacagcg agatcggcat gaagggcgag cggaggcggg gcaagggcca   4020
cgacggcctg tatcagggcc tgtccaccgc caccaaggat acctacgacg ccctgcacat   4080
gcaggccctg cccccaaggc tcgagggcgg cggagagggc agaggaagtc ttctaacatg   4140
cggtgacgtg gaggagaatc ccggccctag gatgcttctc ctggtgacaa gccttctgct   4200
ctgtgagtta ccacacccag cattcctcct gatcccacgc aaagtgtgta acggaatagg   4260
tattggtgaa tttaaagact cactctccat aaatgctacg aatattaaac acttcaaaaa   4320
ctgcacctcc atcagtggcg atctccacat cctgccggtg gcatttaggg gtgactcctt   4380
cacacatact cctcctctgg atccacagga actggatatt ctgaaaaccg taaaggaaat   4440
cacagggttt ttgctgattc aggcttggcc tgaaaacagg acggacctcc atgcctttga   4500
gaacctagaa atcatacgcg gcaggaccaa gcaacatggt cagttttctc ttgcagtcgt   4560
cagcctgaac ataacatcct tgggattacg ctccctcaag gagataagtg atggagatgt   4620
gataatttca ggaaacaaaa atttgtgcta tgcaaataca ataaactgga aaaaactgtt   4680
tgggacctcc ggtcagaaaa ccaaaattat aagcaacaga ggtgaaaaca gctgcaaggc   4740
cacaggccag gtctgccatg ccttgtgctc ccccgagggc tgctggggcc cggagcccag   4800
ggactgcgtc tcttgccgga atgtcagccg aggcagggaa tgcgtggaca agtgcaacct   4860
tctggagggt gagccaaggg agtttgtgga gaactctgag tgcatacagt gccacccaga   4920
gtgcctgcct caggccatga acatcacctg cacaggacgg ggaccagaca actgtatcca   4980
gtgtgcccac tacattgacg gcccccactg cgtcaagacc tgcccggcag gagtcatggg   5040
agaaaacaac accctggtct ggaagtacgc agacgccggc catgtgtgcc acctgtgcca   5100
tccaaactgc acctacggat gcactgggcc aggtcttgaa ggctgtccaa cgaatgggcc   5160
taagatcccg tccatcgcca ctgggatggt gggggccctc ctcttgctgc tggtggtggc   5220
cctggggatc ggcctcttca tgtgagcggc cgctctagac ccgggctgca ggaattcgat   5280
atcaagctta tcgataatca acctctggat tacaaaattt gtgaaagatt gactggtatt   5340
cttaactatg ttgctccttt tacgctatgt ggatacgctg ctttaatgcc tttgtatcat   5400
gctattgctt cccgtatggc tttcattttc tcctccttgt ataaatcctg gttgctgtct   5460
ctttatgagg agttgtggcc cgttgtcagg caacgtggcg tggtgtgcac tgtgtttgct   5520
gacgcaaccc ccactggttg gggcattgcc accacctgtc agctcctttc cgggactttc   5580
```

```
gctttccccc tccctattgc cacggcggaa ctcatcgccg cctgccttgc ccgctgctgg   5640

acaggggctc ggctgttggg cactgacaat tccgtggtgt tgtcggggaa atcatcgtcc   5700

tttccttggc tgctcgcctg tgttgccacc tggattctgc gcgggacgtc cttctgctac   5760

gtcccttcgg ccctcaatcc agcggacctt ccttcccgcg gcctgctgcc ggctctgcgg   5820

cctcttccgc gtcttcgcct tcgccctcag acgagtcgga tctccctttg ggccgcctcc   5880

ccgcatcgat accgtcgact agccgtacct ttaagaccaa tgacttacaa ggcagctgta   5940

gatcttagcc actttttaaa agaaaagggg ggactggaag ggctaattca ctcccaaaga   6000

agacaagatc tgctttttgc ctgtactggg tctctctggt tagaccagat ctgagcctgg   6060

gagctctctg gctaactagg gaacccactg cttaagcctc aataaagctt gccttgagtg   6120

cttcaagtag tgtgtgcccg tctgttgtgt gactctggta actagagatc cctcagaccc   6180

ttttagtcag tgtggaaaat ctctagcaga attcgatatc aagcttatcg ataccgtcga   6240

cctcgagggg gggcccggta cccaattcgc cctatagtga gtcgtattac aattcactgg   6300

ccgtcgtttt acaacgtcgt gactgggaaa accctggcgt tacccaactt aatcgccttg   6360

cagcacatcc ccctttcgcc agctggcgta atagcgaaga ggcccgcacc gatcgccctt   6420

cccaacagtt gcgcagcctg aatggcgaat ggaaattgta agcgttaata ttttgttaaa   6480

attcgcgtta aatttttgtt aaatcagctc attttttaac caataggccg aaatcggcaa   6540

aatcccttat aaatcaaaag aatagaccga gatagggttg agtgttgttc cagtttggaa   6600

caagagtcca ctattaaaga acgtggactc caacgtcaaa gggcgaaaaa ccgtctatca   6660

gggcgatggc ccactacgtg aaccatcacc ctaatcaagt tttttggggt cgaggtgccg   6720

taaagcacta aatcggaacc ctaaagggag cccccgattt agagcttgac ggggaaagcc   6780

ggcgaacgtg gcgagaaagg aagggaagaa agcgaaagga gcgggcgcta gggcgctggc   6840

aagtgtagcg gtcacgctgc gcgtaaccac cacacccgcc gcgcttaatg cgccgctaca   6900

gggcgcgtca ggtggcactt ttcggggaaa tgtgcgcgga acccctattt gtttattttt   6960

ctaaatacat tcaaatatgt atccgctcat gagacaataa ccctgataaa tgcttcaata   7020

atattgaaaa aggaagagta tgagtattca acatttccgt gtcgccctta ttcccttttt   7080

tgcggcattt tgccttcctg tttttgctca cccagaaacg ctggtgaaag taaaagatgc   7140

tgaagatcag ttgggtgcac gagtgggtta catcgaactg gatctcaaca gcggtaagat   7200

ccttgagagt tttcgccccg aagaacgttt tccaatgatg agcactttta aagttctgct   7260

atgtggcgcg gtattatccc gtattgacgc cgggcaagag caactcggtc gccgcataca   7320

ctattctcag aatgacttgg ttgagtactc accagtcaca gaaaagcatc ttacggatgg   7380

catgacagta agagaattat gcagtgctgc cataaccatg agtgataaca ctgcggccaa   7440

cttacttctg acaacgatcg gaggaccgaa ggagctaacc gcttttttgc acaacatggg   7500

ggatcatgta actcgccttg atcgttggga accggagctg aatgaagcca taccaaacga   7560

cgagcgtgac accacgatgc ctgtagcaat ggcaacaacg ttgcgcaaac tattaactgg   7620

cgaactactt actctagctt cccggcaaca attaatagac tggatggagg cggataaagt   7680

tgcaggacca cttctgcgct cggcccttcc ggctggctgg tttattgctg ataaatctgg   7740

agccggtgag cgtgggtctc gcggtatcat tgcagcactg gggccagatg gtaagccctc   7800

ccgtatcgta gttatctaca cgacggggag tcaggcaact atggatgaac gaaatagaca   7860

gatcgctgag ataggtgcct cactgattaa gcattggtaa ctgtcagacc aagtttactc   7920

atatatactt tagattgatt taaaacttca tttttaattt aaaaggatct aggtgaagat   7980
```

```
ccttttgat aatctcatga ccaaaatccc ttaacgtgag ttttcgttcc actgagcgtc   8040
agaccccgta gaaaagatca aaggatcttc ttgagatcct ttttttctgc gcgtaatctg   8100
ctgcttgcaa acaaaaaaac caccgctacc agcggtggtt tgtttgccgg atcaagagct   8160
accaactctt tttccgaagg taactggctt cagcagagcg cagataccaa atactgttct   8220
tctagtgtag ccgtagttag gccaccactt caagaactct gtagcaccgc ctacatacct   8280
cgctctgcta atcctgttac cagtggctgc tgccagtggc gataagtcgt gtcttaccgg   8340
gttggactca agacgatagt taccggataa ggcgcagcgg tcgggctgaa cggggggttc   8400
gtgcacacag cccagcttgg agcgaacgac ctacaccgaa ctgagatacc tacagcgtga   8460
gctatgagaa agcgccacgc ttcccgaagg gagaaaggcg gacaggtatc cggtaagcgg   8520
cagggtcgga acaggagagc gcacgaggga gcttccaggg ggaaacgcct ggtatcttta   8580
tagtcctgtc gggtttcgcc acctctgact tgagcgtcga tttttgtgat gctcgtcagg   8640
ggggcggagc ctatggaaaa acgccagcaa cgcggccttt ttacggttcc tggccttttg   8700
ctggcctttt gctcacatgt tctttcctgc gttatcccct gattctgtgg ataaccgtat   8760
taccgccttt gagtgagctg ataccgctcg ccgcagccga acgaccgagc gcagcgagtc   8820
agtgagcgag gaagcggaag agcgcccaat acgcaaaccg cctctccccg cgcgttggcc   8880
gattcattaa tgcagctggc acgacaggtt tcccgactgg aaagcgggca gtgagcgcaa   8940
cgcaattaat gtgagttagc tcactcatta ggcaccccag gctttacact ttatgcttcc   9000
ggctcgtatg ttgtgtggaa ttgtgagcgg ataacaattt cacacaggaa acagctatga   9060
ccatgattac gccaagctcg aaattaaccc tcactaaagg gaacaaaagc tggagctcca   9120
ccgcggtggc ggcctcgagg tcgagatccg gtcgaccagc aaccatagtc ccgcccctaa   9180
ctccgcccat cccgccccta actccgccca gttccgccca ttctccgccc catggctgac   9240
taattttttt tatttatgca gaggccgagg ccgcctcggc ctctgagcta ttccagaagt   9300
agtgaggagg cttttttgga ggcctaggct tttgcaaaaa gcttcgacgg tatcgattgg   9360
ctcatgtcca acattaccgc catgttgaca ttgattattg actagttatt aatagtaatc   9420
aattacgggg tcattagttc atagcccata tatggagttc cgcgttacat aacttacggt   9480
aaatggcccg cctggctgac cgcccaacga cccccgccca ttgacgtcaa taatgacgta   9540
tgttcccata gtaacgccaa tagggacttt ccattgacgt caatgggtgg agtatttacg   9600
gtaaactgcc cacttggcag tacatcaagt gtatcatatg ccaagtacgc cccctattga   9660
cgtcaatgac ggtaaatggc ccgcctggca ttatgcccag tacatgacct tatgggactt   9720
tcctacttgg cagtacatct acgtattagt catcgctatt accatggtga tgcggttttg   9780
gcagtacatc aatgggcgtg gatagcggtt tgactcacgg ggatttccaa gtctccaccc   9840
cattgacgtc aatgggagtt tgttttggca ccaaaatcaa cgggactttc caaaatgtcg   9900
taacaactcc gccccattga cgcaaatggg cggtaggcgt gtacggaatt cggagtggcg   9960
agccctcaga tcctgcatat aagcagctgc tttttgcctg tactgggtct ctctg      10015
```

<210> SEQ ID NO 44
<211> LENGTH: 1055
<212> TYPE: PRT
<213> ORGANISM: Artificial Sequence
<220> FEATURE:
<223> OTHER INFORMATION: Synthetic sequence

<400> SEQUENCE: 44

```
Met Leu Leu Leu Val Thr Ser Leu Leu Leu Cys Glu Leu Pro His Pro
1               5                   10                  15

Ala Phe Leu Leu Ile Pro Gln Ser Val Lys Glu Ser Glu Gly Asp Leu
            20                  25                  30

Val Thr Pro Ala Gly Asn Leu Thr Leu Thr Cys Thr Ala Ser Gly Ser
        35                  40                  45

Asp Ile Asn Asp Tyr Pro Ile Ser Trp Val Arg Gln Ala Pro Gly Lys
    50                  55                  60

Gly Leu Glu Trp Ile Gly Phe Ile Asn Ser Gly Gly Ser Thr Trp Tyr
65                  70                  75                  80

Ala Ser Trp Val Lys Gly Arg Phe Thr Ile Ser Arg Thr Ser Thr Thr
                85                  90                  95

Val Asp Leu Lys Met Thr Ser Leu Thr Thr Asp Asp Thr Ala Thr Tyr
            100                 105                 110

Phe Cys Ala Arg Gly Tyr Ser Thr Tyr Tyr Gly Asp Phe Asn Ile Trp
        115                 120                 125

Gly Pro Gly Thr Leu Val Thr Ile Ser Ser Gly Gly Gly Gly Ser Gly
    130                 135                 140

Gly Gly Gly Ser Gly Gly Gly Gly Ser Glu Leu Val Met Thr Gln Thr
145                 150                 155                 160

Pro Ser Ser Thr Ser Gly Ala Val Gly Gly Thr Val Thr Ile Asn Cys
                165                 170                 175

Gln Ala Ser Gln Ser Ile Asp Ser Asn Leu Ala Trp Phe Gln Gln Lys
            180                 185                 190

Pro Gly Gln Pro Pro Thr Leu Leu Ile Tyr Arg Ala Ser Asn Leu Ala
        195                 200                 205

Ser Gly Val Pro Ser Arg Phe Ser Gly Ser Arg Ser Gly Thr Glu Tyr
    210                 215                 220

Thr Leu Thr Ile Ser Gly Val Gln Arg Glu Asp Ala Ala Thr Tyr Tyr
225                 230                 235                 240

Cys Leu Gly Gly Val Gly Asn Val Ser Tyr Arg Thr Ser Phe Gly Gly
                245                 250                 255

Gly Thr Glu Val Val Val Lys Glu Ser Lys Tyr Gly Pro Pro Cys Pro
            260                 265                 270

Pro Cys Pro Ala Pro Glu Phe Leu Gly Gly Pro Ser Val Phe Leu Phe
        275                 280                 285

Pro Pro Lys Pro Lys Asp Thr Leu Met Ile Ser Arg Thr Pro Glu Val
    290                 295                 300

Thr Cys Val Val Val Asp Val Ser Gln Glu Asp Pro Glu Val Gln Phe
305                 310                 315                 320

Asn Trp Tyr Val Asp Gly Val Glu Val His Asn Ala Lys Thr Lys Pro
                325                 330                 335

Arg Glu Glu Gln Phe Asn Ser Thr Tyr Arg Val Val Ser Val Leu Thr
            340                 345                 350

Val Leu His Gln Asp Trp Leu Asn Gly Lys Glu Tyr Lys Cys Lys Val
        355                 360                 365

Ser Asn Lys Gly Leu Pro Ser Ser Ile Glu Lys Thr Ile Ser Lys Ala
    370                 375                 380

Lys Gly Gln Pro Arg Glu Pro Gln Val Tyr Thr Leu Pro Pro Ser Gln
385                 390                 395                 400

Glu Glu Met Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
```

```
            420                 425                 430

Glu Asn Asn Tyr Lys Thr Thr Pro Pro Val Leu Asp Ser Asp Gly Ser
        435                 440                 445

Phe Phe Leu Tyr Ser Arg Leu Thr Val Asp Lys Ser Arg Trp Gln Glu
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Leu Gly Lys Met Phe Trp Val
                485                 490                 495

Leu Val Val Val Gly Gly Val Leu Ala Cys Tyr Ser Leu Leu Val Thr
            500                 505                 510

Val Ala Phe Ile Ile Phe Trp Val Lys Arg Gly Arg Lys Lys Leu Leu
        515                 520                 525

Tyr Ile Phe Lys Gln Pro Phe Met Arg Pro Val Gln Thr Thr Gln Glu
    530                 535                 540

Glu Asp Gly Cys Ser Cys Arg Phe Pro Glu Glu Glu Glu Gly Gly Cys
545                 550                 555                 560

Glu Leu Arg Val Lys Phe Ser Arg Ser Ala Asp Ala Pro Ala Tyr Gln
                565                 570                 575

Gln Gly Gln Asn Gln Leu Tyr Asn Glu Leu Asn Leu Gly Arg Arg Glu
            580                 585                 590

Glu Tyr Asp Val Leu Asp Lys Arg Arg Gly Arg Asp Pro Glu Met Gly
        595                 600                 605

Gly Lys Pro Arg Arg Lys Asn Pro Gln Glu Gly Leu Tyr Asn Glu Leu
    610                 615                 620

Gln Lys Asp Lys Met Ala Glu Ala Tyr Ser Glu Ile Gly Met Lys Gly
625                 630                 635                 640

Glu Arg Arg Arg Gly Lys Gly His Asp Gly Leu Tyr Gln Gly Leu Ser
                645                 650                 655

Thr Ala Thr Lys Asp Thr Tyr Asp Ala Leu His Met Gln Ala Leu Pro
            660                 665                 670

Pro Arg Leu Glu Gly Gly Gly Glu Gly Arg Gly Ser Leu Leu Thr Cys
        675                 680                 685

Gly Asp Val Glu Glu Asn Pro Gly Pro Arg Met Leu Leu Leu Val Thr
    690                 695                 700

Ser Leu Leu Leu Cys Glu Leu Pro His Pro Ala Phe Leu Leu Ile Pro
705                 710                 715                 720

Arg Lys Val Cys Asn Gly Ile Gly Ile Gly Glu Phe Lys Asp Ser Leu
                725                 730                 735

Ser Ile Asn Ala Thr Asn Ile Lys His Phe Lys Asn Cys Thr Ser Ile
            740                 745                 750

Ser Gly Asp Leu His Ile Leu Pro Val Ala Phe Arg Gly Asp Ser Phe
        755                 760                 765

Thr His Thr Pro Pro Leu Asp Pro Gln Glu Leu Asp Ile Leu Lys Thr
    770                 775                 780

Val Lys Glu Ile Thr Gly Phe Leu Leu Ile Gln Ala Trp Pro Glu Asn
785                 790                 795                 800

Arg Thr Asp Leu His Ala Phe Glu Asn Leu Glu Ile Ile Arg Gly Arg
                805                 810                 815

Thr Lys Gln His Gly Gln Phe Ser Leu Ala Val Val Ser Leu Asn Ile
            820                 825                 830

Thr Ser Leu Gly Leu Arg Ser Leu Lys Glu Ile Ser Asp Gly Asp Val
        835                 840                 845
```

```
Ile Ile Ser Gly Asn Lys Asn Leu Cys Tyr Ala Asn Thr Ile Asn Trp
    850                 855                 860

Lys Lys Leu Phe Gly Thr Ser Gly Gln Lys Thr Lys Ile Ile Ser Asn
865                 870                 875                 880

Arg Gly Glu Asn Ser Cys Lys Ala Thr Gly Gln Val Cys His Ala Leu
                885                 890                 895

Cys Ser Pro Glu Gly Cys Trp Gly Pro Glu Pro Arg Asp Cys Val Ser
            900                 905                 910

Cys Arg Asn Val Ser Arg Gly Arg Glu Cys Val Asp Lys Cys Asn Leu
        915                 920                 925

Leu Glu Gly Glu Pro Arg Glu Phe Val Glu Asn Ser Glu Cys Ile Gln
    930                 935                 940

Cys His Pro Glu Cys Leu Pro Gln Ala Met Asn Ile Thr Cys Thr Gly
945                 950                 955                 960

Arg Gly Pro Asp Asn Cys Ile Gln Cys Ala His Tyr Ile Asp Gly Pro
                965                 970                 975

His Cys Val Lys Thr Cys Pro Ala Gly Val Met Gly Glu Asn Asn Thr
            980                 985                 990

Leu Val Trp Lys Tyr Ala Asp Ala Gly His Val Cys His Leu Cys His
        995                 1000                1005

Pro Asn Cys Thr Tyr Gly Cys Thr Gly Pro Gly Leu Glu Gly Cys Pro
    1010                1015                1020

Thr Asn Gly Pro Lys Ile Pro Ser Ile Ala Thr Gly Met Val Gly Ala
1025                1030                1035                1040

Leu Leu Leu Leu Leu Val Val Ala Leu Gly Ile Gly Leu Phe Met
                1045                1050                1055
```

<210> SEQ ID NO 45
<211> LENGTH: 10015
<212> TYPE: DNA
<213> ORGANISM: Artificial Sequence
<220> FEATURE:
<223> OTHER INFORMATION: Synthetic sequence

<400> SEQUENCE: 45

```
gttagaccag atctgagcct gggagctctc tggctaacta gggaacccac tgcttaagcc      60

tcaataaagc ttgccttgag tgcttcaagt agtgtgtgcc cgtctgttgt gtgactctgg     120

taactagaga tccctcagac ccttttagtc agtgtggaaa atctctagca gtggcgcccg     180

aacagggact tgaaagcgaa agggaaacca gaggagctct ctcgacgcag gactcggctt     240

gctgaagcgc gcacggcaag aggcgagggg cggcgactgg tgagtacgcc aaaaattttg     300

actagcggag gctagaagga gagagatggg tgcgagagcg tcagtattaa gcgggggaga     360

attagatcga tgggaaaaaa ttcggttaag gccaggggga aagaaaaaat ataaattaaa     420

acatatagta tgggcaagca gggagctaga acgattcgca gttaatcctg gcctgttaga     480

aacatcagaa ggctgtagac aaatactggg acagctacaa ccatcccttc agacaggatc     540

agaagaactt agatcattat ataatacagt agcaaccctc tattgtgtgc atcaaaggat     600

agagataaaa gacaccaagg aagctttaga caagatagag gaagagcaaa acaaaagtaa     660

gaaaaaagca cagcaagcag cagctgacac aggacacagc aatcaggtca gccaaaatta     720

ccctatagtg cagaacatcc aggggcaaat ggtacatcag gccatatcac ctagaacttt     780

aaatgcatgg gtaaaagtag tagaagagaa ggctttcagc ccagaagtga tacccatgtt     840

ttcagcatta tcagaaggag ccaccccaca agatttaaac accatgctaa acacagtggg     900
```

```
gggacatcaa gcagccatgc aaatgttaaa agagaccatc aatgaggaag ctgcaggcaa    960
agagaagagt ggtgcagaga gaaaaaagag cagtgggaat aggagctttg ttccttgggt   1020
tcttgggagc agcaggaagc actatgggcg cagcgtcaat gacgctgacg gtacaggcca   1080
gacaattatt gtctggtata gtgcagcagc agaacaattt gctgagggct attgaggcgc   1140
aacagcatct gttgcaactc acagtctggg gcatcaagca gctccaggca agaatcctgg   1200
ctgtggaaag atacctaaag gatcaacagc tcctggggat ttggggttgc tctggaaaac   1260
tcatttgcac cactgctgtg ccttggatct acaaatggca gtattcatcc acaattttaa   1320
aagaaaaggg gggattgggg ggtacagtgc aggggaaaga atagtagaca taatagcaac   1380
agacatacaa actaaagaat tacaaaaaca aattacaaaa attcaaaatt ttcgggttta   1440
ttacagggac agcagagatc cagtttgggg atcaattgca tgaagaatct gcttagggtt   1500
aggcgttttg cgctgcttcg cgaggatctg cgatcgctcc ggtgcccgtc agtgggcaga   1560
gcgcacatcg cccacagtcc ccgagaagtt ggggggaggg gtcggcaatt gaaccggtgc   1620
ctagagaagg tggcgcgggg taaactggga aagtgatgtc gtgtactggc tccgcctttt   1680
tcccgagggt gggggagaac cgtatataag tgcagtagtc gccgtgaacg ttcttttttcg  1740
caacgggttt gccgccagaa cacagctgaa gcttcgaggg gctcgcatct ctccttcacg   1800
cgcccgccgc cctacctgag gccgccatcc acgccggttg agtcgcgttc tgccgcctcc   1860
cgcctgtggt gcctcctgaa ctgcgtccgc cgtctaggta agtttaaagc tcaggtcgag   1920
accgggcctt tgtccggcgc tcccttggag cctacctaga ctcagccggc tctccacgct   1980
ttgcctgacc ctgcttgctc aactctacgt ctttgtttcg ttttctgttc tgcgccgtta   2040
cagatccaag ctgtgaccgg cgcctacggc tagcgaattc gccaccatgc tgctgctggt   2100
gacaagcctg ctgctgtgcg agctgcccca ccccgccttt ctgctgatcc cccagagcgt   2160
gaaagagtcc gagggcgacc tggtcacacc agccggcaac ctgaccctga cctgtaccgc   2220
cagcggcagc gacatcaacg actaccccat ctcttgggtc cgccaggctc ctggcaaggg   2280
actggaatgg atcggcttca tcaacagcgg cggcagcact tggtacgcca gctgggtcaa   2340
aggccggttc accatcagcc ggaccagcac caccgtggac ctgaagatga caagcctgac   2400
caccgacgac accgccacct acttttgcgc cagaggctac agcacctact acggcgactt   2460
caacatctgg ggccctggca ccctggtcac aatctctagc ggcggaggcg gcagcggagg   2520
tggaggaagt ggcggcggag gatccgagct ggtcatgacc cagaccccca gcagcacatc   2580
tggcgccgtg ggcggcaccg tgaccatcaa ttgccaggcc agccagagca tcgacagcaa   2640
cctggcctgg ttccagcaga agcccggcca gcccccccacc ctgctgatct acagagcctc   2700
caacctggcc agcggcgtgc caagcagatt cagcggcagc agatctggca ccgagtacac   2760
cctgaccatc tccggcgtgc agagagagga cgccgctacc tattactgcc tgggcggcgt   2820
gggcaacgtg tcctacagaa ccagcttcgg cggaggtact gaggtggtcg tcaaatacgg   2880
accgccctgc ccccccttgcc ctgcccccga gttcctgggc ggacccagcg tgttcctgtt   2940
cccccccaag cccaaggaca ccctgatgat cagccggacc cccgaggtga cctgcgtggt   3000
ggtggacgtg agccaggaag atcccgaggt ccagttcaat tggtacgtgg acggcgtgga   3060
agtgcacaac gccaagacca agcccagaga ggaacagttc aacagcacct accgggtggt   3120
gtctgtgctg accgtgctgc accaggactg gctgaacggc aaagaataca agtgcaaggt   3180
gtccaacaag ggcctgccca gcagcatcga aaagaccatc agcaaggcca agggccagcc   3240
```

-continued

```
tcgcgagccc caggtgtaca ccctgcctcc ctcccaggaa gagatgacca agaaccaggt   3300
gtccctgacc tgcctggtga agggcttcta ccccagcgac atcgccgtgg agtgggagag   3360
caacggccag cctgagaaca actacaagac cacccctccc gtgctggaca gcgacggcag   3420
cttcttcctg tacagccggc tgaccgtgga caagagccgg tggcaggaag gcaacgtctt   3480
tagctgcagc gtgatgcacg aggccctgca caaccactac acccagaaga gcctgagcct   3540
gtccctgggc aagatgttct gggtgctggt ggtggtgggc ggggtgctgg cctgctacag   3600
cctgctggtg acagtggcct tcatcatctt ttgggtgaaa cggggcagaa agaaactcct   3660
gtatatattc aaacaaccat ttatgagacc agtacaaact actcaagagg aagatggctg   3720
tagctgccga tttccagaag aagaagaagg aggatgtgaa ctgcgggtga agttcagcag   3780
aagcgccgac gcccctgcct accagcaggg ccagaatcag ctgtacaacg agctgaacct   3840
gggcagaagg gaagagtacg acgtcctgga taagcggaga ggccgggacc ctgagatggg   3900
cggcaagcct cggcggaaga acccccagga aggcctgtat aacgaactgc agaaagacaa   3960
gatggccgag gcctacagcg agatcggcat gaagggcgag cggaggcggg gcaagggcca   4020
cgacggcctg tatcagggcc tgtccaccgc caccaaggat acctacgacg ccctgcacat   4080
gcaggccctg cccccaaggc tcgagggcgg cggagagggc agaggaagtc ttctaacatg   4140
cggtgacgtg gaggagaatc ccggccctag gatgcttctc ctggtgacaa gccttctgct   4200
ctgtgagtta ccacacccag cattcctcct gatcccacgc aaagtgtgta acggaatagg   4260
tattggtgaa tttaaagact cactctccat aaatgctacg aatattaaac acttcaaaaa   4320
ctgcacctcc atcagtggcg atctccacat cctgccggtg gcatttaggg gtgactcctt   4380
cacacatact cctcctctgg atccacagga actggatatt ctgaaaaccg taaaggaaat   4440
cacagggttt ttgctgattc aggcttggcc tgaaaacagg acggacctcc atgcctttga   4500
gaacctagaa atcatacgcg gcaggaccaa gcaacatggt cagttttctc ttgcagtcgt   4560
cagcctgaac ataacatcct tgggattacg ctccctcaag gagataagtg atggagatgt   4620
gataatttca ggaaacaaaa atttgtgcta tgcaaataca ataaactgga aaaaactgtt   4680
tgggacctcc ggtcagaaaa ccaaaattat aagcaacaga ggtgaaaaca gctgcaaggc   4740
cacaggccag gtctgccatg ccttgtgctc ccccgagggc tgctggggcc cggagcccag   4800
ggactgcgtc tcttgccgga atgtcagccg aggcagggaa tgcgtggaca agtgcaacct   4860
tctggagggt gagccaaggg agtttgtgga gaactctgag tgcatacagt gccacccaga   4920
gtgcctgcct caggccatga acatcacctg cacaggacgg ggaccagaca actgtatcca   4980
gtgtgcccac tacattgacg gcccccactg cgtcaagacc tgcccggcag gagtcatggg   5040
agaaaacaac accctggtct ggaagtacgc agacgccggc catgtgtgcc acctgtgcca   5100
tccaaactgc acctacggat gcactgggcc aggtcttgaa ggctgtccaa cgaatgggcc   5160
taagatcccg tccatcgcca ctgggatggt gggggccctc ctcttgctgc tggtggtggc   5220
cctggggatc ggcctcttca tgtgagcggc cgctctagac ccgggctgca ggaattcgat   5280
atcaagctta tcgataatca acctctggat tacaaaattt gtgaaagatt gactggtatt   5340
cttaactatg ttgctccttt tacgctatgt ggatacgctg ctttaatgcc tttgtatcat   5400
gctattgctt cccgtatggc tttcattttc tcctccttgt ataaatcctg gttgctgtct   5460
ctttatgagg agttgtggcc cgttgtcagg caacgtggcg tggtgtgcac tgtgtttgct   5520
gacgcaaccc ccactggttg gggcattgcc accacctgtc agctcctttc cgggactttc   5580
gctttccccc tccctattgc cacggcggaa ctcatcgccg cctgccttgc ccgctgctgg   5640
```

```
acaggggctc ggctgttggg cactgacaat tccgtggtgt tgtcggggaa atcatcgtcc   5700
tttccttggc tgctcgcctg tgttgccacc tggattctgc gcgggacgtc cttctgctac   5760
gtcccttcgg ccctcaatcc agcggacctt ccttcccgcg gcctgctgcc ggctctgcgg   5820
cctcttccgc gtcttcgcct tcgccctcag acgagtcgga tctccctttg ggccgcctcc   5880
ccgcatcgat accgtcgact agccgtacct ttaagaccaa tgacttacaa ggcagctgta   5940
gatcttagcc actttttaaa agaaaagggg ggactggaag ggctaattca ctcccaaaga   6000
agacaagatc tgctttttgc ctgtactggg tctctctggt tagaccagat ctgagcctgg   6060
gagctctctg gctaactagg gaacccactg cttaagcctc aataaagctt gccttgagtg   6120
cttcaagtag tgtgtgcccg tctgttgtgt gactctggta actagagatc cctcagaccc   6180
ttttagtcag tgtggaaaat ctctagcaga attcgatatc aagcttatcg ataccgtcga   6240
cctcgagggg gggcccggta cccaattcgc cctatagtga gtcgtattac aattcactgg   6300
ccgtcgtttt acaacgtcgt gactgggaaa accctggcgt tacccaactt aatcgccttg   6360
cagcacatcc ccctttcgcc agctggcgta atagcgaaga ggcccgcacc gatcgccctt   6420
cccaacagtt gcgcagcctg aatggcgaat ggaaattgta agcgttaata ttttgttaaa   6480
attcgcgtta aatttttgtt aaatcagctc attttttaac caataggccg aaatcggcaa   6540
aatcccttat aaatcaaaag aatagaccga gatagggttg agtgttgttc cagtttggaa   6600
caagagtcca ctattaaaga acgtggactc caacgtcaaa gggcgaaaaa ccgtctatca   6660
gggcgatggc ccactacgtg aaccatcacc ctaatcaagt tttttggggt cgaggtgccg   6720
taaagcacta aatcggaacc ctaaagggag cccccgattt agagcttgac ggggaaagcc   6780
ggcgaacgtg gcgagaaagg aagggaagaa agcgaaagga gcgggcgcta gggcgctggc   6840
aagtgtagcg gtcacgctgc gcgtaaccac cacacccgcc gcgcttaatg cgccgctaca   6900
gggcgcgtca ggtggcactt ttcggggaaa tgtgcgcgga acccctattt gtttattttt   6960
ctaaatacat tcaaatatgt atccgctcat gagacaataa ccctgataaa tgcttcaata   7020
atattgaaaa aggaagagta tgagtattca acatttccgt gtcgccctta ttcccttttt   7080
tgcggcattt tgccttcctg tttttgctca cccagaaacg ctggtgaaag taaaagatgc   7140
tgaagatcag ttgggtgcac gagtgggtta catcgaactg gatctcaaca gcggtaagat   7200
ccttgagagt tttcgccccg aagaacgttt tccaatgatg agcactttta aagttctgct   7260
atgtggcgcg gtattatccc gtattgacgc cgggcaagag caactcggtc gccgcataca   7320
ctattctcag aatgacttgg ttgagtactc accagtcaca gaaaagcatc ttacggatgg   7380
catgacagta agagaattat gcagtgctgc cataaccatg agtgataaca ctgcggccaa   7440
cttacttctg acaacgatcg gaggaccgaa ggagctaacc gcttttttgc acaacatggg   7500
ggatcatgta actcgccttg atcgttggga accggagctg aatgaagcca taccaaacga   7560
cgagcgtgac accacgatgc ctgtagcaat ggcaacaacg ttgcgcaaac tattaactgg   7620
cgaactactt actctagctt cccggcaaca attaatagac tggatggagg cggataaagt   7680
tgcaggacca cttctgcgct cggcccttcc ggctggctgg tttattgctg ataaatctgg   7740
agccggtgag cgtgggtctc gcggtatcat tgcagcactg gggccagatg gtaagccctc   7800
ccgtatcgta gttatctaca cgacggggag tcaggcaact atggatgaac gaaatagaca   7860
gatcgctgag ataggtgcct cactgattaa gcattggtaa ctgtcagacc aagtttactc   7920
atatatactt tagattgatt taaaacttca tttttaattt aaaaggatct aggtgaagat   7980
```

```
cctttttgat aatctcatga ccaaaatccc ttaacgtgag ttttcgttcc actgagcgtc   8040

agaccccgta gaaaagatca aaggatcttc ttgagatcct ttttttctgc gcgtaatctg   8100

ctgcttgcaa acaaaaaaac caccgctacc agcggtggtt tgtttgccgg atcaagagct   8160

accaactctt tttccgaagg taactggctt cagcagagcg cagataccaa atactgttct   8220

tctagtgtag ccgtagttag gccaccactt caagaactct gtagcaccgc ctacatacct   8280

cgctctgcta atcctgttac cagtggctgc tgccagtggc gataagtcgt gtcttaccgg   8340

gttggactca agacgatagt taccggataa ggcgcagcgg tcgggctgaa cggggggttc   8400

gtgcacacag cccagcttgg agcgaacgac ctacaccgaa ctgagatacc tacagcgtga   8460

gctatgagaa agcgccacgc ttcccgaagg gagaaaggcg gacaggtatc cggtaagcgg   8520

cagggtcgga acaggagagc gcacgaggga gcttccaggg ggaaacgcct ggtatcttta   8580

tagtcctgtc gggtttcgcc acctctgact tgagcgtcga tttttgtgat gctcgtcagg   8640

ggggcggagc ctatggaaaa acgccagcaa cgcggccttt ttacggttcc tggccttttg   8700

ctggcctttt gctcacatgt tctttcctgc gttatcccct gattctgtgg ataaccgtat   8760

taccgccttt gagtgagctg ataccgctcg ccgcagccga acgaccgagc gcagcgagtc   8820

agtgagcgag gaagcggaag agcgcccaat acgcaaaccg cctctccccg cgcgttggcc   8880

gattcattaa tgcagctggc acgacaggtt tcccgactgg aaagcgggca gtgagcgcaa   8940

cgcaattaat gtgagttagc tcactcatta ggcaccccag gctttacact ttatgcttcc   9000

ggctcgtatg ttgtgtggaa ttgtgagcgg ataacaattt cacacaggaa acagctatga   9060

ccatgattac gccaagctcg aaattaaccc tcactaaagg gaacaaaagc tggagctcca   9120

ccgcggtggc ggcctcgagg tcgagatccg gtcgaccagc aaccatagtc ccgcccctaa   9180

ctccgcccat cccgccccta actccgccca gttccgccca ttctccgccc catggctgac   9240

taattttttt tatttatgca gaggccgagg ccgcctcggc ctctgagcta ttccagaagt   9300

agtgaggagg cttttttgga ggcctaggct tttgcaaaaa gcttcgacgg tatcgattgg   9360

ctcatgtcca acattaccgc catgttgaca ttgattattg actagttatt aatagtaatc   9420

aattacgggg tcattagttc atagcccata tatggagttc cgcgttacat aacttacggt   9480

aaatggcccg cctggctgac cgcccaacga cccccgccca ttgacgtcaa taatgacgta   9540

tgttcccata gtaacgccaa tagggacttt ccattgacgt caatgggtgg agtatttacg   9600

gtaaactgcc cacttggcag tacatcaagt gtatcatatg ccaagtacgc cccctattga   9660

cgtcaatgac ggtaaatggc ccgcctggca ttatgcccag tacatgacct tatgggactt   9720

tcctacttgg cagtacatct acgtattagt catcgctatt accatggtga tgcggttttg   9780

gcagtacatc aatgggcgtg gatagcggtt tgactcacgg ggatttccaa gtctccaccc   9840

cattgacgtc aatgggagtt tgttttggca ccaaaatcaa cgggactttc caaaatgtcg   9900

taacaactcc gccccattga cgcaaatggg cggtaggcgt gtacggaatt cggagtggcg   9960

agccctcaga tcctgcatat aagcagctgc tttttgcctg tactgggtct ctctg       10015
```

<210> SEQ ID NO 46
<211> LENGTH: 945
<212> TYPE: PRT
<213> ORGANISM: Artificial Sequence
<220> FEATURE:
<223> OTHER INFORMATION: Synthetic sequence

<400> SEQUENCE: 46

Met Leu Leu Leu Val Thr Ser Leu Leu Leu Cys Glu Leu Pro His Pro

```
1               5                   10                  15

Ala Phe Leu Leu Ile Pro Gln Ser Val Lys Glu Ser Glu Gly Asp Leu
            20                  25                  30

Val Thr Pro Ala Gly Asn Leu Thr Leu Thr Cys Thr Ala Ser Gly Ser
        35                  40                  45

Asp Ile Asn Asp Tyr Pro Ile Ser Trp Val Arg Gln Ala Pro Gly Lys
    50                  55                  60

Gly Leu Glu Trp Ile Gly Phe Ile Asn Ser Gly Gly Ser Thr Trp Tyr
65                  70                  75                  80

Ala Ser Trp Val Lys Gly Arg Phe Thr Ile Ser Arg Thr Ser Thr Thr
                85                  90                  95

Val Asp Leu Lys Met Thr Ser Leu Thr Thr Asp Asp Thr Ala Thr Tyr
            100                 105                 110

Phe Cys Ala Arg Gly Tyr Ser Thr Tyr Tyr Gly Asp Phe Asn Ile Trp
        115                 120                 125

Gly Pro Gly Thr Leu Val Thr Ile Ser Ser Gly Gly Gly Gly Ser Gly
    130                 135                 140

Gly Gly Gly Ser Gly Gly Gly Gly Ser Glu Leu Val Met Thr Gln Thr
145                 150                 155                 160

Pro Ser Ser Thr Ser Gly Ala Val Gly Gly Thr Val Thr Ile Asn Cys
                165                 170                 175

Gln Ala Ser Gln Ser Ile Asp Ser Asn Leu Ala Trp Phe Gln Gln Lys
            180                 185                 190

Pro Gly Gln Pro Pro Thr Leu Leu Ile Tyr Arg Ala Ser Asn Leu Ala
        195                 200                 205

Ser Gly Val Pro Ser Arg Phe Ser Gly Ser Arg Ser Gly Thr Glu Tyr
    210                 215                 220

Thr Leu Thr Ile Ser Gly Val Gln Arg Glu Asp Ala Ala Thr Tyr Tyr
225                 230                 235                 240

Cys Leu Gly Gly Val Gly Asn Val Ser Tyr Arg Thr Ser Phe Gly Gly
                245                 250                 255

Gly Thr Glu Val Val Val Lys Glu Ser Lys Tyr Gly Pro Pro Cys Pro
            260                 265                 270

Pro Cys Pro Gly Gln Pro Arg Glu Pro Gln Val Tyr Thr Leu Pro Pro
        275                 280                 285

Ser Gln Glu Glu Met Thr Lys Asn Gln Val Ser Leu Thr Cys Leu Val
    290                 295                 300

Lys Gly Phe Tyr Pro Ser Asp Ile Ala Val Glu Trp Glu Ser Asn Gly
305                 310                 315                 320

Gln Pro Glu Asn Asn Tyr Lys Thr Thr Pro Pro Val Leu Asp Ser Asp
                325                 330                 335

Gly Ser Phe Phe Leu Tyr Ser Arg Leu Thr Val Asp Lys Ser Arg Trp
            340                 345                 350

Gln Glu Gly Asn Val Phe Ser Cys Ser Val Met His Glu Ala Leu His
        355                 360                 365

Asn His Tyr Thr Gln Lys Ser Leu Ser Leu Ser Leu Gly Lys Met Phe
    370                 375                 380

Trp Val Leu Val Val Val Gly Gly Val Leu Ala Cys Tyr Ser Leu Leu
385                 390                 395                 400

Val Thr Val Ala Phe Ile Ile Phe Trp Val Lys Arg Gly Arg Lys Lys
                405                 410                 415

Leu Leu Tyr Ile Phe Lys Gln Pro Phe Met Arg Pro Val Gln Thr Thr
            420                 425                 430
```

```
Gln Glu Glu Asp Gly Cys Ser Cys Arg Phe Pro Glu Glu Glu Glu Gly
        435                 440                 445

Gly Cys Glu Leu Arg Val Lys Phe Ser Arg Ser Ala Asp Ala Pro Ala
    450                 455                 460

Tyr Gln Gln Gly Gln Asn Gln Leu Tyr Asn Glu Leu Asn Leu Gly Arg
465                 470                 475                 480

Arg Glu Glu Tyr Asp Val Leu Asp Lys Arg Arg Gly Arg Asp Pro Glu
                485                 490                 495

Met Gly Gly Lys Pro Arg Arg Lys Asn Pro Gln Glu Gly Leu Tyr Asn
            500                 505                 510

Glu Leu Gln Lys Asp Lys Met Ala Glu Ala Tyr Ser Glu Ile Gly Met
        515                 520                 525

Lys Gly Glu Arg Arg Arg Gly Lys Gly His Asp Gly Leu Tyr Gln Gly
    530                 535                 540

Leu Ser Thr Ala Thr Lys Asp Thr Tyr Asp Ala Leu His Met Gln Ala
545                 550                 555                 560

Leu Pro Pro Arg Leu Glu Gly Gly Gly Glu Gly Arg Gly Ser Leu Leu
                565                 570                 575

Thr Cys Gly Asp Val Glu Glu Asn Pro Gly Pro Arg Met Leu Leu Leu
            580                 585                 590

Val Thr Ser Leu Leu Leu Cys Glu Leu Pro His Pro Ala Phe Leu Leu
        595                 600                 605

Ile Pro Arg Lys Val Cys Asn Gly Ile Gly Ile Gly Glu Phe Lys Asp
    610                 615                 620

Ser Leu Ser Ile Asn Ala Thr Asn Ile Lys His Phe Lys Asn Cys Thr
625                 630                 635                 640

Ser Ile Ser Gly Asp Leu His Ile Leu Pro Val Ala Phe Arg Gly Asp
                645                 650                 655

Ser Phe Thr His Thr Pro Pro Leu Asp Pro Gln Glu Leu Asp Ile Leu
            660                 665                 670

Lys Thr Val Lys Glu Ile Thr Gly Phe Leu Leu Ile Gln Ala Trp Pro
        675                 680                 685

Glu Asn Arg Thr Asp Leu His Ala Phe Glu Asn Leu Glu Ile Ile Arg
    690                 695                 700

Gly Arg Thr Lys Gln His Gly Gln Phe Ser Leu Ala Val Val Ser Leu
705                 710                 715                 720

Asn Ile Thr Ser Leu Gly Leu Arg Ser Leu Lys Glu Ile Ser Asp Gly
                725                 730                 735

Asp Val Ile Ile Ser Gly Asn Lys Asn Leu Cys Tyr Ala Asn Thr Ile
            740                 745                 750

Asn Trp Lys Lys Leu Phe Gly Thr Ser Gly Gln Lys Thr Lys Ile Ile
        755                 760                 765

Ser Asn Arg Gly Glu Asn Ser Cys Lys Ala Thr Gly Gln Val Cys His
    770                 775                 780

Ala Leu Cys Ser Pro Glu Gly Cys Trp Gly Pro Glu Pro Arg Asp Cys
785                 790                 795                 800

Val Ser Cys Arg Asn Val Ser Arg Gly Arg Glu Cys Val Asp Lys Cys
                805                 810                 815

Asn Leu Leu Glu Gly Glu Pro Arg Glu Phe Val Glu Asn Ser Glu Cys
            820                 825                 830

Ile Gln Cys His Pro Glu Cys Leu Pro Gln Ala Met Asn Ile Thr Cys
        835                 840                 845
```

```
Thr Gly Arg Gly Pro Asp Asn Cys Ile Gln Cys Ala His Tyr Ile Asp
    850                 855                 860

Gly Pro His Cys Val Lys Thr Cys Pro Ala Gly Val Met Gly Glu Asn
865                 870                 875                 880

Asn Thr Leu Val Trp Lys Tyr Ala Asp Ala Gly His Val Cys His Leu
                885                 890                 895

Cys His Pro Asn Cys Thr Tyr Gly Cys Thr Gly Pro Gly Leu Glu Gly
            900                 905                 910

Cys Pro Thr Asn Gly Pro Lys Ile Pro Ser Ile Ala Thr Gly Met Val
        915                 920                 925

Gly Ala Leu Leu Leu Leu Leu Val Val Ala Leu Gly Ile Gly Leu Phe
    930                 935                 940

Met
945


<210> SEQ ID NO 47
<211> LENGTH: 9685
<212> TYPE: DNA
<213> ORGANISM: Artificial Sequence
<220> FEATURE:
<223> OTHER INFORMATION: Synthetic sequence

<400> SEQUENCE: 47

gttagaccag atctgagcct gggagctctc tggctaacta gggaacccac tgcttaagcc     60

tcaataaagc ttgccttgag tgcttcaagt agtgtgtgcc cgtctgttgt gtgactctgg    120

taactagaga tccctcagac ccttttagtc agtgtggaaa atctctagca gtggcgcccg    180

aacagggact tgaaagcgaa agggaaacca gaggagctct ctcgacgcag gactcggctt    240

gctgaagcgc gcacggcaag aggcgagggg cggcgactgg tgagtacgcc aaaaattttg    300

actagcggag gctagaagga gagagatggg tgcgagagcg tcagtattaa gcgggggaga    360

attagatcga tgggaaaaaa ttcggttaag gccaggggga aagaaaaaat ataaattaaa    420

acatatagta tgggcaagca gggagctaga acgattcgca gttaatcctg gcctgttaga    480

aacatcagaa ggctgtagac aaatactggg acagctacaa ccatcccttc agacaggatc    540

agaagaactt agatcattat ataatacagt agcaaccctc tattgtgtgc atcaaaggat    600

agagataaaa gacaccaagg aagctttaga caagatagag gaagagcaaa acaaaagtaa    660

gaaaaaagca cagcaagcag cagctgacac aggacacagc aatcaggtca gccaaaatta    720

ccctatagtg cagaacatcc aggggcaaat ggtacatcag gccatatcac ctagaacttt    780

aaatgcatgg gtaaaagtag tagaagagaa ggctttcagc ccagaagtga tacccatgtt    840

ttcagcatta tcagaaggag ccaccccaca agatttaaac accatgctaa acacagtggg    900

gggacatcaa gcagccatgc aaatgttaaa agagaccatc aatgaggaag ctgcaggcaa    960

agagaagagt ggtgcagaga gaaaaaagag cagtgggaat aggagctttg ttccttgggt   1020

tcttgggagc agcaggaagc actatgggcg cagcgtcaat gacgctgacg gtacaggcca   1080

gacaattatt gtctggtata gtgcagcagc agaacaattt gctgagggct attgaggcgc   1140

aacagcatct gttgcaactc acagtctggg gcatcaagca gctccaggca agaatcctgg   1200

ctgtggaaag atacctaaag gatcaacagc tcctggggat ttggggttgc tctggaaaac   1260

tcatttgcac cactgctgtg ccttggatct acaaatggca gtattcatcc acaattttaa   1320

aagaaaaggg gggattgggg ggtacagtgc aggggaaaga atagtagaca taatagcaac   1380

agacatacaa actaaagaat tacaaaaaca aattacaaaa attcaaaatt ttcgggttta   1440
```

-continued

```
ttacagggac agcagagatc cagtttgggg atcaattgca tgaagaatct gcttagggtt   1500
aggcgttttg cgctgcttcg cgaggatctg cgatcgctcc ggtgcccgtc agtgggcaga   1560
gcgcacatcg cccacagtcc ccgagaagtt ggggggaggg gtcggcaatt gaaccggtgc   1620
ctagagaagg tggcgcgggg taaactggga aagtgatgtc gtgtactggc tccgcctttt   1680
tcccgagggt gggggagaac cgtatataag tgcagtagtc gccgtgaacg ttcttttttcg   1740
caacgggttt gccgccagaa cacagctgaa gcttcgaggg gctcgcatct ctccttcacg   1800
cgcccgccgc cctacctgag gccgccatcc acgccggttg agtcgcgttc tgccgcctcc   1860
cgcctgtggt gcctcctgaa ctgcgtccgc cgtctaggta agtttaaagc tcaggtcgag   1920
accgggcctt tgtccggcgc tcccttggag cctacctaga ctcagccggc tctccacgct   1980
ttgcctgacc ctgcttgctc aactctacgt ctttgtttcg ttttctgttc tgcgccgtta   2040
cagatccaag ctgtgaccgg cgcctacggc tagcgaattc gccaccatgc tgctgctggt   2100
gacaagcctg ctgctgtgcg agctgcccca ccccgccttt ctgctgatcc cccagagcgt   2160
gaaagagtcc gagggcgacc tggtcacacc agccggcaac ctgaccctga cctgtaccgc   2220
cagcggcagc gacatcaacg actaccccat ctcttgggtc cgccaggctc ctggcaaggg   2280
actggaatgg atcggcttca tcaacagcgg cggcagcact tggtacgcca gctgggtcaa   2340
aggccggttc accatcagcc ggaccagcac caccgtggac ctgaagatga caagcctgac   2400
caccgacgac accgccacct acttttgcgc cagaggctac agcacctact acggcgactt   2460
caacatctgg ggccctggca ccctggtcac aatctctagc ggcggaggcg gcagcggagg   2520
tggaggaagt ggcggcggag gatccgagct ggtcatgacc cagaccccca gcagcacatc   2580
tggcgccgtg ggcggcaccg tgaccatcaa ttgccaggcc agccagagca tcgacagcaa   2640
cctggcctgg ttccagcaga agcccggcca gccccccacc ctgctgatct acagagcctc   2700
caacctggcc agcggcgtgc caagcagatt cagcggcagc agatctggca ccgagtacac   2760
cctgaccatc tccggcgtgc agagagagga cgccgctacc tattactgcc tgggcggcgt   2820
gggcaacgtg tcctacagaa ccagcttcgg cggaggtact gaggtggtcg tcaaatacgg   2880
accgccctgc ccccttgcc ctggccagcc tcgcgagccc caggtgtaca ccctgcctcc   2940
ctcccaggaa gagatgacca agaaccaggt gtccctgacc tgcctggtga agggcttcta   3000
ccccagcgac atcgccgtgg agtgggagag caacggccag cctgagaaca actacaagac   3060
cacccctccc gtgctggaca gcgacggcag cttcttcctg tacagccggc tgaccgtgga   3120
caagagccgg tggcaggaag gcaacgtctt tagctgcagc gtgatgcacg aggccctgca   3180
caaccactac acccagaaga gcctgagcct gtccctgggc aagatgttct gggtgctggt   3240
ggtggtgggc ggggtgctgg cctgctacag cctgctggtg acagtggcct tcatcatctt   3300
ttgggtgaaa cggggcagaa agaaactcct gtatatattc aaacaaccat ttatgagacc   3360
agtacaaact actcaagagg aagatggctg tagctgccga tttccagaag aagaagaagg   3420
aggatgtgaa ctgcgggtga agttcagcag aagcgccgac gcccctgcct accagcaggg   3480
ccagaatcag ctgtacaacg agctgaacct gggcagaagg gaagagtacg acgtcctgga   3540
taagcggaga ggccgggacc ctgagatggg cggcaagcct cggcggaaga acccccagga   3600
aggcctgtat aacgaactgc agaaagacaa gatggccgag gcctacagcg agatcggcat   3660
gaagggcgag cggaggcggg gcaagggcca cgacggcctg tatcagggcc tgtccaccgc   3720
caccaaggat acctacgacg ccctgcacat gcaggccctg cccccaaggc tcgagggcgg   3780
cggagagggc agaggaagtc ttctaacatg cggtgacgtg gaggagaatc ccggccctag   3840
```

```
gatgcttctc ctggtgacaa gccttctgct ctgtgagtta ccacacccag cattcctcct   3900
gatcccacgc aaagtgtgta acggaatagg tattggtgaa tttaaagact cactctccat   3960
aaatgctacg aatattaaac acttcaaaaa ctgcacctcc atcagtggcg atctccacat   4020
cctgccggtg gcatttaggg gtgactcctt cacacatact cctcctctgg atccacagga   4080
actggatatt ctgaaaaccg taaaggaaat cacagggttt ttgctgattc aggcttggcc   4140
tgaaaacagg acggacctcc atgcctttga gaacctagaa atcatacgcg gcaggaccaa   4200
gcaacatggt cagttttctc ttgcagtcgt cagcctgaac ataacatcct tgggattacg   4260
ctccctcaag gagataagtg atggagatgt gataatttca ggaaacaaaa atttgtgcta   4320
tgcaaataca ataaactgga aaaaactgtt tgggacctcc ggtcagaaaa ccaaaattat   4380
aagcaacaga ggtgaaaaca gctgcaaggc cacaggccag gtctgccatg ccttgtgctc   4440
ccccgagggc tgctggggcc cggagcccag ggactgcgtc tcttgccgga atgtcagccg   4500
aggcagggaa tgcgtggaca agtgcaacct tctggagggt gagccaaggg agtttgtgga   4560
gaactctgag tgcatacagt gccacccaga gtgcctgcct caggccatga acatcacctg   4620
cacaggacgg ggaccagaca actgtatcca gtgtgcccac tacattgacg gcccccactg   4680
cgtcaagacc tgcccggcag gagtcatggg agaaaacaac accctggtct ggaagtacgc   4740
agacgccggc catgtgtgcc acctgtgcca tccaaactgc acctacggat gcactgggcc   4800
aggtcttgaa ggctgtccaa cgaatgggcc taagatcccg tccatcgcca ctgggatggt   4860
gggggccctc ctcttgctgc tggtggtggc cctggggatc ggcctcttca tgtgagcggc   4920
cgctctagac ccgggctgca ggaattcgat atcaagctta tcgataatca acctctggat   4980
tacaaaattt gtgaaagatt gactggtatt cttaactatg ttgctccttt tacgctatgt   5040
ggatacgctg ctttaatgcc tttgtatcat gctattgctt cccgtatggc tttcattttc   5100
tcctccttgt ataaatcctg gttgctgtct ctttatgagg agttgtggcc cgttgtcagg   5160
caacgtggcg tggtgtgcac tgtgtttgct gacgcaaccc ccactggttg gggcattgcc   5220
accacctgtc agctcctttc cgggactttc gctttccccc tccctattgc cacggcggaa   5280
ctcatcgccg cctgccttgc ccgctgctgg acaggggctc ggctgttggg cactgacaat   5340
tccgtggtgt tgtcggggaa atcatcgtcc tttccttggc tgctcgcctg tgttgccacc   5400
tggattctgc gcgggacgtc cttctgctac gtcccttcgg ccctcaatcc agcggacctt   5460
ccttcccgcg gcctgctgcc ggctctgcgg cctcttccgc gtcttcgcct tcgccctcag   5520
acgagtcgga tctccctttg ggccgcctcc ccgcatcgat accgtcgact agccgtacct   5580
ttaagaccaa tgacttacaa ggcagctgta gatcttagcc actttttaaa agaaaagggg   5640
ggactggaag ggctaattca ctcccaaaga agacaagatc tgctttttgc ctgtactggg   5700
tctctctggt tagaccagat ctgagcctgg gagctctctg gctaactagg gaacccactg   5760
cttaagcctc aataaagctt gccttgagtg cttcaagtag tgtgtgcccg tctgttgtgt   5820
gactctggta actagagatc cctcagaccc ttttagtcag tgtggaaaat ctctagcaga   5880
attcgatatc aagcttatcg ataccgtcga cctcgagggg gggcccggta cccaattcgc   5940
cctatagtga gtcgtattac aattcactgg ccgtcgtttt acaacgtcgt gactgggaaa   6000
accctggcgt tacccaactt aatcgccttg cagcacatcc ccctttcgcc agctggcgta   6060
atagcgaaga ggcccgcacc gatcgccctt cccaacagtt gcgcagcctg aatggcgaat   6120
ggaaattgta agcgttaata ttttgttaaa attcgcgtta aatttttgtt aaatcagctc   6180
```

-continued

```
atttttaac caataggccg aaatcggcaa aatcccttat aaatcaaaag aatagaccga   6240
gatagggttg agtgttgttc cagtttggaa caagagtcca ctattaaaga acgtggactc   6300
caacgtcaaa gggcgaaaaa ccgtctatca gggcgatggc ccactacgtg aaccatcacc   6360
ctaatcaagt tttttggggt cgaggtgccg taaagcacta aatcggaacc ctaaagggag   6420
cccccgattt agagcttgac ggggaaagcc ggcgaacgtg gcgagaaagg aagggaagaa   6480
agcgaaagga gcgggcgcta gggcgctggc aagtgtagcg gtcacgctgc gcgtaaccac   6540
cacacccgcc gcgcttaatg cgccgctaca gggcgcgtca ggtggcactt ttcggggaaa   6600
tgtgcgcgga acccctattt gtttattttt ctaaatacat tcaaatatgt atccgctcat   6660
gagacaataa ccctgataaa tgcttcaata atattgaaaa aggaagagta tgagtattca   6720
acatttccgt gtcgccctta ttcccttttt tgcggcattt tgccttcctg tttttgctca   6780
cccagaaacg ctggtgaaag taaaagatgc tgaagatcag ttgggtgcac gagtgggtta   6840
catcgaactg gatctcaaca gcggtaagat ccttgagagt tttcgccccg aagaacgttt   6900
tccaatgatg agcactttta aagttctgct atgtggcgcg gtattatccc gtattgacgc   6960
cgggcaagag caactcggtc gccgcataca ctattctcag aatgacttgg ttgagtactc   7020
accagtcaca gaaaagcatc ttacggatgg catgacagta agagaattat gcagtgctgc   7080
cataaccatg agtgataaca ctgcggccaa cttacttctg acaacgatcg gaggaccgaa   7140
ggagctaacc gcttttttgc acaacatggg ggatcatgta actcgccttg atcgttggga   7200
accggagctg aatgaagcca taccaaacga cgagcgtgac accacgatgc ctgtagcaat   7260
ggcaacaacg ttgcgcaaac tattaactgg cgaactactt actctagctt cccggcaaca   7320
attaatagac tggatggagg cggataaagt tgcaggacca cttctgcgct cggcccttcc   7380
ggctggctgg tttattgctg ataaatctgg agccggtgag cgtgggtctc gcggtatcat   7440
tgcagcactg gggccagatg gtaagccctc ccgtatcgta gttatctaca cgacggggag   7500
tcaggcaact atggatgaac gaaatagaca gatcgctgag ataggtgcct cactgattaa   7560
gcattggtaa ctgtcagacc aagtttactc atatatactt tagattgatt taaaacttca   7620
tttttaattt aaaaggatct aggtgaagat cctttttgat aatctcatga ccaaaatccc   7680
ttaacgtgag ttttcgttcc actgagcgtc agaccccgta gaaaagatca aaggatcttc   7740
ttgagatcct ttttttctgc gcgtaatctg ctgcttgcaa acaaaaaaac caccgctacc   7800
agcggtggtt tgtttgccgg atcaagagct accaactctt tttccgaagg taactggctt   7860
cagcagagcg cagataccaa atactgttct tctagtgtag ccgtagttag gccaccactt   7920
caagaactct gtagcaccgc ctacatacct cgctctgcta atcctgttac cagtggctgc   7980
tgccagtggc gataagtcgt gtcttaccgg gttggactca agacgatagt taccggataa   8040
ggcgcagcgg tcgggctgaa cggggggttc gtgcacacag cccagcttgg agcgaacgac   8100
ctacaccgaa ctgagatacc tacagcgtga gctatgagaa agcgccacgc ttcccgaagg   8160
gagaaaggcg gacaggtatc cggtaagcgg cagggtcgga acaggagagc gcacgaggga   8220
gcttccaggg ggaaacgcct ggtatcttta tagtcctgtc gggtttcgcc acctctgact   8280
tgagcgtcga tttttgtgat gctcgtcagg ggggcggagc ctatggaaaa acgccagcaa   8340
cgcggccttt ttacggttcc tggccttttg ctggcctttt gctcacatgt tctttcctgc   8400
gttatcccct gattctgtgg ataaccgtat taccgccttt gagtgagctg ataccgctcg   8460
ccgcagccga acgaccgagc gcagcgagtc agtgagcgag gaagcggaag agcgcccaat   8520
acgcaaaccg cctctccccg cgcgttggcc gattcattaa tgcagctggc acgacaggtt   8580
```

```
tcccgactgg aaagcgggca gtgagcgcaa cgcaattaat gtgagttagc tcactcatta   8640

ggcaccccag gctttacact ttatgcttcc ggctcgtatg ttgtgtggaa ttgtgagcgg   8700

ataacaattt cacacaggaa acagctatga ccatgattac gccaagctcg aaattaaccc   8760

tcactaaagg gaacaaaagc tggagctcca ccgcggtggc ggcctcgagg tcgagatccg   8820

gtcgaccagc aaccatagtc ccgcccctaa ctccgcccat cccgccccta actccgccca   8880

gttccgccca ttctccgccc catggctgac taattttttt tatttatgca gaggccgagg   8940

ccgcctcggc ctctgagcta ttccagaagt agtgaggagg cttttttgga ggcctaggct   9000

tttgcaaaaa gcttcgacgg tatcgattgg ctcatgtcca acattaccgc catgttgaca   9060

ttgattattg actagttatt aatagtaatc aattacgggg tcattagttc atagcccata   9120

tatggagttc cgcgttacat aacttacggt aaatggcccg cctggctgac cgcccaacga   9180

cccccgccca ttgacgtcaa taatgacgta tgttcccata gtaacgccaa tagggacttt   9240

ccattgacgt caatgggtgg agtatttacg gtaaactgcc cacttggcag tacatcaagt   9300

gtatcatatg ccaagtacgc cccctattga cgtcaatgac ggtaaatggc ccgcctggca   9360

ttatgcccag tacatgacct tatgggactt tcctacttgg cagtacatct acgtattagt   9420

catcgctatt accatggtga tgcggttttg gcagtacatc aatgggcgtg gatagcggtt   9480

tgactcacgg ggatttccaa gtctccaccc cattgacgtc aatgggagtt tgttttggca   9540

ccaaaatcaa cgggactttc caaaatgtcg taacaactcc gccccattga cgcaaatggg   9600

cggtaggcgt gtacggaatt cggagtggcg agccctcaga tcctgcatat aagcagctgc   9660

tttttgcctg tactgggtct ctctg                                         9685
```

<210> SEQ ID NO 48
<211> LENGTH: 838
<212> TYPE: PRT
<213> ORGANISM: Artificial Sequence
<220> FEATURE:
<223> OTHER INFORMATION: Synthetic sequence

<400> SEQUENCE: 48

```
Met Leu Leu Leu Val Thr Ser Leu Leu Leu Cys Glu Leu Pro His Pro
1               5                   10                  15

Ala Phe Leu Leu Ile Pro Gln Ser Val Lys Glu Ser Glu Gly Asp Leu
            20                  25                  30

Val Thr Pro Ala Gly Asn Leu Thr Leu Thr Cys Thr Ala Ser Gly Ser
        35                  40                  45

Asp Ile Asn Asp Tyr Pro Ile Ser Trp Val Arg Gln Ala Pro Gly Lys
    50                  55                  60

Gly Leu Glu Trp Ile Gly Phe Ile Asn Ser Gly Gly Ser Thr Trp Tyr
65                  70                  75                  80

Ala Ser Trp Val Lys Gly Arg Phe Thr Ile Ser Arg Thr Ser Thr Thr
                85                  90                  95

Val Asp Leu Lys Met Thr Ser Leu Thr Thr Asp Asp Thr Ala Thr Tyr
            100                 105                 110

Phe Cys Ala Arg Gly Tyr Ser Thr Tyr Tyr Gly Asp Phe Asn Ile Trp
        115                 120                 125

Gly Pro Gly Thr Leu Val Thr Ile Ser Ser Gly Gly Gly Gly Ser Gly
    130                 135                 140

Gly Gly Gly Ser Gly Gly Gly Gly Ser Glu Leu Val Met Thr Gln Thr
145                 150                 155                 160
```

```
Pro Ser Ser Thr Ser Gly Ala Val Gly Gly Thr Val Thr Ile Asn Cys
                165                 170                 175

Gln Ala Ser Gln Ser Ile Asp Ser Asn Leu Ala Trp Phe Gln Gln Lys
            180                 185                 190

Pro Gly Gln Pro Pro Thr Leu Leu Ile Tyr Arg Ala Ser Asn Leu Ala
        195                 200                 205

Ser Gly Val Pro Ser Arg Phe Ser Gly Ser Arg Ser Gly Thr Glu Tyr
    210                 215                 220

Thr Leu Thr Ile Ser Gly Val Gln Arg Glu Asp Ala Ala Thr Tyr Tyr
225                 230                 235                 240

Cys Leu Gly Gly Val Gly Asn Val Ser Tyr Arg Thr Ser Phe Gly Gly
                245                 250                 255

Gly Thr Glu Val Val Val Lys Glu Ser Lys Tyr Gly Pro Pro Cys Pro
            260                 265                 270

Pro Cys Pro Met Phe Trp Val Leu Val Val Val Gly Gly Val Leu Ala
        275                 280                 285

Cys Tyr Ser Leu Leu Val Thr Val Ala Phe Ile Ile Phe Trp Val Lys
    290                 295                 300

Arg Gly Arg Lys Lys Leu Leu Tyr Ile Phe Lys Gln Pro Phe Met Arg
305                 310                 315                 320

Pro Val Gln Thr Thr Gln Glu Glu Asp Gly Cys Ser Cys Arg Phe Pro
                325                 330                 335

Glu Glu Glu Glu Gly Gly Cys Glu Leu Arg Val Lys Phe Ser Arg Ser
            340                 345                 350

Ala Asp Ala Pro Ala Tyr Gln Gln Gly Gln Asn Gln Leu Tyr Asn Glu
        355                 360                 365

Leu Asn Leu Gly Arg Arg Glu Glu Tyr Asp Val Leu Asp Lys Arg Arg
    370                 375                 380

Gly Arg Asp Pro Glu Met Gly Gly Lys Pro Arg Arg Lys Asn Pro Gln
385                 390                 395                 400

Glu Gly Leu Tyr Asn Glu Leu Gln Lys Asp Lys Met Ala Glu Ala Tyr
                405                 410                 415

Ser Glu Ile Gly Met Lys Gly Glu Arg Arg Arg Gly Lys Gly His Asp
            420                 425                 430

Gly Leu Tyr Gln Gly Leu Ser Thr Ala Thr Lys Asp Thr Tyr Asp Ala
        435                 440                 445

Leu His Met Gln Ala Leu Pro Pro Arg Leu Glu Gly Gly Gly Glu Gly
    450                 455                 460

Arg Gly Ser Leu Leu Thr Cys Gly Asp Val Glu Glu Asn Pro Gly Pro
465                 470                 475                 480

Arg Met Leu Leu Leu Val Thr Ser Leu Leu Leu Cys Glu Leu Pro His
                485                 490                 495

Pro Ala Phe Leu Leu Ile Pro Arg Lys Val Cys Asn Gly Ile Gly Ile
            500                 505                 510

Gly Glu Phe Lys Asp Ser Leu Ser Ile Asn Ala Thr Asn Ile Lys His
        515                 520                 525

Phe Lys Asn Cys Thr Ser Ile Ser Gly Asp Leu His Ile Leu Pro Val
    530                 535                 540

Ala Phe Arg Gly Asp Ser Phe Thr His Thr Pro Pro Leu Asp Pro Gln
545                 550                 555                 560

Glu Leu Asp Ile Leu Lys Thr Val Lys Glu Ile Thr Gly Phe Leu Leu
                565                 570                 575

Ile Gln Ala Trp Pro Glu Asn Arg Thr Asp Leu His Ala Phe Glu Asn
```

```
            580                 585                 590

Leu Glu Ile Ile Arg Gly Arg Thr Lys Gln His Gly Gln Phe Ser Leu
        595                 600                 605

Ala Val Val Ser Leu Asn Ile Thr Ser Leu Gly Leu Arg Ser Leu Lys
    610                 615                 620

Glu Ile Ser Asp Gly Asp Val Ile Ile Ser Gly Asn Lys Asn Leu Cys
625                 630                 635                 640

Tyr Ala Asn Thr Ile Asn Trp Lys Lys Leu Phe Gly Thr Ser Gly Gln
                645                 650                 655

Lys Thr Lys Ile Ile Ser Asn Arg Gly Glu Asn Ser Cys Lys Ala Thr
            660                 665                 670

Gly Gln Val Cys His Ala Leu Cys Ser Pro Glu Gly Cys Trp Gly Pro
        675                 680                 685

Glu Pro Arg Asp Cys Val Ser Cys Arg Asn Val Ser Arg Gly Arg Glu
    690                 695                 700

Cys Val Asp Lys Cys Asn Leu Leu Glu Gly Glu Pro Arg Glu Phe Val
705                 710                 715                 720

Glu Asn Ser Glu Cys Ile Gln Cys His Pro Glu Cys Leu Pro Gln Ala
                725                 730                 735

Met Asn Ile Thr Cys Thr Gly Arg Gly Pro Asp Asn Cys Ile Gln Cys
            740                 745                 750

Ala His Tyr Ile Asp Gly Pro His Cys Val Lys Thr Cys Pro Ala Gly
        755                 760                 765

Val Met Gly Glu Asn Asn Thr Leu Val Trp Lys Tyr Ala Asp Ala Gly
    770                 775                 780

His Val Cys His Leu Cys His Pro Asn Cys Thr Tyr Gly Cys Thr Gly
785                 790                 795                 800

Pro Gly Leu Glu Gly Cys Pro Thr Asn Gly Pro Lys Ile Pro Ser Ile
                805                 810                 815

Ala Thr Gly Met Val Gly Ala Leu Leu Leu Leu Leu Val Val Ala Leu
            820                 825                 830

Gly Ile Gly Leu Phe Met
        835


<210> SEQ ID NO 49
<211> LENGTH: 119
<212> TYPE: PRT
<213> ORGANISM: Artificial Sequence
<220> FEATURE:
<223> OTHER INFORMATION: Synthetic sequence

<400> SEQUENCE: 49

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
```

```
            100                 105                 110

Leu Ser Leu Ser Leu Gly Lys
        115


<210> SEQ ID NO 50
<211> LENGTH: 229
<212> TYPE: PRT
<213> ORGANISM: Artificial Sequence
<220> FEATURE:
<223> OTHER INFORMATION: Synthetic sequence

<400> SEQUENCE: 50

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 51
<211> LENGTH: 9
<212> TYPE: PRT
<213> ORGANISM: Artificial Sequence
<220> FEATURE:
<223> OTHER INFORMATION: Synthetic sequence

<400> SEQUENCE: 51

Tyr Gly Pro Pro Cys Pro Pro Cys Pro
1               5


<210> SEQ ID NO 52
<211> LENGTH: 10
<212> TYPE: PRT
<213> ORGANISM: Artificial Sequence
<220> FEATURE:
```

<223> OTHER INFORMATION: Synthetic sequence

<400> SEQUENCE: 52

Lys Tyr Gly Pro Pro Cys Pro Pro Cys Pro
1 5 10

<210> SEQ ID NO 53
<211> LENGTH: 14
<212> TYPE: PRT
<213> ORGANISM: Artificial Sequence
<220> FEATURE:
<223> OTHER INFORMATION: Synthetic sequence

<400> SEQUENCE: 53

Glu Val Val Val Lys Tyr Gly Pro Pro Cys Pro Pro Cys Pro
1 5 10

<210> SEQ ID NO 54
<211> LENGTH: 2529
<212> TYPE: DNA
<213> ORGANISM: Artificial Sequence
<220> FEATURE:
<223> OTHER INFORMATION: Synthetic sequence

<400> SEQUENCE: 54
atgcttctcc tggtgacaag ccttctgctc tgtgagttac cacacccagc attcctcctg 60
atcccagata tccagatgac ccagtccccg agctccctgt ccgcctctgt gggcgatagg 120
gtcaccatca cctgccgtgc cagtcaggat gtgaatactg ctgtagcctg gtatcaacag 180
aaaccaggaa aagctccgaa actactgatt tactcggcat ccttcctcta ctctggagtc 240
ccttctcgct tctctggttc cagatctggg acggatttca ctctgaccat cagcagtctg 300
cagccggaag acttcgcaac ttattactgt cagcaacatt atactactcc tcccacgttc 360
ggacagggta ccaaggtgga gatcaaaggc agtactagcg gcggtggctc cgggggcgga 420
tccggtgggg gcggcagcag cgaggttcag ctggtggagt ctggcggtgg cctggtgcag 480
ccagggggct cactccgttt gtcctgtgca gcttctggct tcaacattaa agacacctat 540
atacactggg tgcgtcaggc cccgggtaag ggcctggaat gggttgcaag gatttatcct 600
acgaatggtt atactagata tgccgatagc gtcaagggcc gtttcactat aagcgcagac 660
acatccaaaa acacagccta cctgcagatg aacagcctgc gtgctgagga cactgccgtc 720
tattattgtt ctagatgggg aggggacggc ttctatgcta tggactactg gggtcaagga 780
accctggtca ccgtctcgag tgagagcaag tacggaccgc cctgcccccc ttgccctatg 840
ttctgggtgc tggtggtggt cggaggcgtg ctggcctgct acagcctgct ggtcaccgtg 900
gccttcatca tcttttgggt gaaacggggc agaaagaaac tcctgtatat attcaaacaa 960
ccatttatga gaccagtaca aactactcaa gaggaagatg gctgtagctg ccgatttcca 1020
gaagaagaag aaggaggatg tgaactgcgg gtgaagttca gcagaagcgc cgacgcccct 1080
gcctaccagc agggccagaa tcagctgtac aacgagctga acctgggcag aagggaagag 1140
tacgacgtcc tggataagcg gagaggccgg gaccctgaga tgggcggcaa gcctcggcgg 1200
aagaaccccc aggaaggcct gtataacgaa ctgcagaaag acaagatggc cgaggcctac 1260
agcgagatcg gcatgaaggg cgagcggagg cggggcaagg gccacgacgg cctgtatcag 1320
ggcctgtcca ccgccaccaa ggatacctac gacgccctgc acatgcaggc cctgcccccca 1380 aggctcgagg gcggcggaga gggcagagga agtcttctaa catgcggtga cgtggaggag 1440
aatcccggcc ctaggatgct tctcctggtg acaagccttc tgctctgtga gttaccacac 1500
ccagcattcc tcctgatccc acgcaaagtg tgtaacggaa taggtattgg tgaatttaaa 1560
gactcactct ccataaatgc tacgaatatt aaacacttca aaaactgcac ctccatcagt 1620
ggcgatctcc acatcctgcc ggtggcattt aggggtgact ccttcacaca tactcctcct 1680
ctggatccac aggaactgga tattctgaaa accgtaaagg aaatcacagg gtttttgctg 1740
attcaggctt ggcctgaaaa caggacggac ctccatgcct ttgagaacct agaaatcata 1800
cgcggcagga ccaagcaaca tggtcagttt tctcttgcag tcgtcagcct gaacataaca 1860
tccttgggat tacgctccct caaggagata agtgatggag atgtgataat ttcaggaaac 1920
aaaaatttgt gctatgcaaa tacaataaac tggaaaaaac tgtttgggac ctccggtcag 1980
aaaaccaaaa ttataagcaa cagaggtgaa aacagctgca aggccacagg ccaggtctgc 2040
catgccttgt gctcccccga gggctgctgg ggcccggagc ccagggactg cgtctcttgc 2100
cggaatgtca gccgaggcag ggaatgcgtg gacaagtgca accttctgga gggtgagcca 2160
agggagtttg tggagaactc tgagtgcata cagtgccacc cagagtgcct gcctcaggcc 2220
atgaacatca cctgcacagg acggggacca gacaactgta tccagtgtgc ccactacatt 2280
gacggccccc actgcgtcaa gacctgcccg gcaggagtca tgggagaaaa caacaccctg 2340
gtctggaagt acgcagacgc cggccatgtg tgccacctgt gccatccaaa ctgcacctac 2400
ggatgcactg ggccaggtct tgaaggctgt ccaacgaatg ggcctaagat cccgtccatc 2460
gccactggga tggtgggggc cctcctcttg ctgctggtgg tggccctggg gatcggcctc 2520
ttcatgtga 2529

<210> SEQ ID NO 55
<211> LENGTH: 2850
<212> TYPE: DNA
<213> ORGANISM: Artificial Sequence
<220> FEATURE:
<223> OTHER INFORMATION: Synthetic sequence

<400> SEQUENCE: 55
atgcttctcc tggtgacaag ccttctgctc tgtgagttac cacacccagc attcctcctg 60
atcccagata tccagatgac ccagtccccg agctccctgt ccgcctctgt gggcgatagg 120
gtcaccatca cctgccgtgc cagtcaggat gtgaatactg ctgtagcctg gtatcaacag 180
aaaccaggaa aagctccgaa actactgatt tactcggcat ccttcctcta ctctggagtc 240
ccttctcgct tctctggttc cagatctggg acggatttca ctctgaccat cagcagtctg 300
cagccggaag acttcgcaac ttattactgt cagcaacatt atactactcc tcccacgttc 360
ggacagggta ccaaggtgga gatcaaaggc agtactagcg gcggtggctc cgggggcgga 420
tccggtgggg gcggcagcag cgaggttcag ctggtggagt ctggcggtgg cctggtgcag 480
ccagggggct cactccgttt gtcctgtgca gcttctggct tcaacattaa agacacctat 540
atacactggg tgcgtcaggc cccgggtaag ggcctggaat gggttgcaag gatttatcct 600
acgaatggtt atactagata tgccgatagc gtcaagggcc gtttcactat aagcgcagac 660
acatccaaaa acacagccta cctgcagatg aacagcctgc gtgctgagga cactgccgtc 720
tattattgtt ctagatgggg aggggacggc ttctatgcta tggactactg gggtcaagga 780
accctggtca ccgtctcgag tgagagcaag tacggaccgc cctgcccccc ttgccctggc 840
cagcctagag aaccccaggt gtacaccctg cctcccagcc aggaagagat gaccaagaac 900
caggtgtccc tgacctgcct ggtcaaaggc ttctacccca gcgatatcgc cgtggaatgg 960

```
gagagcaacg gccagcccga gaacaactac aagaccaccc cccctgtgct ggacagcgac   1020
ggcagcttct tcctgtactc ccggctgacc gtggacaaga gccggtggca ggaaggcaac   1080
gtcttcagct gcagcgtgat gcacgaggcc ctgcacaacc actacaccca gaagtccctg   1140
agcctgagcc tgggcaagat gttctgggtg ctggtggtgg tcggaggcgt gctggcctgc   1200
tacagcctgc tggtcaccgt ggccttcatc atcttttggg tgaaacgggg cagaaagaaa   1260
ctcctgtata tattcaaaca accatttatg agaccagtac aaactactca agaggaagat   1320
ggctgtagct gccgatttcc agaagaagaa gaaggaggat gtgaactgcg ggtgaagttc   1380
agcagaagcg ccgacgcccc tgcctaccag cagggccaga atcagctgta caacgagctg   1440
aacctgggca gaagggaaga gtacgacgtc ctggataagc ggagaggccg ggaccctgag   1500
atgggcggca agcctcggcg gaagaacccc caggaaggcc tgtataacga actgcagaaa   1560
gacaagatgg ccgaggccta cagcgagatc ggcatgaagg gcgagcggag gcggggcaag   1620
ggccacgacg gcctgtatca gggcctgtcc accgccacca aggataccta cgacgccctg   1680
cacatgcagg ccctgccccc aaggctcgag ggcggcggag agggcagagg aagtcttcta   1740
acatgcggtg acgtggagga gaatcccggc cctaggatgc ttctcctggt gacaagcctt   1800
ctgctctgtg agttaccaca cccagcattc ctcctgatcc cacgcaaagt gtgtaacgga   1860
ataggtattg gtgaatttaa agactcactc tccataaatg ctacgaatat taaacacttc   1920
aaaaactgca cctccatcag tggcgatctc cacatcctgc cggtggcatt taggggtgac   1980
tccttcacac atactcctcc tctggatcca caggaactgg atattctgaa aaccgtaaag   2040
gaaatcacag ggtttttgct gattcaggct tggcctgaaa acaggacgga cctccatgcc   2100
tttgagaacc tagaaatcat acgcggcagg accaagcaac atggtcagtt ttctcttgca   2160
gtcgtcagcc tgaacataac atccttggga ttacgctccc tcaaggagat aagtgatgga   2220
gatgtgataa tttcaggaaa caaaaatttg tgctatgcaa atacaataaa ctggaaaaaa   2280
ctgtttggga cctccggtca gaaaaccaaa attataagca acagaggtga aaacagctgc   2340
aaggccacag gccaggtctg ccatgccttg tgctcccccg agggctgctg gggcccggag   2400
cccagggact gcgtctcttg ccggaatgtc agccgaggca gggaatgcgt ggacaagtgc   2460
aaccttctgg agggtgagcc aagggagttt gtggagaact ctgagtgcat acagtgccac   2520
ccagagtgcc tgcctcaggc catgaacatc acctgcacag gacggggacc agacaactgt   2580
atccagtgtg cccactacat tgacggcccc cactgcgtca agacctgccc ggcaggagtc   2640
atgggagaaa acaacaccct ggtctggaag tacgcagacg ccggccatgt gtgccacctg   2700
tgccatccaa actgcaccta cggatgcact gggccaggtc ttgaaggctg tccaacgaat   2760
gggcctaaga tcccgtccat cgccactggg atggtggggg ccctcctctt gctgctggtg   2820
gtggccctgg ggatcggcct cttcatgtga                                    2850
```

<210> SEQ ID NO 56
<211> LENGTH: 3180
<212> TYPE: DNA
<213> ORGANISM: Artificial Sequence
<220> FEATURE:
<223> OTHER INFORMATION: Synthetic sequence

<400> SEQUENCE: 56

```
atgcttctcc tggtgacaag ccttctgctc tgtgagttac cacacccagc attcctcctg     60
atcccagata tccagatgac ccagtccccg agctccctgt ccgcctctgt gggcgatagg    120
gtcaccatca cctgccgtgc cagtcaggat gtgaatactg ctgtagcctg gtatcaacag    180
```

```
aaaccaggaa aagctccgaa actactgatt tactcggcat ccttcctcta ctctggagtc    240
ccttctcgct tctctggttc cagatctggg acggatttca ctctgaccat cagcagtctg    300
cagccggaag acttcgcaac ttattactgt cagcaacatt atactactcc tcccacgttc    360
ggacagggta ccaaggtgga gatcaaaggc agtactagcg gcggtggctc cgggggcgga    420
tccggtgggg gcggcagcag cgaggttcag ctggtggagt ctggcggtgg cctggtgcag    480
ccagggggct cactccgttt gtcctgtgca gcttctggct tcaacattaa agacacctat    540
atacactggg tgcgtcaggc ccgggtaag ggcctggaat gggttgcaag gatttatcct    600
acgaatggtt atactagata tgccgatagc gtcaagggcc gtttcactat aagcgcagac    660
acatccaaaa acacagccta cctgcagatg aacagcctgc gtgctgagga cactgccgtc    720
tattattgtt ctagatgggg aggggacggc ttctatgcta tggactactg gggtcaagga    780
accctggtca ccgtctcgag tgagagcaag tacggaccgc cctgcccccc ttgccctgcc    840
cccgagttcc tgggcggacc cagcgtgttc ctgttccccc ccaagcccaa ggacaccctg    900
atgatcagcc ggacccccga ggtgacctgc gtggtggtgg acgtgagcca ggaagatccc    960
gaggtccagt tcaattggta cgtggacggc gtggaagtgc acaacgccaa gaccaagccc   1020
agagaggaac agttcaacag cacctaccgg gtggtgtctg tgctgaccgt gctgcaccag   1080
gactggctga acggcaaaga atacaagtgc aaggtgtcca acaagggcct gcccagcagc   1140
atcgaaaaga ccatcagcaa ggccaagggc cagcctcgcg agccccaggt gtacaccctg   1200
cctccctccc aggaagagat gaccaagaac caggtgtccc tgacctgcct ggtgaagggc   1260
ttctacccca gcgacatcgc cgtggagtgg gagagcaacg gccagcctga gaacaactac   1320
aagaccaccc ctcccgtgct ggacagcgac ggcagcttct tcctgtacag ccggctgacc   1380
gtggacaaga gccggtggca ggaaggcaac gtctttagct gcagcgtgat gcacgaggcc   1440
ctgcacaacc actacaccca gaagagcctg agcctgtccc tgggcaagat gttctgggtg   1500
ctggtggtgg tgggcggggt gctggcctgc tacagcctgc tggtgacagt ggccttcatc   1560
atcttttggg tgaaacgggg cagaaagaaa ctcctgtata tattcaaaca accatttatg   1620
agaccagtac aaactactca agaggaagat ggctgtagct gccgatttcc agaagaagaa   1680
gaaggaggat gtgaactgcg ggtgaagttc agcagaagcg ccgacgcccc tgcctaccag   1740
cagggccaga atcagctgta caacgagctg aacctgggca gaagggaaga gtacgacgtc   1800
ctggataagc ggagaggccg ggaccctgag atgggcggca agcctcggcg gaagaacccc   1860
caggaaggcc tgtataacga actgcagaaa gacaagatgg ccgaggccta cagcgagatc   1920
ggcatgaagg gcgagcggag gcggggcaag ggccacgacg gcctgtatca gggcctgtcc   1980
accgccacca aggataccta cgacgccctg cacatgcagg ccctgccccc aaggctcgag   2040
ggcggcggag agggcagagg aagtcttcta acatgcggtg acgtggagga gaatcccggc   2100
cctaggatgc ttctcctggt gacaagcctt ctgctctgtg agttaccaca cccagcattc   2160
ctcctgatcc cacgcaaagt gtgtaacgga ataggtattg gtgaatttaa agactcactc   2220
tccataaatg ctacgaatat taaacacttc aaaaactgca cctccatcag tggcgatctc   2280
cacatcctgc cggtggcatt taggggtgac tccttcacac atactcctcc tctggatcca   2340
caggaactgg atattctgaa aaccgtaaag gaaatcacag ggtttttgct gattcaggct   2400
tggcctgaaa acaggacgga cctccatgcc tttgagaacc tagaaatcat acgcggcagg   2460
accaagcaac atggtcagtt ttctcttgca gtcgtcagcc tgaacataac atccttggga   2520
```

```
ttacgctccc tcaaggagat aagtgatgga gatgtgataa tttcaggaaa caaaaatttg   2580

tgctatgcaa atacaataaa ctggaaaaaa ctgtttggga cctccggtca gaaaaccaaa   2640

attataagca acagaggtga aaacagctgc aaggccacag gccaggtctg ccatgccttg   2700

tgctcccccg agggctgctg gggcccggag cccagggact gcgtctcttg ccggaatgtc   2760

agccgaggca gggaatgcgt ggacaagtgc aaccttctgg agggtgagcc aagggagttt   2820

gtggagaact ctgagtgcat acagtgccac ccagagtgcc tgcctcaggc catgaacatc   2880

acctgcacag gacggggacc agacaactgt atccagtgtg cccactacat tgacggcccc   2940

cactgcgtca agacctgccc ggcaggagtc atgggagaaa acaacaccct ggtctggaag   3000

tacgcagacg ccggccatgt gtgccacctg tgccatccaa actgcaccta cggatgcact   3060

gggccaggtc ttgaaggctg tccaacgaat gggcctaaga tcccgtccat cgccactggg   3120

atggtggggg ccctcctctt gctgctggtg gtggccctgg ggatcggcct cttcatgtga   3180
```

```
<210> SEQ ID NO 57
<211> LENGTH: 11
<212> TYPE: PRT
<213> ORGANISM: Artificial Sequence
<220> FEATURE:
<223> OTHER INFORMATION: Synthetic sequence

<400> SEQUENCE: 57

Arg Ala Ser Gln Asp Ile Ser Lys Tyr Leu Asn
1               5                   10


<210> SEQ ID NO 58
<211> LENGTH: 7
<212> TYPE: PRT
<213> ORGANISM: Artificial Sequence
<220> FEATURE:
<223> OTHER INFORMATION: Synthetic sequence

<400> SEQUENCE: 58

Ser Arg Leu His Ser Gly Val
1               5


<210> SEQ ID NO 59
<211> LENGTH: 9
<212> TYPE: PRT
<213> ORGANISM: Artificial Sequence
<220> FEATURE:
<223> OTHER INFORMATION: Synthetic sequence

<400> SEQUENCE: 59

Gly Asn Thr Leu Pro Tyr Thr Phe Gly
1               5


<210> SEQ ID NO 60
<211> LENGTH: 16
<212> TYPE: PRT
<213> ORGANISM: Artificial Sequence
<220> FEATURE:
<223> OTHER INFORMATION: Synthetic sequence

<400> SEQUENCE: 60

Val Ile Trp Gly Ser Glu Thr Thr Tyr Tyr Asn Ser Ala Leu Lys Ser
1               5                   10                  15


<210> SEQ ID NO 61
<211> LENGTH: 7
<212> TYPE: PRT
<213> ORGANISM: Artificial Sequence
```

<220> FEATURE:
<223> OTHER INFORMATION: Synthetic sequence

<400> SEQUENCE: 61

Tyr Ala Met Asp Tyr Trp Gly
1 5

<210> SEQ ID NO 62
<211> LENGTH: 11
<212> TYPE: PRT
<213> ORGANISM: Artificial Sequence
<220> FEATURE:
<223> OTHER INFORMATION: Synthetic sequence

<400> SEQUENCE: 62

Ala Ser Gly Phe Asp Phe Ser Ala Tyr Tyr Met
1 5 10

<210> SEQ ID NO 63
<211> LENGTH: 7
<212> TYPE: PRT
<213> ORGANISM: Artificial Sequence
<220> FEATURE:
<223> OTHER INFORMATION: Synthetic sequence

<400> SEQUENCE: 63

Thr Ile Tyr Pro Ser Ser Gly
1 5

<210> SEQ ID NO 64
<211> LENGTH: 9
<212> TYPE: PRT
<213> ORGANISM: Artificial Sequence
<220> FEATURE:
<223> OTHER INFORMATION: Synthetic sequence

<400> SEQUENCE: 64

Ala Asp Arg Ala Thr Tyr Phe Cys Ala
1 5

<210> SEQ ID NO 65
<211> LENGTH: 6
<212> TYPE: PRT
<213> ORGANISM: Artificial Sequence
<220> FEATURE:
<223> OTHER INFORMATION: Synthetic sequence

<400> SEQUENCE: 65

Asp Thr Ile Asp Trp Tyr
1 5

<210> SEQ ID NO 66
<211> LENGTH: 16
<212> TYPE: PRT
<213> ORGANISM: Artificial Sequence
<220> FEATURE:
<223> OTHER INFORMATION: Synthetic sequence

<400> SEQUENCE: 66

Val Gln Ser Asp Gly Ser Tyr Thr Lys Arg Pro Gly Val Pro Asp Arg
1 5 10 15

<210> SEQ ID NO 67
<211> LENGTH: 8
<212> TYPE: PRT
<213> ORGANISM: Artificial Sequence
<220> FEATURE:

<223> OTHER INFORMATION: Synthetic sequence

<400> SEQUENCE: 67

Tyr Ile Gly Gly Tyr Val Phe Gly
1               5

<210> SEQ ID NO 68
<211> LENGTH: 11
<212> TYPE: PRT
<213> ORGANISM: Artificial Sequence
<220> FEATURE:
<223> OTHER INFORMATION: Synthetic sequence

<400> SEQUENCE: 68

Ser Gly Ser Asp Ile Asn Asp Tyr Pro Ile Ser
1               5                   10

<210> SEQ ID NO 69
<211> LENGTH: 7
<212> TYPE: PRT
<213> ORGANISM: Artificial Sequence
<220> FEATURE:
<223> OTHER INFORMATION: Synthetic sequence

<400> SEQUENCE: 69

Ile Asn Ser Gly Gly Ser Thr
1               5

<210> SEQ ID NO 70
<211> LENGTH: 8
<212> TYPE: PRT
<213> ORGANISM: Artificial Sequence
<220> FEATURE:
<223> OTHER INFORMATION: Synthetic sequence

<400> SEQUENCE: 70

Tyr Phe Cys Ala Arg Gly Tyr Ser
1               5

<210> SEQ ID NO 71
<211> LENGTH: 5
<212> TYPE: PRT
<213> ORGANISM: Artificial Sequence
<220> FEATURE:
<223> OTHER INFORMATION: Synthetic sequence

<400> SEQUENCE: 71

Ser Asn Leu Ala Trp
1               5

<210> SEQ ID NO 72
<211> LENGTH: 16
<212> TYPE: PRT
<213> ORGANISM: Artificial Sequence
<220> FEATURE:
<223> OTHER INFORMATION: Synthetic sequence

<400> SEQUENCE: 72

Arg Ala Ser Asn Leu Ala Ser Gly Val Pro Ser Arg Phe Ser Gly Ser
1               5                   10                  15

<210> SEQ ID NO 73
<211> LENGTH: 8
<212> TYPE: PRT
<213> ORGANISM: Artificial Sequence
<220> FEATURE:
<223> OTHER INFORMATION: Synthetic sequence

```
<400> SEQUENCE: 73

Asn Val Ser Tyr Arg Thr Ser Phe
1               5


<210> SEQ ID NO 74
<211> LENGTH: 5
<212> TYPE: PRT
<213> ORGANISM: Artificial Sequence
<220> FEATURE:
<223> OTHER INFORMATION: Synthetic sequence

<400> SEQUENCE: 74

Asp Tyr Gly Val Ser
1               5
```